US012357278B2

(12) United States Patent
Ellinor, II et al.

(10) Patent No.: US 12,357,278 B2
(45) Date of Patent: Jul. 15, 2025

(54) ECHOCARDIOGRAPHY DEEP LEARNING AND CARDIOVASCULAR OUTCOMES

(71) Applicants: The General Hospital Corporation, Boston, MA (US); Beth Israel Deaconess Medical Center, Inc., Boston, MA (US); The Broad Institute, Inc., Cambridge, MA (US)

(72) Inventors: Patrick T. Ellinor, II, Brookline, MA (US); Emily S. Lau, Boston, MA (US); Jennifer Ho, Cambridge, MA (US); Mostafa Al-Alusi, Cambridge, MA (US); Paolo Di Achille, Cambridge, MA (US); Puneet Batra, Cambridge, MA (US); Steven Lubitz, Boston, MA (US)

(73) Assignees: The General Hospital Corporation, Boston, MA (US); Beth Israel Deaconess Medical Center, Inc., Boston, MA (US); The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 18/913,937

(22) Filed: Oct. 11, 2024

(65) Prior Publication Data
US 2025/0120676 A1 Apr. 17, 2025

Related U.S. Application Data

(60) Provisional application No. 63/590,324, filed on Oct. 13, 2023.

(51) Int. Cl.
*A61B 8/00* (2006.01)
*A61B 8/08* (2006.01)
(Continued)

(52) U.S. Cl.
CPC .......... *A61B 8/5223* (2013.01); *A61B 8/0883* (2013.01); *G06T 7/0012* (2013.01);
(Continued)

(58) Field of Classification Search
CPC ........ G06T 7/0012; G06T 2207/10016; G06T 2207/20081; G06T 2207/20084;
(Continued)

(56) References Cited

U.S. PATENT DOCUMENTS

2019/0183366 A1* 6/2019 Dehghan Marvast ... A61B 5/72

FOREIGN PATENT DOCUMENTS

| CN | 115620183 A | 1/2023 |
| WO | 2025081112 A1 | 4/2025 |

OTHER PUBLICATIONS

Abadi, Martin , "TensorFlow: Large-Scale Machine Learning on Heterogeneous Distributed Systems", , Mar. 16, 2016, 19 pages.
(Continued)

*Primary Examiner* — Amelie R Davis
(74) *Attorney, Agent, or Firm* — FIG. 1 Patents

(57) ABSTRACT

Echocardiography deep learning and cardiovascular outcomes are described. An echocardiogram analysis module may include a deep learning model to generate a video output for an input echocardiogram video, the deep learning model comprising a convolutional neural network and at least one dense layer. The echocardiogram analysis module may further include a cardiac prediction generator to generate a cardiac prediction based on video outputs generated for a plurality of input echocardiogram videos of an echocardiogram study, the cardiac prediction comprising a measurement prediction or a classification prediction.

26 Claims, 51 Drawing Sheets

(51) Int. Cl.
    *G06T 7/00*     (2017.01)
    *G06V 10/774*     (2022.01)
    *G06V 10/776*     (2022.01)
    *G06V 10/82*     (2022.01)
    *G06V 20/40*     (2022.01)
    *G16H 50/20*     (2018.01)

(52) U.S. Cl.
CPC .......... *G06V 10/774* (2022.01); *G06V 10/776* (2022.01); *G06V 10/82* (2022.01); *G06V 20/41* (2022.01); *G06V 20/46* (2022.01); *G16H 50/20* (2018.01); *G06T 2207/10016* (2013.01); *G06T 2207/20081* (2013.01); *G06T 2207/20084* (2013.01); *G06T 2207/30048* (2013.01); *G06V 2201/031* (2022.01)

(58) Field of Classification Search
CPC ........ G06T 2207/30048; G06V 10/774; G06V 10/776; G06V 10/82; G06V 20/41; G06V 20/46; G06V 2201/031; G16H 50/20; A61B 8/5223; A61B 8/0883
See application file for complete search history.

(56) References Cited

OTHER PUBLICATIONS

Agarwal, Sunil , "Prediction of Incident Heart Failure in General Practice: The ARIC Study", NIH Public Access; Circ Heart Fail., Jul. 1, 2012, 17 pages.
Akbilgic, Oguz , "ECG-AI: electrocardiogramtificial intelligencemodel for prediction of heart failure", European Society of Cardiology, Oct. 9, 2021, 9 pages.
Attia, Zachi , "An artificial intelligence-enabled ECG algorithm for the identification of patients with atrial fibrillation during sinus rhythm: a retrospective analysis of outcome prediction", www.thelancet.com, vol. 394, Sep. 7, 2019, 7 pages.
Attia, Zachi , "Screening for cardiac contractile dysfunction using an artificial intelligence—enabled electrocardiogram", Nature Medicine, vol. 25, Jan. 2019, 9 pages.
Austin, Peter , "Graphical calibration curves and the integrated calibration index (ICI) for survival models", Statistics in Medicine, Wiley, Apr. 17, 2020, 29 pages.
Booth, John , "Masked Hypertension and Cardiovascular Disease Events in a Prospective Cohort of African Americans: the Jackson Heart Study", HHS Public Access, Author manuscript, Hypertension, Aug. 1, 2017, 22 pages.
Butler, Javed , "Incident Heart Failure Prediction in the Elderly: The Health ABC Heart Failure Score", NIH Public Access; Circ Heart Fail. Author manuscript, Sep. 22, 2009, 18 pages.
Casale, Paul N, "Value of Echocardiographic Measurement of Left Ventricular Mass in Predicting Cardiovascular Morbid Events in Hypertensive Men", Annals of Internal Medicine, 1986, 7 pages.
Chen, Jersey , "National and regional trends in heart failure hospitalization and mortality rates for Medicare beneficiaries: 1998-2008", NIH Public Access, JAMA, Oct. 19, 2011, 19 pages.
Cowie, Martin , "Electronic health records to facilitate clinical research", Clin Res Cardiol, vol. 106, 2017, 9 pages.
Cunningham, Jonathan , "Natural Language Processing for Adjudication of Heart Failure Hospitalizations in a Multi-Center Clinical Trial", Running Title: NLP for HF Adjudication; medRxiv preprint doi: https://doi.org/10.1101/2023.08.17.23294234;, Aug. 23, 2023, 25 pages.
Cunningham, Jonathan , "Natural Language Processing for Adjudication of Heart Failure Hospitalizations in a Multi-Center Clinical Trial", HHS Public Access, JACC Heart Fail, Dec. 4, 2023, 4 pages.
Duffy, Grant , "High-Throughput Precision Phenotyping of Left Ventricular Hypertrophy With Cardiovascular Deep Learning", JAMA Cardiology, 2022, 10 pages.
Elias, Pierre , "Deep Learning Electrocardiogramalysis for Detection of Left-Sided Valvular Heart Disease", Journal of the American College of Cardiology, vol. 80 , No. 6, Aug. 9, 2022, 14 pages.
Friedman, Sam , "broadinstitute/ml4h: v0.0.18", Retrieved at <<https://zenodo.org/records/13910018>> on Mar. 27, 2025, Oct. 9, 2024, 5 pages.
GBD 2017 Disease and Injury Inci , "Global, regional, and national incidence, prevalence, and years lived with disability for 354 diseases and injuries for 195 countries and territories, 1990-2017: a systematic analysis for the Global Burden of Disease Study 2017", Global Health Metrics, www.thelancet.com vol. 392, Nov. 10, 2018, 70 pages.
Gensheimer, Michael , "A scalable discrete-time survival model for neural networks", PeerJ, Jan. 15, 2019, 19 pages.
Ghorbani, Amirata , "Deep learning interpretation of echocardiograms", npj, Digital Medicine, www.nature.com/npjdigitalmed, 2020, 10 pages.
He, Bryan , "Blinded, randomized trial of sonographer versus AI cardiac function assessment", Nature, vol. 615, Apr. 20, 2023, 9 pages.
Hwang, Kevin , "Barriers to Accurate Blood Pressure Measurement in the Medical Office", Journal of Primary Care & Community Health; vol. 9, 2018.
Iandola, Forrest , "DenseNet: Implementing Efficient ConvNet Descriptor Pyramids", Technical Report, Apr. 7, 2014, 11 pages.
Jain, Piyush , "A two-stage deep CNN architecture for the classification of low-risk and high-risk hypertension classes using multi-lead ECG signals", Informatics in Medicine Unlocked 21, Nov. 8, 2020, 8 pages.
Jeffrey, Zhang , "Fully Automated Echocardiogram Interpretation in Clinical Practice", Circulation DOI: 10.1161/CIRCULATIONAHA. 118.034338, Oct. 16, 2018, 13 pages.
Joshua, Bundy , "Systolic Blood Pressure Reduction and Risk of Cardiovascular Disease and Mortality: A Systematic Review and Network Meta-analysis", JAMA Cardiology, American Medical Association, May 31, 2017, 7 pages.
Kasser, Irwin , "The Relationship of Increased Left Atrial vol. and Pressure to Abnormal P Waves on the Electrocardiogram", Circulation, vol. XXXIX, Mar. 1969, 5 pages.
Khan, Sadiya , "10-Year Risk Equations for Incident Heart Failure in the General Population", HHS Public Access; J Am Coll Cardiol., May 21, 2020, 20 pages.
Khurshid, Shaan , "A Simple and Portable Algorithm for Identifying Atrial Fibrillation in the Electronic Medical Record", HHS Public Access; Published in final edited form as: Am J Cardiol., Jan. 15, 2017, 13 pages.
Khurshid, Shaan , "Cohort design and natural language processing to reduce bias in electronic health records research", npj Digital Medicine, 2022, 14 pages.
Khurshid, Shaan , "Deep Learning to Predict Cardiac Magnetic Resonance-Derived Left Ventricular Mass and Hypertrophy From 12-Lead ECGs", Circ Cardiovasc Imaging, American Heart Association, Inc., Jun. 2021, 11 pages.
Khurshid, Shaan , "Electrocardiogram-based Deep Learning and Clinical Risk Factors to Predict Atrial Fibrillation", HHS Public Access, Circulation, Jan. 11, 2022, 23 pages.
Khurshid, Shaan , "GitHub, JEDI", Retrieved at <<https://github.com/broadinstitute/jedi-public?tab=readme-ov-file>> on Mar. 31, 2025, 2021, 4 pages.
Kingma, Diederik , "Adam: A Method for Stochastic Optimization", Published as a conference paper at ICLR 2015, Jan. 30, 2017, 15 pages.
Kingma, Diederik P, "Adam: A Method for Stochastic Optimization", Cornell University, arXiv Preprint, arXiv.org [retrieved Aug. 9, 2023]. Retrieved from the Internet <https://arxiv.org/pdf/1412.6980.pdf>., Jan. 30, 2017, 15 pages.
Kirk, Jonathan , "Electromechanical Dyssynchrony and Resynchronization of the Failing Heart", NIH Public Access, Author Manuscript, Circ Res., Aug. 30, 2013, 27 pages.
Kondratyuk, Dan , "MoViNets: Mobile Video Networks for Efficient Video Recognition", Cornell University arXiv, arXiv.org [retrieved Feb. 8, 2022]. Retrieved from the Internet <https://arxiv.org/pdf/2103.11511.pdf>., Apr. 18, 2021, 21 Pages.

(56) References Cited

OTHER PUBLICATIONS

Kwon, Joon-myoung, "Development and Validation of Deep-Learning Algorithm for Electrocardiogramased Heart Failure Identification", Korean Circulation Journal, Feb. 19, 2019, 11 pages.

Lang, Roberto M., "Recommendations for cardiac chamber quantification by echocardiography in adults: an update from the American Society of Echocardiography and the European Association of Cardiovascular Imaging", Journal of the American Society of Echocardiography, Jan. 2015, 53 pages.

Lehtonen, Arttu, "Prevalence and prognosis of ECGabnormalities in normotensive and hypertensive individuals", Journal of Hypertension, 34, Jan. 18, 2016, 8 pages.

Liu, Liyuan, "On the Variance of the Adaptive Learning Rate and Beyond", Cornell University arXiv, arXiv.org [retrieved Feb. 14, 2022]. Retrieved from the Internet <https://arxiv.org/pdf/1908.03265.pdf>., Oct. 26, 2021, 14 Pages.

Lu, Yang, "Quantifying Blood Pressure Visit-to-Visit Variability in the Real-World Setting: A Retrospective Cohort Study", Circulation: Cardiovascular Quality and Outcomes, Apr. 2023, 11 pages.

Lu, Yao, "Bidirectionally Self-Normalizing Neural Networks", , Dec. 3, 2021, 23 pages.

Madani, Ali, "Fast and accurate view classification of echocardiograms using deep learning", npj Digital Medicine, 2018, 8 pages.

Mitchell, Carol, "Guidelines for Performing a Comprehensive Transthoracic Echocardiographic Examination in Adults: Recommendations from the American Society of Echocardiography", Journal of the American Society of Echocardiography, Jan. 2019, 64 pages.

Nagueh, Sherif, "Interobserver Variability in Applying American Society of Echocardiography/European Association of Cardiovascular Imaging 2016 Guidelines for Estimation of Left Ventricular Filling Pressure", Circ Cardiovasc Imaging., Jan. 2019, 8 pages.

Ouyang, David, "Video-based AI for beat-to-beat assessment of cardiac function", HHS Public Access; Nature; PMC 2022, Apr. 4, 2022, 22 pages.

Papolos, Alexander, "U.S. Hospital Use of Echocardiography : Insights From the Nationwide Inpatient Sample", Journal of the American College of Cardiology, vol. 67, No. 5, 2016, 9 pages.

Park, Sungheon, "Analysis on the Dropout Effect in Convolutional Neural Networks", SCCV, Part II, LNCS 10112, 2017, 16 pages.

Patel, Shivan, "Cardiovascular Mortality Associated With 5 Leading Risk Factors: National and State Preventable Fractions Estimated From Survey Data", Annals of Internal Medicine, American College of Physicians, Jun. 30, 2015, 47 pages.

Pencina, Michael, "Extensions of net reclassification improvement calculations to measure usefulness of new biomarkers", NIH Public Access; Stat Med. Author manuscript, Jan. 15, 2011, 18 pages.

Pencina, Michael, "Quantifying Importance of Major Risk Factors for Coronary Heart Disease. Circulation", Circulation, vol. 139, Mar. 26, 2019, 9 pages.

Raghunath, Sushravya, "Deep Neural Networks Can Predict New—Onset Atrial Fibrillation From the 12-Lead ECG and Help Identify Those at Risk of Atrial Fibrillation-Related Stroke", Circulation 2021, Mar. 30, 2021, 12 pages.

Ramachandran, Prajit, "Searching for Activation Functions", Google Brain, Oct. 27, 2017, 13 pages.

Rapsomaniki, Eleni, "Blood pressure and incidence of twelve cardiovascular diseases: lifetime risks, healthy life-years lost, and age-specifi c associations in 1•25 million people", www.thelancet.com vol. 383, May 31, 2014, 13 pages.

Robins, James, "Correcting for Noncompliance and Dependent Censoring in an—AIDS Clinical Trial with Inverse Probability of Censoring Weighted (IPCW) Log-Rank Tests", Biometrics 56, Sep. 2000, 10 pages.

Samad, Manar, "Predicting Survival From Large Echocardiography and Electronic Health Record Datasets", JACC: Cardiovascular Imaging, vol. 12 No 4, 2019, 9 pages.

Savarese, Gianluigi, "Global burden of heart failure: a comprehensive and updated review of epidemiology", Cardiovascular Research, European Society of Cardiology, 118, Feb. 12, 2022, 16 pages.

Scott, D. Solomon, "Influence of ejection fraction on outcomes and efficacy of spironolactone in patients with heart failure with preserved ejection fraction", European Heart Journal, 37, 2016, 8 pages.

Shah, Amil, "Echocardiographic Features of Patients With Heart Failure and Preserved Left Ventricular Ejection Fraction", Journal of the American College of Cardiology, vol. 74, No. 23, 2019, 16 pages.

Shimbo, Daichi, "The Use of Ambulatory Blood Pressure Monitoring Among Medicare Beneficiaries in 2007-2010", NIH Public Access; American Society of Hypertension, Dec. 1, 2015, 14 pages.

Singh, Pulkit, "One Clinician Is All You Need-Cardiac Magnetic Resonance Imaging Measurement Extraction: Deep Learning Algorithm Development", JMIR Medical Informatics, vol. 10, Issue 9, 2022, 15 pages.

Sinha, Arjun, "Race- and Sex-Specific Population Attributable Fractions of Incident Heart Failure", A Population-Based Cohort Study From the Lifetime Risk Pooling Project, Circulation: Heart Failure is available at www.ahajournals.org/journal/circheartfailure, Apr. 2021, 8 pages.

Snoek, Jasper, "Practical Bayesian Optimization of Machine Learning Algorithms", , 2012, 12 pages.

Soh, Desmond, "Automated diagnostic tool for hypertension using convolutional neural network", Computers in Biology and Medicine 126, Sep. 17, 2020, 7 pages.

Solomon, Scott, "Influence of ejection fraction on cardiovascular outcomes in a broad spectrum of heart failure patients", Circulation. 2005;112:3738-3744, Sep. 7, 2005, 7 pages.

Srivastava, Nitish, "Dropout: A Simple Way to Prevent Neural Networks from Overfitting", Journal of Machine Learning Research[retrieved Nov. 20, 2022]. [retrieved from the Internet <https://www.jmlr.org/papers/volume15/srivastava14a/srivastava14a.pdf?utm_campaign=buffer&utm_content=buffer79b43&utm_medium=social&utm_source=twitter.com>., Jan. 2014, 30 Pages.

Stergiou, George S., "2021 European Society of Hypertension practice guidelines for office and out-of-office blood pressure measurement", Journal of Hypertension, Wolters Kluwer Health, Inc., Feb. 14, 2021, 10 pages.

Tromp, Jasper, "A formal validation of a deep learning-based automated workflow for the interpretation of the echocardiogram", Nature Communications, Nov. 9, 2022.

Tromp, Jasper, "Automated interpretation of systolic and diastolic function on the echocardiogram: a multicohort study", The Lancet Digital Health, Dec. 1, 2021, 9 pages.

Tsao, Connie, "Heart Disease and Stroke Statistics—2023 Update: A Report From the American Heart Association", AHA Statistical Update, Circulation is available at ww.ahajournals.org/journal/circ, Feb. 21, 2023, 529 pages.

Unger, Thomas, "2020 International Society of Hypertension Global Hypertension Practice Guidelines", Hypertension is available at https://www.ahajournals.org/journal/hyp, 2020, 24 pages.

Von Jeinsen, Beatrice, "Prognostic Significance of Echocardiographic Measures of Cardiac Remodeling", HHS Public Access; J Am Soc Echocardiogr, Jan. 2020, 22 pages.

Wang, Elizabeth, "Initial Precipitants and Recurrence of Atrial Fibrillation", HHS Public Access; Author manuscript; Circ Arrhythm Electrophysiol., Mar. 1, 2021, 18 pages.

Whelton, Paul, "2017 ACC/AHA/AAPA/ABC/ACPM/AGS/APhA/ASH/ASPC/NMA/PCNA Guideline for the Prevention, Detection, Evaluation, and Management of High Blood Pressure in Adults: A Report of the American College of Cardiology/American Heart Association Task Force on Clinical Pra", Hypertension is available at http://hyper.ahajournals.org, Jun. 2018, 103 pages.

Wright, Alison, "Primary Prevention of Cardiovascular and Heart Failure Events With SGLT2 Inhibitors, GLP-1 Receptor Agonists, and Their Combination in Type 2 Diabetes", MACCE and HF Risk With Antidiabetic Drugs, Diabetes Care vol. 45, Apr. 2022, 10 pages.

Yuan, Yan, "Threshold-free measures for assessing the performance of medical screening tests", Frontiers in Public Health, vol. 3, Article 57, Apr. 20, 2015, 9 pages.

Zhang, Dong-Yan, "A comparative meta-analysis of prospective observational studies on masked hypertension and masked uncon-

(56) References Cited

OTHER PUBLICATIONS trolled hypertension defined by ambulatory and home blood pressure", Journal of Hypertension 2019,, Mar. 8, 2019, 11 pages.
Ge, et al., "PV-LVNet: Direct left 1-40 ventricle multitype indices estimation from 2D echocardiograms of paired apical views with deep neural networks", Medical Image Analysis, Oxford University Press, vol. 58, 2019, 12 pages.
Lau, et al., "Deep Learning-Enabled Assessment of Left Heart Structure and Function Predicts Cardiovascular Outcomes", Journal of the American College of Cardiology, vol. 82, No. 20, Nov. 6, 2023, pp. 1936-1945.
"International Search Report and Written Opinion", International Application No. PCT/US2024/051138, Feb. 4, 2025, 19 pages.
Zeng, et al., "MAEF-Net: Multi-attention efficient feature fusion network for left ventricular segmentation and quantitative analysis in two-dimensional echocardiography", Ultrasonics, vol. 127, 2023, 14 pages.

\* cited by examiner

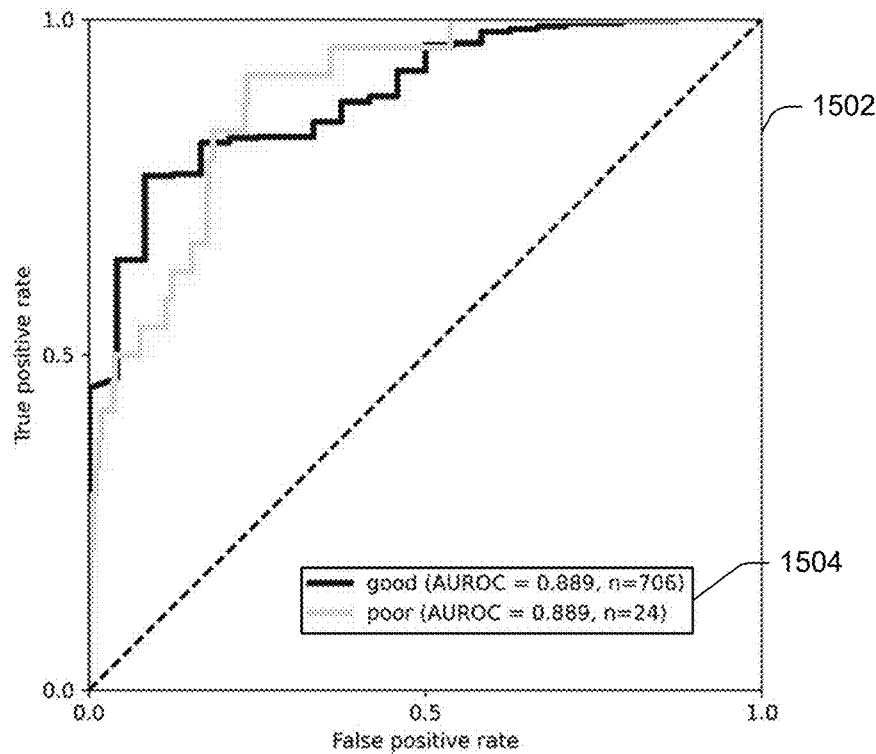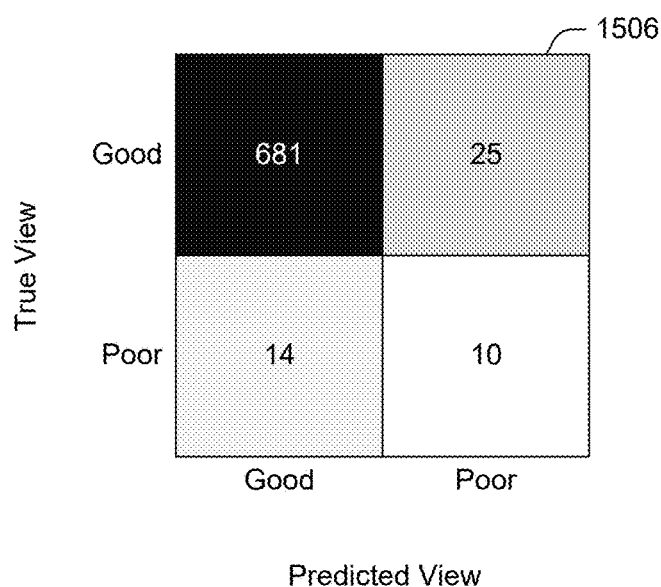
FIG. 15

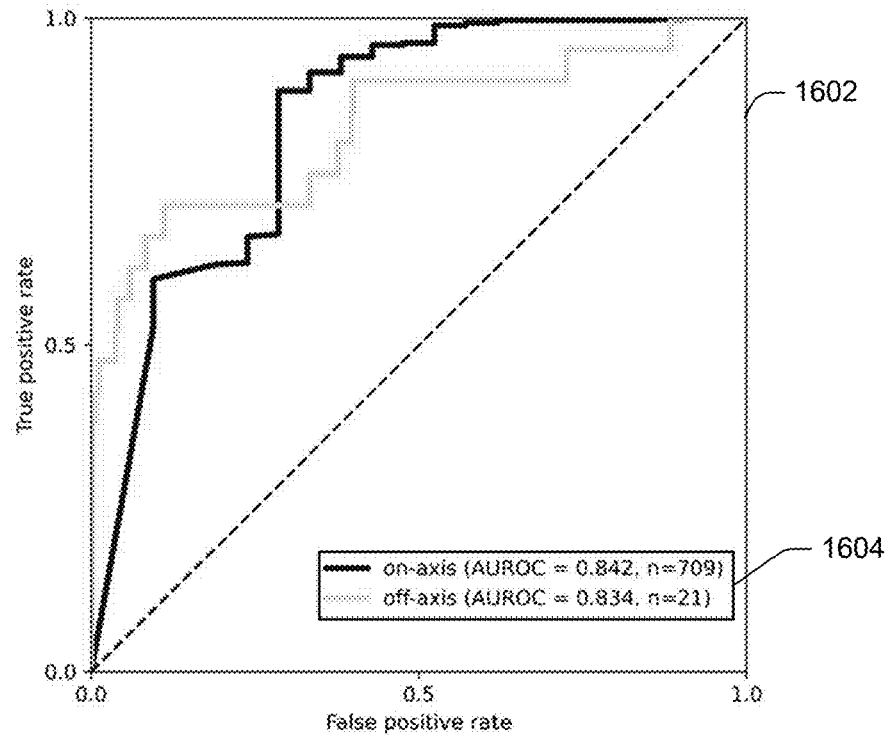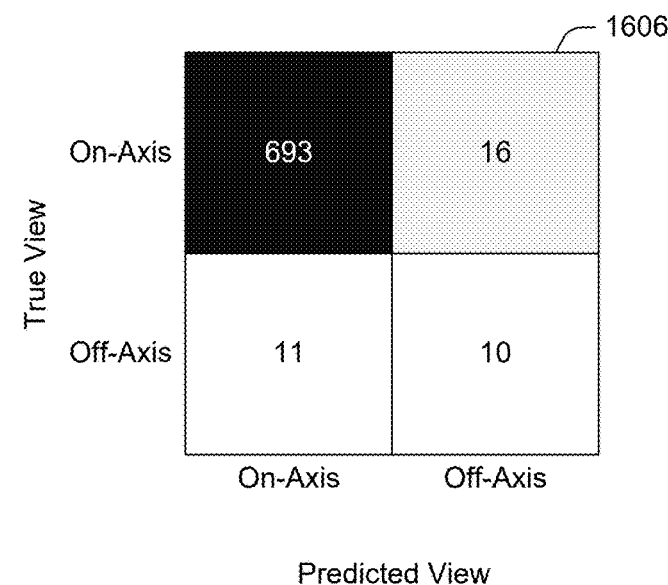
FIG. 16

| True View \ Predicted View | PLAX | Asc. Aorta | RV Inflow | RV Focused | Pulm. Artery | PSAX AV | PSAX MV | PSAX Pap. | PSAX Apex | A4C | A5C | A3C | A2C | Suprast. | Subcostal |
|---|---|---|---|---|---|---|---|---|---|---|---|---|---|---|---|
| PLAX | 130 | 5 | 0 | 0 | 0 | 0 | 1 | 0 | 3 | 0 | 1 | 1 | 0 | 0 | 5 |
| Asc. Aorta | 4 | 8 | 0 | 0 | 0 | 0 | 0 | 0 | 0 | 0 | 0 | 0 | 0 | 0 | 1 |
| RV Inflow | 0 | 0 | 14 | 0 | 0 | 0 | 0 | 1 | 3 | 0 | 0 | 1 | 0 | 0 | 2 |
| RV Focused | 0 | 0 | 0 | 10 | 1 | 0 | 0 | 0 | 0 | 1 | 0 | 0 | 0 | 0 | 0 |
| Pulm. Artery | 1 | 2 | 0 | 0 | 32 | 0 | 0 | 0 | 1 | 0 | 0 | 1 | 1 | 1 | 1 |
| PSAX AV | 8 | 4 | 0 | 0 | 1 | 46 | 1 | 1 | 2 | 1 | 0 | 0 | 0 | 0 | 0 |
| PSAX MV | 1 | 2 | 0 | 0 | 0 | 0 | 19 | 6 | 1 | 0 | 1 | 0 | 0 | 0 | 2 |
| PSAX Pap. | 0 | 0 | 0 | 0 | 0 | 0 | 3 | 17 | 2 | 0 | 0 | 0 | 0 | 1 | 2 |
| PSAX Apex | 1 | 0 | 0 | 0 | 0 | 0 | 0 | 0 | 34 | 0 | 0 | 0 | 3 | 1 | 1 |
| A4C | 1 | 0 | 0 | 0 | 0 | 3 | 0 | 1 | 2 | 98 | 0 | 0 | 5 | 0 | 3 |
| A5C | 1 | 0 | 0 | 0 | 2 | 0 | 0 | 1 | 3 | 5 | 29 | 2 | 5 | 0 | 1 |
| A3C | 0 | 0 | 0 | 0 | 0 | 0 | 0 | 0 | 0 | 2 | 1 | 27 | 7 | 0 | 0 |
| A2C | 0 | 0 | 2 | 0 | 0 | 0 | 0 | 0 | 7 | 1 | 0 | 0 | 49 | 0 | 0 |
| Suprast. | 0 | 0 | 0 | 0 | 0 | 0 | 0 | 0 | 0 | 0 | 0 | 1 | 0 | 36 | 1 |
| Subcostal | 2 | 0 | 0 | 0 | 0 | 0 | 0 | 0 | 3 | 1 | 2 | 2 | 0 | 4 | 104 |

FIG. 17B

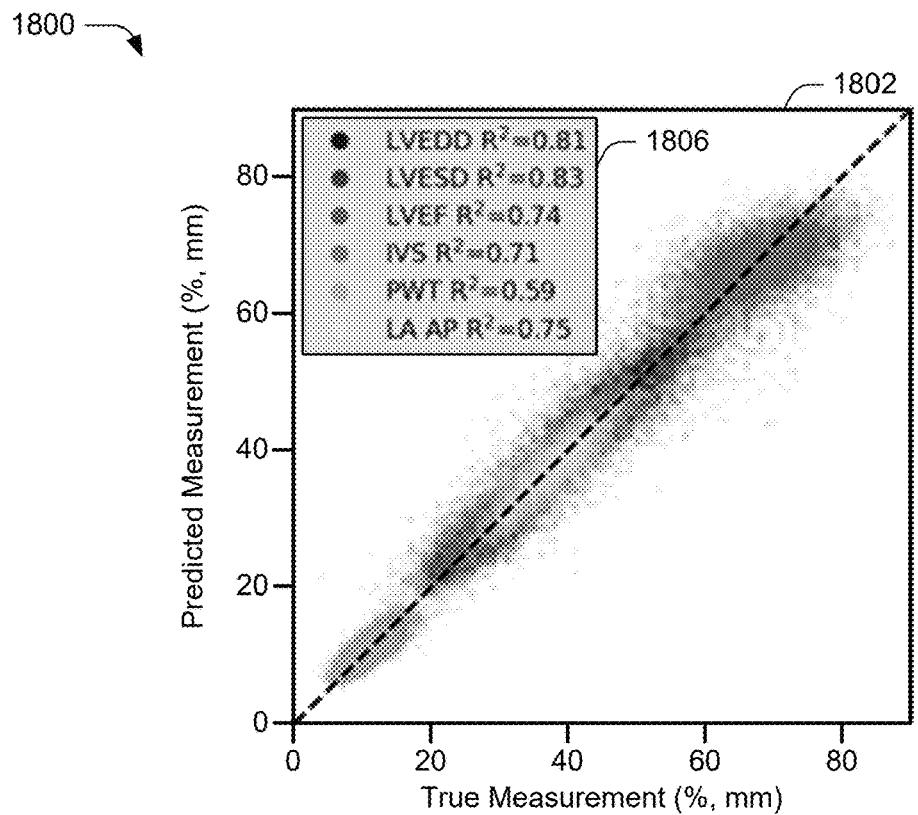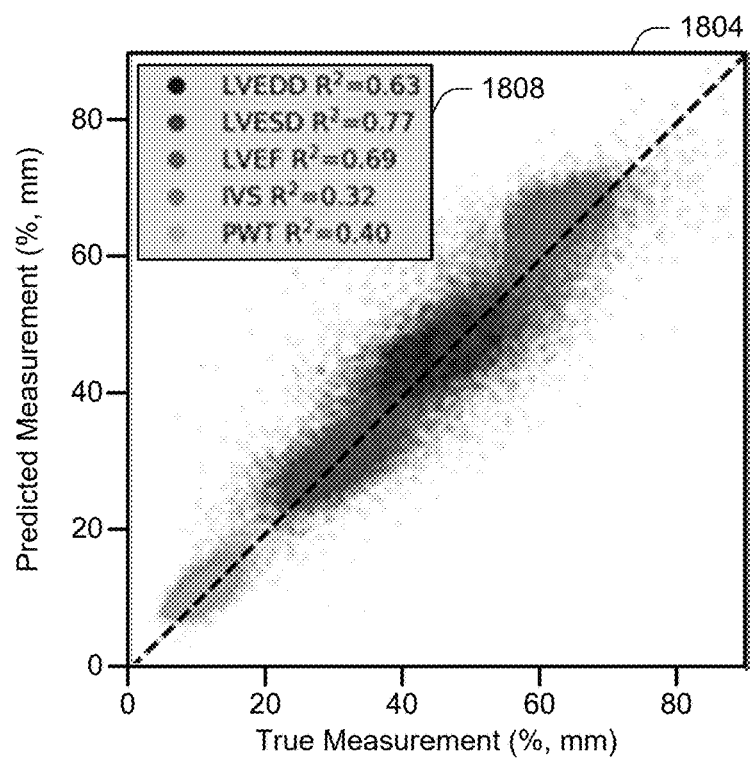
FIG. 18A

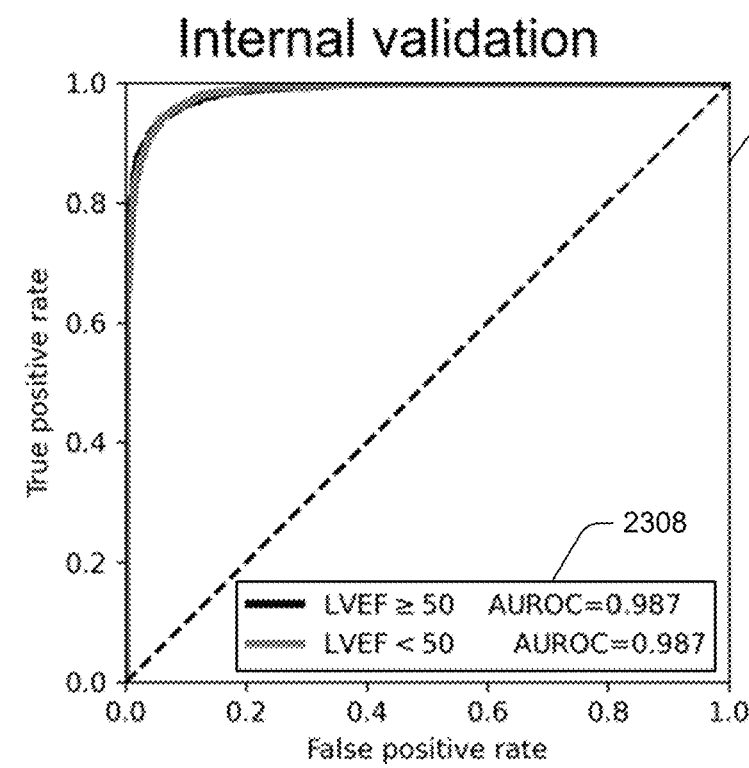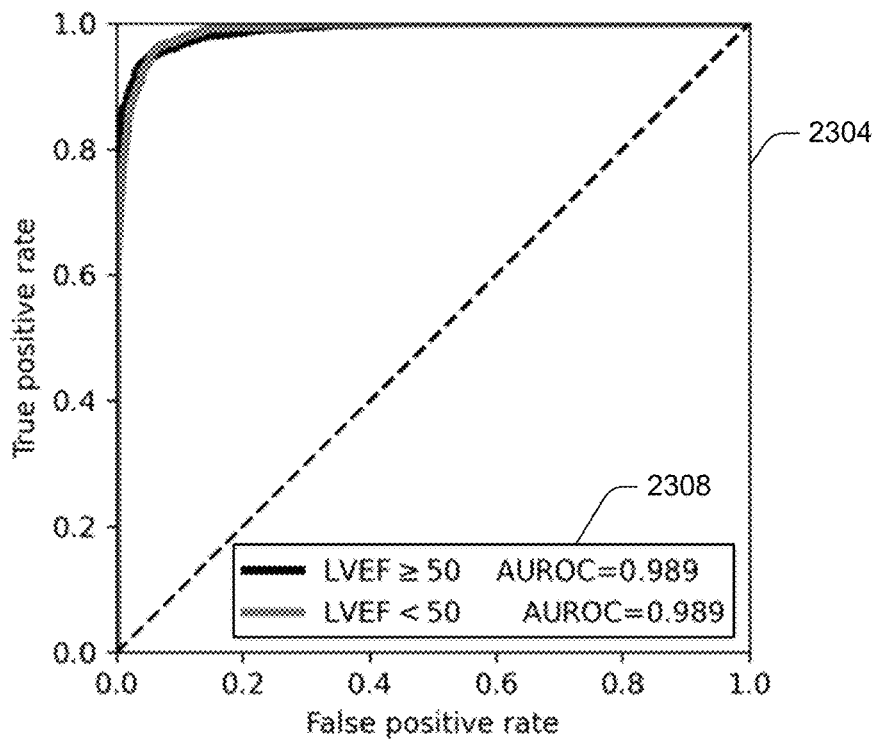
FIG. 23A

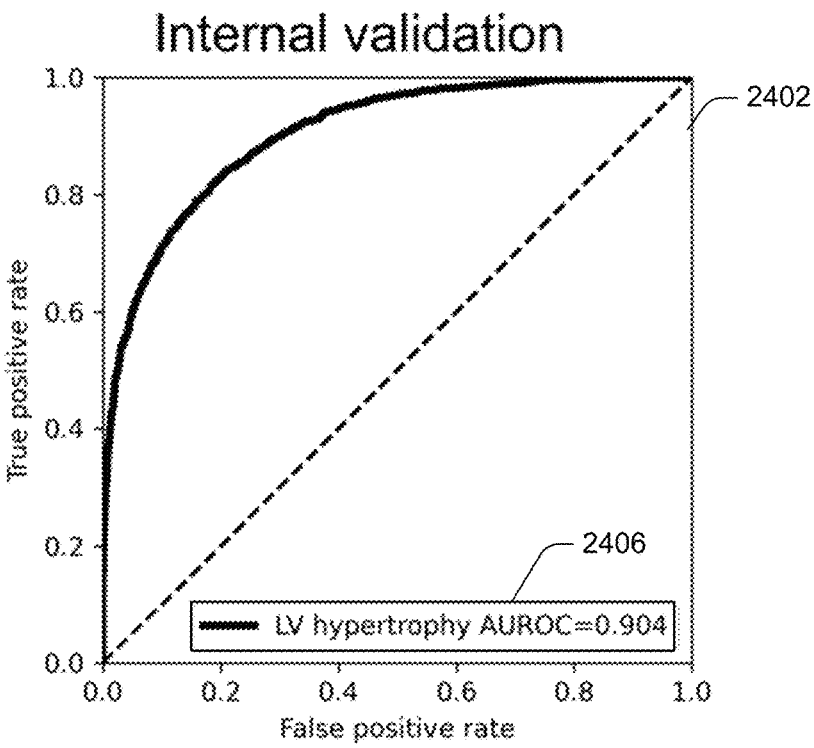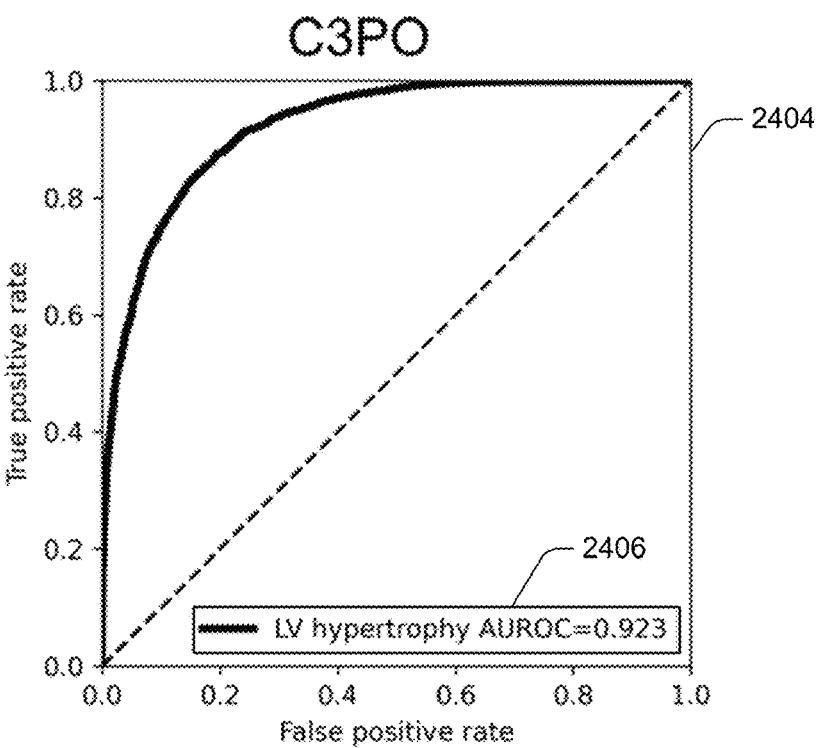
FIG. 24

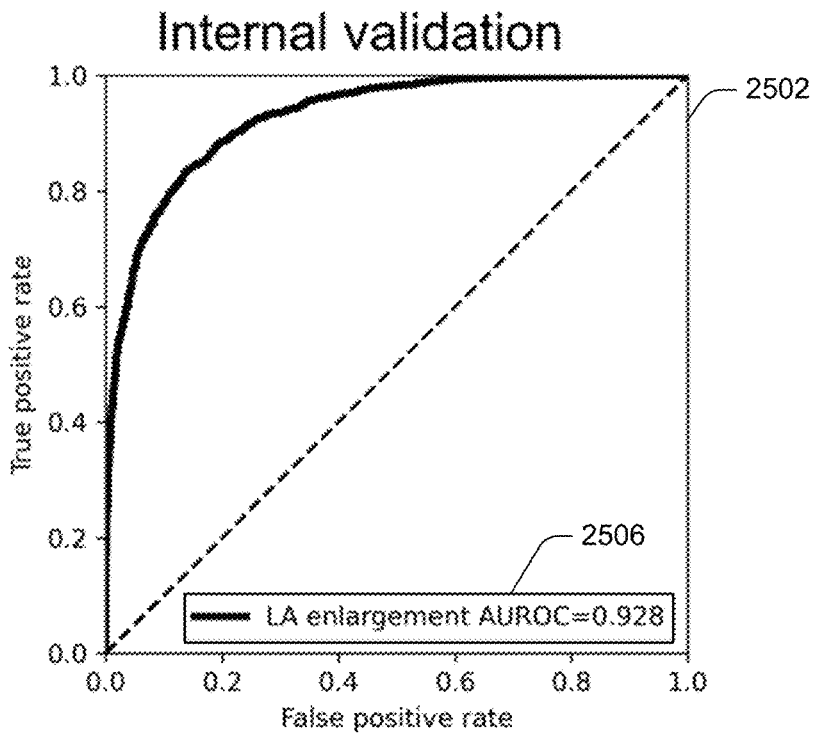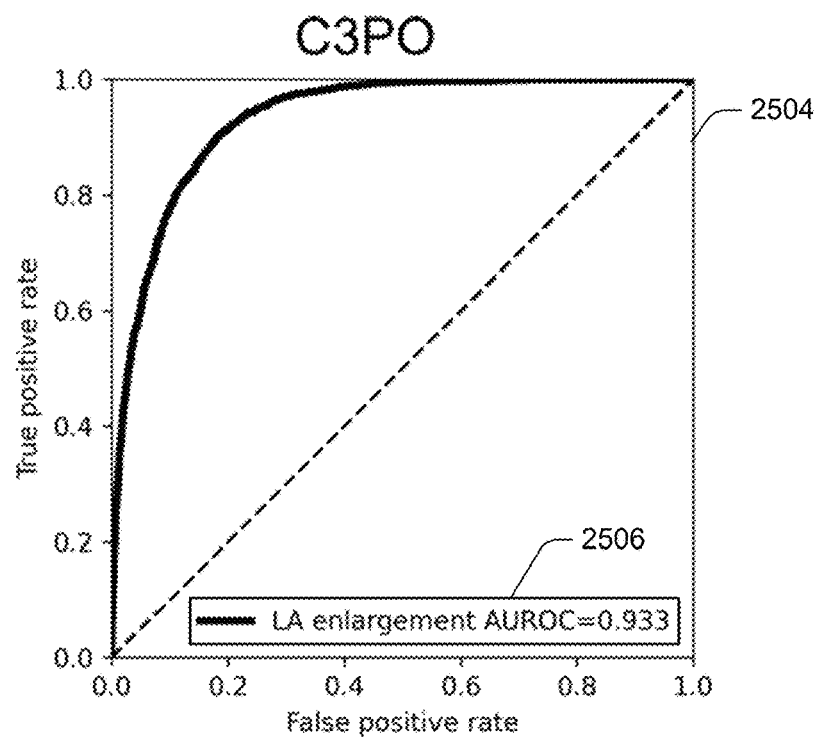
FIG. 25

ECHOCARDIOGRAPHY DEEP LEARNING AND CARDIOVASCULAR OUTCOMES

RELATED APPLICATIONS

This application claims priority to U.S. Provisional Patent Application Ser. No. 63/590,324, filed Oct. 13, 2023, entitled "Echocardiography Deep Learning and Cardiovascular Outcomes," the entire disclosure of which is hereby incorporated by reference herein in its entirety.

STATEMENT REGARDING GOVERNMENT SUPPORT

This invention was made with government support under Grant Nos. HL007208, HL092577, HL153669, HL157635, HL159243, HL160003, HL139791, HL105780, HL134894, and HL140224 awarded by the National Institutes of Health. The government has certain rights in the invention.

BACKGROUND

Echocardiography is a widely used noninvasive imaging technique that utilizes ultrasound waves to visualize the heart and assess its structure, function, and blood flow. By way of example, echocardiography may be used in evaluating various cardiovascular conditions, including heart valve disorders (e.g., mitral valve prolapse), heart disease, myocardial infarction, and heart failure. During an echocardiography scan, an operator (e.g., a sonographer) may acquire echocardiographic imaging data using an ultrasound probe (e.g., a transducer) configured to transmit and receive ultrasound signals that are processed into an echocardiogram image and/or a series of images (e.g., an echocardiogram video) by a computing device. Example modes of echocardiography include transthoracic echocardiography (TTE), where an ultrasound transducer is placed on the chest in one or more views, and transesophageal echocardiography (TEE), where the transducer is positioned in the esophagus. Additionally, Doppler echocardiography may be used to measure a speed and direction of blood flow. Once obtained, the sonographer and/or a supervising clinician (e.g., a cardiologist) may manually evaluate the echocardiogram image(s) via visual assessment and/or using measurement tools in order to assess one or more various cardiovascular conditions, cardiovascular functions, and so forth.

SUMMARY

Echocardiography deep learning and cardiovascular outcomes are described. An echocardiogram analysis module may include a deep learning model to generate a video output for an input echocardiogram video, the deep learning model comprising a convolutional neural network and at least one dense layer. The echocardiogram analysis module may further include a cardiac prediction generator to generate a cardiac prediction based on video outputs generated for a plurality of input echocardiogram videos of an echocardiogram study, the cardiac prediction comprising a measurement prediction or a classification prediction.

This Summary introduces a selection of concepts in a simplified form that are further described below in the Detailed Description. As such, this Summary is not intended to identify essential features of the claimed subject matter, nor is it intended to be used as an aid in determining the scope of the claimed subject matter.

BRIEF DESCRIPTION OF THE DRAWINGS

The detailed description is described with reference to the accompanying figures.

FIG. 15 shows an example analysis of echocardiographic image quality by echocardiography deep learning models trained for left heart measurement predictions.

FIG. 16 shows an example analysis of echocardiographic image axis classification by echocardiography deep learning models trained for left heart measurement predictions.

FIGS. 17A and 17B show an example analysis of echocardiographic image view by echocardiography deep learning models trained for left heart measurement predictions.

FIGS. 18A-18C show an example analysis of measurement prediction performance by echocardiography deep learning models trained for left heart measurement predictions.

FIGS. 23A and 23B show an example analysis of preserved versus reduced left ventricular ejection fraction categories in the internal and external validation sets.

FIG. 24 shows an example analysis of classifying left ventricular hypertrophy in the internal and external validation sets.

FIG. 25 shows an example analysis of classifying left atrial enlargement in the internal and external validation sets.

DETAILED DESCRIPTION

Overview

Figure 1:
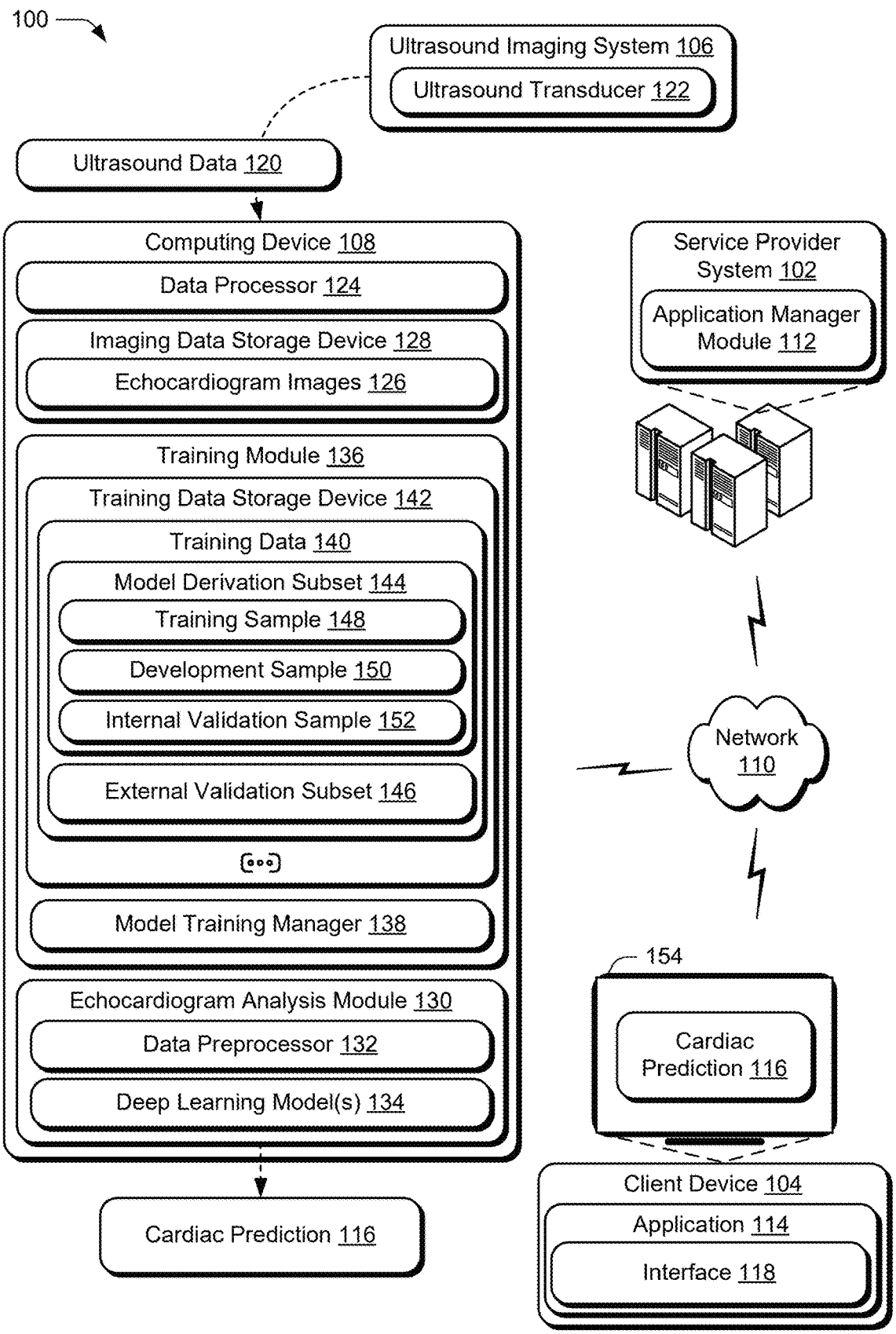
FIG. 1 is an illustration of an environment in an example implementation that is operable to employ echocardiography deep learning for cardiac predictions.

The heart (e.g., the human heart) is a four-chambered organ that is responsible for pumping blood throughout a body. The heart has two atria (upper chambers) and two ventricles (lower chambers). Blood enters the heart through the right atrium (RA), passes into the right ventricle (RV), and is then pumped to the lungs for oxygenation. The oxygenated blood returns to the left atrium (LA), moves into the left ventricle (LV), and is pumped out through the aorta to the rest of the body. The heart also contains four major valves (tricuspid, pulmonary, mitral, and aortic valves) that regulate blood flow between the chambers and ensure proper circulation.

Echocardiography is the most widely available noninvasive imaging modality for the assessment of cardiac structure and function. By way of example, echocardiographic imaging data may be obtained from one or more views during an echocardiography scan. Example transthoracic echocardiography (TTE) views include a parasternal long-axis view (PLAX), a parasternal short-axis view (PSAX), an apical four-chamber view (A4C), an apical three-chamber view (A3C), an apical two-chamber view (A2C), and a subcostal view.

Using echocardiography, clinicians may diagnose and/or monitor a wide range of cardiovascular disease (CVD) conditions. Echocardiographic measures have been demonstrated to predict clinical outcomes in both healthy community-based samples and among patients with CVD. As one example, the left heart, comprising the left atrium and left ventricle, pumps oxygenated blood to the body's tissues. The structure and function of the left heart may be assessed as a part of diagnosing various cardiovascular conditions, such as heart failure (HF), and predicting patient outcomes. By way of example, this assessment may be performed by trained clinicians (e.g., cardiologists) manually interpreting echocardiogram images. Standard echocardiographic measures of cardiac structure and function, including left ventricular ejection fraction (LVEF), dimensions, volumes, and mass as well as left atrial volume have all been shown to be associated with incident disease in healthy participants and clinical outcomes (including all-cause mortality, cardiovascular death, and risk of hospitalization) in disease states like HF. However, this process can be time-consuming and subject to interobserver variability. Moreover, only certain views lend themselves to interpretation by the trained clinician for the assessment of a particular structural or functional feature of the left heart.

As another example, right ventricular dilation and systolic dysfunction are known prognostic markers across a range of cardiovascular diseases, including atrial fibrillation (AF) and HF. Routine assessment of RV size and function is recommended by clinical guidelines as part of comprehensive two-dimensional TTE exams. However, while TTE is the most widely available modality for RV measurement, the crescentic geometry of the RV and its position under the sternum make accurate imaging and measurement challenging. Guidelines therefore recommend assessing the RV using multiple acoustic windows and reporting RV size and function using both qualitative descriptions and multiple quantitative parameters. As a result, RV measurement by TTE is time-consuming, relies on significant expertise, and is limited by high interobserver variability. Given the limited availability and high cost of advanced imaging modalities, there is a need for a rapid and accurate method of assessing RV structure and function in order to facilitate both TTE interpretation workflows and the use of RV measures to stratify cardiovascular risk.

As yet another example, mitral valve prolapse (MVP) is a condition in which the two leaflets of the mitral valve (located between the left atrium and left ventricle of the heart) do not close properly. Instead, one or both bulge (or "prolapse") back into the left atrium during contraction of the left ventricle, which is called systole. This improper closure can lead to mitral valve regurgitation, where some blood leaks backward into the left atrium instead of moving forward into the aorta. MVP affects an estimated 2-3% of the population and has been associated with HF, atrial and ventricular arrhythmias, and sudden cardiac death. However, MVP diagnosis by TTE takes time and clinical expertise. By way of example, diagnostic criteria for MVP focus on the degree of systolic displacement of the mitral valve (MV) into the left atrium on the PLAX or A3C view because of the saddle-shaped geometry of the MV and the desire to standardize MVP diagnosis across providers. While the development of distinct diagnostic criteria for MVP in other views may be possible, they would be impractical to implement and standardize across echocardiography imaging locations. Further, this would complicate already burdensome echocardiogram interpretation workflows to improve diagnostic yield of a relatively uncommon feature.

Overall, while rapid image acquisition, relative low cost, and lack of ionizing radiation make echocardiography an effective noninvasive imaging modality, the acquisition and interpretation of echocardiograms takes significant time, resources, and expertise. Moreover, assessment of cardiac structure and function from echocardiography is limited by substantial inter- and intra-observer variability.

Automated deep learning approaches have the potential to enable reproducible echocardiogram capture and interpretation at scale. However, conventional echocardiogram analysis systems may struggle to efficiently process and interpret complex echocardiogram data from multiple views to generate comprehensive cardiac predictions. Moreover, these systems typically rely on separate models for different measurements and/or utilize manual segmentation of specific videos, leading to inefficient operation and potentially inconsistent results.

To overcome these issues, echocardiography deep learning and cardiovascular outcomes are disclosed herein. In accordance with the described techniques, a deep learning model is used to process echocardiographic imaging data, such as echocardiogram videos, and generate a cardiac prediction, which may provide a measure of cardiac structure, a measure of cardiac function, and/or a cardiac classification with respect to a disease or condition (e.g., MVP). The deep learning model is trained on vast quantities of echocardiographic imaging data to create models that can output the cardiac prediction without image segmentation.

Moreover, the techniques described herein provide a model architecture that may be adapted to output different types of cardiac predictions, non-limiting examples of which include a first model to output left ventricular structural and/or functional measurement(s), a second model to output left atrial structural and/or functional measurement(s), a third model to output right ventricular structural and/or functional measurement(s), and a fourth model to output a mitral valve prolapse classification.

By way of example, the techniques described herein enable generation of a machine learning model (e.g., a deep learning model) that is able to output an accurate cardiac prediction from one or a plurality of echocardiogram videos obtained for an echocardiography study. By including multiple views, including those that are not typically used during a manual clinical analysis workflow, and avoiding image segmentation, the machine learning model "learns" how to interpret latent information from echocardiogram videos that may not be readily interpretable by human observers. By way of example, via the training process described herein, the machine learning model may learn to identify complex patterns and features that go beyond what is physically measurable. For instance, the machine learning model may include a three-dimensional convolutional neural network (3D CNN) that, through training, learns to extract features of an input echocardiogram video that are relevant to a particular cardiac prediction (or predictions) for which the deep learning model is being trained. These features, which may be captured in video embeddings output by the 3D CNN, represent a high-dimensional abstraction of the echocardiogram video. The information extracted in this way from a plurality of echocardiogram videos of a single study, including from views that may be considered suboptimal or non-diagnostic for human analysis, may be combined to output a study-level cardiac prediction. By leveraging this information, the machine learning model may learn to make accurate predictions about cardiac function, structure, and/or the presence of cardiac conditions that may not be evident from visual inspection or manual measurement performed by a human.

The techniques described herein represent an advance in computer engineering and provide a substantial advancement over existing practices. The data acquired to prepare the machine learning models are technical data relating to echocardiogram imaging data. The methods and systems described herein are more consistent, accurate, and efficient than manual/human analysis, which is prone to bias and does not scale to the amount of qualitative data that is generated today.

Moreover, the techniques described herein also enable non-expert providers to obtain clinically relevant information from an echocardiography scan. For instance, echocardiography scans rely on interpretation by experts, but such experts may be unavailable at the point of care, particularly in resource-limited or time-sensitive settings. As such, the machine learning models described herein may be used as a part of identifying cardiac abnormalities as soon as the echocardiography scan is completed for enhanced clinical decision support. This may also reduce specialist dependency, enabling the specialists to devote more time to higher-level patient care decisions and less time on manual echocardiography scan interpretation.

In the following discussion, an example environment is first described that may employ the techniques described herein. Example implementation details and procedures are then described that may be performed in the example environment as well as other environments. Consequently, performance of the example procedures is not limited to the example environment and the example environment is not limited to performance of the example procedures.

As used herein, the singular forms "a," "an," and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less from the specified value, insofar as such variations are appropriate to perform in the disclosed techniques. It is to be understood that the value to which the modifier "about" or "approximately" refers is itself also specifically disclosed.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

In the description of the figures, like numerals represent like (but not necessarily identical) elements throughout the figures.

Example Environment

FIG. 1 is an illustration of an environment 100 in an example implementation that is operable to employ echocardiography deep learning for cardiac predictions as described herein. The illustrated environment 100 includes a service provider system 102, a client device 104, an ultrasound imaging system 106, and a computing device 108 that are communicatively coupled, one to another, via a network 110. The network 110 may enable wired and/or wireless electronic communication, for example. Although the computing device 108 is illustrated as separate from the service provider system 102 and the client device 104, this functionality may be incorporated as part of the service provider system 102 and/or the client device 104, further divided among other entities, and so forth. By way of example, an entirety of or portions of the functionality of the computing device 108 may be incorporated as part of the service provider system 102 and/or the client device 104. Additionally or alternatively, an entirety of or portions of the client device 104 may be incorporated as part of the service provider system 102 and/or the computing device 108.

Computing devices that are usable to implement the service provider system 102, the client device 104, and the computing device 108 may be configured in a variety of ways. A computing device, for instance, may be configured as a desktop computer, a laptop computer, a mobile device (e.g., assuming a handheld configuration such as a tablet or mobile phone), and so forth. Thus, the computing device may range from full resource devices with substantial memory and processor resources (e.g., personal computers, game consoles) to a low-resource device with limited memory and/or processing resources (e.g., mobile devices). Additionally, a computing device may be representative of a plurality of different devices, such as multiple servers utilized to perform operations "over the cloud," as further described in relation to FIG. 9.

The service provider system 102 is illustrated as including an application manager module 112 that is representative of functionality to provide access to the computing device 108 to a user of the client device 104 via the network 110. The application manager module 112, for instance, may expose content or functionality of the computing device 108 that is accessible via the network 110 by an application 114 of the client device 104. The application 114 may be configured as a network-enabled application, a browser, a native application, and so on, that exchanges data with the service provider system 102 via the network 110. The data can be employed by the application 114 to enable the user of the client device 104 to communicate with the service provider system 102, such as to receive application updates and features when the service provider system 102 provides functionality to manage the application 114.

In the context of the described techniques, the application 114 includes functionality to train and/or use a machine learning model to analyze echocardiogram images (e.g., videos) and output a cardiac prediction 116, as will be elaborated herein. In the illustrated example, the application 114 includes an interface 118 that is implemented at least partially in hardware of the client device 104 for facilitating communication between the client device 104 and the computing device 108. By way of example, the interface 118 includes functionality to receive inputs to the computing device 108 from the client device 104 (e.g., from a user of the client device 104) and output information, data, and so forth from the computing device 108 to the client device 104, including the cardiac prediction 116.

The computing device 108 illustrated in FIG. 1 is further configured to receive ultrasound data 120 from the ultrasound imaging system 106. The ultrasound imaging system 106 includes an ultrasound transducer 122 (e.g., an ultrasound probe) configured to emit pulsed ultrasonic signals into a body of a subject (e.g., a patient) during an echocardiography scan. By way of example, the ultrasound transducer 122 may include one or more transducer elements that contract and expand when voltage is applied, emitting an ultrasound wave. Ultrasound waves are sinusoidal fluctuations in pressure; the size of each pressure wave is termed the amplitude, the distance between the two waves is the wavelength, and the number of waves per second is the frequency. For medical applications, the frequency of ultrasound tends to lie within the range of 2-20 million cycles per second (MHz). By way of example, echocardiography may be performed in a frequency range between 2.5-10 MHz. After the ultrasound transducer 122 emits the pulsed ultrasonic signals into the body, the pulsed ultrasonic signals are backscattered from structures within an interior of the body, like blood cells and muscular tissue, to produce echoes that return to ultrasound transducer 122. The echoes are converted into electrical signals by the transducer elements and converted to the ultrasound data 120 via a beamforming operation. The ultrasound data 120 may be in the form of a radiofrequency (RF) signal, for instance.

The terms "scan" or "scanning" may be used herein to refer to acquiring data through the process of transmitting and receiving ultrasonic signals. The term "data" may be used herein to refer to one or more datasets acquired with an ultrasound imaging system, such as the ultrasound imaging system 106. In at least one implementation, data acquired via the ultrasound imaging system 106 is processed via a data processor 124 of the computing device 108 to generate echocardiogram images 126, which may be stored in an imaging data storage device 128. The echocardiogram images 126 comprise still images as well as sequences of images, e.g., video clips. The imaging data storage device 128 may represent one or more databases and other types of storage capable of storing the echocardiogram images 126. The imaging data storage device 128 may also store a variety of other data, such as patient demographic information, electronic health record information, and so forth.

By way of example, the data processor 124 may process the ultrasound data 120 in real-time during a scanning session (e.g., a period of time where a healthcare provider, such as a sonographer, acquires the ultrasound data 120 via the ultrasound imaging system 106), as the echo signals are received and transmitted to the computing device 108. The term "real-time" is defined to include a procedure that is performed without intentional delay (e.g., substantially at the time of occurrence). In the context of echocardiography, for instance, real-time denotes generating the echocardiogram images 126 substantially as the ultrasound data 120 is acquired. As a non-limiting example, the ultrasound imaging system 106 may acquire images at a real-time frame rate ranging between 10 and 30 frames/sec. In at least one variation, the ultrasound imaging system 106 may acquire two-dimensional (2D) data of one or more planes at a faster rate. However, it should be understood that the real-time frame rate may be dependent on a length (e.g., duration) of time that it takes to acquire and/or process each frame of data for display. Accordingly, when acquiring a relatively large amount of data, the real-time frame rate may be slower. Thus, some implementations may have real-time frame rates that are considerably faster than 30 frames/sec (e.g., Hertz), while other embodiments may have real-time frame rates slower than 10 frames/sec. In at least one variation, the data may be stored temporarily in a buffer (not shown) during a scanning session and processed in less than real-time by the data processor 124 in an off-line operation.

The echocardiogram images 126 generated by the computing device 108 from the ultrasound data 120 may be refreshed at a same or similar frame rate at which the ultrasound data 120 is acquired. The imaging data storage device 128 may store the processed frames of acquired data, e.g., the echocardiogram images 126. In at least one implementation, the echocardiogram images 126 are stored in a manner to facilitate retrieval thereof according to its order or time of acquisition. The imaging data storage device 128 may comprise any known data storage medium. It is to be appreciated that while the data processor 124 and the imaging data storage device 128 are illustrated as part of the computing device 108, in at least one variation, the data processor 124 and/or the imaging data storage device 128 are part of the ultrasound imaging system 106 and/or another computing device.

In one or more implementations, the data processor 124 may process the ultrasound data 120 in different mode-related modules (e.g., B-mode, Color Doppler, M-mode, Color M-mode, spectral Doppler, elastography, tissue velocity imaging, strain, strain rate, and the like) to form 2D or three-dimensional (3D) images. When multiple images are obtained, the data processor 124 may also be configured to stabilize or register the images. For example, one or more modules may generate B-mode, color Doppler, M-mode, color M-mode, color flow imaging, spectral Doppler, elastography, tissue velocity imaging (TVI), strain (e.g., speckle tracking echocardiography), strain rate, and the like, and combinations thereof. As one example, the one or more modules may process B-mode data, which may include 2D and/or 3D B-mode data, and the like. The modules may include, for example, a scan conversion module to perform scan conversion operations to convert the acquired ultrasound data 120 from beam space coordinates to display space coordinates. In B-mode, for instance, dense structures, such as the pericardium and calcified valves, may appear bright (white) in corresponding portions of the echocardiogram images 126, whereas blood filled cavities (atria, ventricles) are almost echo free and may appear dark (black). A video processor module may be provided that reads the echocardiogram images 126 from the imaging data storage device 128 and displays a video or image loop in real-time while a procedure (e.g., an echocardiographic imaging procedure) is being performed on the patient and/or after completion of the procedure.

Further, the components of the ultrasound imaging system 106 and/or the computing device 108 may be coupled to one another to form a single structure, may be separate but located within a common room, or may be remotely located with respect to one another. For example, one or more of the modules described herein may operate in a data server that has a distinct and remote location with respect to other components of the ultrasound imaging system 106 and/or the computing device 108, such as the ultrasound transducer 122. Optionally, the ultrasound imaging system 106 may be a unitary system that is capable of being moved (e.g., portably) from room to room. For example, the ultrasound imaging system 106 may include wheels, may be transported (e.g., on a cart), or may comprise a handheld device.

In at least one implementation, the echocardiogram images 126, or a portion thereof, may be processed by an echocardiogram analysis module 130. By way of example, the echocardiogram analysis module 130 is representative of the functionality implemented at least partially in hardware of the computing device 108 to analyze the echocardiogram images 126, such as one or more video clips of the echocardiogram images 126, and output the cardiac prediction 116. In the example shown in FIG. 1, the echocardiogram analysis module 130 includes a data preprocessor 132 and at least one deep learning model 134 for analyzing the echocardiogram images 126 to generate the cardiac prediction 116. The at least one deep learning model 134 is a trained machine learning model. By way of example, the echocardiogram analysis module 130 may include multiple different deep learning models that correspond to different types of machine learning models, where the underlying models learn using different approaches (e.g., supervised learning, unsupervised learning, and/or reinforcement learning), and/or multiple different deep learning models having a same model architecture but that are trained using different input data and/or to output a different type of cardiac prediction 116. By way of example, these models may include regression models (e.g., linear, polynomial, and/or logistic regression models), classifiers, neural networks, and reinforcement learning based models, to name just a few.

The at least one deep learning model 134 may be configured as (or include) other types of models without departing from the spirit or scope of the described techniques. These different machine learning models may be built or trained (or the model otherwise learned), respectively, using different inputs and/or different algorithms due, at least in part, to different architectures and/or learning paradigms. Accordingly, it is to be appreciated that the following discussion of the functionality of the echocardiogram analysis module 130 is applicable to a variety of machine learning models. For explanatory purposes, however, the functionality of the at least one deep learning model 134 will be described generally with respect to a convolutional neural network (CNN). The CNN, for instance, may include two spatial dimensions and one temporal dimension. By way of example, the at least one deep learning model 134 may be based on the Mobile Video Network (MoViNet) A2 architecture that uses a 3D CNN to process spatiotemporal information in videos. Additional details of the CNN will be described herein, e.g., with respect to FIG. 2. In one or more implementations, the CNN is combined with additional architectures and/or model portions to produce the cardiac prediction 116. Moreover, the cardiac prediction 116 may be different based on the particular deep learning model 134 used, as elaborated herein.

The computing device 108 further includes a training module 136 that is implemented at least partially in hardware of the computing device, at least in part, to deploy deep learning to generate the at least one deep learning model 134. By way of example, the training module 136 includes a model training manager 138 that is configured to manage the at least one deep learning model 134. This model management may include, for example, building the at least one deep learning model 134, training the at least one deep learning model 134, updating the model(s), and so forth. For instance, the model training manager 138 may be configured to carry out this model management using, at least in part, training data 140 maintained in a training data storage device 142. As illustrated in the environment 100 of FIG. 1, the training data 140 may include a model derivation subset 144 and an external validation subset 146. For example, the model training manager 138 may use at least a portion of the model derivation subset 144 of the training data 140 as input for training the at least one deep learning model 134 and may use at least a portion of the external validation subset 146 for evaluating performance of the at least one deep learning model 134 after the at least one deep learning model 134 is at least initially trained. The model derivation subset 144 and the external validation subset 146 may include echocardiogram videos from different data sources, for example. As such, the external validation subset 146 may be used to verify that the at least one deep learning model 134 achieves performance goals on data from diverse sources. Moreover, although the training data 140 may include multiple echocardiogram videos (including different views) from a single patient, each separate video may be treated as a separate training sample. Ellipses denote that more than one training data set may be stored in the training data storage device 142.

It is to be appreciated that although the model derivation subset 144 and the external validation subset 146 are shown stored in the same training data storage device 142, in at least one variation, the model derivation subset 144 and the external validation subset 146 are distributed among multiple storage locations. Alternatively, or in addition, the training data storage device 142 may be stored in a location that is external to the computing device 108 and accessed by the computing device 108 (e.g., over the network 110). As such, it is to be appreciated that the relative arrangement of the various modules and data storage devices in FIG. 1 is non-limiting, and variations are possible.

In one or more implementations, the model derivation subset 144 is further subdivided into a training sample 148, a development sample 150, and an internal validation sample 152. By way of example, the training sample 148 may comprise a largest portion of the of the model derivation subset 144, while the internal validation sample 152 may comprise a smallest portion of the model derivation subset 144. As a non-limiting example, the training sample 148 comprises 70% of the model derivation subset 144, the development sample 150 comprises 20% of the model derivation subset 144, and the internal validation sample 152 comprises 10% of the model derivation subset 144, although other divisions are possible. The training sample 148, for instance, may comprise between 50% and 80% of the model derivation subset 144, the development sample 150 may comprise between 10% and 40% of the model derivation subset 144, and the internal validation sample 152 may comprise between 5% and 30% of the model derivation subset 144.

Broadly speaking, the training sample 148 may be input to the at least one deep learning model 134 during a training process, where the at least one deep learning model 134 learns patterns and relationships in the data. During the training process, weights and parameters of the at least one deep learning model 134 may be adjusted to reduce (e.g., minimize) errors between an output of the model and a ground truth label associated with a corresponding echocardiogram video (e.g., the cardiac prediction, as determined by a clinician). Following completion of the training process, the at least one deep learning model 134 is able to accurately predict the cardiac prediction 116 of the training sample 148.

The development sample 150 may be input to the at least one deep learning model 134 during a model refinement (e.g., fine-tuning) process, where the at least one deep learning model 134 is adjusted to prevent or reduce overfitting/underfitting of the model to the training sample 148. By way of example, the model refinement process may be performed following each round (or epoch) of training to evaluate how well the at least one deep learning model 134 performs on data that is different from the training sample 148. During the model refinement process, for instance, a complexity, learning rate, and/or regularization of the at least one deep learning model 134 may be adjusted (e.g., by the model training manager 138, automatically and/or based on user input) based on the performance of the at least one deep learning model 134 with the development sample 150. As an illustrative example, if the at least one deep learning model 134 accurately predicts the cardiac prediction 116 of the training sample 148 but not the development sample 150, overfitting of the at least one deep learning model 134 to the training sample 148 is indicated. As such, the model refinement process enables settings of the at least one deep learning model 134 and/or its training to be fine-tuned so that the at least one deep learning model 134 can be generalized to unseen data (e.g., data that the at least one deep learning model 134 has not been trained on).

The internal validation sample 152 may be input to the at least one deep learning model 134 during an internal validation process that is performed after the at least one deep learning model 134 is trained and fine-tuned. The internal validation sample 152 comprises data that was unseen by the at least one deep learning model 134 during the training and model refinement processes described above but that is derived from the same dataset (e.g., the model derivation subset 144). The internal validation process evaluates the performance of the at least one deep learning model 134 on similar data as to that used during the training and model refinement processes. If the at least one deep learning model 134 does not meet acceptable or desired performance criteria (e.g., as defined by model developers) during the internal validation process, the at least one deep learning model 134 may be returned to the training and/or model refinement processes so that changes can be made. For example, changes may be made to feature selection, the model architecture, regularization techniques, hyperparameter tuning, and the like.

The model training manager 138 may leverage the functionality of the data preprocessor 132 to process the training data 140 during the training, refinement, and validation processes described above. The data preprocessor 132, for instance, may remove patient identifying information, superimposed labels (e.g., added by scanning equipment, sonographers, or echocardiographers), and/or non-ultrasound data (e.g., respirometer and electrocardiogram tracings). Additionally, or alternatively, the data preprocessor 132 may standardize echocardiogram videos input into the at least one deep learning model 134, such as by resizing, normalizing, and so forth in order to provide consistent inputs.

In at least one implementation, the at least one deep learning model 134 is trained to classify the training data 140 in order to select echocardiogram videos for inclusion or exclusion in the training, refinement, and validation processes regarding the cardiac prediction 116. As a non-limiting example, a separate deep learning model may be trained to identify which of the standard echocardiographic views a video represents; whether the clip is on-axis or off-axis; whether the clip represents a standard 2-dimensional B-mode clip, Doppler clip, or 3-dimensional clip; and whether the clip is of interpretable quality. In at least one implementation, the data preprocessor 132 labels individual electrocardiogram videos of the training data 140 accordingly using outputs of such deep learning models, and these labels may be used to select clips for inclusion during the training, refinement, and validation of the at least one deep learning model 134 with respect to the cardiac prediction 116.

Once the at least one deep learning model 134 is at least initially trained and internally validated, the model training manager 138 may use the external validation subset 146 of the training data 140 to evaluate generalizability of the at least one deep learning model 134. As mentioned above, the external validation subset 146 comprises echocardiogram data (e.g., videos) from a different data source, such as a different imaging clinic and/or patient population. By way of example, the external validation subset 146 may be input into the at least one deep learning model 134, and the at least one deep learning model 134 may output the cardiac prediction 116 for respective echocardiogram videos. The cardiac prediction 116 may be compared to the ground truth labels to evaluate an accuracy of the at least one deep learning model 134 on this novel dataset. The external validation subset 146, for instance, may be used to verify that the performance of at least one deep learning model 134 is not specific to the data source of the model derivation subset 144.

In response to the at least one deep learning model 134 meeting desired or acceptable performance metrics, the at least one deep learning model 134 may be deployed for determining the cardiac prediction 116 of newly obtained echocardiogram data, including echocardiogram data for which there is no ground truth label. By way of example, the echocardiogram images 126 may correspond to echocardiogram videos that have not been evaluated by a clinician or technician with respect to the cardiac prediction 116. The echocardiogram images 126 may be input into the (trained and validated) at least one deep learning model 134 at or around the time of acquisition, and the at least one deep learning model 134 may output the cardiac prediction 116 accordingly, thus enabling a streamlined echocardiography workflow.

In at least one implementation, the cardiac prediction 116 includes an estimated physical measurement of a portion of the heart (e.g., a left atrial anterior-posterior dimension, a left ventricular end-diastolic dimension, a left ventricular end-systolic dimension, a right ventricular end-diastolic dimension, a interventricular septal wall thickness, and/or a posterior wall thickness), which may be linked to a particular timing with respect to systole or diastole. Additionally or alternatively, the cardiac prediction 116 includes an indication of a functional status of at least a portion of the heart (e.g., a left ventricular ejection fraction and/or a right ventricular ejection fraction). In at least one variation, the cardiac prediction 116 includes a probability score indicating a likelihood that a cardiac condition is present (e.g., a probability of mitral valve prolapse).

Although the above discussion is focused on video inputs to the at least one deep learning model 134 and receiving the cardiac prediction 116 as the output, it is to be appreciated that additional inputs and/or outputs are possible. By way of example, the at least one deep learning model 134 may be trained on auxiliary (e.g., secondary) tasks that may help the at least one deep learning model 134 learn shared representations of the input data, which increase the performance of the at least one deep learning model 134 for the cardiac prediction 116. Examples of auxiliary tasks include predicting age, sex, and/or other demographic features. Additional or alternative auxiliary tasks may be discussed herein below with respect to example model applications.

The client device 104 is shown displaying, via a display device 154, cardiac prediction 116. Alternatively, or in addition, the client device 104 may display, via the display device 154, the echocardiogram images 126. It is to be appreciated that the cardiac prediction 116 may be also stored in a memory of the computing device 108 and/or the client device 104 for subsequent access.

In this way, the echocardiogram analysis module 130 enables automated echocardiography scan analysis for identifying and/or monitoring a plurality of different cardiovascular conditions or disease states, which may be used in patient stratification, risk assessment, and/or treatment monitoring.

Echocardiography Deep Learning Example Implementations

Figure 2:
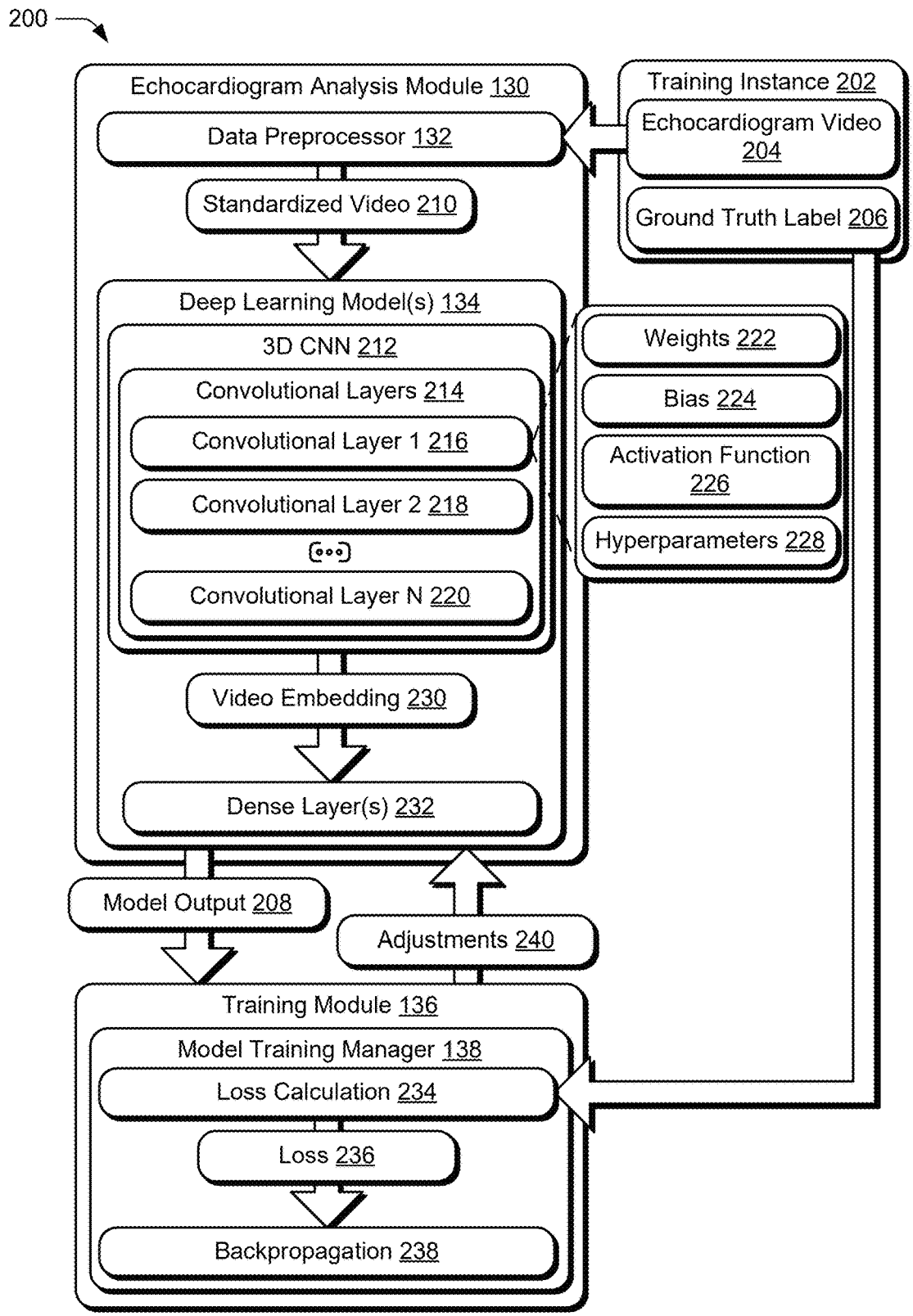
FIG. 2 depicts an example training process that may be used in generating the at least one deep learning model of the echocardiogram analysis module of FIG. 1.

FIG. 2 depicts an example training process 200 that may be used in generating the at least one deep learning model 134 of the echocardiogram analysis module 130 of FIG. 1. It is to be appreciated that the example training process 200 denotes one implementation of a training process that may be used in generating at least a portion of the at least one deep learning model 134.

In the example training process 200, a training instance 202 includes an echocardiogram video 204 and a ground truth label 206 associated with the echocardiogram video 204. The echocardiogram video 204, for instance, includes a sequence of echocardiogram image frames obtained for a single view during a single acquisition process (e.g., where the ultrasound transducer 122 is commanded to emit and receive ultrasound signals at a desired acquisition frame rate). By way of example, an echocardiogram scan may include acquiring a plurality of still images and a plurality of videos, which may have different view angles with respect to each other. Example views include a parasternal long-axis view (PLAX), a parasternal short-axis view (PSAX), an apical four-chamber view (A4C), an apical three-chamber view (A3C), an apical two-chamber view (A2C), and a subcostal view. During the training, the echocardiogram video 204 is part of a corresponding portion of the training data 140 (e.g., the training sample 148).

Each echocardiogram video 204 may be separately evaluated by the at least one deep learning model 134 to generate a model output 208, which corresponds to the single echocardiogram video 204. As such, the training instance 202 includes an input portion (e.g., the echocardiogram video 204) and an associated expected output portion (e.g., the ground truth label 206), and a great many training instances 202 may be used during the training process. The model output 208 corresponds to a prediction for a particular classification and/or measurement task(s) the at least one deep learning model 134 is being trained for. By way of example, a first model of the at least one deep learning model 134 may be trained to output (e.g., as the model output 208) left ventricular structural and/or functional measurements, while a second model of the at least one deep learning model 134 may be trained to output left atrial structural and/or functional measurements. As another example, a third model of the at least one deep learning model 134 may be trained to output right heart (e.g., right ventricle and/or right atrium) structural and/or functional measurements, while a fourth model of the at least one deep learning model 134 may be trained to output a probability that mitral valve prolapse (MVP) is present. Alternatively, or in addition, the at least one deep learning model 134 may be trained as a classification model to identify an echocardiographic view (e.g., PLAX, A4C, etc.), video type (e.g., 2-dimensional Doppler versus 3-dimensional), image quality, and image axis. The ground truth label 206 defines a true or expected output of the deep learning model 134 for the echocardiogram video 204. By way of example, the ground truth label 206 may be or may be derived from clinical labels adjudicated by an expert (e.g., a clinical echocardiographer) for comparison to the model output 208 during training.

In the example shown in FIG. 2, the echocardiogram video 204 is input to the data preprocessor 132, which generates a standardized video 210. As mentioned above with respect to FIG. 1, the data preprocessor 132 may remove patient identifying information, superimposed labels, and/or non-ultrasound data. The data preprocessor 132 may further resize and normalize the echocardiogram video 204 to generate the standardized video 210. By way of example, different echocardiogram videos 204 may have different lengths (e.g., numbers of frames) and resolutions. The standardization process performed by the data preprocessor 132 may ensure a consistent input to the at least one deep learning model 134. By way of example, the standardized video 210 generated for a first echocardiogram video 204 may have a same resolution and frame number as the standardized video 210 that is generated a second echocardiogram video 204, even when the second echocardiogram video 204 has a different resolution and video length.

Moreover, the data preprocessor 132 may be configured to use continuous or intermittent input frame sampling. Continuous frame input sampling comprises selecting frames from the echocardiogram video 204 in a sequential, consecutive manner, without skipping frames. In contrast, intermittent input frame sampling comprises selecting frames at regular intervals (e.g., every nth frame), and skipping frames between the ones that are selected. Examples intermittent input frame sampling rates include take 1/skip 1 (where one frame is skipped between selected frames), take 1/skip 2 (where two frames are skipped between selected frames), take 1/skip 3 (where three frames are skipped between selected frames), and so forth. As such, continuous input frame sampling may capture smooth, fast-changing dynamics and may be useful when frame-to-frame information is highly relevant to the task for which the at least one deep learning model 134 is being trained, whereas intermittent input frame sampling may provide a coarser representation of the overall trend or structure depicted in the echocardiogram video 204. It is to be appreciated that intermittent input frame sampling may reduce computational costs for covering a larger temporal portion of the echocardiogram video 204.

As an illustrative, non-limiting example, the standardized video 210 may comprise a 16-frame input with a resolution of 224 by 224 pixels and a take 1/skip 3 intermittent input frame sampling strategy. As such, the standardized video 210 may have a tensor shape of (16, 224, 224, 3), corresponding to 16 frames, each frame being a 224 pixel height by 224 pixel width image having 3 color channels (e.g., RGB). However, other input strategies may be used for the standardized video 210, such as by including more or fewer frames, a different resolution, or a different frame sampling strategy. For instance, in at least one variation, a 32-frame input is used. However, increasing the frame number may decrease computational efficiency. As such, the strategy used by the data preprocessor 132 for generating the standardized video 210 from the echocardiogram video 204 may be selected to balance model performance with computational efficiency.

The standardized video 210 is input to the at least one deep learning model 134. In the example training process 200 shown in FIG. 2, the at least one deep learning model 134 comprises a 3D CNN 212 having convolutional layers 214. The convolutional layers 214 are shown as including a first convolutional layer 216 (e.g., "convolutional layer 1"), a second convolutional layer 218 (e.g., "convolutional layer 2"), and an $N^{th}$ convolutional layer 220 (e.g., "convolutional layer N"), where N is an integer representing the total number of convolutional layers. Ellipses denote that additional convolutional layers may be present between the second convolutional layer 218 and the $N^{th}$ convolutional layer 220. In general, the convolutional layers 214 are configured to extract features of the standardized video 210.

It is to be appreciated that one or more of the convolutional layers 214 may be grouped together in blocks. By way of example, a block may comprise multiple convolutional layers that are stacked together with operations such as pooling, batch normalization, and activation functions to form a unit that is able to extract more complex or abstract features than a single convolutional layer alone. For instance, the first convolutional layer 216 may be a single convolutional layer, while the second convolutional layer 218 through the $N^{th}$ convolutional layer 220 may be arranged in blocks. In at least one non-limiting example, the first convolutional layer 216 is followed by five blocks. The first convolutional layer 216, for example, may apply a kernel (e.g., a filter) to the standardized video 210, which scans across the spatial (2D) dimensions of the frames and the temporal (time-based) dimension to extract low-level features like edges across frames. The features detected by the first convolutional layer 216 are fed to the subsequent convolutional layers 214 (e.g., the blocks) in sequence, allowing the 3D CNN 212 to detect increasingly complex patterns in the standardized video 210. For example, the second convolutional layer 218 (e.g., in combination with other convolutional layers in a corresponding block) may use the edge information from the first convolutional layer 216 to extract features like shapes, textures, and simple movements, while later layers such as the $N^{th}$ convolutional layer 220 may extract more complex patterns like valve movement and cardiac motion across time.

The first convolutional layer 216, as well as others of the convolutional layers 214, may comprise weights 222, a bias 224, an activation function 226, and hyperparameters 228. By way of example, the weights 222 and the bias 224 may be randomly initialized and then "learned" during the training process, as elaborated below. The 3D CNN 212, for instance, performs a series of convolutions. A convolution is a mathematical operation where the kernel slides over an input image of the standardized video 210 and performs element-wise multiplication with the values of the image at each position. The results are summed up to produce a single output value for that location, and this process is repeated across the image to produce a feature map. The kernel comprises a matrix of numbers, which are the weights 222 of the kernel, that is applied to the input. The bias 224 is a single number added to the result of the convolution. After each convolution, the feature map may be passed through the activation function 226, e.g., a non-linear function such as ReLU (Rectified Linear Unit), which replaces negative values with zero. After several convolution operations, a pooling layer may be used to reduce the size of the feature map.

The hyperparameters 228 are not learned during the training process but can be adjusted to increase performance. The hyperparameters 228 may comprise depth, stride, and zero-padding. Depth controls the number of neurons within a given convolutional layer of the convolutional layers 214. Reducing the depth may increase the speed of the 3D CNN 212 but may also reduce the accuracy of the 3D CNN 212. Stride determines how much the kernel moves or "slides" across the input. A stride of two, for example, means that the kernel skips one pixel and moves to every other position. A higher stride value would thus enable the 3D CNN 212 to process data more quickly and reduces the spatial dimensions of the feature map. Zero-padding controls the border padding in the input, ensuring that the kernel can be applied to edge pixels for which the kernel does not perfectly fit the pixel dimensions. For example zero-padding may add zeros for missing portions so that the output of the convolution remains the same size as the input.

In at least one implementation, the 3D CNN 212 outputs a video embedding 230, which may be a flattened representation of the feature maps discussed above. The video embedding 230 comprises a one-dimensional vector that summarizes the features or characteristics of the standardized video 210 that have been learned by the 3D CNN 212. The video embedding 230 is input into one or more dense layers 232, which are fully connected layers where every neuron (node) is fully connected to every neuron in the previous and next layer. The one or more dense layers 232 function to aggregate information learned by previous layers and make final predictions for the model output 208.

Similar to the convolutional layers 214, the one or more dense layers 232 may comprise the weights 222, the bias 224, the activation function 226, and the hyperparameters 228. It is to be appreciated that values of at least a portion of these parameters and/or type of activation function used are specific to a given convolutional layer 214 or dense layer 232. The one or more dense layers 232, for instance, may take the video embedding 230 as an input vector, multiply it by a matrix of the weights 222, add the bias 224, and then apply the activation function 226 to produce the model output 208.

The model output 208 is received by the model training manager 138, which may perform a loss calculation 234. The loss calculation 234 may use a loss function to compute the difference between the model output 208 and the ground truth label 206, e.g., a loss 236. The loss 236, for instance, is a measure of the error of the given deep learning model of the at least one deep learning model 134 in determining the model output 208. The loss function used in the loss calculation 234 may depend on a type of the model output 208. As non-limiting examples, mean squared error loss may be used for regression problems (where a continuous value is predicted), whereas cross-entropy loss may be used for classification problems.

A goal of the training is to minimize the loss 236 by adjusting the weights 222 and biases 224 of the given deep learning model of the at least one deep learning model 134. In order to do so, the model training manager 138 may employ backpropagation 238 to compute how the parameters are to be updated based on a gradient of the loss 236 with respect to each parameter. By way of example, the backpropagation 238 process may utilize an optimization algorithm such as gradient descent. The backpropagation 238 results in adjustments 240, which are used to update the weights 222 and biases 224 of the deep learning model 134.

As such, following many rounds of training with a large number of training instances 202, the model output 208 becomes consistent with the ground truth label 206 due to the at least one deep learning model 134 "learning" to minimize the loss 236 between the model output 208 and the ground truth label 206.

In one or more implementations, the training process 200 is a multi-step training process that enables the at least one deep learning model 134 to "learn" from both qualitative and quantitative ground truth labels 206. As a non-limiting example, in a first training step of the training process 200 referred to as "pre-training," the at least one deep learning model 134 may be trained predict qualitative size (e.g., dilated or normal) and/or function (e.g., hypokinetic or normal) as the model output 208 using an entirety of the model derivation subset 144. Then, in a second, subsequent training step of the training process 200, the least one deep learning model 134 is "fine-tuned" to give quantitative estimates as the model output 208 using a portion of the model derivation subset 144 in which quantitative measurements are available. The result of the second training step is that the final at least one deep learning model 134 may provide estimates of both qualitative and quantitative size and function. The advantage of the multi-step training process is that the at least one deep learning model 134 can learn general features of heart size and/or function from a large sample of qualitative descriptions and then learn how to more precisely estimate measurements from a smaller number of studies with quantitative labels. For instance, the at least one deep learning model 134 may include randomly initialized weights 222 and bias 224 values prior to the first training step, and the at least one deep learning model 134 may include the weights 222 and bias 224 values learned during the first training step at the beginning of the second training step.

In various implementations, the model output 208 for a plurality of videos of an echocardiography scan may be combined, such as will be elaborated herein, to produce the cardiac prediction 116. In some instances, additional components, such as classification head(s), are included and also trained via the process described above.

The training process 200 thus provides a general framework for further model adaptation to generate specific cardiac prediction 116 outputs, such as those described herein. By way of example, the 3D CNN 212 may provide an encoder backbone that can be combined with additional architectures to produce the cardiac prediction 116, such as further described below with respect to FIGS. 3-6. Moreover, by using this example training process 200, the at least one deep learning model 134 does not rely on manual segmentation but instead "learns" which portions of the echocardiogram video 204 are relevant to any given task. This also enables the at least one deep learning model 134 to identify interpretable data patterns in echocardiogram videos beyond what is interpretable by a human and/or used in manual measurement workflows. For instance, the at least one deep learning model 134 may be trained to output a measurement regarding a specific anatomical location of the heart (e.g., a cardiac chamber). However, the measurement output by the at least one deep learning model 134 is an estimation/prediction, as the at least one deep learning model 134 does not perform a physical measurement on the input data. Because the at least one deep learning model 134 does not perform a physical measurement, the at least one deep learning model 134 may be able to estimate the measurement in part using latent information from other cardiac chambers.

Deep Learning for Assessing Left Heart Structure and Function

Figure 3:
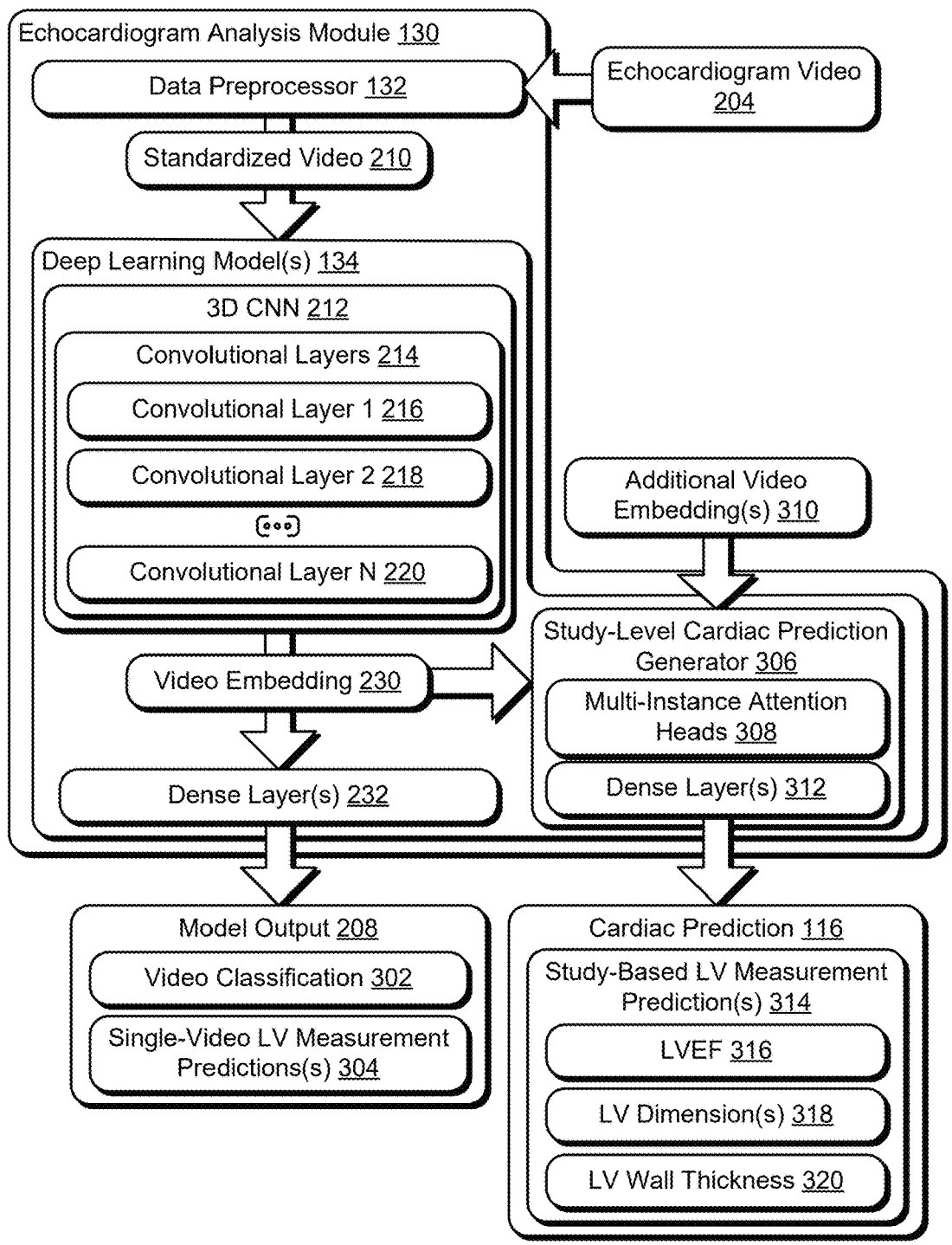
FIG. 3 depicts an example implementation of generating and using at least one deep learning model to assess left ventricular heart structure and function.

FIG. 3 depicts an example implementation 300 of generating and using at the least one deep learning model 134 to assess left ventricular heart structure and function. Components previously introduced in FIGS. 1 and 2 are numbered the same and function as previously described.

In the implementation 300, the at least one deep learning model 134 is a two-part model including the 3D CNN 212 as an encoder backbone. In the example shown, the at least one deep learning model 134 is trained to output, as the model output 208 from the one or more dense layers 232, a video classification 302 and single-video left ventricle (LV) measurement prediction(s) 304. The video classification 302, for instance, may indicate an image type, an image quality, an axis, a view classification, or any combination thereof. The image type, for instance, may differentiate between 2-dimensional, 2-dimensional B-mode, Doppler, and 3-dimensional echocardiographic videos. As another example, the image quality may be classified using a binary system that denotes good image quality or poor image quality. The axis may denote whether the corresponding echocardiogram video is on-axis or off-axis. On-axis images may comprise images from standard transducer positions (e.g., of the ultrasound transducer 122), such as parasternal (right and left), apical, subcostal, and suprasternal positions. Off-axis images may comprise nonstandard transducer positions where the image does not conform to the standard view (e.g., foreshortened, tangential cuts, etc.), as delineated by the American Society of Echocardiography guidelines. The view classification may differentiate between, for example, parasternal long axis (PLAX), ascending aorta, right ventricular inflow, right ventricular focused, pulmonary artery, parasternal short axis aortic valve level, parasternal short axis mitral valve level, parasternal short axis papillary muscle level, parasternal short axis apex, apical 5-chamber (A5C), apical 4-chamber (A4C), apical 3-chamber (A3C), apical 2-chamber (A2C), suprasternal notch, subcostal, other views, or any combination thereof.

For instance, during training of the at least one deep learning model 134 to output the video classification 302, a board-certified echocardiographer may manually review the echocardiogram videos 204 in the training data 140 and assign the following labels to each video as the ground truth label 206: (1) 2-dimensional B mode, Doppler, or 3-dimensional image, (2) good quality or poor quality, (3) on-axis or off-axis, and (4) the standard echocardiographic view (e.g., PLAX, A4C, A2C, etc.). The image quality may be considered "poor" if the echocardiographer is unable to identify the standard view or key structures; all other images may be considered "good."

In at least one implementation, after the echocardiogram videos 204 are classified via the video classification 302, specific video clips are selected for further processing by the at least one deep learning model 134 to generate the single-video LV measurement prediction(s) 304. By way of example, PLAX, A4C, and A2C echocardiographic videos may be used to generate per-video predictions for distinct measurements of left ventricle structure and function, including left ventricle ejection fraction (LVEF), LV end-diastolic dimension (LVEDD), LV end-systolic dimension (LVESD), interventricular septal wall thickness (IVS), and posterior wall thickness (PWT), which will be further explained below. It is to be understood that as used herein, "single-video" corresponds to one or more predictions generated from an input echocardiogram video 204 and is not meant to limit the predictions to a single output. Accordingly, a "single-video output" corresponds to one or more predictions generated by the at least one deep learning model 134 for a given input echocardiogram video 204.

However, echocardiography studies typically include acquiring a plurality of images and video clips during a single scanning session. For instance, an echocardiogram study may include capturing images and/or videos from a plurality of different views (e.g., parasternal long-axis, parasternal short-axis, apical four-chamber, apical three-chamber, apical two-chamber, subcostal, etc.) and/or using different imaging modalities (e.g., two-dimensional, three-dimensional, Doppler, etc.) during a scanning session. As such, the implementation 300 further includes a study-level cardiac prediction generator 306. The study-level cardiac prediction generator 306 is representative of the functionality to aggregate information generated for individual echocardiogram videos 204 to an overall prediction that summarizes the plurality of images and video clips obtained during the echocardiography study, which is output as the cardiac prediction 116.

In the example shown in FIG. 3, the study-level cardiac prediction generator 306 includes multi-instance attention heads 308 that are trained to generate fine-tuned study-based predictions. By way of example, the multi-instance attention heads 308 may translate sequences of encoded representations (e.g., the video embedding 230) from the same echocardiogram scanning session. Accordingly, the multi-instance attention heads 308 may receive the video embedding 230 as well as video embedding(s) from other videos of the same scanning session, represented in FIG. 3 as additional video embedding(s) 310. As a non-limiting example, the multi-instance attention heads 308 are configured to process up to forty embeddings. Because echocardiogram videos in a given scan may not be equally informative, the multi-instance attention heads 308 may determine which embeddings are the most informative for outputting the cardiac prediction 116. By way of example, if one view shows the left ventricle more clearly, the multi-instance attention heads 308 may assign higher importance to the corresponding video embedding 230. In the implementation 300, the study-level cardiac prediction generator 306 further includes one or more dense layers 312 (e.g., two dense layers), which may receive aggregated information from the multi-instance attention heads 308 and make final predictions regarding the cardiac prediction 116.

The cardiac prediction 116 includes study-based LV measurement prediction(s) 314 in the present example. The study-based LV measurement prediction(s) 314 may comprise predictions for a LVEF 316, left ventricle dimension(s) 318, and LV wall thickness 320. By way of example, the multi-instance attention heads 308 may comprise three separate attention heads, where a first multi-instance attention head outputs predictions for the LVEF 316, a second multi-instance attention head outputs predictions for the left ventricle dimension(s) 318, and a third multi-instance attention head outputs predictions for the LV wall thickness 320.

The LVEF 316 corresponds to how much blood the left ventricle pumps out during each contraction (e.g., heartbeat). In general, a lower ejection fraction corresponds to weaker pumping actions of the heart. As such, the LVEF 316 may provide one indication of the function or dysfunction of the left side of the heart. A low ejection fraction (e.g., less than 50%), for instance, may indicate a higher risk of heart failure.

The left ventricle dimension(s) 318 may comprise one or both of the LVEDD and the LVESD. The LVEDD corresponds to the diameter of the left ventricle at the end of diastole, when the left ventricle is filled with blood and is expected to be at its largest diameter, while the LVESD corresponds to the diameter of the left ventricle at the end of systole, after the left ventricle has contracted to pump blood and is expected to be at its smallest diameter. A larger LVEDD may indicate that the left ventricle is dilated, which may suggest conditions like heart failure, cardiomyopathy, or volume overload. A larger LVESD may indicate poor left ventricular function or systolic dysfunction, where the heart struggles to contract effectively. As such, the LV dimension(s) 318 may provide another indication of the function and/or dysfunction of the left side of the heart.

The LV wall thickness 320 may include one or both of the IVS and PWT. The IVS refers to the thickness of the wall that separates the left and right ventricles, whereas the PWT corresponds to the thickness of the left ventricle at its posterior end. An increased IVS and/or PWT may suggest left ventricular hypertrophy or hypertrophic cardiomyopathy. For instance, hypertrophy may be a response to chronic stress on the heart that causes the heart to work harder to pump blood (e.g., due to hypertension), which may be a risk factor for heart failure. Accordingly, the LV wall thickness 320 may provide yet another indication of the function and/or dysfunction of the left side of the heart, alone or together with one or more or each of the LVEF 316 and the LV dimension(s) 318.

It is to be appreciated that the study-based LV measurement prediction(s) 314 may include one or more additional or alternative measurements of left ventricle structure and/or function from those explicitly listed without departing from the spirit or scope of the described techniques.

Thus, the implementation 300 shown in FIG. 3 may allow the echocardiogram analysis module 130 to process multiple views and instances of echocardiogram data to generate comprehensive cardiac structure and function predictions regarding the left ventricle from the input echocardiogram video 204 as well as other echocardiogram videos from the same study. For instance, the study-based LV measurement prediction(s) 314 may provide an estimation of an individual's heart function and/or risk of heart failure, which may be used by a clinician in risk assessment and/or in determining a course of treatment for an individual. Additional example details of the usage of the study-based LV measurement prediction(s) 314 are described herein with respect to Example 1.

Figure 4:
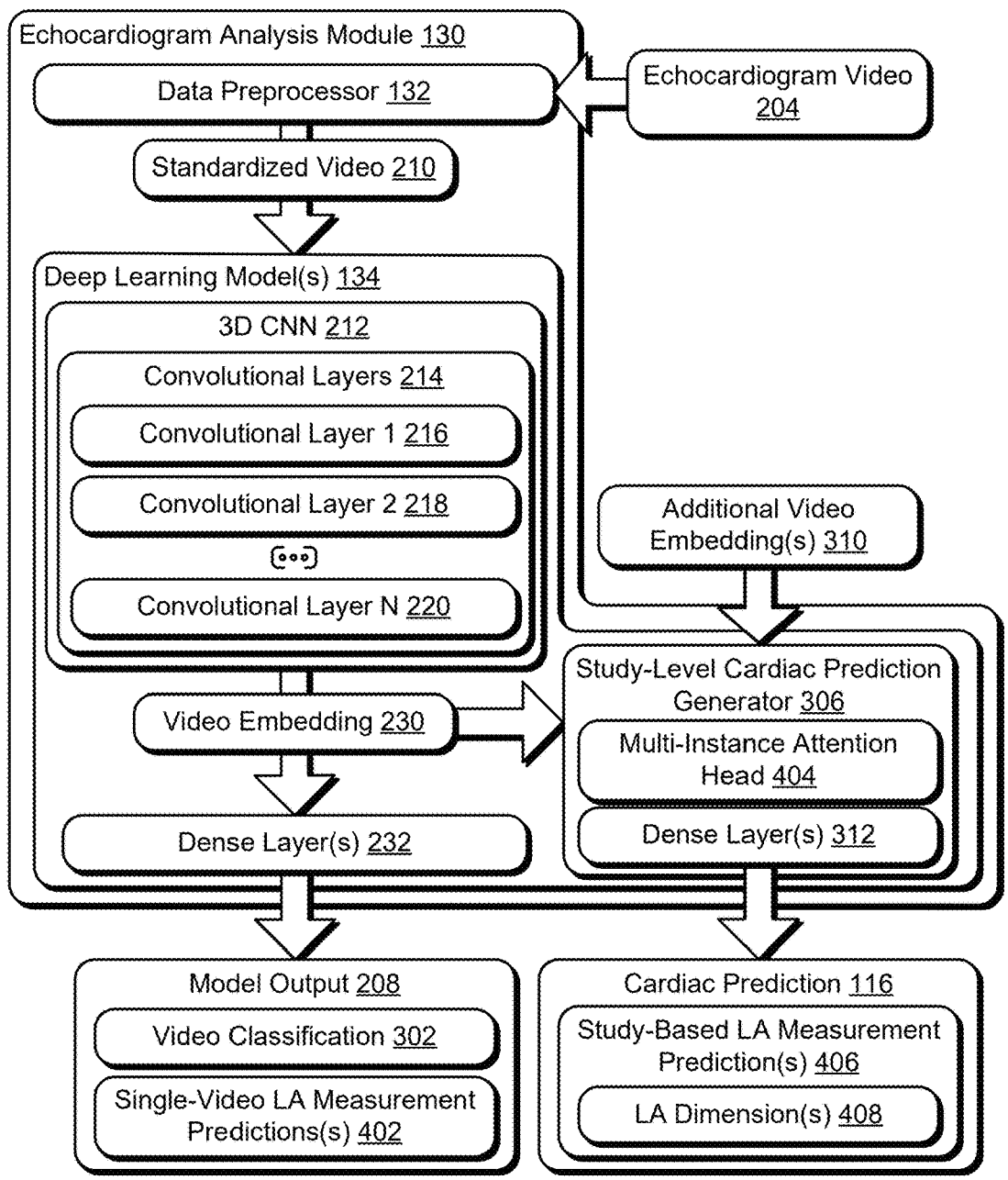
FIG. 4 depicts an example implementation of generating and using at least one deep learning model to assess left atrial heart structure and function.

FIG. 4 depicts an example implementation 400 of generating and using at least one deep learning model 134 to assess left atrial heart structure and function. Components previously introduced in FIGS. 1-3 are numbered the same and function as previously described.

Similar to the implementation 300 of FIG. 3, in the implementation 400, the at least one deep learning model 134 is a two-part model including the 3D CNN 212 as an encoder backbone. Therefore, for simplicity, the differences between the implementation 300 and the implementation 400 will be highlighted below.

In the example shown in FIG. 4, the at least one deep learning model 134 is trained to output, as the model output 208 from the one or more dense layers 232, the video classification 302 and single-video left atrium (LA) measurement prediction(s) 402. In at least one implementation, after the videos are classified via the video classification 302, specific video clips are selected for further processing by the at least one deep learning model 134 to generate the single-video LA measurement prediction(s) 402. By way of example, PLAX, A4C, and A2C echocardiographic videos may be used to generate at least one per-video prediction for measures of left atrium structure and function, including left atrium anteroposterior dimension (LA AP), as further explained below.

It is to be appreciated that the information included in the video embedding 230 may vary in the implementation 400 compared to the implementation 300 due to the different training. For instance, the training process may result in different values for the weights 222 and bias 224 (see FIG. 2) when the at least one deep learning model 134 is trained to output the single-video LA measurement prediction(s) 402 compared to when it is trained to output the single-video LV measurement prediction(s) 304 of FIG. 3. For example, a first deep learning model of the at least one deep learning model 134 may be trained to output the single-video LV measurement prediction(s) 304, and a second, separate deep learning model of the at least one deep learning model 134 may be trained to output the single-video LA measurement prediction(s) 402.

The implementation 400 includes the study-level cardiac prediction generator 306, which includes a multi-instance attention head 404 (e.g., a single multi-instance attention head) configured to receive the video embedding 230 and the additional video embedding(s) 310 to generate, as the cardiac prediction 116, study-based LA measurement prediction(s) 406. In at least one variation, however, a plurality of multi-instance attention heads 404 may be used, similar to the implementation 300. By way of example, the 3D CNN 212 may generate video embeddings 230 for PLAX, A4C, and A2C echocardiogram videos 204 on a per-video basis, and the multi-instance attention head 404 may integrate the video embeddings 230 for each video to generate the study-based LA measurement prediction(s) 406.

In the example shown in FIG. 4, the study-based LA measurement prediction(s) 406 include LA dimension(s) 408, which includes one or more predictions regarding the size of the left atrium. As mentioned above, the LA dimension(s) 408 may include the LA AP. The LA AP is the distance from the front (anterior) to the back (posterior) of the left atrium, typically determined at the level of the aortic valve. LA enlargement, for instance, may indicate increased pressure or volume load, as may occur in conditions such as atrial fibrillation, left ventricular diastolic dysfunction, mitral valve disease, or chronic hypertension, which may result in heart failure. Accordingly, the LA dimension(s) 408 may provide yet another indication of the function and/or dysfunction of the left side of the heart, alone or together with the study-based LV measurement prediction(s) 314 of FIG. 3.

It is to be appreciated that the study-based LA measurement prediction(s) 406 may include one or more additional or alternative measurements of left atrium structure and/or function from those explicitly listed without departing from the spirit or scope of the described techniques.

Thus, the implementation 400 shown in FIG. 4 may allow the echocardiogram analysis module 130 to process multiple views and instances of echocardiogram data to generate one or more cardiac structure and function predictions regarding the left atrium from the input echocardiogram video 204 as well as other echocardiogram videos from the same study. For instance, the study-based LA measurement prediction(s) 406 may provide an estimation of an individual's heart function and/or risk of heart failure, which may be used by a clinician in risk assessment and/or in determining a course of treatment for an individual. Additional example details of the usage of the study-based LA measurement prediction(s) 406 are described herein with respect to Example 1.

Deep Learning for Assessing Right Heart Structure and Function

Figure 5:
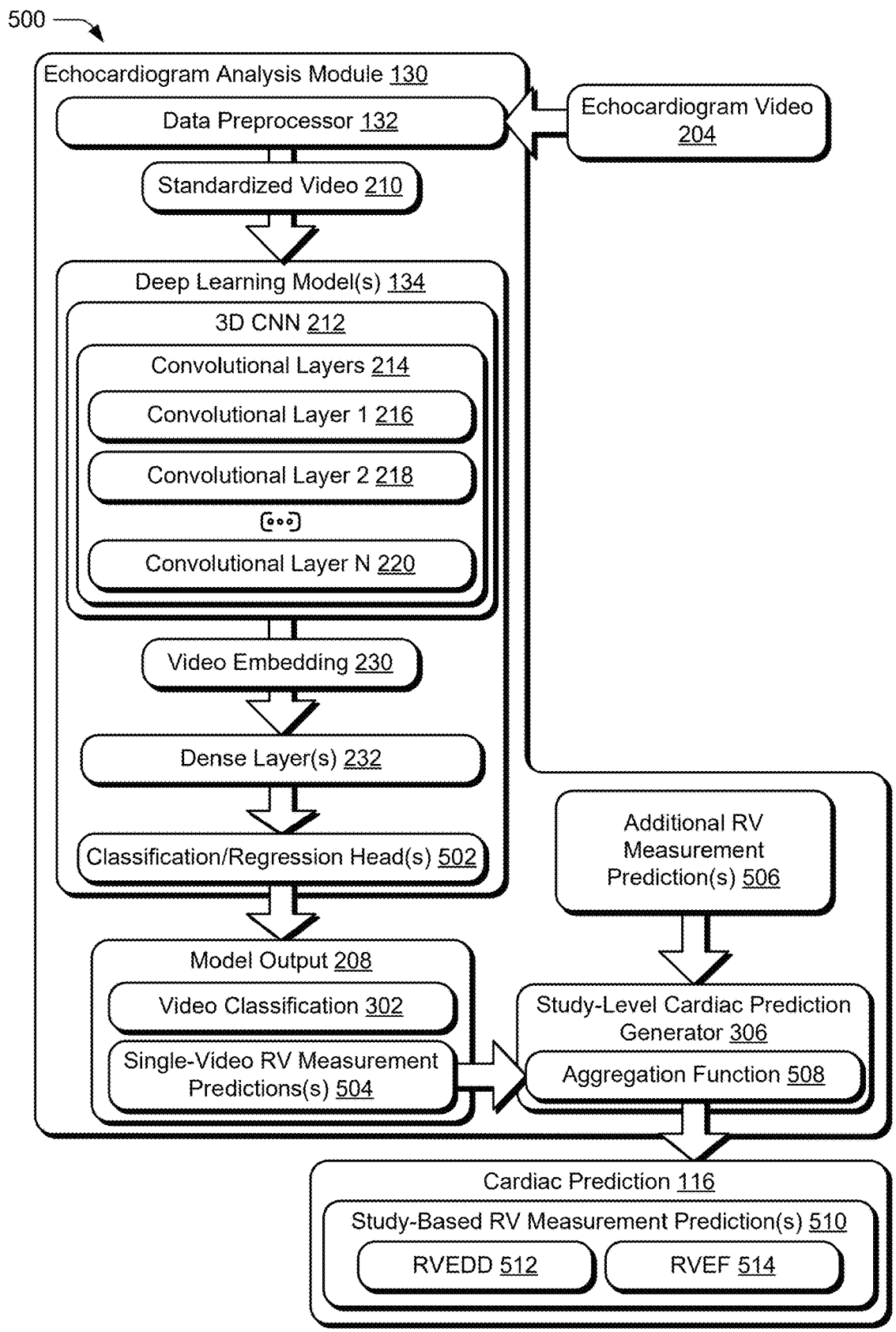
FIG. 5 depicts an example implementation of generating and using at least one deep learning model to assess right ventricular heart structure and function.

FIG. 5 depicts an example implementation 500 of generating and using at least one deep learning model 134 to assess right ventricular heart structure and function. Components previously introduced in FIGS. 1-4 are numbered the same and function as previously described.

Similar to the implementation 300 of FIG. 3 and the implementation 400 of FIG. 4, in the implementation 500, the at least one deep learning model 134 includes the 3D CNN 212 as an encoder backbone. Therefore, for simplicity, the differences between the implementation 500 and the implementation 300 will be highlighted below.

In the implementation 500, the output of the one or more dense layers 232 is input into one or more classification and/or regression heads 502. By way of example, in the implementation 500, the at least one deep learning model 134 may be configured for multitask learning, where the at least one deep learning model 134 simultaneously performs classification and regression tasks. Each classification and/or regression head, for instance, may serve a different prediction task, thus enabling the at least one deep learning model 134 to predict multiple outputs. By way of example, the classification head(s) may be configured to predict a categorical label, whereas the regression head(s) may be configured to predict quantitative values (e.g., numerical outputs). The categorical label may be a qualitative label regarding the right ventricle (RV) size or function, such as normal, reduced, dilated, and so forth.

The one or more classification and/or regression heads 502 output the qualitative labels and/or quantitative values as single-video RV measurement prediction(s) 504, which may be included in the model output 208. The single-video RV measurement prediction(s) 504 for the echocardiogram video 204 may be aggregated with the single-video RV prediction(s) 504 for other echocardiogram videos of the same study, represented in FIG. 5 as additional RV measurement prediction(s) 506, via the study-level cardiac prediction generator 306. In the implementation 500, the study-level cardiac prediction generator 306 includes an aggregation function 508. By way of example, the aggregation function 508 may take the median of the single-video RV measurement prediction(s) 504 and the additional RV measurement prediction(s) 506 to output, as the cardiac prediction 116, study-based RV measurement prediction(s) 510.

In at least one implementation, the study-based RV measurement prediction(s) 510 includes RV end-diastolic diameter (RVEDD) 512 and/or RV ejection fraction (RVEF) 514. By way of example, the single-video RV measurement prediction(s) 504 for the RVEDD for relevant views of the same study (e.g., A4C and RV-focused views) are input into the aggregation function 508, and the aggregation function 508 outputs the RVEDD 512 as the per-study prediction. Separately, the single-video RV measurement prediction(s) 504 for the RVEF for the relevant views of the same study are input into the aggregation function 508, which outputs the RVEF 514 as the per-study prediction. The RVEDD 512, for example, is a measurement of the right ventricle at the end of diastole at its widest area, typically near the tricuspid valve. Right ventricular dilation, where the RVEDD is larger than 41 millimeters, for example, is associated with chronic lung diseases, pulmonary hypertension, pulmonary embolism, and right-sided heart failure. The RVEF 514 is an indicator of how effectively the right ventricle pumps blood with each heartbeat, represented as a percentage of the proportion of blood ejected from the right ventricle during systole relative to the amount present at the end of diastole. Reduced RVEF (e.g., less than 45%) may indicate right ventricular dysfunction, which may be due to pulmonary hypertension, right-sided heart failure, or a myocardial infarction affecting the right heart.

In one or more implementations, separate models are trained to output the RVEDD 512 and the RVEF 514. By way of example, a first model may be trained to predict the RVEDD 512, and a second model may be separately trained to output the RVEF 514. As such, the first model and the second model may have different weights 222 and biases 224 (see FIG. 2) with respect to each other and with respect to other deep learning models trained to output other predictions, such as those described with respect to FIGS. 3, 4, and 6.

It is to be appreciated that the study-based RV measurement prediction(s) 510 may include one or more additional or alternative measurements of right ventricle structure and/or function from those explicitly listed without departing from the spirit or scope of the described techniques.

Thus, the implementation 500 shown in FIG. 5 may allow the echocardiogram analysis module 130 to process multiple views and instances of echocardiogram data to generate one or more cardiac structure and function predictions regarding the right ventricle from the input echocardiogram video 204 as well as other echocardiogram videos from the same study. For instance, the study-based RV measurement prediction(s) 510 may provide an estimation of an individual's heart function and/or risk of heart failure or other pulmonary conditions, which may be used by a clinician in risk assessment and/or in determining a course of treatment for an individual. Additional example details regarding the usage of the study-based RV measurement prediction(s) 510 are described herein with respect to Example 2.

Deep Learning for Assessing Mitral Valve Prolapse

Figure 6:
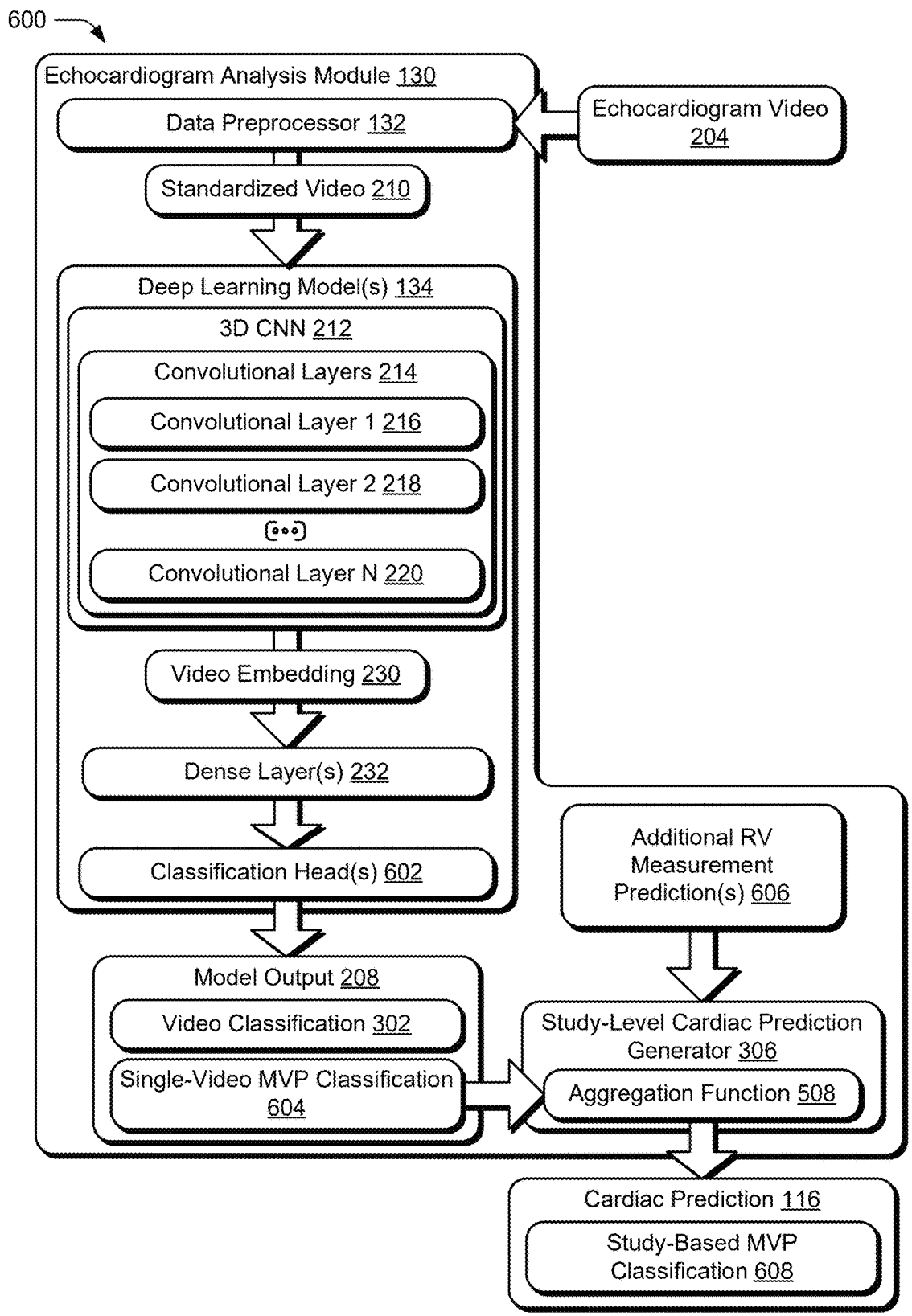
FIG. 6 depicts an example implementation of generating and using at least one deep learning model to assess whether mitral valve prolapse is present.

FIG. 6 depicts an example implementation 600 of generating and using at least one deep learning model 134 to assess whether or not mitral valve prolapse is present. Components previously introduced in FIGS. 1-5 are numbered the same and function as previously described.

Similar to the implementation 500 of FIG. 5, in the implementation 600, the at least one deep learning model 134 includes the 3D CNN 212 as an encoder backbone and uses the aggregation function 508 to output study-based predictions. Therefore, for simplicity, the differences between the implementation 600 and the implementation 500 will be highlighted below.

In the implementation 600, the at least one deep learning model 134 includes at least one classification head 602 and is trained to output, as part of the model output 208, a single-video mitral valve prolapse (MVP) classification 604. By way of example, unlike in the implementation 500 of FIG. 5, the at least one deep learning model 134 may not include regression head(s). In at least one implementation, the single-video MVP classification 604 includes a probability score (e.g., value) indicating a likelihood that MVP is present. The probability score, for instance, may range from 0 (e.g., MVP is not detected) to 1 (e.g., a highest likelihood that MVP is present).

Alternatively, or in addition, the single-video MVP classification 604 is a binary classification output indicating either the presence of MVP (e.g., MVP is detected) or the absence of MVP (e.g., MVP is not detected). Alternatively, or in addition, when MVP is detected, the single-video MVP classification 604 further indicates a type of MVP detected. By way of example, the at least one deep learning model 134 may classify the mitral valve imaged in the echocardiogram video 204 as one of unspecified MVP, anterior leaflet prolapse, posterior leaflet prolapse, bileaflet prolapse, superior displacement of the mitral valve not meeting criteria for MVP, or normal. In this example, unspecified MVP, anterior leaflet prolapse, posterior leaflet prolapse, and bileaflet prolapse correspond to classifications indicating MVP is present, whereas superior displacement of the mitral valve not meeting criteria for MVP and normal correspond to classifications indicating MVP is not present.

The aggregation function 508 of the study-level cardiac prediction generator 306 receives the single-video MVP classification 604 from the echocardiogram video 204 as well as from other echocardiogram videos of the same study, represented in FIG. 6 as additional RV measurement prediction(s) 606, and outputs, as the cardiac prediction 116, a study-based MVP classification 608. The aggregation function 508 may utilize the same or a different function than in the implementation 500 of FIG. 5, for instance, to generate the study-based MVP classification 608. By way of example, the aggregation function 508 may aggregate video-level predictions into study-level predictions (e.g., the study-based MVP classification 608) by taking the median of all single-video MVP classifications 604 for the given study. Similar to the single-video MVP classification 604, the study-based MVP classification 608 may include a probability score and/or a binary classification of MVP.

In at least one implementation, a threshold is used to determine whether MVP is present based on the probability score. As an illustrative example, the threshold is a value in a range between 0.4 and 0.6 (e.g., 0.470). The threshold may be determined during training based on maximizing classification accuracy in the model derivation subset 144, for instance. Using the threshold, the echocardiogram analysis module 130 may classify individuals having probability scores less than the threshold as not having MVP (e.g., the study-based MVP classification 608 indicates MVP is not present) and may classify individuals having probability scores greater than or equal to the threshold has having MVP (e.g., the study-based MVP classification 608 indicates MVP is present).

In at least one implementation, the probability score may also serve as a marker to stratify a severity of MVP. In some instances, MVP is an asymptomatic, benign condition. In other instances, however, MVP can lead to mitral valve regurgitation, where blood leaks backward from the left ventricle into the left atrium due to improper valve closure. Mitral valve regurgitation can lead to, for example, left ventricular dilation, heart failure symptoms, and/or atrial fibrillation. Therefore, the study-based MVP classification 608 may be used for patient risk stratification. Probability score-based study-based MVP classifications may extend the amount of clinically relevant information obtained (e.g., compared with binary MVP classification), as the probability score may help clinicians identify a degree of degeneration of the mitral valve and/or indicate which individuals are more likely to develop mitral valve regurgitation.

In at least one implementation, the video classification 302 may be used to select which video clips to analyze for the single-video MVP classification 604. By way of example, the selected video clips may include on-axis, interpretable, 2-dimensional B-mode (non-Doppler) video clips representing PLAX, A4C, A3C, and A2C views. It is to be appreciated that although PLAX or A3C views are typically used in clinical MVP diagnosis, at least one deep learning model 134 described herein is not limited to evaluating the PLAX and A3C views. Accordingly, a larger number of views may be evaluated by the at least one deep learning model 134 for generating the study-based MVP classification 608 than may be used in a manual MVP classification workflow.

It is to be appreciated that the at least one deep learning model 134 trained to output the single-video MVP classification 604 may have different weights 222 and bias 224 values (see FIG. 2) with respect to other deep learning models trained to output the other different predictions described herein.

Thus, the implementation 600 shown in FIG. 6 may allow the echocardiogram analysis module 130 to process multiple views and instances of echocardiogram data to generate a prediction regarding whether MVP is present from the input echocardiogram video 204 as well as other echocardiogram videos from the same study, which may be used by a clinician in risk assessment and/or in determining a course of treatment for an individual. Additional example details regarding usage of the study-based MVP classification 608 are further described herein with respect to Example 3.

Having discussed example details of the techniques for echocardiography deep learning and cardiovascular outcomes, consider now example procedures to illustrate additional aspects of the techniques.

Example Procedures

This section describes example procedures for echocardiography deep learning and cardiovascular outcomes in one or more implementations. Aspects of the procedures may be implemented in hardware, firmware, or software, or a combination thereof. The procedures are shown as a set of blocks that specify operations performed by one or more devices and are not necessarily limited to the orders shown for performing the operations by the respective blocks. In at least some implementations, at least a portion of the procedure is performed by a suitably configured device, such as the computing device 108 of FIG. 1, by executing instructions stored in a non-transitory computer-readable storage medium.

Figure 7:
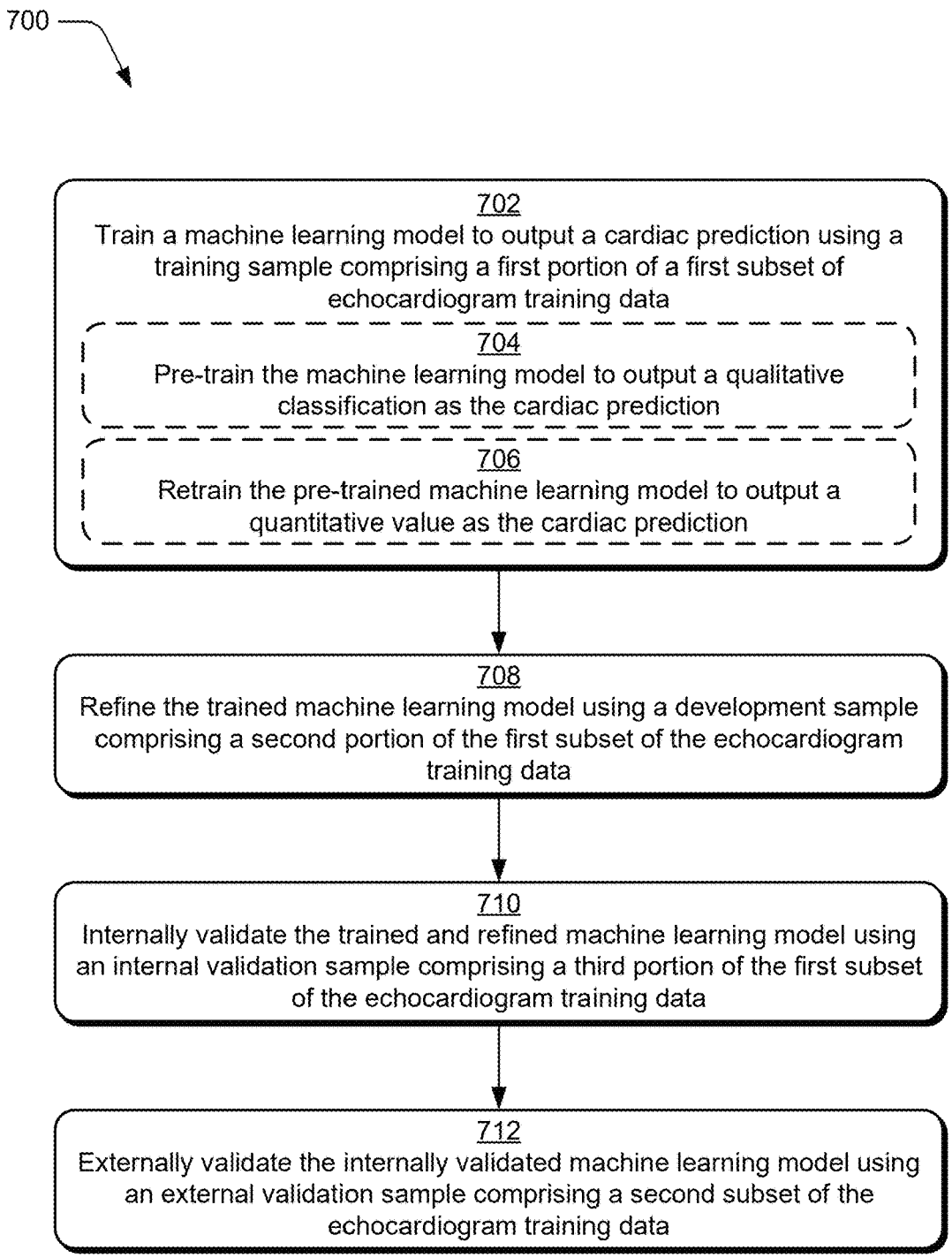
FIG. 7 depicts an example procedure for training and validating a machine learning model to output a cardiac prediction according to one or more implementations.

FIG. 7 depicts an example procedure 700 for training and validating a machine learning model to output a cardiac prediction according to one or more implementations. Where appropriate, reference will be made to components previously introduced in FIGS. 1-6.

A machine learning model is trained to output a cardiac prediction using a training sample comprising a first portion of a first subset of echocardiogram training data (block 702). By way of example, the machine learning model may be included in the at least one deep learning model 134 introduced with respect to FIG. 1. For example, the training module 136 may train the machine learning model using the training sample 148 of the model derivation subset 144 of the training data 140. In one or more implementations, the machine learning model may include the 3D CNN 212 with multiple convolutional layers 214 for extracting features from standardized echocardiogram videos.

In at least one implementation, the training process involves exposing the machine learning model to a diverse set of echocardiogram videos from model derivation subset 144, allowing it to "learn" patterns and features in the echocardiogram videos that are associated with a specific training task. For instance, the machine learning model "learns" via the adjustment of the weights 222 and biases 224, which may be adjusted through backpropagation 238 based on the calculated loss 236 between the model output 208, corresponding to the cardiac prediction of the machine learning model for a single-video input, and the ground truth labels 206. This iterative process continues until the model achieves satisfactory performance on the model derivation subset 144 of the training data 140.

In at least one implementation, as depicted in FIG. 3, the machine learning model may be trained to output left ventricular (LV) measurement predictions as the cardiac prediction 116. The machine learning model may include the multi-instance attention heads 308 to aggregate predictions across multiple videos in an echocardiogram study. The model may be trained to output study-based LV measurement predictions 314, such as the LVEF 316, LV dimension(s) 318, and/or LV wall thickness 320. As such, the ground truth labels 206 may include manually measured LVEF values, LV dimension measurements (e.g., the LVEDD and/or the LVESD), and/or LV wall thickness measurements (e.g., the IVS and/or the PWT) for the echocardiogram videos in the training data 140. Given this, the model training manager 138 may form a training instance that includes an input portion corresponding to a given echocardiogram video and an associated output portion with a measured value and/or a structural/functional classification (e.g., dilated, normal, etc.).

In at least one other implementation, as shown in FIG. 4, the machine learning model may be trained to generate left atrial (LA) measurement predictions as the cardiac prediction 116. This model architecture may include the multi-instance attention head 404 to produce study-based LA measurement predictions 406, such as LA dimension(s) 408. As such, the ground truth labels 206 may include manually measured LA dimension(s) (e.g., the LA AP) for the echocardiogram videos in the training data 140. Given this, the model training manager 138 may form a training instance that includes an input portion corresponding to a given echocardiogram video and an associated output portion with a measured value and/or a structural/functional classification (e.g., dilated, normal, etc.).

In one or more other implementations, as shown in FIG. 5, the machine learning model may be trained to output right ventricular (RV) measurements as the cardiac prediction 116. This model architecture may use the one or more classification and/or regression heads 502 and an aggregation function 508 to produce study-based RV measurement prediction(s) 510, which may include the RVEDD 512 and/or the RVEF 514. In such implementations, the ground truth labels 206 may include manually measured RVEDD and RVEF values for the echocardiogram videos in the training data 140. Given this, the model training manager 138 may form a training instance that includes an input portion corresponding to a given echocardiogram video and an associated output portion with a measured value and/or a structural/functional classification (e.g., dilated, normal, etc.).

In at least one other implementation, as shown in FIG. 6, the machine learning model may be trained to output a mitral valve prolapse (MVP) classification as the cardiac prediction 116. In this scenario, the ground truth labels 206 may comprise known MVP classifications (e.g., presence or absence of MVP) for the echocardiogram videos in the training data 140. By way of example, each electrocardiogram video of the training data 140 may be classified (e.g., by an echocardiographer or other clinician) into one of the following categories: unspecified MVP, anterior leaflet prolapse, posterior leaflet prolapse, bileaflet prolapse, superior displacement of the mitral valve not meeting criteria for MVP, and normal. In at least one implementation, for model training and evaluation purposes, patients with prolapse of any leaflet were classified as "MVP," and patients labeled as superior displacement of the MV or normal were classified as "normal." As such, the training data 140 may be associated with ground truth labels 206 regarding the presence or absence of MVP. Given this, the model training manager 138 may form a training instance that includes an input portion corresponding to a given echocardiogram video and an associated output portion with a first value indicating the patient has MVP (e.g., "1" or some other corresponding value) or a second value indicating the patient does not have MVP (e.g., "0").

Optionally, training the machine learning model to output the cardiac prediction includes pre-training the machine learning model to output a qualitative classification as the cardiac prediction (block 704) and retraining the pre-trained machine learning model to output a quantitative value as the cardiac prediction (block 706). By way of example, in the pre-training, the machine learning model may be trained to predict qualitative size (e.g., dilated or normal) and/or function (e.g., hypokinetic or normal). Subsequently, the pre-trained machine learning model may be retrained to predict quantitative values. For instance, this multi-step training process may be utilized when there is a relatively large available training dataset that includes qualitative ground truth labels 206, but a relatively smaller portion includes quantitative ground truth labels 206. Accordingly, the initial weights 222 and bias 224 values learned from the larger dataset during the pre-training may be further fine-tuned during the retraining with the smaller dataset, which may result in more accurate model outputs and more efficient training compared to training with the smaller dataset from randomly initialized values.

The trained machine learning model is refined using a development sample comprising a second portion of the first subset of the echocardiogram training data (block 708). By way of example, the model training manager 138 may use the development sample 150 to fine-tune the model hyperparameters 228 and adjust the model weights 222 and biases 224. During the refinement process, for instance, the machine learning model is exposed to new echocardiogram data from the development sample 150, which is not seen by the machine learning model during the initial training process (e.g., as performed at block 702). This process helps identify and correct any overfitting that may have occurred during the training process. The hyperparameters 228, such as the learning rate, batch size, and/or regularization strength, may be adjusted to achieve a desirable performance on the development sample 150 while maintaining good generalization to unseen data, for instance.

The trained and refined machine learning model is internally validated using an internal validation sample comprising a third portion of the first subset of the echocardiogram training data (block 710). By way of example, the model performance may be evaluated on the internal validation sample 152 to assess generalization. The internal validation process may provide an initial measure of an ability of the machine learning model to make accurate cardiac predictions on data from a same data source as the training sample 148 and the development sample 150 (e.g., the model derivation subset 144) but that was not used during the training (block 702) or refinement (block 708) processes described above.

During the internal validation process, for instance, outputs of the machine learning model are compared against the ground truth label 206 for the internal validation sample 152. Various performance metrics, such as accuracy, precision, recall, and F1 score for classification tasks, or mean absolute error and root mean squared error for regression tasks, may be calculated. The internal validation process may help identify any potential issues with the performance of the machine learning model and guide further refinement if the performance is not adequate.

The internally validated machine learning model is externally validated using an external validation sample comprising a second subset of the echocardiogram training data (block 712). By way of example, in response to the machine learning model meeting an acceptable or desired performance criteria, an external validation process may be performed using the external validation subset 146. During the external validation process, the external validation subset 146 is input to the internally validated machine learning model. The external validation subset 146 may be used to verify that the performance of at least one deep learning model 134 is not specific to the data source of the model derivation subset 144. The external validation subset 146, for instance, comprises echocardiogram data from a separate cohort, often collected from a different institution and/or different patient population. The external validation process may provide a robust evaluation of the machine learning model with respect to a real-world scenario and may help identify biases or limitations that were not apparent in the internal validation. The external validation may provide confidence in the ability of the machine learning model to make accurate cardiac predictions across diverse patient populations and clinical settings.

In this way, the procedure 700 enables generation of a machine learning model that is able to output an accurate cardiac prediction 116 from one or a plurality of echocardiogram videos obtained for an echocardiography study. By including multiple views, including those that are not typically used during a manual clinical analysis workflow, and avoiding image segmentation, the machine learning model learns how to interpret latent information from echocardiogram videos that may not be readily interpretable by human observers. By way of example, via the training process described above, the machine learning model may learn to identify complex patterns and features that go beyond what is physically/manually measurable. These features, captured in the video embeddings, represent a high-dimensional abstraction of the echocardiogram data, including from views that may be considered suboptimal or non-diagnostic for manual human analysis. By leveraging this information, the machine learning model may learn to make accurate predictions about cardiac function, structure, and/or the presence of cardiac conditions that may not be evident from visual inspection or manual measurement performed by a human. Moreover, the procedure 700 is adaptable for a plurality of different training tasks to enable a plurality of different specialized machine learning models to be developed for different cardiac structure, function, and classification predictions.

Figure 8:
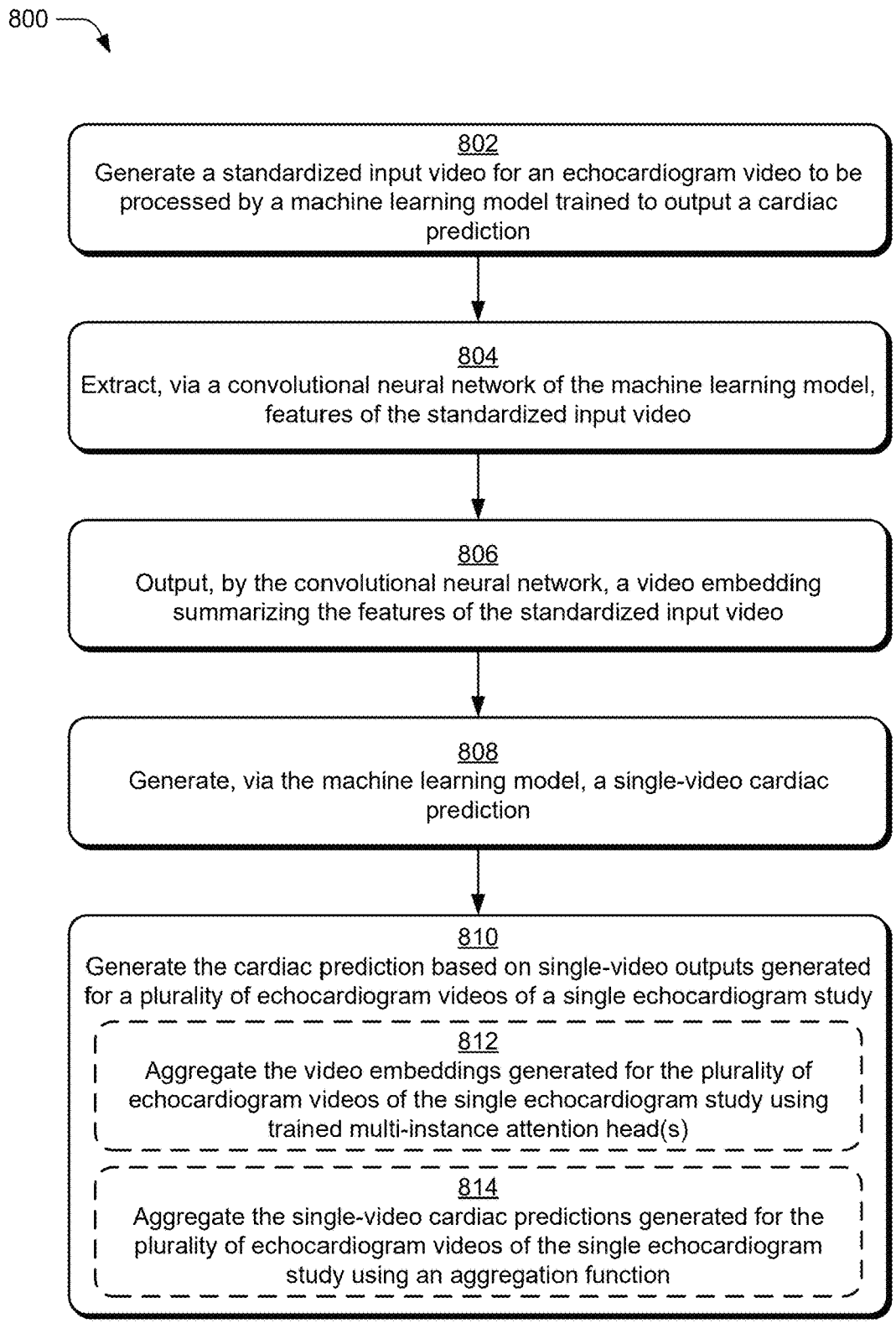
FIG. 8 depicts an example procedure for generating a cardiac prediction from an echocardiogram study using a machine learning model according to one or more implementations.

FIG. 8 depicts an example procedure 800 for generating a cardiac prediction from an echocardiogram study using a machine learning model according to one or more implementations. Where appropriate, reference will be made to components previously introduced in FIGS. 1-6.

A standardized input video is generated for an echocardiogram video to be processed by a machine learning model trained to output a cardiac prediction (block 802). By way of example, the data preprocessor 132 may generate the standardized video 210 from the echocardiogram video 204. The standardized video 210 may be processed to have consistent dimensions, frame rate, and other characteristics to ensure uniform input to the machine learning model. Moreover, data overlays and non-echocardiogram data (e.g., patient information, text, electrocardiogram tracings, and respirometer tracings) may be removed to generate the standardized video 210.

Features of the standardized input video are extracted via a convolutional neural network of the machine learning model (block 804). By way of example, the machine learning model (e.g., the at least one deep learning model 134) may utilize the 3D CNN 212 to extract features from the standardized video 210. These features may represent various aspects of cardiac structure and/or function depicted in the echocardiogram video. The particular features extracted depend on the specific task(s) for which the machine learning model is trained. By way of example, during training, if a particular feature helps to minimize the loss 236, the training may reinforce this feature by adjusting the corresponding weights 222 and bias 224. In contrast, a feature that does not contribute to reducing the loss 236 may not be emphasized.

As such, the 3D CNN 212 may be trained to extract task-relevant features such that the extracted features may vary from model to model of the at least one deep learning model 134. For instance, a first machine learning model trained to output LV measurement prediction(s), such as in the implementation 300 of FIG. 3, may extract a first group of features; a second machine learning model trained to output LA measurement prediction(s), such as in the implementation 400 of FIG. 4, may extract a second group of features; a third machine learning model trained to output RV measurement prediction(s), such as in the implementation 500 of FIG. 5, may extract a third group of features; and a fourth machine learning model trained to output an MVP classification, such as in the implementation 600 of FIG. 6, may extract a fourth group of features. There may be overlap between the first group of features, the second group of features, the third group of features, and/or the fourth group of features.

The convolutional neural network outputs a video embedding summarizing the features of the standardized input video (block 806). By way of example, the 3D CNN 212 may output the video embedding 230, which encapsulates the extracted features in a compact representation (e.g., a 1D vector of fixed length). The video embedding 230, for instance, may capture both spatial and temporal information to distill the information of the standardized video 210 into a lower-dimensional, meaningful representation that can be used for downstream tasks like classification or regression.

The machine learning model generates a single-video cardiac prediction (block 808). By way of example, the video embedding 230 may be fed to one or more dense layers 232 and/or one or more task-specific classification/regression heads (e.g., the one or more classification and/or regression heads 502 of FIG. 5, or the one or more classification heads 602 of FIG. 6), which output the single-video cardiac prediction.

In at least one implementation, such as depicted in FIG. 3, the one or more dense layers 232 may generate single-video LV measurement prediction(s) 304 based on the video embedding 230. These predictions may include estimates of the LVEF 316, the LV dimension(s) 318 (e.g., the LVEDD and/or the LVESD), and/or the LV wall thickness 320 (e.g., the IVS and/or the PWT). In at least one other implementation, such as depicted in FIG. 4, the dense layer(s) 232 may produce single-video LA measurement prediction(s) 402, such as LA dimension(s) 408 (e.g., the LA AP), based on the video embedding 230. In one or more other implementations, such as illustrated in FIG. 5, the dense layer(s) 232 and the one or more classification and/or regression heads 502 may generate single-video RV measurement prediction(s) 504. These may include predictions of right ventricular end-diastolic diameter (RVEDD) and/or the right ventricular ejection fraction (RVEF). For mitral valve prolapse classification, as shown in FIG. 6, the dense layer(s) 232 and classification head(s) 602 may produce a single-video MVP classification 604 based on the video embedding 230.

The cardiac prediction is generated based on single-video outputs generated for a plurality of echocardiogram videos of a single echocardiogram study (block 810). By way of example, the information from multiple echocardiogram videos may be aggregated by the machine learning model to produce a study-level cardiac prediction.

In at least one implementation, generating the cardiac prediction based on the single-video outputs includes aggregating the video embeddings generated for the plurality of echocardiogram videos of the single echocardiogram study using trained multi-instance attention head(s) (block 812). By way of example, the multi-instance attention head(s) (e.g., the multi-instance attention heads 308 of FIG. 3 or the multi-instance attention head 404 of FIG. 4) may receive the video embeddings 230 generated by the 3D CNN 212 for the plurality of echocardiogram videos to capture relationships between the videos as well as generalize relevant information across the multiple video inputs. The output of the attention head(s), for instance, may be a single representation that is then passed to the one or more dense layers 312, which may output the cardiac prediction 116.

For example, in at least one implementation where the LV measurement(s) are predicted (e.g., FIG. 3), the multi-instance attention heads 308 may aggregate the video embedding 230 and the additional video embedding(s) 310 to produce the study-based LV measurement prediction(s) 314. Similarly, in at least one implementation where LA measurement(s) are predicted (FIG. 4), the multi-instance attention head 404 may aggregate single-video LA measurement predictions 402 to generate study-based LA measurement prediction(s) 406.

By using the using trained multi-instance attention head(s) to aggregate the single-video outputs, such as the video embedding 230 produced for the plurality of echocardiogram videos, the machine learning model may learn how to aggregate information in a task-specific manner that takes into account spatial and temporal relationships between the videos that may be difficult to capture using statistical aggregation methods.

In at least one other implementation, generating the cardiac prediction based on the single-video outputs includes aggregating the single-video cardiac predictions generated for the plurality of echocardiogram videos of the single echocardiogram study using an aggregation function (block 814). By way of example, the aggregation function 508 may receive the single-video cardiac predictions and use a statistical aggregation method, such as by taking the median or the mean, to combine information from the plurality of echocardiogram videos. The aggregation function 508 may not take into account spatial or temporal relationships between the videos but may instead assume that the single-video cardiac predictions are independently valid. Unlike the trained multi-instance attention head(s) described above, the aggregation function 508 may not "learn" from specific patterns in the data, for instance.

For example, in at least one implementation where the RV measurement(s) are predicted (FIG. 5), the aggregation function 508 may combines single-video RV measurement prediction 504 with the additional RV measurement prediction(s) 506 to produce the study-based RV measurement prediction(s) 510. Similarly, for MVP classification (FIG. 6), the aggregation function 508 may combine single-video MVP classifications 604 with the additional RV measurement prediction(s) 606 to generate the study-based MVP classification 608.

By using the aggregation function to aggregate the single-video outputs, such as the single-video cardiac predictions produced for the plurality of echocardiogram videos, a complexity of the model and its training may be reduced, and computational efficiency may be increased.

In this way, the procedure 800 enables use of a machine learning model that is trained to output an accurate cardiac prediction 116 based on one or a plurality of echocardiogram videos obtained for an echocardiography study. By including multiple views, including those that are not typically used during a manual clinical analysis workflow, and avoiding image segmentation, an amount of information on which the cardiac prediction 116 is based may be increased. By leveraging this information, the machine learning model may make accurate predictions about cardiac function, structure, and/or the presence of cardiac conditions that may not be evident from visual inspection or manual measurement performed by a human, thus increasing the information that can be obtained from echocardiography studies and reducing the occurrence of repeat examinations. Moreover, the procedure 800 may enable echocardiographers to increase the number of echocardiography scans that can be performed by reducing an amount of analysis time spent on a single scan and reducing human error.

The procedure 800 also enables non-expert providers to obtain clinically relevant information from an echocardiography scan. For instance, echocardiography scans rely on expert interpretation (e.g., by a cardiologist or other specialist), but such experts may be unavailable at the point of care, particularly in resource-limited or time-sensitive settings. As such, the procedure 800 may be used to identify cardiac abnormalities as soon as the scan is completed for enhanced decision support. This may also reduce specialist dependency, enabling the specialists to devote more time to higher-level patient care decisions and less time on manual echocardiography scan interpretation.

Having described example procedures in accordance with one or more implementations, consider now an example system and device that can be utilized to implement the various techniques described herein.

Example System and Device

Figure 9:
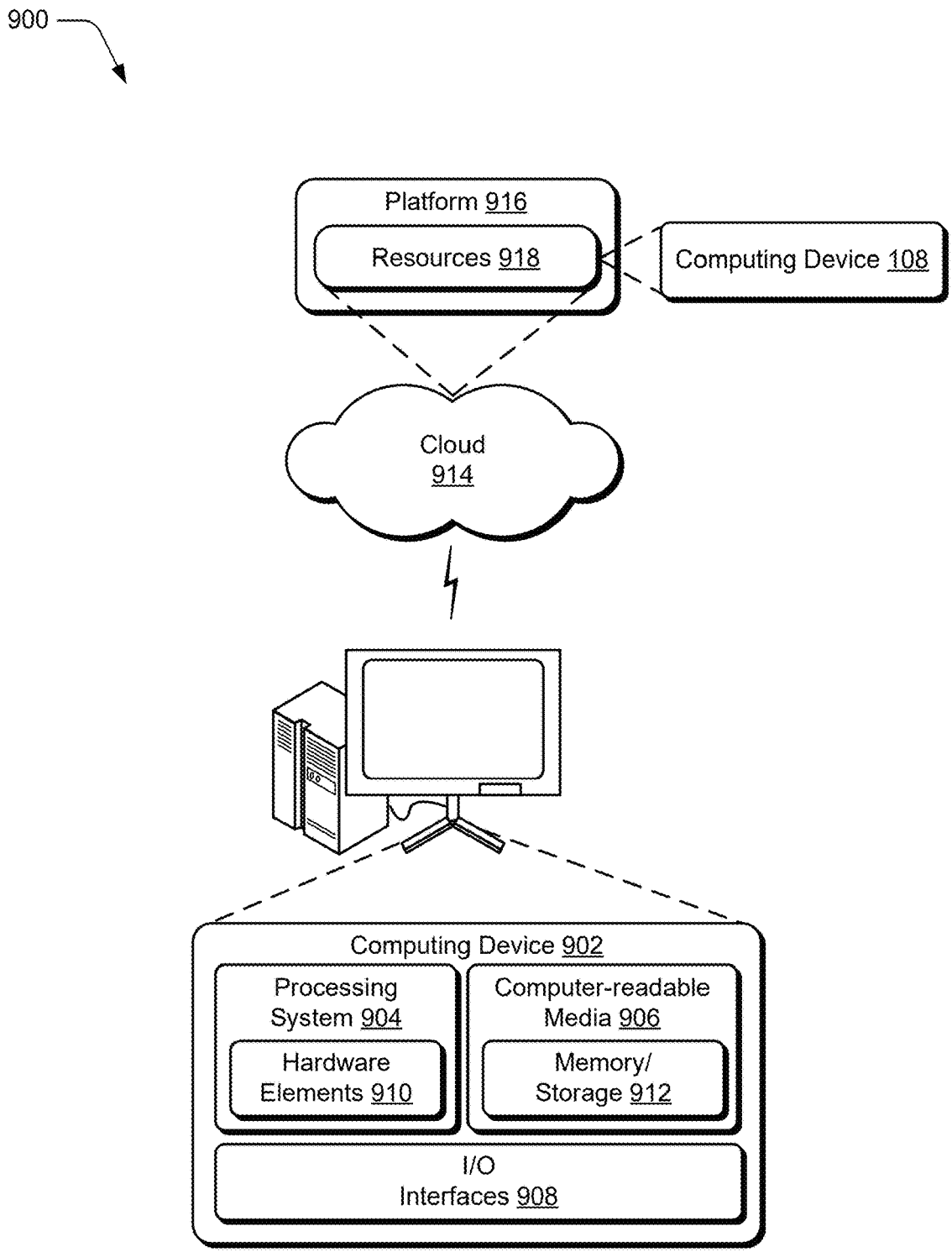
FIG. 9 illustrates an example system including various components of an example device that can be implemented as any type of computing device as described and/or utilized with reference to FIGS. 1-8 to implement the techniques described herein.

FIG. 9 illustrates an example system generally at 900 that includes an example computing device 902 that is representative of one or more computing systems and/or devices that may implement the various techniques described herein. This is illustrated through inclusion of the computing device 108. The computing device 902 may be, for example, a server of a service provider, a device associated with a client (e.g., a client device), an on-chip system, and/or any other suitable computing device or computing system.

The example computing device 902 as illustrated includes a processing system 904, one or more computer-readable media 906, and one or more I/O interfaces 908 that are communicatively coupled, one to another. Although not shown, the computing device 902 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 904 is representative of functionality to perform one or more operations using hardware. Accordingly, the processing system 904 is illustrated as including hardware elements 910 that may be configured as processors, functional blocks, and so forth. This may include implementation in hardware as an application specific integrated circuit or other logic device formed using one or more semiconductors. The hardware elements 910 are not limited by the materials from which they are formed or the processing mechanisms employed therein. For example, processors may be comprised of semiconductor(s) and/or transistors (e.g., electronic integrated circuits (ICs)). In such a context, processor-executable instructions may be electronically executable instructions.

The computer-readable storage media 906 is illustrated as including memory/storage 912. The memory/storage 912 represents memory/storage capacity associated with one or more computer-readable media. The memory/storage 912 may include volatile media (such as random-access memory (RAM)) and/or nonvolatile media (such as read only memory (ROM), Flash memory, optical disks, magnetic disks, and so forth). The memory/storage 912 may include fixed media (e.g., RAM, ROM, a fixed hard drive, and so on) as well as removable media (e.g., flash memory, a removable hard drive, an optical disc, and so forth). The computer-readable media 906 may be configured in a variety of other ways as further described below.

Input/output interface(s) 908 are representative of functionality to allow a user to enter commands and information to computing device 902, and also allow information to be presented to the user and/or other components or devices using various input/output devices. Examples of input devices include a keyboard, a cursor control device (e.g., a mouse), a microphone, a scanner, touch functionality (e.g., capacitive or other sensors that are configured to detect physical touch), a camera (e.g., which may employ visible or non-visible wavelengths such as infrared frequencies to recognize movement as gestures that do not involve touch), and so forth. Examples of output devices include a display device (e.g., a monitor or projector), speakers, a printer, a network card, tactile-response device, and so forth. Thus, the computing device 902 may be configured in a variety of ways as further described below to support user interaction.

Various techniques may be described herein in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. The features of the techniques described herein are platform-independent, meaning that the techniques may be implemented on a variety of commercial computing platforms having a variety of processors.

For instance, the terms "module," "functionality," and "component" may include a hardware and/or software system that operates to perform one or more functions. For example, a module, functionality, or component may include a computer processor, a controller, or another logic-based device that performs operations based on instructions stored on a tangible and non-transitory computer-readable storage medium, such as a computer memory. Alternatively, a module, functionality, or component may include a hard-wired device that performs operations based on hard-wired logic of the device. Various modules, systems, and components shown in the attached figures may represent the hardware that operates based on software or hardwired instructions, the software that directs hardware to perform the operations, or a combination thereof.

An implementation of the described modules and techniques may be stored on or transmitted across some form of computer-readable media. The computer-readable media may include a variety of media that may be accessed by the computing device 902. By way of example, and not limitation, computer-readable media may include "computer-readable storage media" and "computer-readable signal media."

"Computer-readable storage media" may refer to media and/or devices that enable persistent and/or non-transitory storage of information in contrast to mere signal transmission, carrier waves, or signals per se. Thus, computer-readable storage media refers to non-signal bearing media. The computer-readable storage media includes hardware such as volatile and non-volatile, removable and non-removable media, and/or storage devices implemented in a method or technology suitable for storage of information such as computer readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable signal media" may refer to a signal-bearing medium that is configured to transmit instructions to the hardware of the computing device 902, such as via a network. Signal media typically may embody computer readable instructions, data structures, program modules, or other data in a modulated data signal, such as carrier waves, data signals, or other transport mechanism. Signal media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media.

As previously described, hardware elements 910 and computer-readable media 906 are representative of modules, programmable device logic and/or fixed device logic implemented in a hardware form that may be employed in some examples to implement at least some aspects of the techniques described herein, such as to perform one or more instructions. Hardware may include components of an integrated circuit or on-chip system, an application-specific integrated circuit (ASIC), a field-programmable gate array (FPGA), a complex programmable logic device (CPLD), and other implementations in silicon or other hardware. In this context, hardware may operate as a processing device that performs program tasks defined by instructions and/or logic embodied by the hardware as well as a hardware utilized to store instructions for execution, e.g., the computer-readable storage media described previously.

Combinations of the foregoing may also be employed to implement various techniques described herein. Accordingly, software, hardware, or executable modules may be implemented as one or more instructions and/or logic embodied on some form of computer-readable storage media and/or by one or more hardware elements 910. The computing device 902 may be configured to implement particular instructions and/or functions corresponding to the software and/or hardware modules. Accordingly, implementation of a module that is executable by the computing device 902 as software may be achieved at least partially in hardware, e.g., through use of computer-readable storage media and/or hardware elements 910 of the processing system 904. The instructions and/or functions may be executable/operable by one or more articles of manufacture (for example, one or more computing devices 902 and/or processing systems 904) to implement techniques, modules, and examples described herein.

The techniques described herein may be supported by various configurations of the computing device 902 and are not limited to the specific examples of the techniques described herein. This functionality may also be implemented all or in part through use of a distributed system, such as over a "cloud" 914 via a platform 916 as described below.

The cloud 914 includes and/or is representative of a platform 916 for resources 918, which are depicted including the computing device 108. The platform 916 abstracts underlying functionality of hardware (e.g., servers) and software resources of the cloud 914. The resources 918 may include applications and/or data that can be utilized while computer processing is executed on servers that are remote from the computing device 902. The resources 918 can also include services provided over the Internet and/or through a subscriber network, such as a cellular or Wi-Fi network.

The platform 916 may abstract resources and functions to connect the computing device 902 with other computing devices. The platform 916 may also serve to abstract scaling of resources to provide a corresponding level of scale to encountered demand for the resources 918 that are implemented via the platform 916. Accordingly, in an interconnected device example, implementation of functionality described herein may be distributed throughout the system 900. For example, the functionality may be implemented in part on the computing device 902 as well as via the platform 916 that abstracts the functionality of the cloud 914.

Having discussed example details of the techniques for echocardiography deep learning and cardiovascular outcomes, consider now the following examples to illustrate usage of the techniques.

EXAMPLE APPLICATIONS

Example 1: Deep Learning-Enabled Assessment of Left Heart Structure and Function Predicts Cardiovascular Outcomes Overview A deep learning echocardiogram interpretation model referred to as Dimensional Reconstruction of Imaging Data (DROID) was developed and used to automate standard measurements of left atrial (LA) and left ventricular (LV) structure and function. The association of these measurements with incident cardiovascular outcomes was then determined by leveraging two longitudinal multi-institutional electronic health record (EHR)-based cohorts of >500,000 ambulatory patients with echocardiographic studies and linked EHR data for the robust assessment of clinical outcomes.

Methods

Study Cohorts

The Enterprise Warehouse of Cardiology (EWOC) is a retrospective community-based ambulatory cardiology sample of 99,253 adults aged 18 years or older receiving longitudinal cardiology care within the Mass General Brigham (MGB) healthcare system. Participants who had at least one TTE performed at the Massachusetts General Hospital (MGH) were included in the EWOC cohort. The EWOC cohort may correspond to the model derivation subset 144 introduced with respect to FIG. 1, for example.

With respect to the model derivation subset 144, longitudinal cardiology care was defined as ≥2 cardiology clinic visits within 1-3 years between 2000-2019. Cardiology clinic visits were identified using a validated rule-based heuristic tool based on Current Procedural Terminology codes and a manually curated list of 143 cardiology clinic locations. The EWOC cohort was validated using manual chart review. Data were processed using the "JEDI" Extractive Data Infrastructure 1.

Model performance was validated in two external samples. The MGB Community Care Cohort Project (C3PO) cohort is an EHR cohort of 523,445 individuals receiving longitudinal primary care within MGB. Participants enrolled in the C3PO cohort with at least one transthoracic echocardiogram (TTE) performed at MGH within 3 years prior to the start of follow-up were included in the C3PO external validation cohort. Individuals who belonged to both EWOC and C3PO were included in the C3PO cohort only. C3PO and EWOC study protocols were approved by the MGB Institutional Review Board and adhere to the principles of the Declaration of Helsinki. Cohort construction detailed further below. The C3PO external validation cohort comprises a first external sample of the external validation subset 146 introduced with respect to FIG. 1, for example.

With respect to the MGB C3PO Cohort of the external validation subset 146, individuals receiving longitudinal primary care within MGB (defined as having at least one pair of ambulatory care visits between 1-3 years apart) were identified among >3.6 million individuals with at least one ambulatory visit within MGB between 2000 to 2018. Primary care office visits were identified using a validated rule-based heuristic tool based on Current Procedural Terminology codes and a manually curated list of 431 primary care clinic locations. The C3PO cohort was validated using manual chart review and implementation of two existing risk prediction models, the Pooled Cohort Equations and the Cohorts for Aging and Genomic Epidemiology Atrial Fibrillation (CHARGE-AF) score. Start of follow-up for each study participant was defined as the second primary care visit of that individual's earliest qualifying pair.

The EchoNet-Dynamic and EchoNet-LVH datasets are publicly available research datasets. EchoNet-Dynamic comprises 10,030 apical-4 chamber (A4C) echocardiography videos, and EchoNet-LVH comprises 12,000 parasternal-long axis (PLAX) echocardiography videos from individuals who underwent TTE imaging between 2016 and 2018 as part of clinical care at Stanford University Hospital. Use of the EchoNet datasets complied with the Stanford University School of Medicine Research Use Agreement and Terms of Use. The EchoNet-Dynamic and EchoNet-LVH datasets comprise a second external sample of the external validation subset 146 introduced with respect to FIG. 1, for example.

Figure 10:
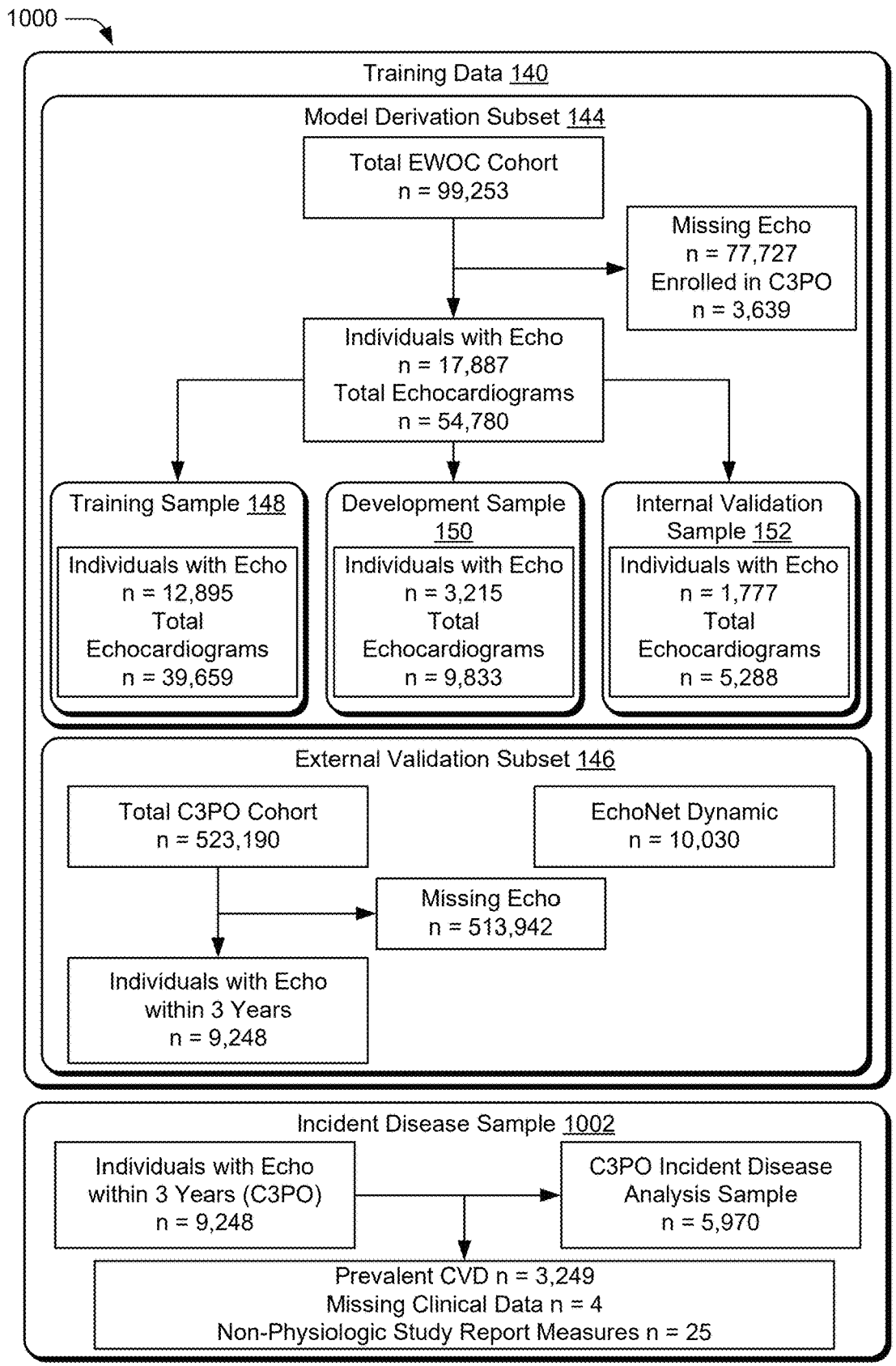
FIG. 10 illustrates a summary of the training data used for developing deep learning models for the assessment of left heart structure and function.

FIG. 10 illustrates a summary 1000 of the training data 140 used for developing deep learning models for the assessment of left heart structure and function. By way of example, the training sample 148 included 39,659 echocardiogram videos obtained for 12,995 individuals, the development sample 150 included 9,833 echocardiogram videos obtained for 3,215 individuals, and the internal validation sample 152 included 5,288 echocardiogram videos obtained for 1,777 individuals. The external validation subset 146 included 9,248 individuals in the C3PO cohort and 10,030 individuals in the EchoNet-Dynamic cohort.

The summary 1000 further includes an incident disease sample 1002, which was used to evaluate model outputs (e.g., the cardiac prediction 116) with incident cardiovascular outcomes. The incident disease sample 1002 includes a subset of the C3PO cohort of the external validation subset 146. Participants with prevalent heart failure (HF) (n=1,063), atrial fibrillation (AF) (n=1,483), myocardial infarction (MI) (n=703), missing clinical data (n=4), and non-physiologic EchoLab measures (n=25) were excluded, yielding a final sample of 5,970 individuals. Participants with HF, AF, and MI are collectively referred to as having prevalent cardiovascular disease (CVD) in the incident disease sample 1002.

Echocardiogram Dataset and Pre-Processing

Individuals included in EWOC and C3PO who had undergone TTE were identified and cross-referenced using the Massachusetts General Hospital (MGH) Echocardiography Laboratory Database (EchoLab), a well-curated dataset of all clinically indicated echocardiograms performed at the MGH from 1980 to 2020. The EchoLab Dataset for the study period of 2001 to 2020 comprises raw echocardiographic images, clinical data, and physician reports for a total of 234,137 echocardiograms representing 91,680 patients. A custom data processing pipeline was implemented to remove identifying information, unintended human labels, and information beyond the scanning sector (e.g., via the data preprocessor 132 of FIG. 1, and as further described below).

Echocardiograms were performed by trained sonographers in accordance with American Society of Echocardiography (ASE) guidelines using Philips Medical Systems IE399, EPIQ 7C, and EPIQCVx and General Electric Vivid7 and E95 ultrasound machines. Raw transthoracic echocardiograms were extracted and downloaded from the clinical echocardiography server (Syngo Dynamics picture archiving and communication system) onto the Mass General Brigham (MGB) ERISOne high performance computing cluster for ingestion and preprocessing. Standard resting echocardiograms consist of a series of approximately 50-150 still images and video clips visualizing the heart. The sampling rate for video clips was at least 30 frames per second. Echocardiogram movies were converted from Digital Imaging and Communications in Medicine (DICOM) format into audio video interleave (AVI) files using custom Python routines, enabling efficient video storage.

The custom data processing pipeline was then implemented to remove identifying information, unintended human labels, and information beyond the scanning sector (including text and electrocardiogram and respirometer tracings). In this example of implementing the data preprocessor 132, all identifying information, unintended human labels, and text was removed by identifying and removing all static elements of the echocardiographic video. Then, electrocardiogram and respirometer tracings were removed by removing all elements that were green in color. A random sample of echocardiographic videos were visually manually inspected to ensure that the scanning sector had been fully retained in the data processing pipeline.

Videos were then cropped into a square aspect ratio. Resulting square images were 600×600 pixels and down sampled by cubic interpolating using the OpenCV Python package (version 4.5.4) into standardized 16-frame videos of size 224×224 pixels. Intensity normalization was performed by converting 8-bit gray scale intensity to 32-bit floating numbers within the 0-1 range. The standardized videos (e.g., the standardized video 210 introduced with respect to FIG. 2) captured the initial ~2.1 s (i.e., at 7.5 frames per second) of the original raw echocardiogram clips. Leveraging parallel computing capabilities of a cluster (e.g., the computing device 108 of FIG. 1) used to process the echocardiogram videos, a total of ~5.5 million echocardiogram movies from 64,028 echocardiogram studies were processed. To facilitate data handling, AVIs from movies acquired during the same session were grouped into a single LMDB Lightning Database.

Model Training, Development, and Validation

For model development, the TTEs performed on EWOC cohort patients were randomly split into independent training (39,659 echocardiograms/12,895 patients), test (9,833 echocardiograms/3,215 patients), and validation (Internal Validation: 5,288 echocardiograms/1,777 patients) sets, such as shown in the model derivation subset 144 of the summary 1000 of FIG. 10. Multiple TTE studies were used per patient during model training. The models were validated in a separate set of patients from the C3PO cohort who were not used for model training (C3PO External Validation, n=9,248 echocardiograms/patients) and in an independent sample from Stanford University Hospital (EchoNet-Dynamic, n=10,030 echocardiograms/patients), as shown in the external validation subset 146 of the summary 1000 of FIG. 10. A single TTE study was used per patient in each of the external validation datasets.

Clinical Variables

Weight, height, systolic and diastolic blood pressure (SBP and DBP), and pulse were derived from tabular EHR data extracted from clinical encounters. Given significant missingness for baseline vital signs in the EHR (>40%), Applicants used a natural language processing (NLP) algorithm to recover vital signs from unstructured notes. For weight, the value most closely adjacent to the start of follow-up was used. Any value for height in the EHR was accepted. For individuals with residual missing height or weight values after NLP recovery, Applicants used height and weight ascertained at time of echocardiogram capture. Diabetes mellitus (DM) was defined as the presence of an International Classification of Diseases, 9th and 10th revision (ICD-9 and 10) code for DM and use of anti-diabetes medication. Hypertension (HTN) was defined as ICD-9 or 10 code for HTN and use of anti-hypertensive medication 30 days prior to the start of follow-up.

Incident Cardiovascular Outcomes

For the incident disease analysis, all individuals from the C3PO with an MGH echocardiogram performed within 3 years prior to start of follow-up were included. Participants with prevalent heart failure (HF) (n=1,063), atrial fibrillation (AF) (n=1,483), myocardial infarction (MI) (n=703), missing clinical data (n=4), and non-physiologic EchoLab measures (n=25) were excluded, yielding a final sample of n=5,970 individuals, as shown in the incident disease sample 1002 of FIG. 10. Outcomes of interest included incident HF, AF, MI, and all-cause death.

Both HF and MI were defined as presence of ≥2 ICD-9 or ICD-10 codes applied in the inpatient setting based on previously published code sets (PPV ≥85%). 3 AF was defined ≥1 ICD-9 or ICD-10 diagnostic or procedural code based on previously validated code sets (PPV ≥85%). Atrial flutter was considered equivalent to AF. The dates of incident HF, AF, and MI were defined as the date of first presence of an ICD-9 or ICD-10 code corresponding to a primary diagnosis for an inpatient encounter. All-cause death was ascertained from the Social Security Death Index or MGB internal documentation of death.

Classification Model

A classification model was developed to perform four classification tasks at scale: (1) detection of image type (2-dimensional B mode versus Doppler versus 3-dimensional echocardiographic images), (2) assessment of image quality (good versus poor quality), (3) determination of axis (on-versus off-axis images), and (4) view classification, such as described with respect to the video classification 302 of FIG. 3.

First, the classification model was trained to identify echocardiographic view (e.g., PLAX, A4C, etc.), video type (e.g., 2-dimensional, Doppler versus 3-dimensional), image quality, and image axis. For each of these classification tasks, a board-certified echocardiographer manually reviewed echocardiogram videos and assigned the following labels to each video: (1) 2-dimensional B mode or Doppler or 3-dimensional image, (2) good quality or poor quality, (3) on-axis or off-axis, and (4) 1 of 15 standard echocardiographic views (e.g., parasternal long axis [PLAX], apical 4-chamber [A4C], apical 2-chamber [A2C]). The image quality was considered "poor" if the echocardiographer was unable to identify the standard view or key structures; all other images were labeled as "good." The image axis was considered "off-axis" if the image did not conform to the standard view (e.g., foreshortened, tangential cuts, etc.) as delineated by the American Society of Echocardiography guidelines. A multi-head convolutional neural network (CNN) model was then trained, developed, and internally validated for the simultaneous performance of the four classification tasks. The optimized model was then applied to all digital image clips included in the training cohort.

The classification model comprises a Movinet-A2 3D convolutional neural network (CNN) encoder (e.g., the 3D CNN 212 introduced with respect to FIG. 2) connected with four classification heads and trained on 80 randomly selected studies from the training cohort, as annotated by a board-certified echocardiographer. The model was given 10 video frames spanning the first 2 seconds of the echocardiographic movie. During training, the model was optimized to simultaneously perform the classification of: 1) echo view type (e.g., PLAX versus A4C etc.); 2) video modality (e.g., standard vs. Doppler vs. 3D); 3) image quality (e.g., good versus poor); and 4) off-axis acquisition (e.g., on-axis versus off-axis). The weights of the encoder were initialized according to the default checkpoint provided in the Tensor Flow Hub (tfhub.dev/tensorflow/movinet/a2/base/kinetics-600/classification/3). Model performance was evaluated on 730 videos from 5 additional echo studies annotated by the expert echocardiographer. As such, the classification model comprises one of the deep learning models 134 described herein.

Predicting Standard Measures of Left Heart Structure and Function

Several model architectures were tested to predict standard measures of left heart structure and function from TTE videos. Left ventricular (LV) and left atrial (LA) measures of interest included LV ejection fraction (LVEF), LV end-diastolic dimension (LVEDD), LV end-systolic dimension (LVESD), interventricular septal wall thickness (IVS), posterior wall thickness (PWT), and left atrial anteroposterior dimension (LA AP).

Figure 11:
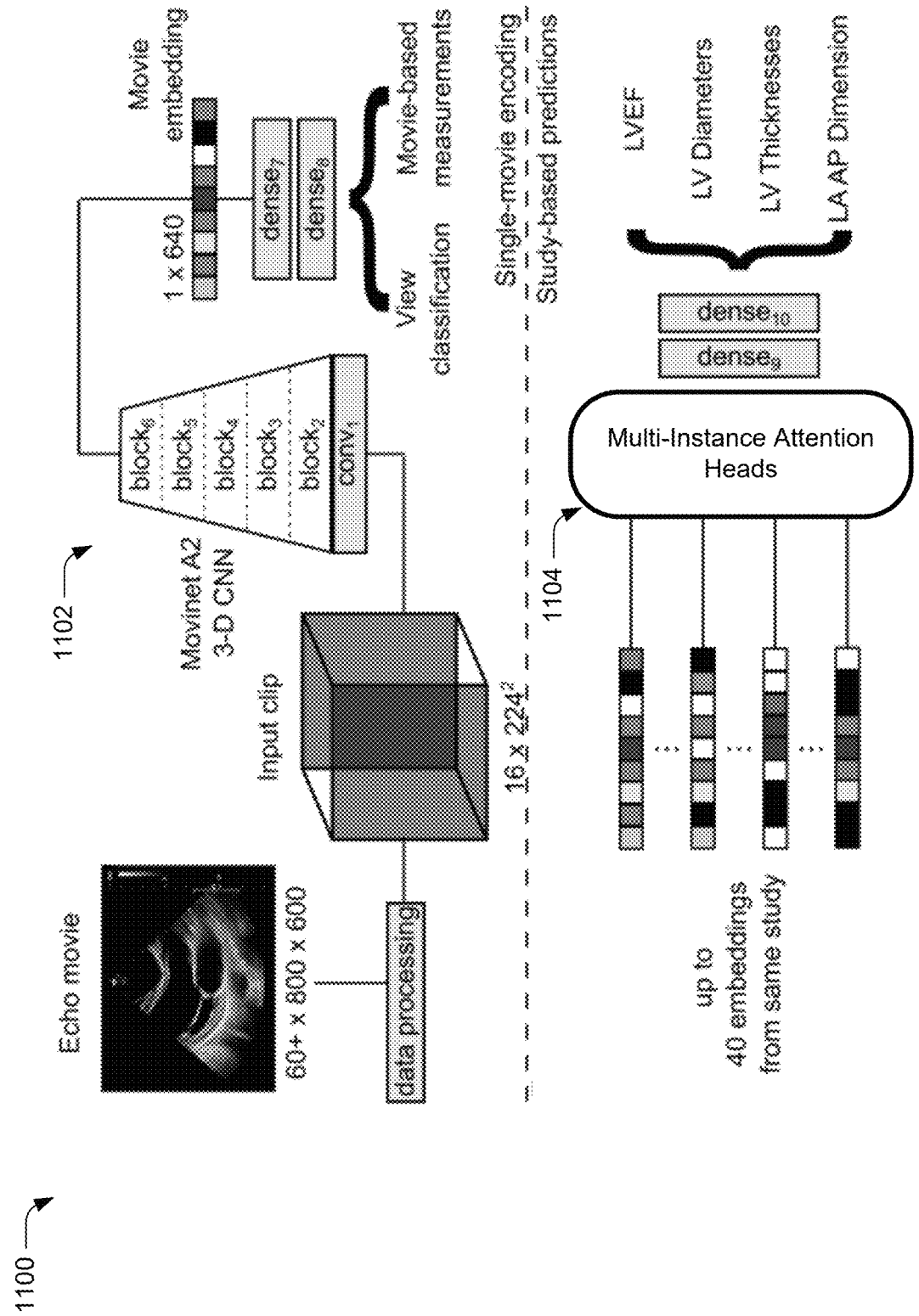
FIG. 11 shows an overview of a model architecture, hereafter named Dimensional Reconstruction of Imaging Data (DROID), that was selected and used for deep learning models trained to access left heart structure and function.

FIG. 11 shows an overview of a model architecture 1100, hereafter named Dimensional Reconstruction of Imaging Data (DROID), that was selected and used for deep learning models trained to access left heart structure and function. DROID comprises a first model portion 1102 having an encoder backbone based on the Movinet-A2 CNN (e.g., the 3D CNN 212) to extract 640-element representations of echo videos via multi-task training and a second model portion 1104 having multi-instance attention heads (e.g., the multi-instance attention heads 308) that translate sequences of encoded representations from the same echocardiogram into study-based predictions. The two-part model architecture of DROID is a manual segmentation-free approach that mimics the clinical echocardiographer interpretation workflow by first encoding important information from all available video clips (via 3D CNNs), and then using attention heads to incorporate information from the most relevant videos to predict the target measurements. See, for example, FIG. 3. Two specific DROID models were trained to predict standard LA and LV measures (DROID-LA and DROID-LV, respectively), as further elaborated below.

FIG. 11 summarizes the workflow sequence for encoding each echocardiographic video via the first model portion 1102. Clinical echocardiogram videos are resized into standardized clips of 16×224×224 pixels. Batches of clips are then input to the 3D CNN, with the individual echocardiogram videos processes individually in parallel, for instance. The weights of the network are progressively optimized to minimize mean square error between model predictions (e.g., the model output 208) and gold standard EchoLab measurements (e.g., the ground truth label 206), such as described with respect to the training process 200 of FIG. 2, for example.

In the Example 1, the first model portion 1102 was trained to generate predictions for measures of left heart structure and function from raw echocardiographic videos. In developing the first model portion 1102, several encoder input strategies were compared, including: (1) 32-frame versus 16-frame inputs and (2) continuous frame sampling versus intermittent frame sampling (take 1/skip 1, take 1/skip 2, take 1/skip 3 . . . ). Model performance for 32-frame versus 16-frame inputs was comparable, so a 16-frame input strategy was selected for further optimizations given the superior computational efficiency for the 16-frame input (Table 1). Comparison of continuous versus intermittent input sampling identified the best model performance for a take 1/skip 3 frames input strategy (Table 1). Encoder output performance for a single-task versus multi-task prediction was then compared (Table 2). While performance of the single-task encoder was marginally better than the multi-task encoder, the multi-task encoder was ultimately preferred for its ability to generate multiple predictions within one model.

TABLE 1

| Input | Input type | $R^2$ | Mean absolute error |
|---|---|---|---|
| 32-frame vs 16-frame inputs | 16-frames | 0.80 | 4.9091 |
| | 32-frames | 0.80 | 4.9102 |
| | Take 1/skip 1 | 0.79 | 5.0083 |
| | Take 1/skip 3 | 0.80 | 4.9091 |

FIG. 11 further depicts the model refinement workflow performed by the second model portion 1104. The second model portion 1104 was used to fine-tune the deep learning model to more precisely predict standard LA and LV measures. The 640-element encodings (e.g., the video embedding 230) of up to forty echocardiogram videos captured from the same echocardiogram study are collected from the embedding layer of the 3D CNN. The encodings are then input into a multi-instance attention head model that generates study-level predictions that account for the weighted contributions from the different encodings.

During model development, the multi-instance attention-head was tested against a transformer-based head. The attention head incorporates up to forty 640-element embeddings from a single study and selects the videos that are most salient to the prediction task. In a similar fashion, the transformer heads were also trained to attend over sequences of up to forty embeddings from a single study. It was found that fine-tuning with either the attention head or transformer head improved model performance compared with a model without fine-tuning (e.g., including the first model portion 1102 alone). Model performance between the attention head or transformer head was similar, and the attention head was selected as the final prediction head given greater clinical interpretability (Table 2). As such, it is to be appreciated that in variations, transformer heads may be used.

TABLE 2

| Input | Input type | $R^2$ | Mean absolute error |
|---|---|---|---|
| Single vs multi-task encoder | Single-task | 0.80 | 4.8352 |
| | Multi-task | 0.80 | 4.9091 |
| Regression heads | Standard head | 0.80 | 4.9091 |
| | MIL attention | 0.81 | 4.6112 |
| | Transformer | 0.82 | 4.5701 |

Model performance was evaluated across a spectrum of heart rates. As summarized in Table 3, the model architecture 1100 showed good performance across varying heart rates, with lowest performance for heart rates above 100 bpm.

TABLE 3

| | MAE (95% CI) | | | | | | | |
|---|---|---|---|---|---|---|---|---|
| | 40-50 bpm | 50-60 bpm | 60-70 bpm | 70-80 bpm | 80-90 bpm | 90-100 bpm | 100-110 bpm | 110-120 bpm |
| LVEF | 4.20 (4.19, 4.21) | 4.08 (4.06, 4.09) | 4.08 (4.07, 4.10) | 4.14 (4.13, 4.15) | 4.44 (4.42, 4.46) | 4.72 (4.69, 4.75) | 4.65 (4.59, 4.70) | 4.87 (4.78, 4.96) |
| LVEDD | 2.03 (2.03, 2.04) | 2.10 (2.09, 2.11) | 2.10 (2.09, 2.11) | 2.08 (2.08, 2.09) | 2.12 (2.11, 2.13) | 2.24 (2.22, 2.25) | 2.31 (2.28, 2.34) | 2.57 (2.53, 2.62) |
| LVESD | 2.01 (2.00, 2.01) | 2.02 (2.01, 2.02) | 1.99 (1.99, 2.00) | 2.01 (2.01, 2.02) | 2.06 (2.05, 2.07) | 2.19 (2.17, 2.21) | 2.17 (2.14, 2.19) | 2.45 (2.41, 2.50) |
| IVS | 1.00 (1.00, 1.01) | 1.00 (0.99, 1.00) | 0.98 (0.97, 0.98) | 0.98 (0.97, 0.98) | 1.00 (1.00, 1.01) | 1.00 (0.99, 1.00) | 1.08 (1.07, 1.10) | 1.07 (1.05, 1.09) |
| PWT | 0.93 (0.92, 0.93) | 0.93 (0.92, 0.93) | 0.92 (0.92, 0.92) | 0.93 (0.92, 0.93) | 0.96 (0.96, 0.97) | 0.96 (0.95, 0.96) | 1.01 (1.00, 1.02) | 1.00 (0.98, 1.02) |
| LA AP | 2.50 (2.49, 2.51) | 2.44 (2.43, 2.45) | 2.59 (2.58, 2.60) | 2.51 (2.50, 2.52) | 2.70 (2.68, 2.72) | 2.65 (2.62, 2.67) | 2.70 (2.66, 2.75) | 2.81 (2.73, 2.88) |

With the model architecture 1100 selected, two models were trained: DROID-LA to predict standard LA measures (which may correspond to the implementation 400 shown in FIG. 4), and DROID-LV (which may correspond to the implementation 300 of FIG. 3) to predict standard LV measures. The DROID-LA model encoder processes PLAX, A4C, and A2C raw echocardiographic videos to generate predictions for LA anteroposterior dimension (LA AP) per video. A multi-instance attention head then integrates up to forty embeddings from the encoder for clips from the same echocardiogram to generate a single per-study prediction of LA AP. The DROID-LV model employs a similar framework and uses a multi-task encoder that integrates inputs from raw PLAX, A4C, and A2C echocardiographic videos to generate per-video predictions for 5 distinct measures of left heart structure and function including LVEF, LV end-diastolic dimension (LVEDD), LV end-systolic dimension (LVESD), interventricular septal wall thickness (IVS), and posterior wall thickness (PWT). Three separate multi-instance attention heads were trained to generate more fine-tuned per-study predictions for (1) LVEF, (2) LV dimensions (LVEDD and LVESD), and (3) wall thickness (IVS and PWT) based on clinical labels adjudicated by expert clinical echocardiographers in the EchoLab database. Both DROID-LA and DROID-LV models process all PLAX, A4C, and A2C videos when available, but can estimate left heart measurements even when one or two of the three are available for a given patient.

Figure 12A:
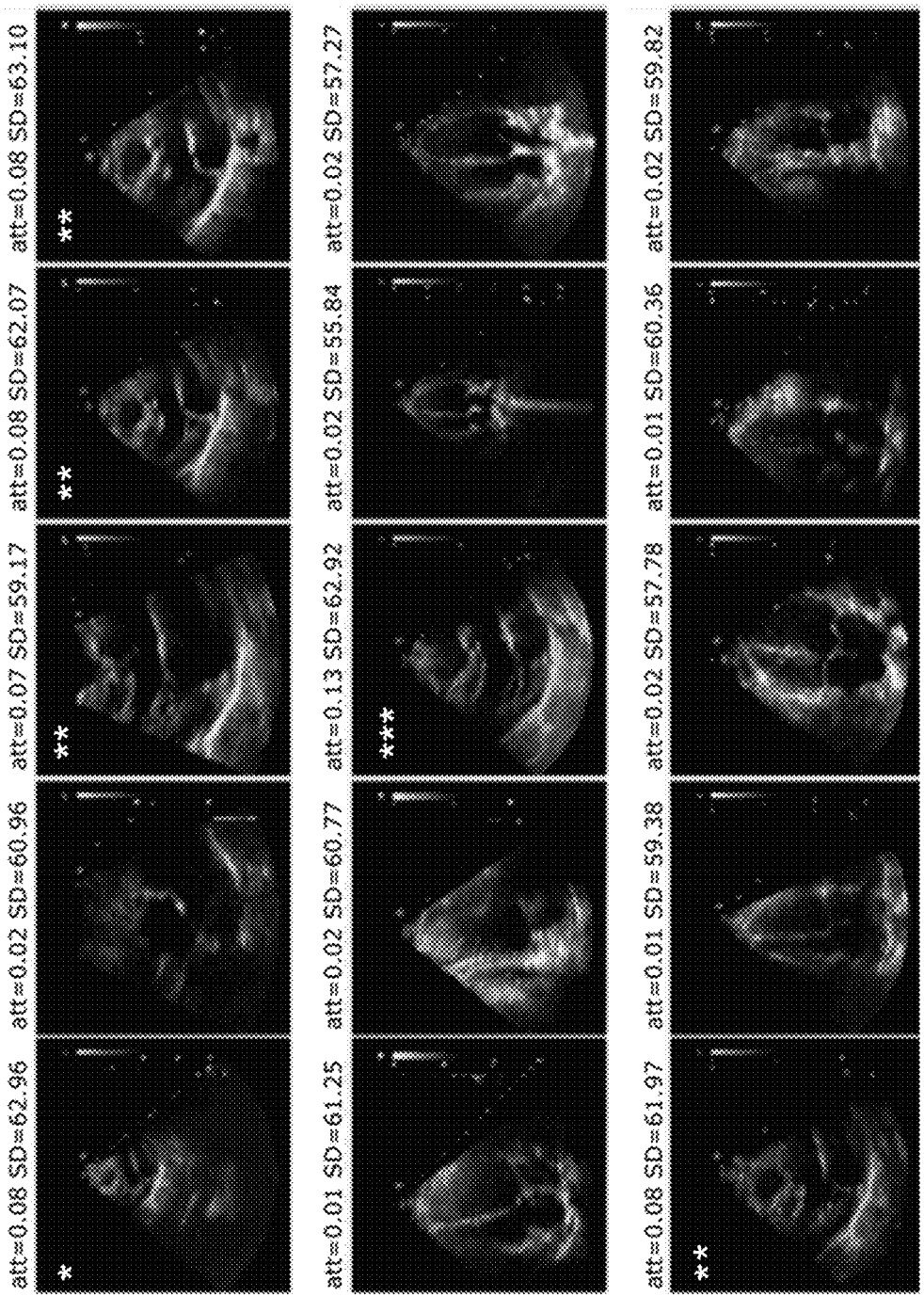
FIGS. 12A and 12B show an example of the relative weights each video input embedding contributes to overall model prediction using attention heads.
Figure 12B:
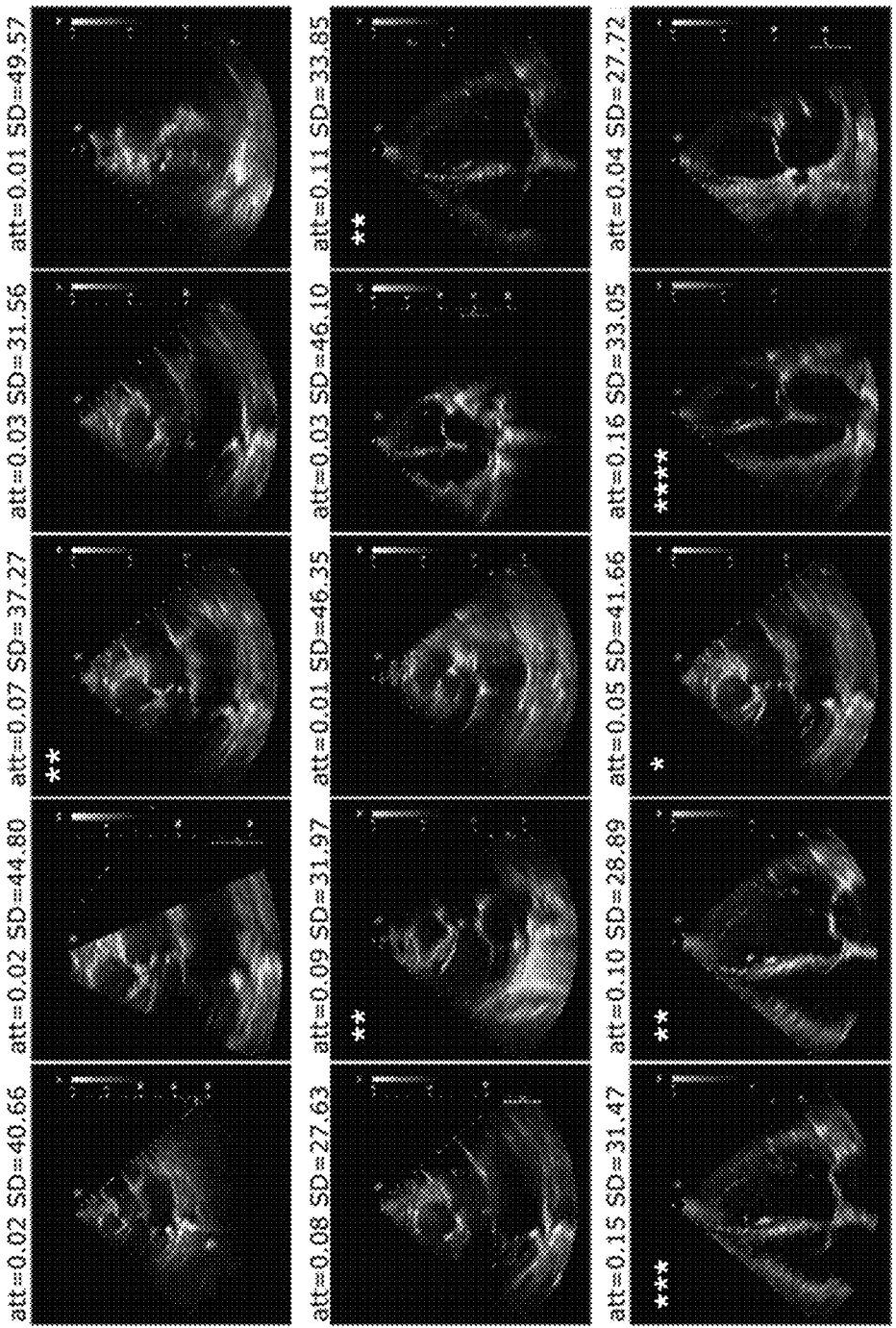

FIGS. 12A and 12B show an example 1200 of the relative weights each video input embedding contributes to overall model prediction using attention heads. Asterisks indicate the relative weight, with input movies having more asterisks contributing larger attention weights to the model while input movies having no asterisks contribute less attention weight to the model. FIG. 12A displays a model prediction of LVEF 68%, where the model reserves most attention weight to good quality parasternal long axis videos. FIG. 12B displays a model prediction of LVEF 16%, where the attention weights are more diffusely distributed across views including apical 4-chamber and apical 3-chamber views. The views also include an associated attention value (att) and standard deviation (SD).

Statistical Analysis

The performance of classification tasks (image type, quality, axis, and view) was evaluated by comparing one-vs-rest area under the receiver operator curve (AUROC) and confusion matrices.

Figure 13:
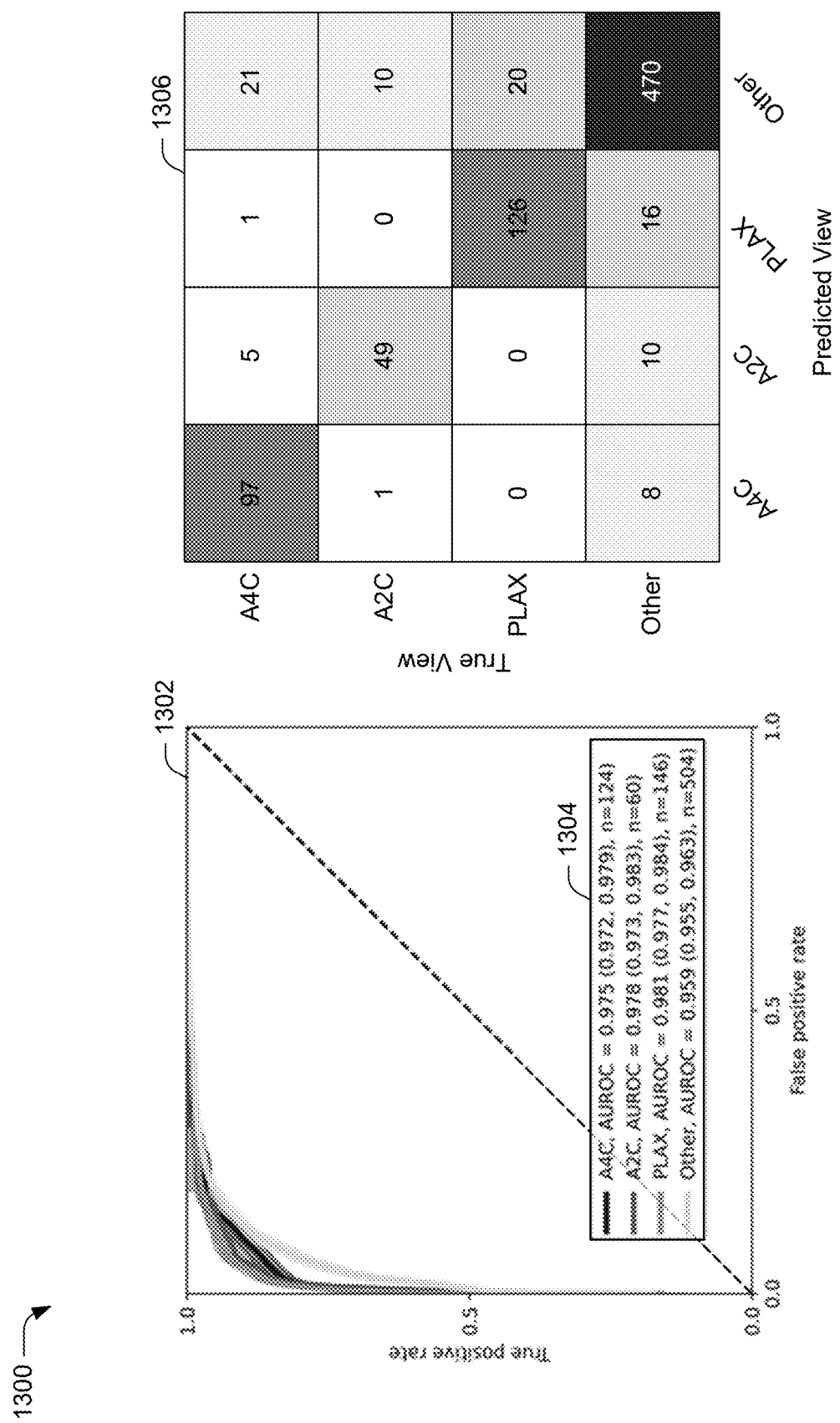
FIG. 13 shows an example analysis of classification tasks (image type, quality, axis, and view) by echocardiography deep learning models trained for left heart measurement predictions.

FIG. 13 shows an example analysis 1300 of classification tasks (image type, quality, axis, and view) by echocardiography deep learning models trained for left heart measurement predictions. The analysis 1300 includes an AUROC plot 1302 for the classification of PLAX, A4C, and A2C echocardiographic views in the EWOC internal validation set. The horizontal axis of the AUROC plot 1302 represents a false positive rate (which may provide a measure of specificity), whereas the vertical axis represents a true positive rate (which may provide a measure of sensitivity). A legend 1304 indicates a line darkness for the AUROC corresponding to the different echocardiographic views and further gives a summary value, a value range, and a sample size (n) for each curve. In general, an AUROC of 1 would represent a model that classifies the view without error, while an AUROC of 0.5 (represented by a dashed diagonal line in the AUROC plot 1302) would represent random guessing (e.g., no discriminatory ability). An AUROC of less than 0.5 thus would represent a model that performs worse than random guessing. The dashed diagonal line through the AUROC plot 1302 thus distinguishes models that perform better than random guessing (e.g., having curves above the diagonal line) from those that perform worse than random guessing (e.g., having curves below the diagonal line). In the present example, the model is able to distinguish the echocardiography views with discrimination.

The analysis 1300 further includes a confusion matrix 1306 displaying accurate and inaccurate view classifications within the EWOC internal validation set. Diagonal entries represent accurate classifications, while off-diagonal entries represent misclassifications.

Figure 14:
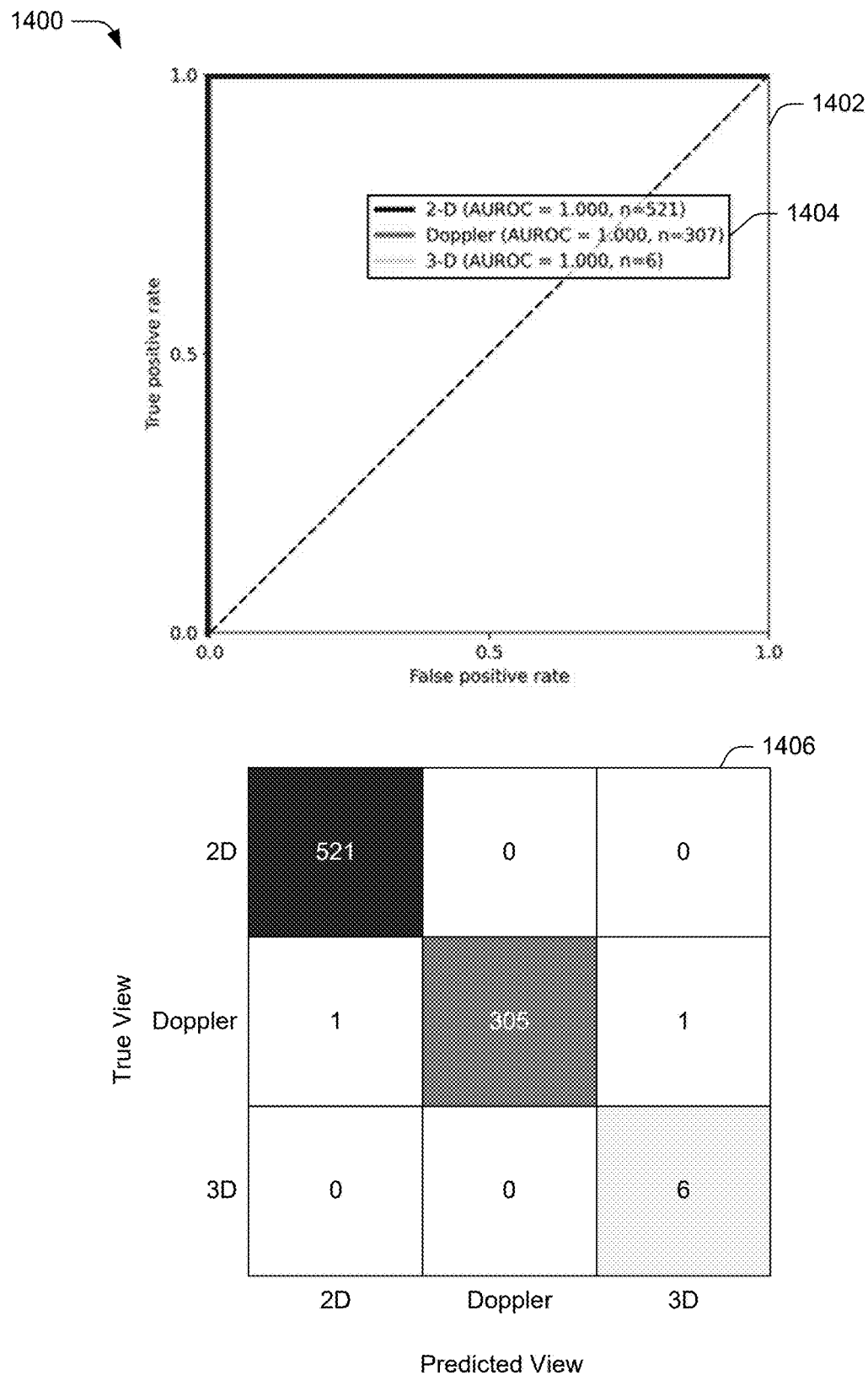
FIG. 14 shows an example analysis of echocardiographic image type by echocardiography deep learning models trained for left heart measurement predictions.

FIG. 14 shows an example analysis 1400 of echocardiographic image type by echocardiography deep learning models trained for left heart measurement predictions. The analysis 1400 includes an AUROC plot 1402 for the classification of 2D, Doppler, and 3D echocardiographic image types in the EWOC internal validation set. The horizontal axis of the AUROC plot 1402 represents a false positive rate (which may provide a measure of specificity), whereas the vertical axis represents a true positive rate (which may provide a measure of sensitivity). A legend 1404 indicates a line darkness for the AUROC corresponding to the different echocardiographic image types and further gives a sample size (n) for each curve. A dashed diagonal line represents perfect discrimination, and the C-statistic for each classification task is displayed.

In the present example, the AUROC is 1 for each curve, indicating that the model that classifies the image types substantially without error. Because the AUROC is 1 for all three image types, the curves are stacked atop one another, with the darkest curve (e.g., corresponding to 2D) visible in the AUROC plot 1402. By way of example, the curves have a true positive rate of 1 and a false positive rate of 0.

The analysis 1400 further includes a confusion matrix 1406 displaying accurate and inaccurate image type classifications within the EWOC internal validation set. Diagonal entries represent accurate classifications, while off-diagonal entries represent misclassifications.

FIG. 15 shows an example analysis 1500 of echocardiographic image quality by echocardiography deep learning models trained for left heart measurement predictions. The analysis 1500 includes an AUROC plot 1502 for the classification of good versus poor quality echocardiographic images in the EWOC internal validation set. The horizontal axis of the AUROC plot 1502 represents a false positive rate (which may provide a measure of specificity), whereas the vertical axis represents a true positive rate (which may provide a measure of sensitivity). A legend 1504 indicates a line darkness for the AUROC corresponding to the different echocardiographic image quality types (e.g., darker for good and lighter for poor) and further gives a sample size (n) for each curve. A dashed diagonal line represents perfect discrimination, and the C-statistic for each classification task is displayed.

The analysis 1500 further includes a confusion matrix 1506 displaying accurate and inaccurate image quality classifications within the EWOC internal validation set. Diagonal entries represent accurate classifications, while off-diagonal entries represent misclassifications.

FIG. 16 shows an example analysis 1600 of echocardiographic image axis classification by echocardiography deep learning models trained for left heart measurement predictions. The analysis 1600 includes an AUROC plot 1602 for the classification of good versus poor quality echocardiographic images in the EWOC internal validation set. The horizontal axis of the AUROC plot 1602 represents a false positive rate (which may provide a measure of specificity), whereas the vertical axis represents a true positive rate (which may provide a measure of sensitivity). A legend 1604 indicates a line darkness for the AUROC corresponding to the different echocardiographic image axis (e.g., darker for on-axis and lighter for off-axis) and further gives a sample size (n) for each curve. A dashed diagonal line represents perfect discrimination, and the C-statistic for each classification task is displayed.

The analysis 1600 further includes a confusion matrix 1606 displaying accurate and inaccurate image axis classifications within the EWOC internal validation set. Diagonal entries represent accurate classifications, while off-diagonal entries represent misclassifications.

Figure 17A:
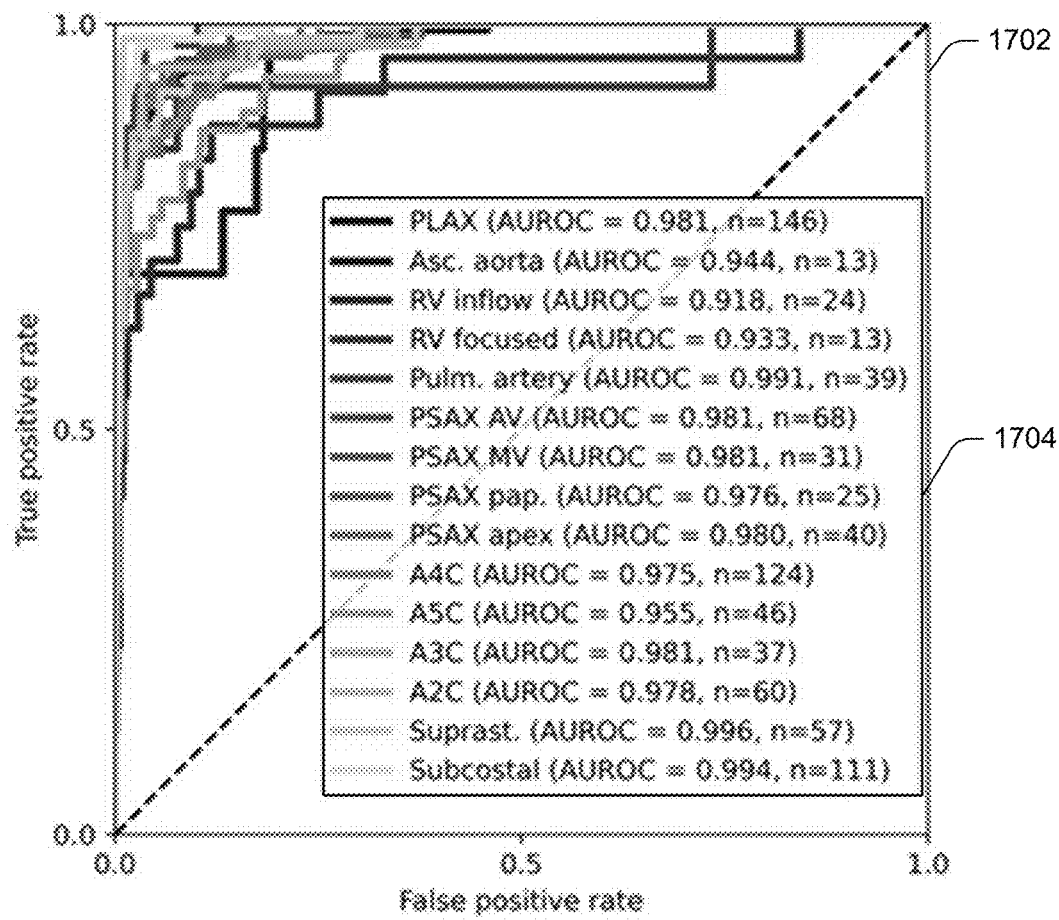

FIGS. 17A and 17B show an example analysis 1700 of echocardiographic image view by echocardiography deep learning models trained for left heart measurement predictions. The analysis 1700 includes an AUROC plot 1702 (FIG. 17A) for the classification of fifteen standard echocardiographic views in the EWOC internal validation set. The horizontal axis of the AUROC plot 1702 represents a false positive rate (which may provide a measure of specificity), whereas the vertical axis represents a true positive rate (which may provide a measure of sensitivity). A legend 1704 indicates a line darkness for the AUROC corresponding to the different echocardiographic view and further gives a sample size (n) for each curve. A dashed diagonal line represents perfect discrimination, and the C-statistic for each classification task is displayed.

The analysis 1700 further includes a confusion matrix 1706 (FIG. 17B) displaying accurate and inaccurate echocardiographic view classifications within the EWOC internal validation set. Diagonal entries represent accurate classifications, while off-diagonal entries represent misclassifications. In FIGS. 17A and 17B, A2C=apical 2-chamber, A3C=apical 3-chamber, A4C=apical 4-chamber, A5C=apical 5-chamber, AUROC=area under the receiver operator characteristic curve, Asc. Aorta=ascending aorta, PLAX=parasternal long axis, PSAX AV=parasternal short axis aortic valve level, PSAX MV=parasternal short axis mitral valve level, PSAX Pap.=parasternal short axis papillary muscle level, PSAX apex=parasternal short axis apex, Pulm. artery=pulmonary artery, RV=right ventricular, Suprast.=suprasternal notch.

Figure 18B:
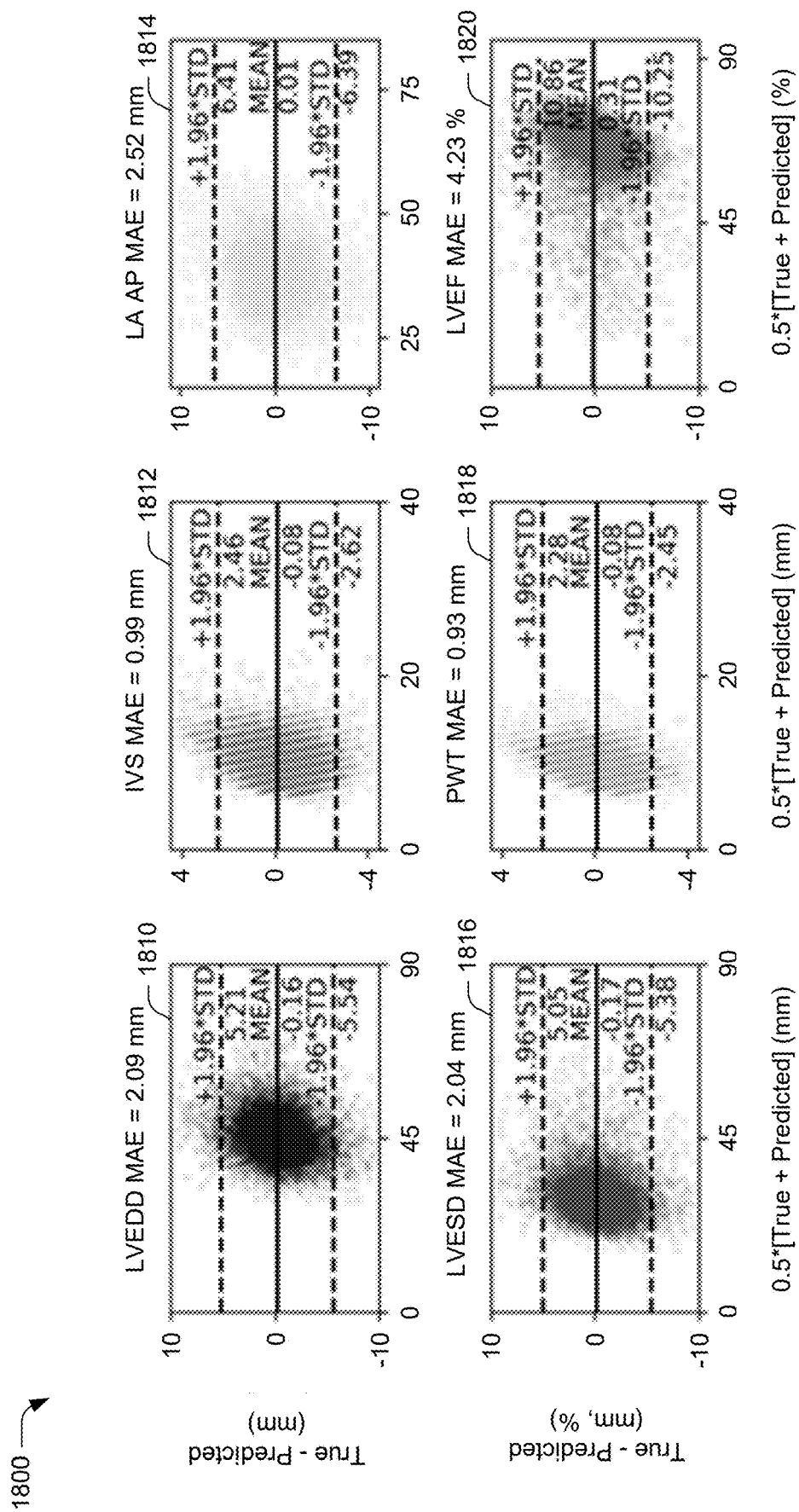
Figure 18C:
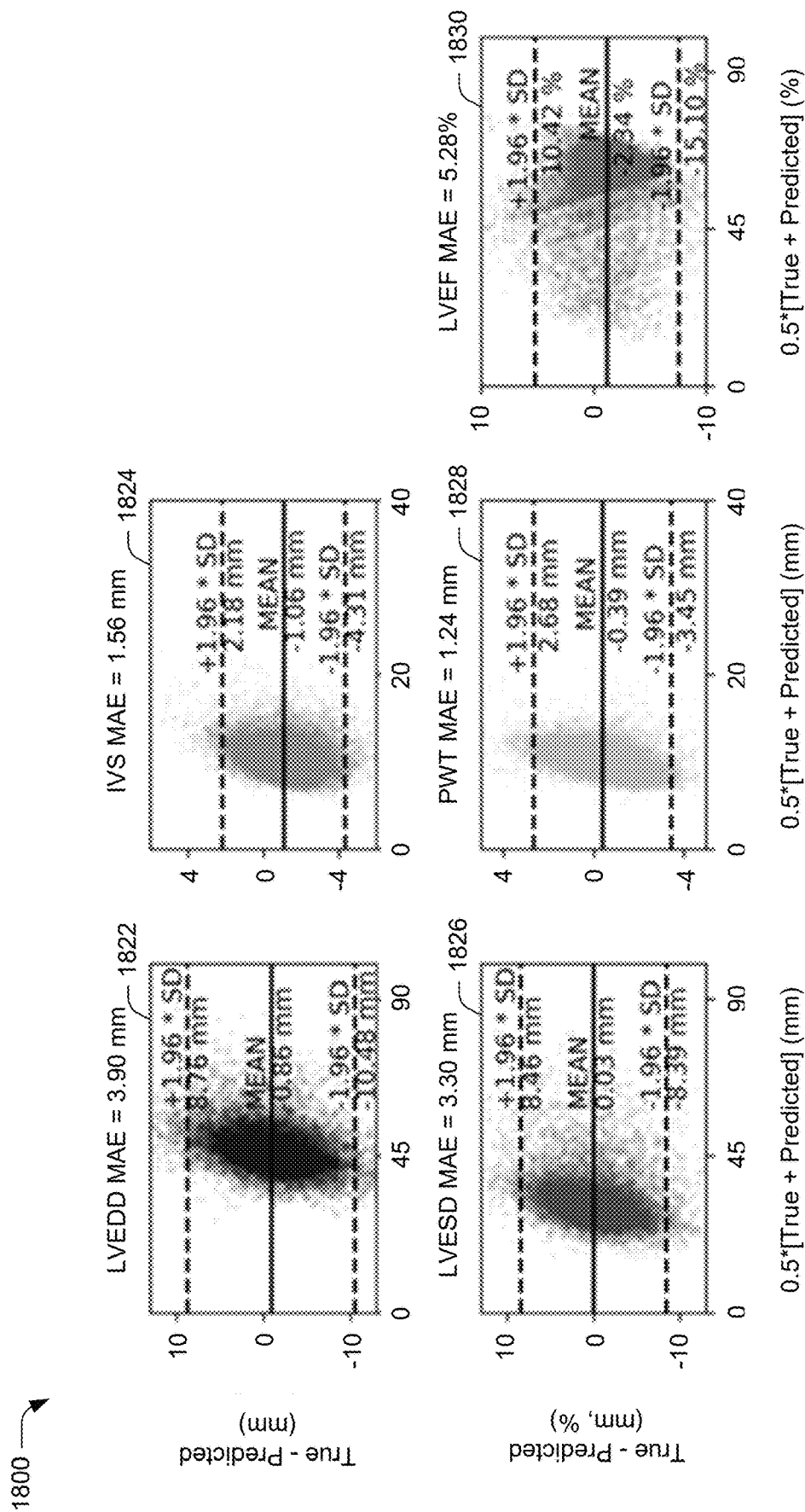

FIGS. 18A-18C show an example analysis 1800 of measurement prediction performance by echocardiography deep learning models trained for left heart measurement predictions. Referring first to FIG. 18A, the performance of the measurement prediction task by the DROID models was evaluated by calculating the mean absolute errors and $R^2$ values. A first correlation plot 1802 shows DROID-derived ("predicted measurement," vertical axis) versus gold standard EchoLab left heart measures ("true measurement," horizontal axis) for the C3PO external validation dataset, while a second correlation plot 1804 shows DROID-derived ("predicted measurement," vertical axis) versus gold standard EchoLab left heart measures ("true measurement," horizontal axis) for the EchoNet-Dynamic external validation dataset.

A first legend 1806 on the first correlation plot 1802 indicates a pixel darkness and corresponding left heart measurements for the first correlation plot 1802, as well as the $R^2$ values. The $R^2$ values denote how well the DROID-derived measurements correlate to the gold standard EchoLab left heart measures for the C3PO external validation dataset. A diagonal line indicates a perfect fit between the DROID-derived measurements and the gold standard EchoLab left heart measures. Higher $R^2$ values (e.g., closer to 1) indicate a stronger correlation between the predicted and true measurements for the C3PO external validation dataset.

A second legend 1808 on the second correlation plot 1804 indicates a pixel darkness and corresponding left heart measurements for the second correlation plot 1804, as well as the $R^2$ values. The $R^2$ values denote how well the DROID-derived measurements correlate to the gold standard EchoLab left heart measures for the EchoNet-Dynamic external validation dataset. A diagonal line indicates a perfect fit between the DROID-derived measurements and the gold standard EchoLab left heart measures. Higher $R^2$ values (e.g., closer to 1) indicate a stronger correlation between the predicted and true measurements for the EchoNet-Dynamic external validation dataset.

FIG. 18B shows Bland-Altman plots of agreement between DROID-derived versus gold standard EchoLab left heart measures for the C3PO external validation dataset, and FIG. 18C shows Bland-Altman plots of agreement between DROID-derived versus gold standard EchoLab left heart measures for the EchoNet-Dynamic external validation dataset. For each plot, the horizontal (x-axis) depicts the mean of paired values for an individual, and the vertical (y-axis) plots the difference (e.g., DROID-derived minus EchoLab). The solid horizontal line depicts the overall mean difference, and the dashed lines depict the estimated 95% limits of agreement. For instance, FIG. 18B shows an LVEDD plot 1810, an IVS plot 1812, an LA AP plot 1814, an LVESD plot 1816, a PWT plot 1818, and a LVEF plot 1820. FIG. 18C shows an LVEDD plot 1822, an IVS plot 1824, and LVESD plot 1826, a PWT plot 1828, and a LVEF plot 1830. A mean absolute error (MAE) value is also given for each plot.

As can be appreciated through the analysis 1800, DROID-LA and DROID-LV accurately predicted LA and LV linear measures (MAE for LA AP=2.52 mm, LVEDD=2.09 mm, LVESD=2.04 mm, IVS=0.99 mm, PWT=0.93 mm, $R^2$ for LVEDD=0.81, LVESD=0.83, IVS=0.71, PWT=0.59, LA AP=0.75), and LVEF (MAE=4.23% points, $R^2$=0.74) in the C3PO external validation dataset. Bland-Altman plots also demonstrated conservative estimation errors for LVEF, IVS, and PWT (95% limits of agreement for LVEF=−10.3% to 10.9%, IVS=−2.6 mm to 2.5 mm, and PWT=−2.5 mm to 2.3 mm) and no systematic bias for LV dimensions and LA AP (FIG. 18B).

Model performance was slightly lower in EchoNet-Dynamic and EchoNet-LVH (FIG. 18C) but accurately predicted LV measures (MAE for LVEDD=3.90 mm, LVESD=3.30 mm, IVS=1.56 mm, PWT=1.24 mm, LVEF=5.28%, $R^2$ for LVEDD=0.63, LVESD=0.77, IVS=0.32, PWT=0.40, LVEF=0.69, FIG. 18A). Bland-Altman plots again showed conservative estimation errors for IVS and PWT (95% limits of agreement for IVS=−4.31 mm to 2.18 mm and PWT=−3.45 mm to 2.68 mm) without systematic bias for LV dimensions and LVEF.

Figure 19A:
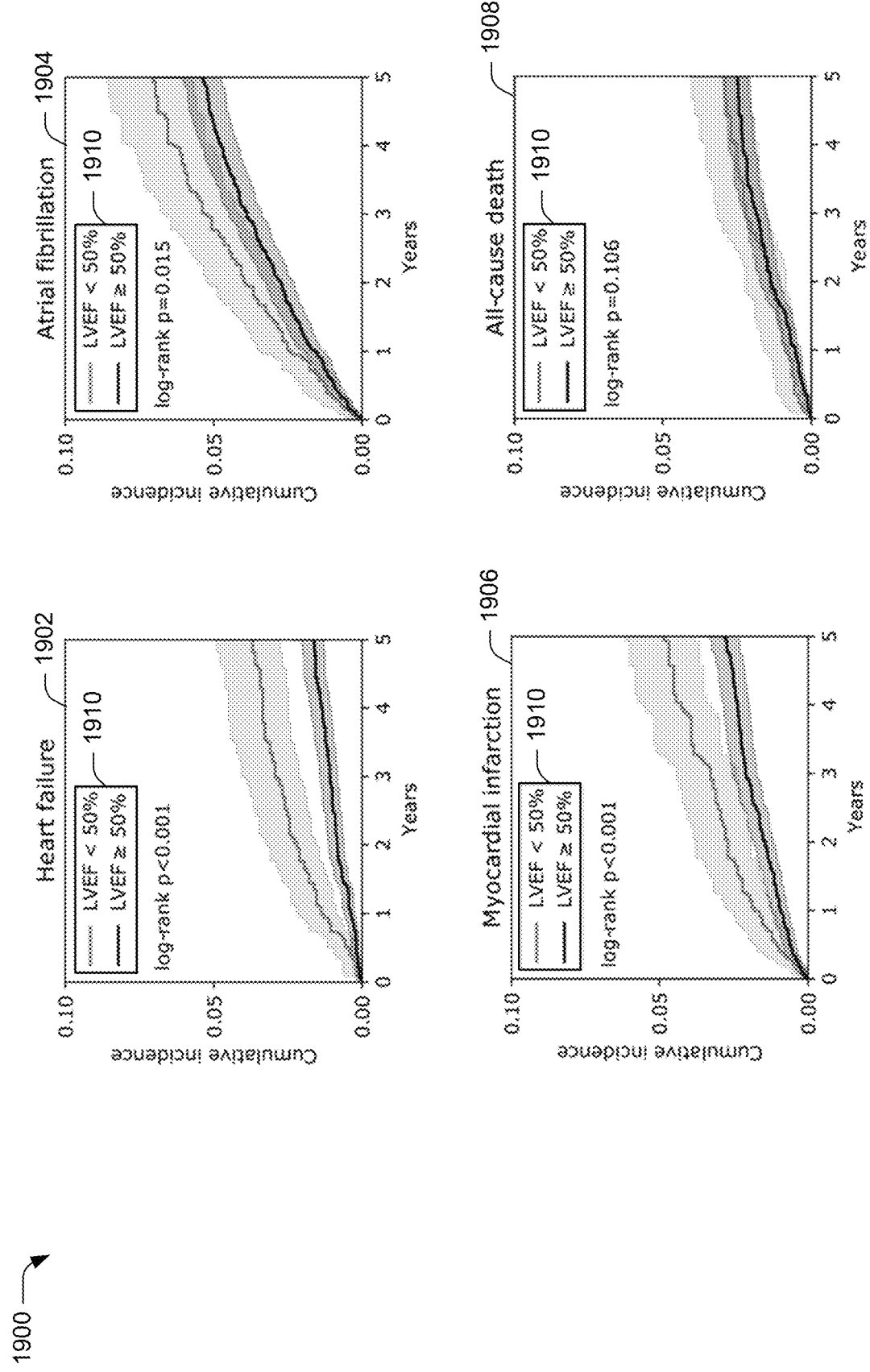
FIGS. 19A-19C show an example analysis of deep learning-derived left heart measurements with respect to clinical outcomes.
Figure 19B:
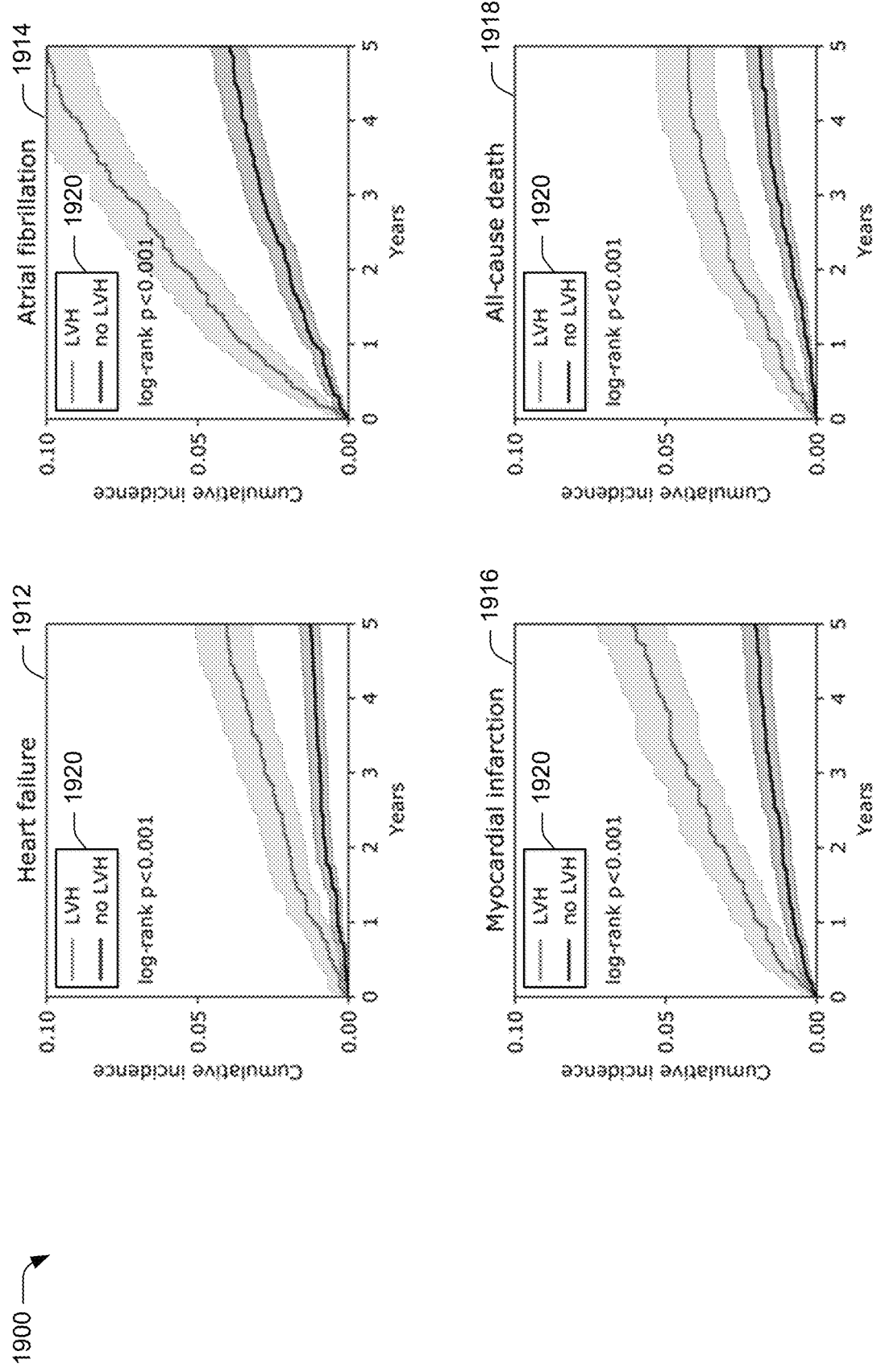
Figure 19C:
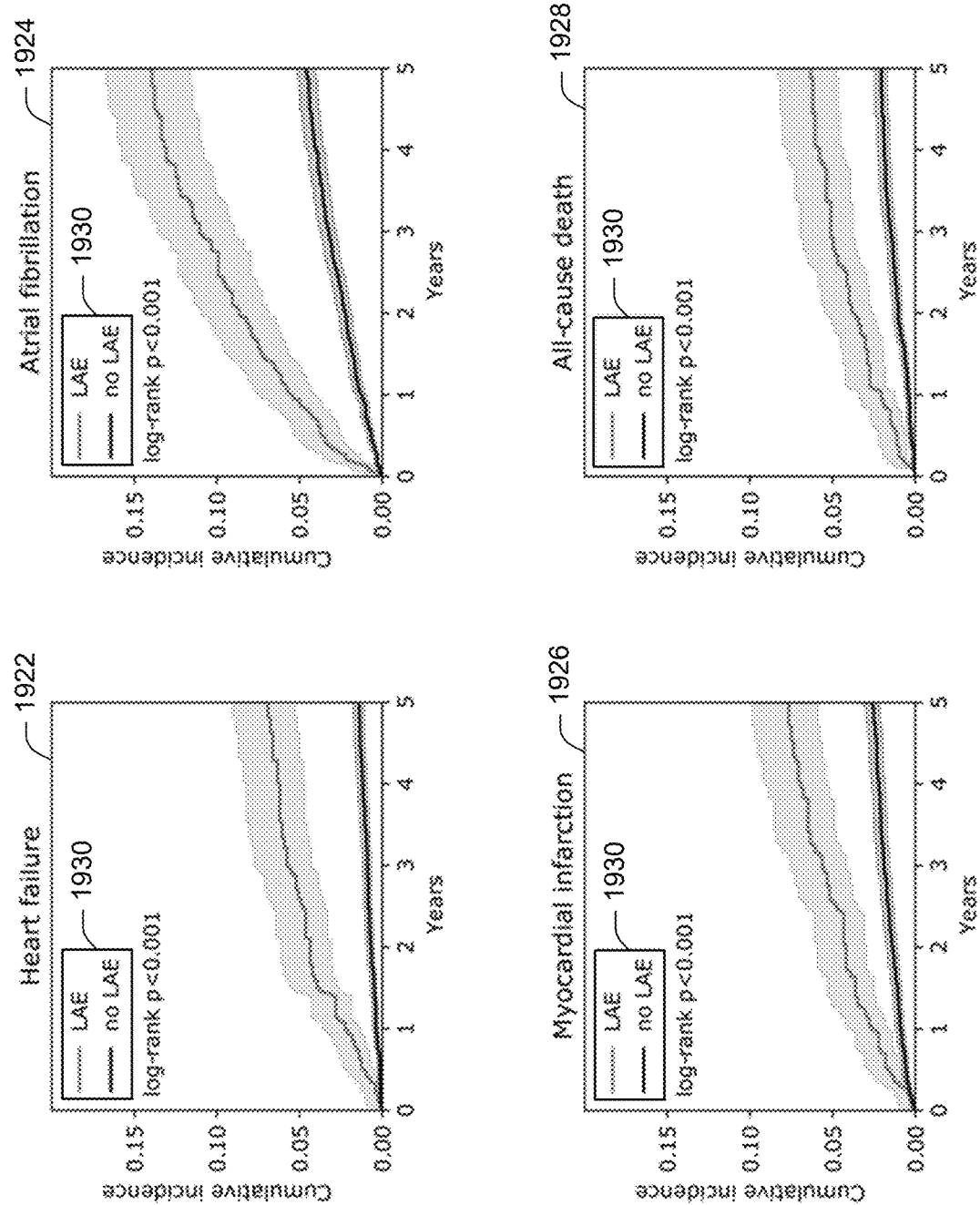

FIGS. 19A-19C show an example analysis 1900 of deep learning-derived left heart measurements with respect to clinical outcomes. In particular, FIG. 19A shows Kaplan-Meier cumulative incidence curves stratified by deep learning-derived LV ejection fraction, FIG. 19B shows Kaplan-Meier cumulative incidence curves stratified by presence versus absence of deep learning-predicted LV hypertrophy (LVH), and FIG. 19C shows Kaplan-Meier cumulative incidence curves stratified by deep learning-predicted presence or absence of LV hypertrophy.

Referring first to FIG. 19A, a first plot 1902 shows Kaplan-Meier cumulative incidence curves for heart failure, a second plot 1904 shows Kaplan-Meier cumulative incidence curves for atrial fibrillation, a third plot 1906 shows Kaplan-Meier cumulative incidence curves for myocardial infarction, and a fourth plot 1908 shows Kaplan-Meier cumulative incidence curves for all-cause death. These incidences are stratified by DROID-LVEF≥50% (darker line) versus DROID-LVEF<50% (lighter line), as indicated by a first legend 1910 on each of the first plot 1902, the second plot 1904, the third plot 1906, and the fourth plot 1908. Lower LVEF (e.g., less than 50%) correlates with higher incidences of heart failure (the first plot 1902), atrial fibrillation (the second plot 1904), and myocardial infarction (the third plot 1906).

As shown in FIG. 19B, a fifth plot 1912 shows Kaplan-Meier cumulative incidence curves for heart failure, a sixth plot 1914 shows Kaplan-Meier cumulative incidence curves for atrial fibrillation, a seventh plot 1916 shows Kaplan-Meier cumulative incidence curves for myocardial infarction, and an eighth plot 1918 shows Kaplan-Meier cumulative incidence curves for all-cause death. These incidences are stratified by no LVH (darker line) versus LVH (lighter line), as indicated by a second legend 1920 on each of the fifth plot 1912, the sixth plot 1914, the seventh plot 1916, and the eighth plot 1918. LVH is defined as PWT and/or IVS>11 mm. LVH correlates with higher incidences of heart failure (the fifth plot 1912), atrial fibrillation (the sixth plot 1914), myocardial infarction (the seventh plot 1916), and all-cause death (the eighth plot 1918).

As shown in FIG. 19C, a ninth plot 1922 shows Kaplan-Meier cumulative incidence curves for heart failure, a tenth plot 1924 shows Kaplan-Meier cumulative incidence curves for atrial fibrillation, an eleventh plot 1926 shows Kaplan-Meier cumulative incidence curves for myocardial infarction, and a twelfth plot 1928 shows Kaplan-Meier cumulative incidence curves for all-cause death. These incidences are stratified by no LAE (darker line) versus LAE (lighter line), as indicated by a third legend 1930 on each of ninth plot 1922, the tenth plot 1924, the eleventh plot 1926, and the twelfth plot 1928. LAE correlates with higher incidences of heart failure (the ninth plot 1922), atrial fibrillation (the tenth plot 1924), myocardial infarction (the eleventh plot 1926), and all-cause death (the twelfth plot 1928).

Figure 20:
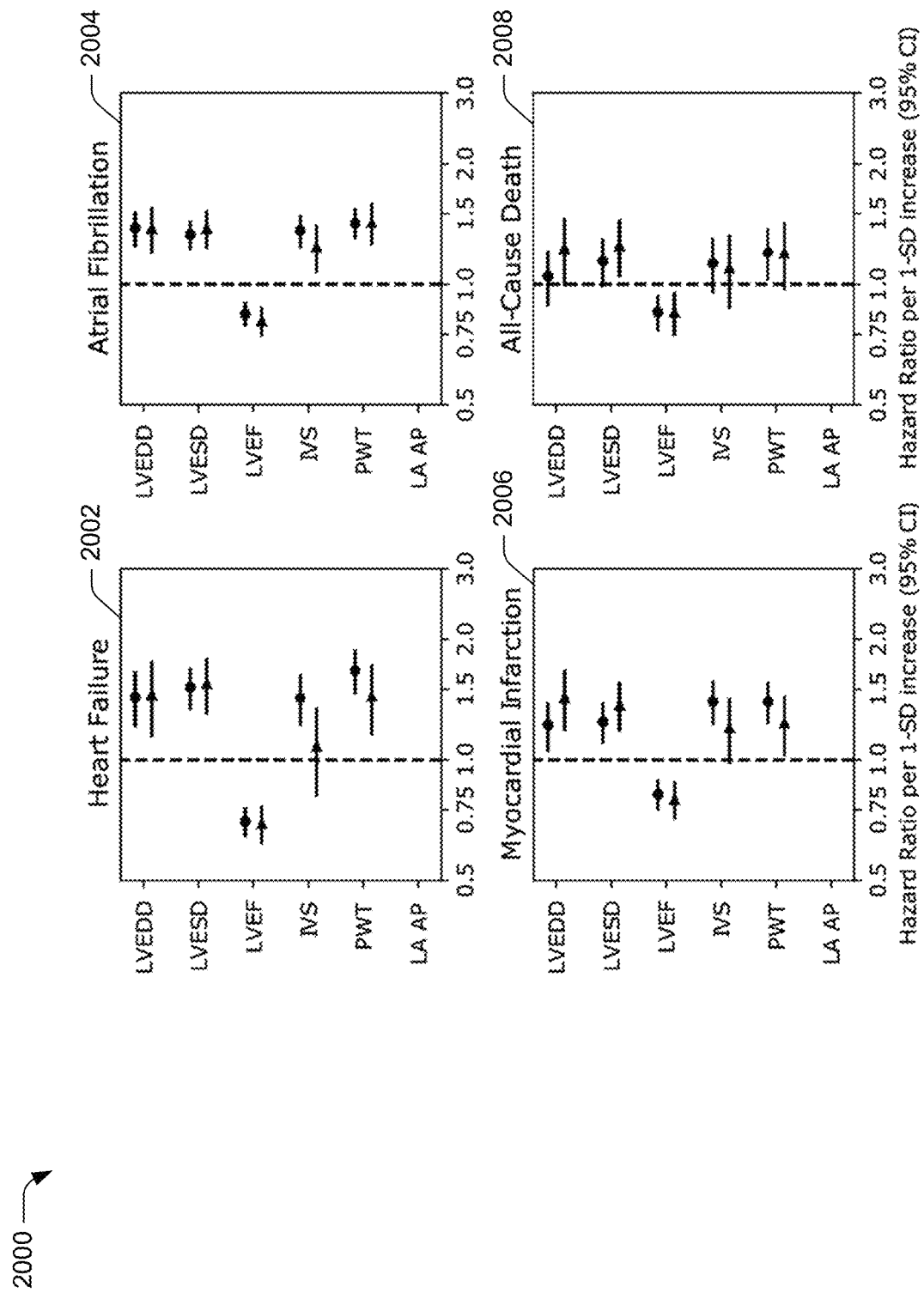
FIG. 20 shows an example analysis of the association of deep learning-derived measurements with incident outcomes using Cox proportional hazards models.

FIG. 20 shows an example analysis 2000 of the association of deep learning-derived measurements with incident outcomes using Cox proportional hazards models. The Cox proportional hazards models were adjusted for age and sex, and then further adjusted for body mass index (BMI), diabetes mellitus (DM), systolic blood pressure (SBP), and hypertension (HTN) treatment. The analysis 2000 includes a plurality of Forest Plots depicting the age- and sex-adjusted (circles) and multivariable-adjusted (triangles) associations of DROID-derived left heart measures with incident heart failure (HF) (a first plot 2002), atrial fibrillation (AF) (a second plot 2004), myocardial infarction (MI) (a third plot 2006), and all-cause death (a fourth plot 2008). Follow-up began at time of echocardiogram capture. The vertical axis of each plot shows the deep learning-derived measurement type, and the horizontal axis shows the hazard ratio per 1-SD increase in the continuous echocardiographic measure (95% confidence interval, CI).

For incident HF, AF, and MI analyses, participants were censored either at date of death or date of last clinical encounter. For mortality analyses, participants were censored at time of death or at time of last clinical encounter (for individuals who survived). Inspection of Schoenfeld residuals did not suggest substantive deviations from proportional hazards in the Cox regressions. Separate models were performed for each outcome of interest. Model discrimination was also evaluated by calculating c-indices. All tests performed were 2-sided, and p-values of <0.05 were considered significant. All analyses were performed using python (version 3.6.9) with packages pandas (version 1.1.5), lifelines (version 0.26.4), and scikit-learn (version 0.24.2).

Saliency Mapping

Figure 21A:
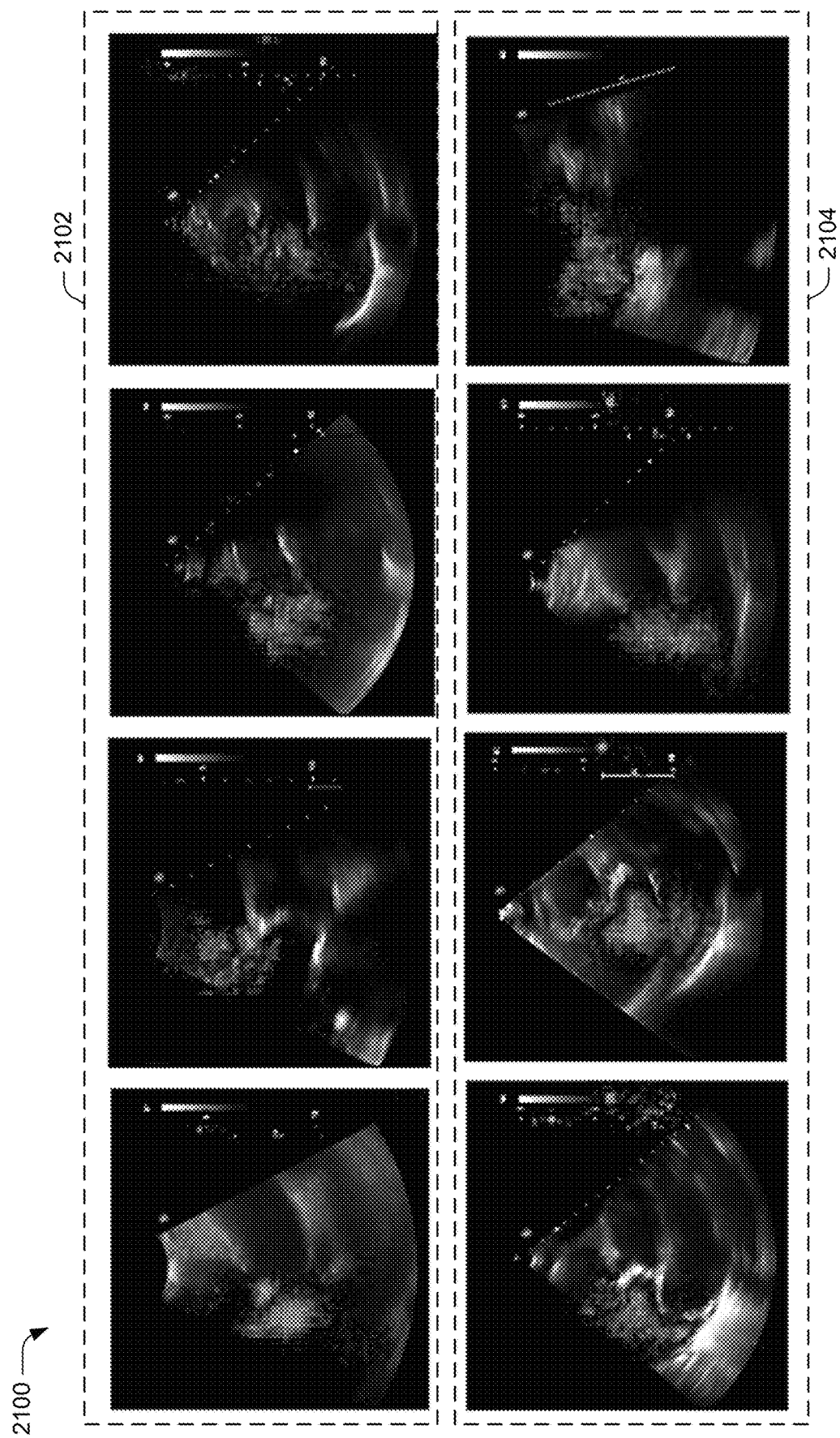
FIGS. 21A-21C depict saliency maps illustrating areas of the echocardiogram with the greatest influence on deep learning model predictions for left heart structure and function
Figure 21B:
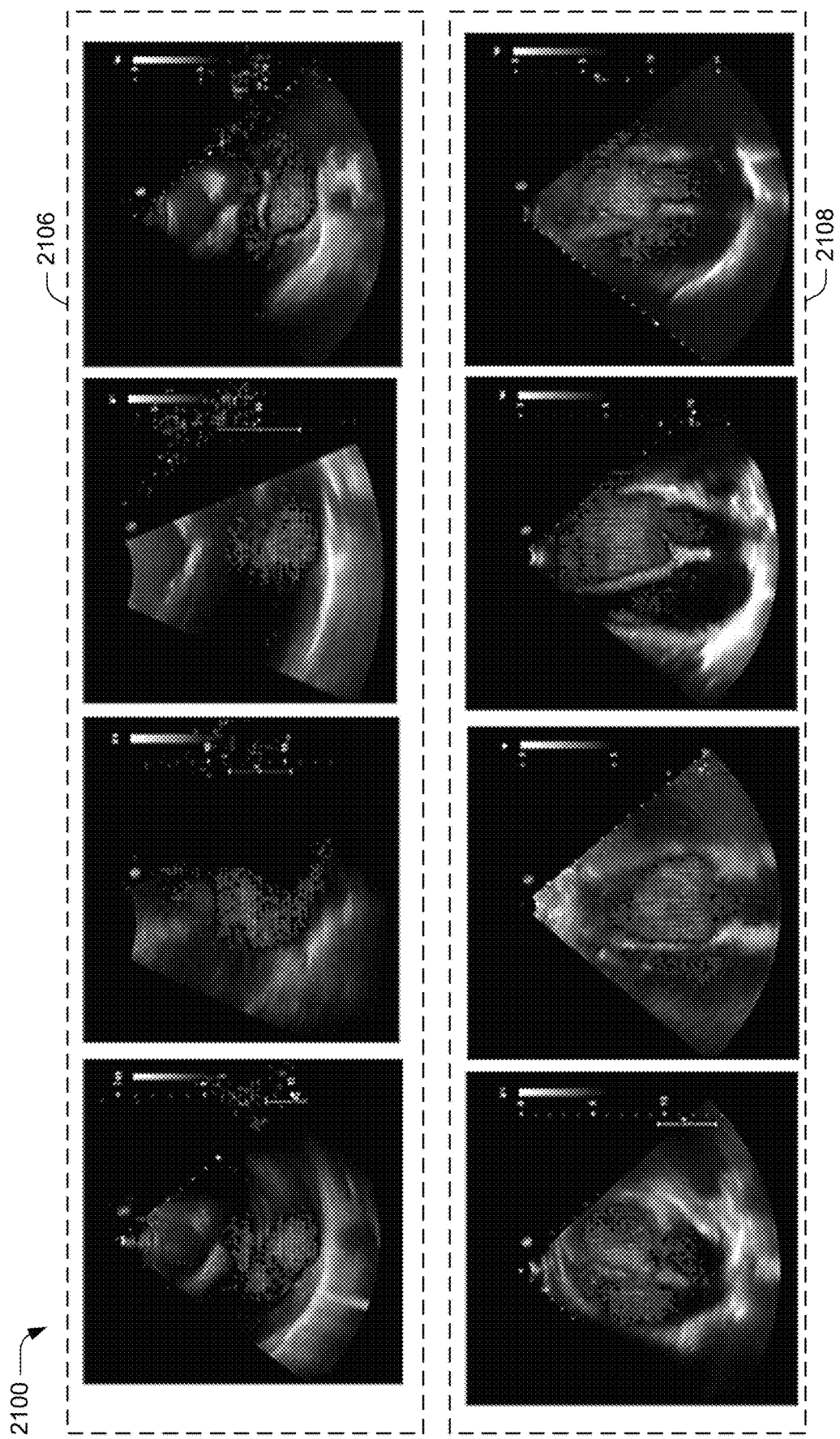
Figure 21C:
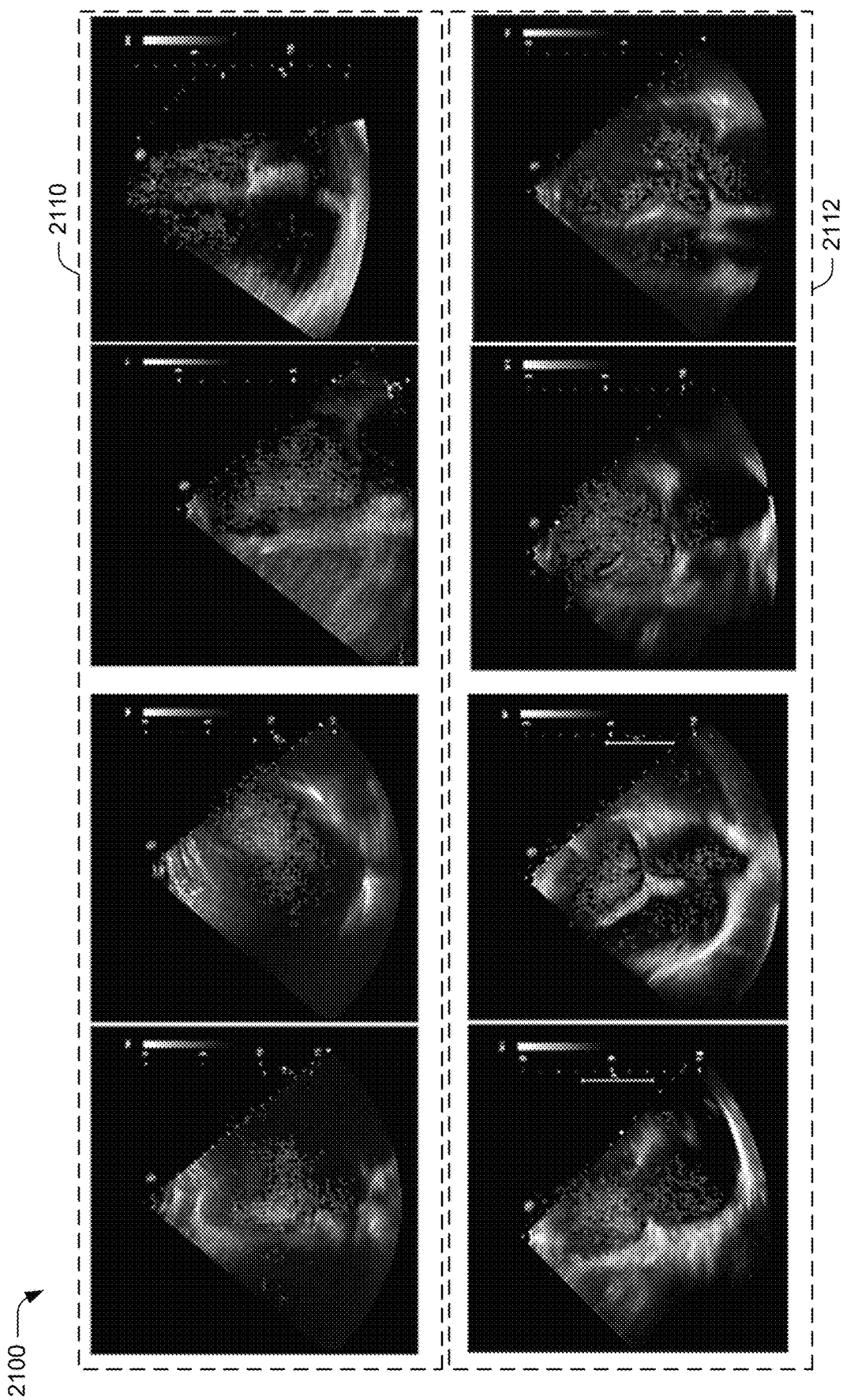

FIGS. 21A-21C depict saliency maps 2100 illustrating areas of the echocardiogram with the greatest influence on deep learning model predictions for left heart structure and function. The saliency maps 2100 highlight the cardiac structures of the echocardiogram that most strongly influenced DROID predictions of left heart structure and function. Saliency is defined as the model output gradient with respect to an input echocardiogram video. Saliency gradients were computed via custom routines using TensorFlow's automatic differentiation utilities. To summarize the saliency patterns as a single snapshot per video, the most salient pixels (e.g., in the upper quintile of average saliency) are overlaid on top of the first frame of the video as coarser pixels in comparison to the echocardiogram video data.

In particular, the saliency maps 2100 depict areas of the echocardiogram which had the greatest influence on DROID-LA and DROID-LV predictions. Each group, as further defined below, includes saliency maps for four unique echocardiograms. Lighter shades depict areas of the echocardiogram that most strongly influence DROID predictions. FIG. 21A displays a first group 2102 of the saliency maps 2100 for DROID-LV prediction of interventricular septal wall and posterior wall thickness from parasternal long axis views and a second group 2104 for DROID-LV prediction of left ventricular end-diastolic and end-systolic dimensions from parasternal long axis views. FIG. 21B displays a third group 2106 of the saliency maps 2100 for DROID-LA predictions of left atrial anteroposterior dimension from parasternal long axis views and a fourth group 2108 for DROID-LV predictions of left ventricular ejection fraction from apical 4-chamber views. FIG. 21C displays the saliency maps 2100 for DROID-LV predictions of left ventricular fraction from stitched together apical 2-chamber (a fifth group 2110) and apical 4-chamber views (a sixth group 2112).

Application of EchoNet-Dynamic to C3PO External Validation Set

The EchoNet-Dynamic model operates on AVI movies of A4C views of 112×112 size normalized within 0-1 range. Applicants modified the dataloader to select only A4C views and scaled down the videos by 50% at runtime. As EchoNet-Dynamic can integrate a variable number of frames, Applicants provided 16 frames sampled with a take 1/skip 3 approach that was employed in the DROID-LV inputs. EchoNet-Dynamic predictions were collected for all A4C videos available from the C3PO external validation cohort. The final EchoNet-Dynamic model-derived study-based prediction was ascertained by taking the median prediction across all A4C views obtained for a given study.

Results

DROID was trained, developed, and validated on 54,780 echocardiograms from 17,887 patients and externally validated on 9,248 patients and echocardiograms from the C3PO External Validation Set and 10,030 patients and echocardiograms from the EchoNet-Dynamic sample (e.g., see FIG. 10).

The deep learning models accurately distinguished between 2-dimensional B mode versus Doppler versus 3-dimensional echocardiographic images (AUROC 2-dimensional: 1.0, Doppler: 1.0, three-dimensional 1.0, FIG. 14). Deep learning also demonstrated good discrimination of good versus poor-quality studies (AUROC 0.889, FIG. 15) and classified on-axis versus off-axis images (AUROC 0.842, 0.834, FIG. 16). Finally, the deep learning model accurately discriminated each of the standard echocardiographic views (PLAX: AUROC 0.98, accuracy 0.96, A4C: AUROC 0.98, accuracy 0.96, A2C: AUROC 0.98, accuracy 0.97, Other: AUROC 0.96, accuracy 0.90, FIG. 13 and FIGS. 17A and 17B). Among a total of 4,734,140 videos, videos that were classified as Doppler (1,675,419 videos, 35.4%), 3-dimensional (18,194 videos, 0.4%), poor quality (218,565 videos, 4.6%), and off-axis (111,276 videos, 2.4%) were not used for training.

Predicting Standard Measures of LV Structure and Function

Figure 22A:
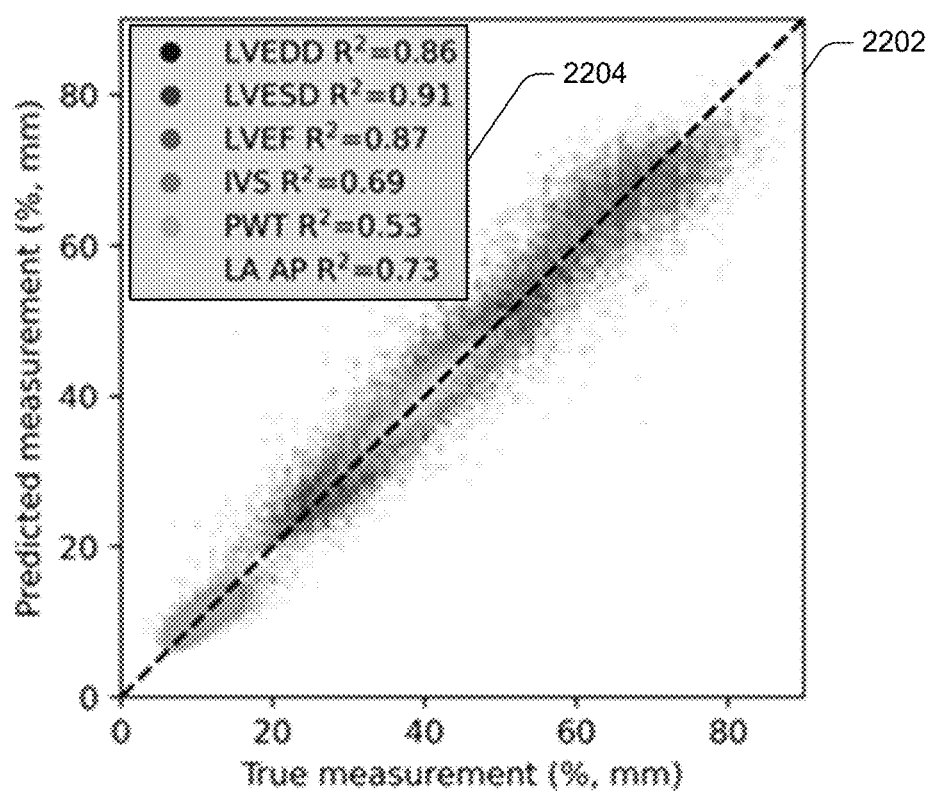
FIGS. 22A and 22B show an example analysis of measurement prediction performance by echocardiography deep learning models for left heart measurement predictions in the internal validation dataset.
Figure 22B:
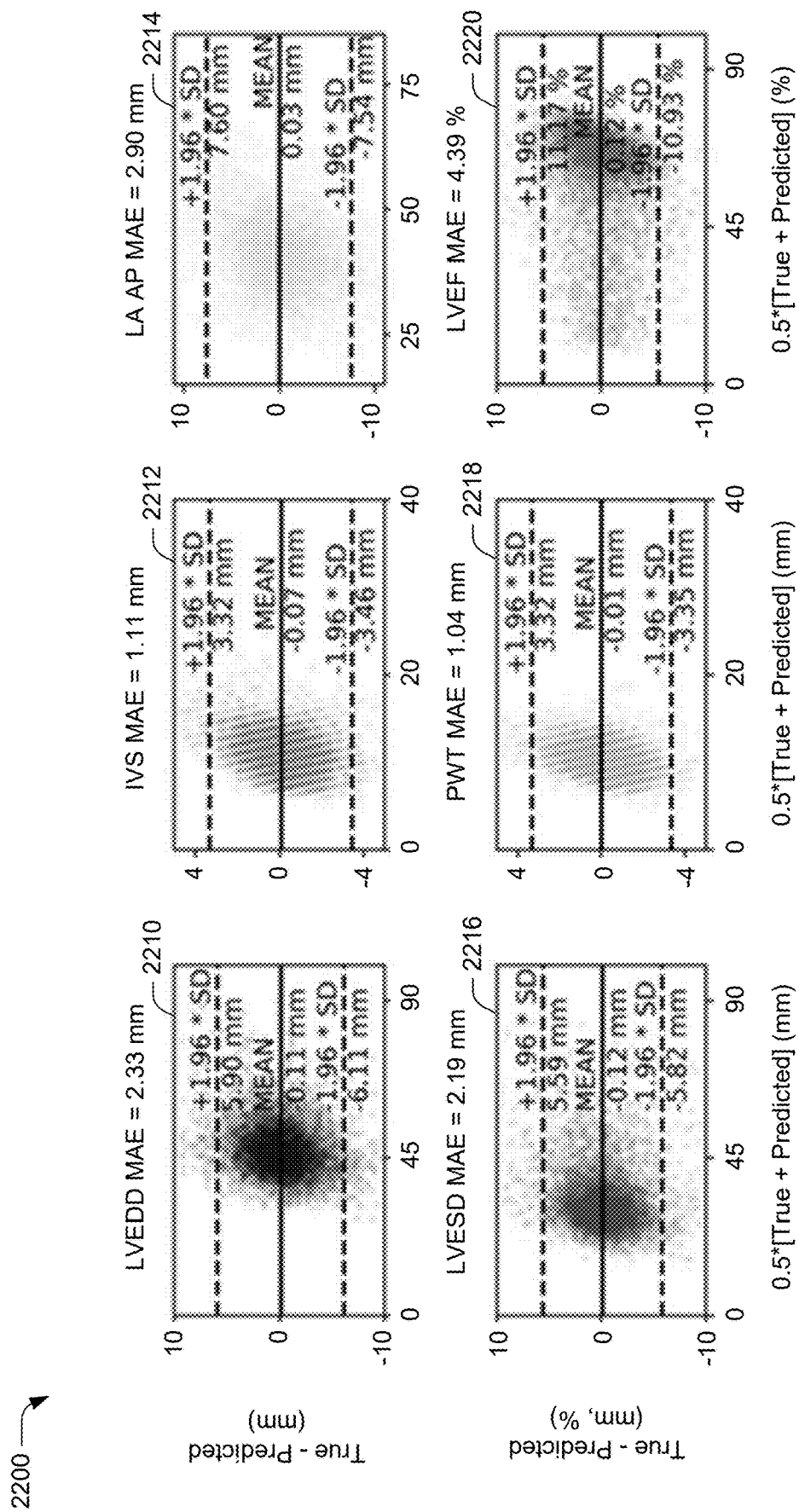

FIGS. 22A and 22B show an example analysis 2200 of measurement prediction performance by echocardiography deep learning models for left heart measurement predictions in the internal validation dataset. Referring first to FIG. 22A, the performance of the measurement prediction task by the DROID models was evaluated by calculating the mean absolute errors and $R^2$ values. A correlation plot 2202 shows DROID-derived ("predicted measurement," vertical axis) versus gold standard EchoLab left heart measures ("true measurement," horizontal axis) for the EWOC internal validation dataset (e.g., the internal validation sample 152 introduced with respect to FIG. 1). A legend 2204 indicates a pixel darkness and corresponding left heart measurements for the correlation plot 2202, as well as the $R^2$ values. The $R^2$ values denote how well the DROID-derived measurements correlate to the gold standard EchoLab left heart measures for the EWOC internal validation dataset. A diagonal line indicates a perfect correlation between the DROID-derived measurements and the gold standard EchoLab left heart measures. Higher $R^2$ values (e.g., closer to 1) indicate a stronger correlation between the predicted and true measurements for the EWOC internal validation dataset.

FIG. 22B shows Bland-Altman plots of agreement between DROID-derived versus gold standard EchoLab left heart measures for the EWOC internal validation dataset. For each plot, the horizontal (x-axis) depicts the mean of paired values for an individual, and the vertical (y-axis) plots the difference (e.g., DROID-derived minus EchoLab). Positive y-axis values demonstrate underestimations by the model, and negative y-axis values demonstrate overestimations by the model. The solid horizontal line depicts the overall mean difference, and the hashed lines depicts the estimated 95% limits of agreement. An accurate model has y-axis values close to zero. An unbiased model displays no systematic pattern along the x-axis (e.g. random scatter).

FIG. 22B shows an LVEDD plot 2210, an IVS plot 2212, an LA AP plot 2214, an LVESD plot 2216, a PWT plot 2218, and a LVEF plot 2220. A mean absolute error (MAE) value is also given for each plot. In the internal validation set, DROID-LA accurately predicted LA AP (mean absolute error [MAE]=2.90 mm, $R^2$=0.73). DROID-LV also accurately predicted LV dimensions (MAE for LVEDD=2.33 mm, LVESD=2.19 mm; $R^2$ for LVEDD=0.86, LVESD=0.91), LV wall thickness, (MAE for IVS=1.11 mm, PWT=1.04 mm; $R^2$ for IVS=0.69, PWT=0.53), and LVEF (MAE=4.39% points, $R^2$=0.87). Bland-Altman plots demonstrated conservative estimation errors for LVEF, IVS, and PWT (95% limits of agreement −10.9% to 11.2% for LVEF, −3.5 mm to 3.3 mm for IVS, and −3.4 mm to 3.3 mm for PWT). Bland-Altman plots did not suggest systematic bias for LV dimensions and LA AP.

DROID-LV accurately predicted preserved versus reduced LVEF (AUROC=0.99, FIG. 19A) and LVH (AUROC=0.90, FIG. 19B). DROID-LA accurately predicted LAE (AUROC=0.93, FIG. 19C).

Model Performance in Internal and External Validation Sets

Figure 23B:
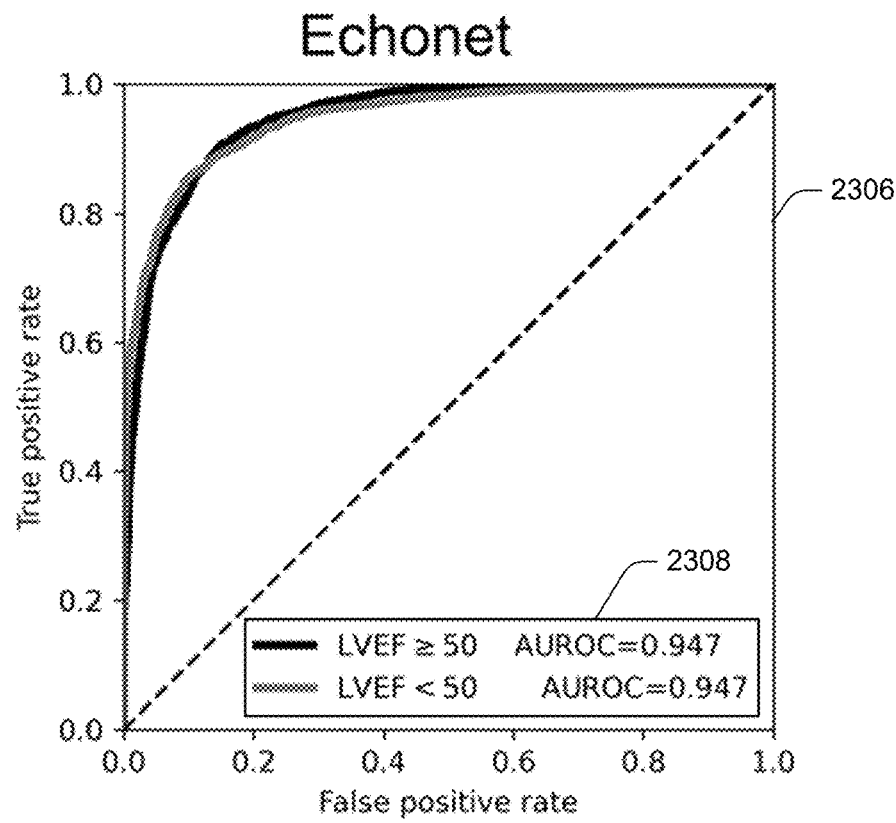

FIGS. 23A and 23B show an example analysis 2300 of preserved versus reduced LVEF categories in the internal and external validation sets. The analysis 2300 includes a first plot 2302 (FIG. 23A) showing receiver operator characteristic (ROC) curves for the accurate and inaccurate classification of LVEF for the EWOC internal validation dataset (e.g., the internal validation sample 152), a second plot 2304 (FIG. 23A) showing ROC curves for the accurate and inaccurate classification of LVEF for the C3PO external validation dataset (e.g., part of the external validation subset 146), and a third plot 2306 (FIG. 23B) showing ROC curves for the accurate and inaccurate classification of LVEF for the EchoNet external validation dataset (e.g., part of the external validation subset 146). The dotted diagonal line in the ROC curves represent perfect discrimination and the C-statistic for each classification task is displayed. A legend 2308 on each plot stratifies DROID-LVEF≥50% (darker line) versus DROID-LVEF<50% (lighter line). In external validation, DROID-LV predicted preserved versus reduced LVEF for the C3PO external validation dataset (AUROC=0.99).

FIG. 24 shows an example analysis 2400 of classifying left ventricular hypertrophy in the internal and external validation sets. The analysis 2400 includes a first plot 2402 showing a receiver operator characteristic (ROC) curve for the accurate and inaccurate classification of left ventricular hypertrophy for the EWOC internal validation dataset (e.g., the internal validation sample 152) and a second plot 2404 showing a ROC curve for the accurate and inaccurate classification of left ventricular hypertrophy for the C3PO external validation dataset (e.g., part of the external validation subset 146). The dotted diagonal line in each plot represents perfect discrimination, and the C-statistic for each classification task is displayed. A legend 2406 on each plot indicates the associated AUROC. In external validation, DROID-LV accurately predicted the presence of LVH (AUROC=0.92).

FIG. 25 shows an example analysis 2500 of classifying left atrial enlargement in the internal and external validation sets. The analysis 2500 includes a first plot 2502 showing a receiver operator characteristic (ROC) curve for the accurate and inaccurate classification of left atrial enlargement (LAE) for the EWOC internal validation dataset (e.g., the internal validation sample 152) and a second plot 2504 showing a ROC curve for the accurate and inaccurate classification of LAE for the C3PO external validation dataset (e.g., part of the external validation subset 146). The dotted diagonal line in each plot represents perfect discrimination, and the C-statistic for each classification task is displayed. A legend 2506 on each plot indicates the associated AUROC. In external validation, DROID-LA accurately predicted LAE (AUROC=0.93).

Deep Learning-Derived Left Heart Measures Associate with Incident Cardiovascular Outcomes For disease association analyses, a total of 5,970 individuals were included in C3PO (mean age 51±18, 57% women). Mean DROID-derived LA AP was 36±6 mm, LVEF was 67±8%, LVEDD 45±6 mm, LVESD 29±5 mm, IVS 10±2 mm, and PWT 9±2 mm. During a median follow-up time of 5 years, 438 participants developed AF, 168 developed HF, 243 developed MI, and 198 died.

Deep learning derived measures were consistently associated with incident outcomes. Compared with patients with DROID-LVEF≥50%, individuals with DROID-LVEF<50% were at greater risk of new-onset HF, AF, MI, and all-cause death (FIG. 19A). A one-standard deviation (SD) lower DROID-derived LVEF was associated with a 42% greater risk of HF (age- and sex-adjusted HR 1.42, 95% CI 1.32-1.56, p-value <0.001), 19% greater risk of AF (HR 1.19, 95% CI 1.10-1.27, p-value <0.001), 22% greater risk of MI (HR 1.22, 95% CI 1.11-1.33, p-value <0.001) and 18% greater risk of death (HR 1.18, 95% CI 1.05-1.30, p-value=0.003). DROID-LA AP, LVEDD, LVESD, IVS, and PWT also predicted incident CV outcomes (see FIG. 20, Table 4). DROID-predicted LVH was associated with 59% greater risk of AF (HR 1.59, 95% CI 1.28-1.96), 99% greater risk of HF (HR 1.99, 95% CI 1.41-2.82), and 55% greater risk of MI (HR 1.55, 95% CI 1.17-2.06). DROID-predicted LAE was associated with greater risk of incident outcomes (AF: HR 2.29, 95% CI 1.84-2.85, HF: HR 3.57, 95% CI 2.56-4.99, MI: HR 1.85, 95% CI 1.38-2.49, and death: HR 2.22, 95% CI 1.61-3.08, see FIG. 19C). Findings persisted after further adjustment of key clinical covariates (see FIG. 20, Table 5).

TABLE 4

| | N events/ N total | Hazard Ratio (95% CI) | | | | | |
|---|---|---|---|---|---|---|---|
| | | LVEF* | LVEDD** | LVESD** | IVS** | PWT** | LA AP** |
| Heart failure | 168/5,970 | 1.42 (1.32, 1.56) | 1.44 (1.22, 1.69) | 1.51 (1.34, 1.71) | 1.43 (1.23, 1.63) | 1.67 (1.47, 1.91) | 1.91 (1.61, 2.27) |
| Atrial fibrillation | 438/5,970 | 1.19 (1.10, 1.27) | 1.38 (1.24, 1.53) | 1.33 (1.22, 1.45) | 1.36 (1.24, 1.50) | 1.42 (1.30, 1.55) | 1.77 (1.59, 1.97) |
| Myocardial infarction | 243/5,970 | 1.22 (1.11, 1.33) | 1.22 (1.06, 1.40) | 1.24 (1.10, 1.40) | 1.40 (1.23, 1.59) | 1.40 (1.24, 1.58) | 1.45 (1.26, 1.67) |
| All-cause mortality | 198/5,970 | 1.18 (1.05, 1.30) | 1.05 (0.89, 1.23) | 1.14 (0.99, 1.31) | 1.13 (0.96, 1.32) | 1.20 (1.03, 1.40) | 1.33 (1.14, 1.55) |

TABLE 5

|  | N events/ N total | Hazard Ratio (95% CI) | | | | | |
| --- | --- | --- | --- | --- | --- | --- | --- |
|  |  | LVEF* | LVEDD** | LVESD** | IVS** | PWT** | LA AP** |
| Heart failure | 102/4,020 | 1.44 (1.29, 1.61) | 1.45 (1.17, 1.80) | 1.55 (1.32, 1.82) | 1.08 (0.84, 1.39) | 1.44 (1.18, 1.77) | 1.76 (1.38, 2.25) |
| Atrial fibrillation | 278/4,020 | 1.24 (1.14, 1.35) | 1.38 (1.21, 1.57) | 1.38 (1.23, 1.54) | 1.24 (1.08, 1.42) | 1.43 (1.26, 1.61) | 1.66 (1.37, 2.00) |
| Myocardial infarction | 151/4,020 | 1.26 (1.13, 1.40) | 1.43 (1.20, 1.70) | 1.37 (1.19, 1.58) | 1.20 (0.99, 1.45) | 1.23 (1.04, 1.47) | 1.44 (1.18, 1.75) |
| All-cause mortality | 136/4,020 | 1.18 (1.04, 1.33) | 1.23 (1.01, 1.49) | 1.25 (1.06, 1.47) | 1.09 (0.89, 1.35) | 1.20 (0.98, 1.46) | 1.53 (1.24, 1.89) |

Association of Echocardiographic Measures with Cardiovascular Outcomes is Greater for Deep Learning-Derived Versus Study Report Measures The associations of LA and LV linear measures with incident cardiovascular outcomes were greater in magnitude for deep learning-derived echocardiographic measures compared with gold standard EchoLab study report values, with c-indices that were comparable or higher (Table 6 and Table 7). A 1-SD increase in DROID-derived LVEDD was associated with a 44% greater risk of incident HF (DROID-LVEDD: HR 1.44, 95% CI 1.22-1.69) compared with 39% greater risk of HF for a 1-SD increase in human annotated LVEDD (EchoLab-LVEDD: HR 1.39, 95% CI 1.19-1.64). The associations of DROID-LVEF and EchoLab-LVEF with incident outcomes were similar.

TABLE 6

| Left heart measures | Hazard Ratio (95% CI) | | | | | | | |
| --- | --- | --- | --- | --- | --- | --- | --- | --- |
|  | Heart Failure | | Atrial Fibrillation | | Myocardial infarction | | All-cause mortality | |
|  | DROID | EchoLab | DROID | EchoLab | DROID | EchoLab | DROID | EchoLab |
| LVEF* | 1.43 (1.31, 1.56) | 1.42 (1.28, 1.58) | 1.18 (1.10, 1.27) | 1.17 (1.08, 1.26) | 1.22 (1.11, 1.33) | 1.19 (1.07, 1.31) | 1.17 (1.06, 1.31) | 1.25 (1.12, 1.39) |
| LVEDD** | 1.44 (1.22, 1.69) | 1.39 (1.19, 1.64) | 1.38 (1.24, 1.53) | 1.29 (1.16, 1.42) | 1.22 (1.06, 1.40) | 1.16 (1.01, 1.33) | 1.05 (0.89, 1.23) | 0.99 (0.85, 1.15) |
| LVESD** | 1.52 (1.34, 1.71) | 1.45 (1.27, 1.65) | 1.33 (1.22, 1.45) | 1.27 (1.16, 1.38) | 1.24 (1.10, 1.40) | 1.19 (1.06, 1.35) | 1.14 (0.99, 1.31) | 1.14 (0.99, 1.31) |
| IVS** | 1.43 (1.23, 1.66) | 1.29 (1.13, 1.49) | 1.36 (1.24, 1.50) | 1.25 (1.15, 1.37) | 1.40 (1.23, 1.59) | 1.32 (1.17, 1.48) | 1.13 (0.96, 1.32) | 1.12 (0.96, 1.29) |
| PWT** | 1.67 (1.47, 1.91) | 1.52 (1.32, 1.74) | 1.42 (1.30, 1.55) | 1.28 (1.17, 1.40) | 1.40 (1.24, 1.58) | 1.29 (1.14, 1.45) | 1.20 (1.03, 1.40) | 1.09 (0.94, 1.25) |
| LA AP** | 2.27 (1.77, 2.92) | 1.78 (1.43, 2.22) | 2.23 (1.90, 2.62) | 1.66 (1.44, 1.91) | 1.74 (1.39, 2.19) | 1.39 (1.70, 1.14) | 1.89 (1.47, 2.42) | 1.65 (1.33, 2.06) |

TABLE 7

| Left heart measures | c-index | | | | | | | |
| --- | --- | --- | --- | --- | --- | --- | --- | --- |
|  | Heart Failure | | Atrial Fibrillation | | Myocardial infarction | | All-cause mortality | |
|  | DROID | EchoLab | DROID | EchoLab | DROID | EchoLab | DROID | EchoLab |
| LVEF | 0.729 | 0.725 | 0.725 | 0.723 | 0.745 | 0.740 | 0.722 | 0.725 |
| LVEDD | 0.720 | 0.720 | 0.730 | 0.727 | 0.740 | 0.739 | 0.714 | 0.715 |
| LVESD | 0.727 | 0.724 | 0.730 | 0.727 | 0.742 | 0.740 | 0.717 | 0.716 |
| IVS | 0.722 | 0.719 | 0.731 | 0.727 | 0.748 | 0.747 | 0.716 | 0.716 |
| PWT | 0.748 | 0.737 | 0.738 | 0.728 | 0.749 | 0.748 | 0.718 | 0.715 |
| LA AP | 0.767 | 0.743 | 0.762 | 0.741 | 0.753 | 0.738 | 0.733 | 0.728 |

Comparison with Existing Models

Figure 26:
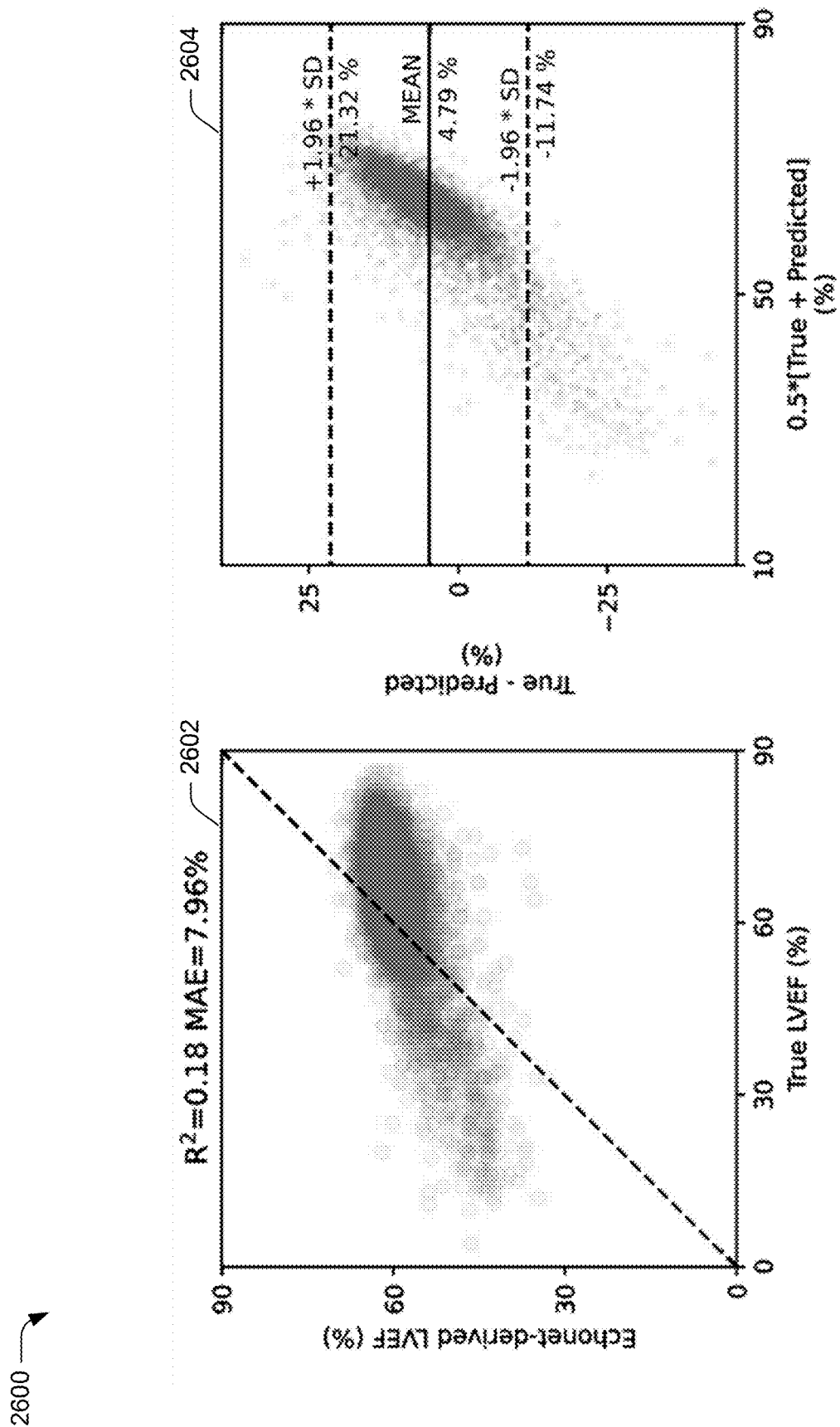
FIG. 26 shows an example analysis of the performance of an alternative model on the external validation cohort.

FIG. 26 shows an example analysis 2600 of the performance of EchoNet-Dynamic on the C3PO external validation cohort. The analysis 2600 includes a correlation plot 2602 comparing LVEF measurement predictions from the EchoNet-Dynamic model (on the vertical, or y-axis) versus gold standard EchoLab LVEF measurements (on the horizontal, or x-axis) in the C3PO external validation cohort. The application of EchoNet-Dynamic on the C3PO external validation cohort demonstrated good correlation with the gold-standard EchoLab LVEF measurement (Pearson r=0.69), but overall poor performance ($R^2$=0.18), covering a conservative LVEF range (32%-62%).

The analysis 2600 further includes a Bland-Altman plot 2604 of agreement between EchoNet-Dynamic derived versus EchoLab gold standard LVEF. The patterns demonstrate that EchoNet-Dynamic is poorly calibrated to the dataset, with pronounced underestimation for echocardiograms with high LVEF and pronounced overestimations for echocardiograms with low LVEF. The Bland-Altman plot 2604 shows conservative LVEF estimation errors with EchoNet-Dynamic (mean bias 4.79%, 95% CI 4.61%-4.97%).

Notably, EchoNet-Dynamic-derived LVEF was consistently associated with incident outcomes, and the associations with incident events were again greater in magnitude when compared with gold standard report values. A one-SD lower EchoNet-Dynamic LVEF was associated with a 46% greater risk of HF (age- and sex-adjusted HR 1.46, 95% CI 1.33-1.61), 17% greater risk of AF (HR 1.17, 95% CI 1.09-1.27), 22% greater risk of MI (HR 1.22, 95% CI 1.11-1.35), and 17% greater risk of death (HR 1.18, 95% CI 1.05-1.31) (Table 8).

Foundational work has demonstrated feasibility of deep learning of echocardiographic images for view classification, measurement of cardiac structure and function, detection of specific myocardial diseases, and prediction of cardiovascular risk factors. Refinement of these deep learning models has enabled increasingly reliable and precise automated classification of standard views, segmentation of cardiac chambers, and quantification of cardiac structure and function. For example, it has been shown that a deep learning model (trained and validated on 277 and 8666 echocardiograms, respectively) accurately classified the PLAX view with 96% accuracy and predicted standard cardiac structural measures including LV mass, LV diastolic volume, and LA volume with mean absolute deviations of 15-17%. Another model (trained and validated on 7,465 and 1,288 echocardiograms respectively) accurately predicted LVEF ($R^2$ 0.81 and MAE 4.1% versus human annotation) and reliably predicted HF with reduced ejection fraction (AUROC 0.97). These previous models were trained on modest numbers of echocardiographic videos (1,000-7,000 echocardiograms) and relied heavily on cardiac segmentation to guide downstream tasks like estimation of standard measures of cardiac structure and function.

To address this current limitation, the large size of the sample (>40,000 echocardiograms) was leveraged to develop a deep learning model to accurately predict cardiac structure and function without the need for resource intensive quality control steps such as manual segmentation. Moreover, the model employs a unique architecture that was designed to simulate the echocardiographic interpretation clinical workflow. The model comprises a multi-task encoder combined with a multi-instance attention head that

TABLE 8

|  | Heart Failure | | Atrial Fibrillation | | Myocardial infarction | | All-cause mortality | |
| --- | --- | --- | --- | --- | --- | --- | --- | --- |
|  | DROID | EchoNet-Dynamic | DROID | EchoNet-Dynamic | DROID | EchoNet-Dynamic | DROID | EchoNet-Dynamic |
| HR (95% CI) | 1.42 (1.32, 1.56) | 1.46 (1.33, 1.61) | 1.19 (1.10, 1.27) | 1.17 (1.09, 1.27) | 1.22 (1.11, 1.33) | 1.22 (1.11, 1.35) | 1.18 (1.05, 1.30) | 1.17 (1.05, 1.31) |
| c-index | 0.729 | 0.732 | 0.725 | 0.724 | 0.745 | 0.741 | 0.722 | 0.728 |

Discussion

A deep learning model (DROID) was developed for the automated measurement of left heart structure and function from echocardiographic images. The association of these measurements was evaluated with incident cardiovascular outcomes in a large multi-institutional EHR cohort of >500,000 individuals receiving longitudinal care with over a decade of follow-up. The model accurately classified views and quantified standard measures of LA dimension, LV wall thickness, chamber diameter, and ejection fraction as compared with gold standard clinical report values. DROID-derived LA and LV measures were in turn independently associated with important cardiovascular outcomes including HF, AF, MI, and all-cause death. Finally, the association between echocardiographic measures with incident outcomes was greater in magnitude for deep learning-derived echocardiographic measures compared with gold standard study report measures. Taken together, this novel approach to integrate automated interpretation of echocardiograms within an EHR-based cohort with well-curated clinical data and longitudinal outcomes highlights the direct clinical relevance of deep learning models for echocardiogram interpretation.

enables the model to integrate information across numerous echocardiographic views (e.g., A4C, A2C, and PLAX) to provide the most accurate prediction of standard measures of cardiac structure and function in a single model without the need for separate models for individual predictions or manual selection of specific videos for segmentation. The deep learning approach represents a significant advancement in deep learning echocardiographic interpretation, as fully automated end-to-end models may be translated to practice at scale with superior performance to existing models.

An underexplored application of deep learning echocardiographic interpretation is its role in disease prediction and prognostication. Standard echocardiographic measures of cardiac structure and function including LVEF, dimensions, volumes, and mass as well as LA volume have all been shown to be associated with incident disease in healthy participants and clinical outcomes (including all-cause mortality, cardiovascular death, and risk of hospitalization) in disease states like HF. To date, machine learning echocardiographic interpretation has been limited to identifying local cardiac structures, diagnosing specific conditions, differentiating causes of LVH, and predicting clinical characteristics, and has not been evaluated with respect to outcomes. The techniques described herein show that the deep learning model-derived LA and LV measures are strongly and consistently associated with incident outcomes including HF, AF, MI, and all-cause death, highlighting the ability of deep learning echocardiographic models to identify clinically relevant disease.

The association of deep learning derived measures of cardiac structure and function with cardiovascular outcomes was greater than the associations seen with gold standard human annotated study report measures. This finding may be explained by the greater reproducibility of deep learning over human echocardiographic measurements as demonstrated in previous studies. Deep learning may also integrate latent information from the echocardiogram that may inform disease risk. For example, DROID-LA may incorporate information from other cardiac chambers to generate a prediction for LA size, which may provide additional predictive value for disease risk.

Finally, one advantage of the study is the integration of deep learning echocardiographic interpretation into a well curated EHR cohort with rigorously defined longitudinal outcomes. EHR datasets are powerful tools with the potential to enable large scale discovery and risk prediction but are limited because of susceptibility to ascertainment bias and data missingness. C3PO was designed to closely mirror an epidemiologic study to overcome these limitations through sampling of only patients receiving longitudinal primary care in MGB and recovery of missing data via natural language processing. Leveraging the rigorous and intentional design of the C3PO EHR cohort, Example 1 shows that deep learning derived measures of left heart structure and function predict incident cardiovascular outcomes among individuals without existing CVD, consistent with previous epidemiologic studies.

Conclusions

A deep learning approach is described for automated echocardiographic interpretation applied to an EHR cohort of >500,000 individuals receiving longitudinal care across a multi-institutional healthcare network. The fully automated end-to-end model accurately quantified standard measures of left heart structure and function, which in turn were associated with future clinical outcomes including HF, AF, MI, and all-cause death. Machine learning of echocardiograms has the potential to scale echocardiogram interpretation and enable disease prediction and further biologic discovery.

Example 2: Deep Learning-Enabled Assessment of Right Ventricular Size and Function Predicts Cardiovascular Outcomes Background Right ventricular (RV) dilation and systolic dysfunction are relevant prognostic markers across a range of cardiovascular diseases, including atrial fibrillation (AF) and heart failure (HF). Routine assessment of RV size and function is recommended by clinical guidelines as part of every comprehensive two-dimensional transthoracic echocardiography (TTE) exam. However, while TTE is the most widely available modality for RV measurement, the crescentic geometry of the RV and its position under the sternum make accurate imaging and measurement challenging. Guidelines therefore recommend assessing the RV using multiple acoustic windows and reporting RV size and function using both qualitative descriptions and multiple quantitative parameters. As a result RV measurement by TTE is time-consuming, relies on significant expertise, and is limited by high interobserver variability. Given the limited availability and high cost of advanced imaging modalities, there is a need for a rapid and accurate method of assessing RV structure and function, to facilitate both TTE interpretation workflows and the use of RV measures to stratify cardiovascular risk.

Deep learning has been used to automate prediction of left heart measures from TTE videos, including in the development of Dimensional Reconstruction of Imaging Data (DROID) model with respect to left atrial and ventricular cavity size, wall thickness, and function described above with respect to Example 1 (see also, the implementation 300 of FIG. 3 and the implementation 400 of FIG. 4). Several studies have also explored the application of deep learning to the RV. However, RV-focused deep learning models to date have been limited by small sample sizes, selected patient populations, a lack of external validation, or unavailability of baseline comorbidities and longitudinal outcomes. One barrier to development of RV deep learning models is the relative unavailability of quantitative RV measurements, particularly for RV function, which is difficult to assess by 2-dimensional TTE.

Described herein is DROID-RV (e.g., the implementation 500 of FIG. 5), a deep learning model trained to estimate the basal RV end-diastolic diameter (RVEDD) and predict RV systolic dysfunction from TTE videos using over 380,000 video clips, 50,000 echocardiogram studies, and 17,000 patients from a longitudinal cardiology cohort. A multi-step training process is employed to leverage both qualitative and quantitative descriptions of RV size and function. DROID-RV predictions are in two external datasets, including longitudinal primary care patients and patients with indications for RV functional assessment. The advantages of the multi-step training approach are demonstrated using both qualitative and quantitative labels by adapting DROID-RV to RVEF estimation using an external sample of patients with RVEF measurements. Finally, DROID-RV is used to estimate RVEDD and probability of RV dysfunction in a longitudinal primary care population, demonstrating that DROID-RV predictions stratify longitudinal risk of AF, HF, and mortality.

Methods

Study Populations

The Enterprise Warehouse of Cardiology (EWOC) cohort is an electronic health record (EHR)-based cohort of 97,251 patients between the age of 18 and 90 years who received longitudinal cardiovascular care ($\geq 2$ clinic visits) in the Mass General Brigham (MGB) healthcare system between 2000 and 2019. Patients with 1) at least one TTE study performed at Massachusetts General Hospital (MGH), 2) at least one apical 4 chamber (A4C) or RV-focused view, and 3) available descriptions of RV systolic function or cavity size (n=17,141). The EWOC cohort corresponds to the model derivation subset 144 introduced with respect to FIG. 1, for example.

External validation of DROID-RV was performed in patients derived from 2 cohorts: 1) the Community Care Cohort Project (C3PO) and 2) RVENet. C3PO is an EHR-based cohort including 520,868 individuals aged 18 to 90 years receiving longitudinal primary care ($\geq 2$ primary care clinic visits) in the MGB healthcare system between 2000 and 2018. Patients in the C3PO population (n=9,112) were included in the validation sample if they had 1) at least one TTE study performed at MGH within 3 years before the start of follow up, 2) at least one A4C or RV-focused view, and 3) available descriptions of RV systolic function or cavity size (n=9,112). Patients belonging to both the EWOC and C3PO cohorts (i.e., those receiving both longitudinal primary and cardiology care; n=3,639) were included in the validation and outcomes sample only.

RVENet is a previously published TTE dataset which includes A4C and RV-focused views with corresponding RVEF labels from patients who underwent 3-dimensional echocardiography at the Heart and Vascular Center of Semmelweis University (Budapest, Hungary). The RVENet dataset was utilized in accordance with its Research Use Agreement. DROID-RV predictions of RV systolic dysfunction were externally validated using the entire RVENet sample. As described below, the RVENet dataset was also used to train and internally validate a second model (DROID-RVEF) to estimate RVEF. When used as training data, the RVENet sample was divided using the same patient-level training and validation splits from the original RVENet model. The C3PO and RVENet cohorts correspond to the external validation subset 146 of FIG. 1, for example.

An outcomes assessment sample included patients in the C3PO external validation sample with at least one follow-up encounter and available covariate data (n=8,941).

Figure 27:
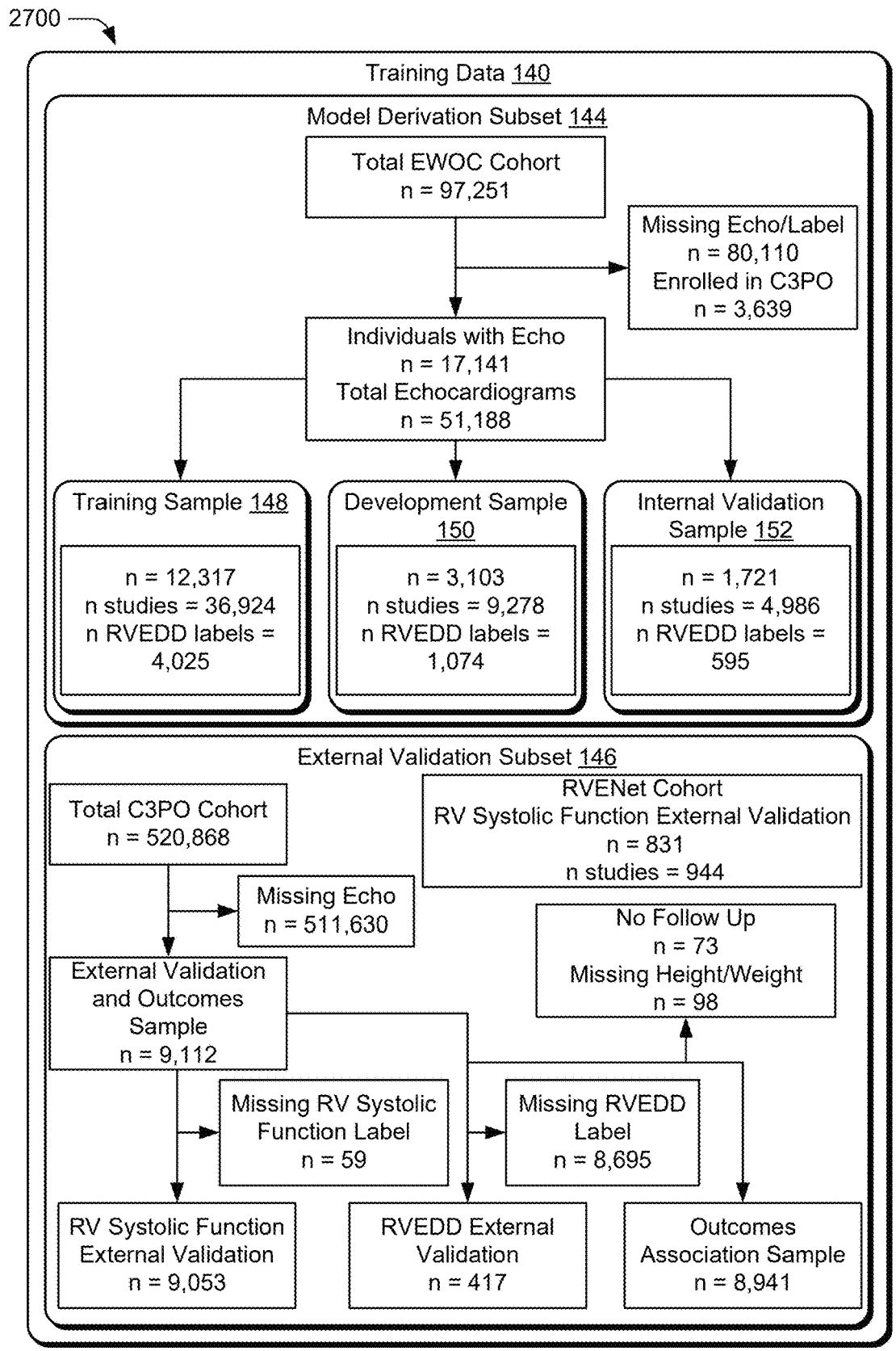
FIG. 27 illustrates a summary of the training data used for developing deep learning models for the assessment of right heart structure and function.

FIG. 27 illustrates a summary 2700 of the training data 140 used for developing deep learning models for the assessment of right heart structure and function. In Example 2, the training sample 148 included 36,924 echocardiogram videos obtained for 12,317 individuals, the development sample 150 included 9,278 echocardiogram videos obtained for 3,103 individuals, and the internal validation sample 152 included 4,986 echocardiogram videos obtained for 1,721 individuals. The external validation subset 146 included 9,052 individuals in the C3PO cohort for RV systolic function external validation, 417 individuals in the C3PO cohort for RVEDD external validation, and 831 individuals in the RVENet dataset. The summary 2700 further indicates the outcomes association sample, which includes 8,941 individuals.

Echocardiogram and Training Label Acquisition and Preprocessing

Digital TTE videos and interpretations were obtained for studies performed on patients in the EWOC and C3PO cohorts at MGH from the MGH Echocardiography Lab database, as previously described with respect to Example 1. The MGH Echocardiography Lab database is a curated dataset containing echocardiogram measurements and clinical interpretations performed by MGH cardiologists as part of routine clinical care.

Echocardiogram preprocessing was performed to remove identifying information and data overlays such as electrocardiogram and respirometer tracings (e.g., via the data preprocessor 132 of FIG. 1). First, a custom pipeline was developed to remove protected health information and data overlaid by scanning equipment, including electrocardiogram and respirometer tracings.

A distinct model (e.g., of the one or more deep learning models 134) was trained to classify each video clip based on quality, view, and imaging type, which was used to identify videos for DROID-RV training. This deep learning model was used to classify clips according to study quality (usable or poor), use of Doppler imaging (Doppler or standard imaging), axis (canonical or off-axis), and standardized TTE view (i.e., apical 4 chamber [A4C], RV-focused, etc.). This model was then applied to all available clips, and outputs were used for clip selection for training of the DROID-RV model.

A4C views and RV-focused views were identified with areas under the receiver-operator curve of 0.975 and 0.933, respectively. TTE clips were processed to standardize resolution to 224 by 224 pixels, and 16 frames were chosen from each clip by selecting a starting frame and every 4th subsequent frame. During model training, if the total video length was greater than 64 (4×16) frames, the starting frame was selected from the initial n frames where n=total # of frames−64. If the video length was shorter than 64 frames, the first frame was used as the starting frame and the clip was padded using frames from the beginning of the clip. During model evaluation, the first frame of each clip was always used as the starting frame to ensure reproducible results. The final input tensor to the model has the shape (16, 224, 224, 3).

RV cavity size (dilated versus normal) and systolic function (hypokinetic versus normal) were treated as binary variables and available for nearly all studies (99.8% for RV size and 99.7% for RV function), whereas RVEDD as a continuous variable was available for only 10.2% of studies. During training, all studies with available RV labels, including multiple studies per patient, were used. For validation and outcomes assessment, only the most recent study per patient within the 3 years prior to the start of follow up was included.

Binary variables for qualitative RV size and function were created by collapsing categories available in the MGH Echolab database. For qualitative RV size, the categories "Dilated" and "Mildly Dilated" were considered dilated, and "Normal," "Upper Limit of Normal," and "Small" were considered normal. For qualitative RV function, the categories "Abnormal" and "Hypokinetic" were considered hypokinetic, and "Normal," "Low Normal," and "Hyperdynamic" were considered normal. "Small" and "Hyperdynamic" were included in their respective normal categories due to the greater clinical relevance of detecting RV dilation and low systolic function, and due to their overall low prevalence (<0.1% each). These labels were used as the ground truth label 206 associated with the echocardiogram video 204 in a training instance 202, e.g., as described with respect to FIG. 2.

Patient Characteristics and Outcomes

Presence of baseline comorbidities was determined by presence of a single International Classification of Disease (ICD) 9, ICD-10, or Current Procedural Terminology (CPT) code, corresponding to the comorbidity on or before the start of follow up, except for AF and HF which were defined as described below.

Longitudinal associations with AF, HF, and all-cause mortality were examined. AF was defined using a previously published algorithm which determines the date of incidence of AF based on ICD codes, CPT codes, and electrocardiogram reports. The date of incident HF was defined as the date of first presence of an ICD-9 or ICD-10 code corresponding to a primary diagnosis of HF for an inpatient encounter. All-cause mortality was determined from EHR records and the social security death index.

When reported at the patient level, the available echocardiogram measurement closest to the start of follow up was used, and the height and weight at the start of follow up were used, if available. Height and weight values were processed to reconcile units, remove non-physiologic values, and limit missingness. Height and weight values were obtained from multiple sources: electronic health record-derived tabular data, natural language processing of clinical notes, and tabular data acquired as part of echocardiography studies. Height and weight values were converted to kilograms and centimeters, respectively, and filtered to exclude non-physiologic values (i.e., height <121.92 cm [4 ft] or height >304.8 cm [10 ft]; weight <13.6 kg [30 lbs] or weight >454.5 kg [1000 lbs]). When height and/or weight were unavailable from C3PO sources, the value from the echocardiogram study most proximal to the start of follow up was used. Height and weight at the time of echocardiogram study were explored as potential co-training tasks for DROID-RV but were not included in the final model. When height and weight were used as co-training tasks patients were excluded if height or weight were missing.

Age at the time of echocardiogram was rounded down to the nearest integer. Prior to model, training continuous output labels (i.e., age and RV end-diastolic dimension) were normalized to mean 0 and standard deviation 1. Final model predictions were generated by multiplying DROID-RV output by the corresponding pre-normalization standard deviation and adding the pre-normalization mean.

DROID-RV Model Development

The DROID-RV model architecture is a 3-dimensional convolutional neural network with two spatial dimensions and one temporal dimension based on the MoViNet architecture. See, for example, the implementation 500 of FIG. 5.

The training population was divided into training, development, and internal validation samples by patient using a 70%/20%/10% split (FIG. 27). The training and development splits were used for selection of hyperparameters, input views, and co-training tasks. Model performance and associations with incident disease were assessed using study-level predictions, which were obtained by taking the median of all video-level predictions for each study. Model training was performed using Python version 3.6.9 with modules TensorFlow 2.5.0 and ml4 h 0.0.7.

As mentioned above, the DROID-RV model architecture comprises a MoViNet-A2 backbone, which is flattened after the final convolutional layer to shape. This is connected to a dense layer with 256 hidden units, and subsequently to a single regression head that contains a number of nodes equal to the number of regression tasks, as well as to one classification head for each classification task. Each classification head has a number of nodes equal to the number of categories for that task, and a softmax activation function is applied. The pre-trained MoViNet weights were used for layers derived from MoViNet-A2, and other layer weights were initialized randomly.

For categorical tasks, the categorical cross-entropy loss function was used, and for regression tasks the mean square error loss function was used. Loss for each classification or regression head was summed and jointly minimized using the Adam optimizer with an initial learning rate of 1 e−4. A batch size of 16 was used during training. Early stopping was employed if the validation set loss failed to improve for 10 epochs, and the checkpoint with the lowest validation loss was used. During fine-tuning for RV end-diastolic diameter regression (i.e., the primary DROID-RV model), each epoch was limited to 400 training steps to allow for more frequent evaluation for early stopping.

Multiple models were developed to test candidate hyperparameters, input views, and co-training tasks. Hyperparameter selection was informed by previous work developing the DROID-LV and DROID-LA models of Example 1. Hyperparameters included the number of input frames and the cadence of selected frames from input videos. Based on previous work, the choice of 16 frames per video best balanced model performance with computational cost, and using every 4th frame resulted in the best model performance.

To improve DROID-RV performance for RV end-diastolic diameter (RVEDD) regression, the addition of other co-training tasks was explored. Sets of co-training tasks that were investigated included RVEDD plus 1) age and sex and 2) age, sex, body surface area, height, and weight. The latter did not improve performance for RVEDD regression, so age and sex alone were chosen for subsequent models. The use of other echocardiographic views during model training, in addition to A4C and RV focused views, was also explored. Other candidate views included the parasternal short axis view (PSAX) at the mitral valve level, the PSAX view at the aortic valve level, the parasternal long axis view, and the subcostal view. None of these views improved model performance when compared to a base model including only A4C and RV focused views, so none were used during training of the final model.

A multi-step training procedure was used to help DROID-RV learn from both qualitative and quantitative RV labels. In the first step, "pre-training," DROID-RV was trained to predict qualitative RV size and function using the full training sample. While the pre-trained model can give predictions of qualitative RV size, it cannot estimate RVEDD. In the second step, DROID-RV was "fine-tuned" to give quantitative estimates of RVEDD, using the subset of the training sample in which RVEDD measurements were available. The result of the second training step is that the final DROID-RV model can provide estimates of both continuous RVEDD and qualitative RV size and function. The advantage of the multi-step training process is that DROID-RV can learn general features of RV dilation from a large sample of qualitative descriptions of RV size, and then learn how to more precisely estimate RVEDD from a smaller number of studies with RVEDD labels.

Direct training (i.e., from random initial weights aside from MoViNet weights) of a model to regress RVEDD was also explored as compared to the two-stage approach involving pre-training using a different set of tasks for which a larger sample size was available, followed by fine-tuning using continuous RVEDD measurements, as described above. Pre-training was assessed using both the DROID-LV model as initial weights, as well as a model trained to predict categorical RV size and function, age, and sex. The pre-training approach using categorical RV size and function improved performance for RVEDD regression, which was further improved by including both categorical RV size and function as co-training tasks during the fine-tuning step.

DROID-RVEF Model Development

A multi-step training approach was also used to train a second model, DROID-RVEF, to estimate RVEF. DROID-RVEF was trained by fine-tuning the DROID-RV model to estimate RVEF using RVEF labels from the training split of the RVENet dataset (n=764). The performance of DROID-RVEF for RVEF estimation and classification of RVEF<45% was validated at the study level in the RVENet validation split (n=180). To facilitate model comparison, the same model training and validation splits were used as employed in previous studies.

The DROID-RVEF model was trained using an identical architecture and hyperparameters to the final DROID-RV model. Due to the availability of different RV parameters in the RVENet dataset used to train DROID-RVEF, the output tasks included R VEF as a primary task and RV end-diastolic and RV end-systolic volumes, age, and sex as auxiliary tasks.

RVENet data was provided as deidentified DICOM files, which were processed using the same data processing pipeline as described above (e.g., via the data preprocessor 132). Since RVENet data included only A4C and RV-focused views that were already quality-controlled, the entire dataset was utilized and was not filtered based on view and quality predictions, as was done for MGH data. RVENet included a majority of clips using the Mayo orientation of A4C views with the right ventricle on the right of the image, whereas MGH data was exclusively in the Stanford orientation with the right ventricle on the left of the image. Prior to input into the DROID-RV model, clips in the Mayo orientation were horizontally flipped to approximate acquisition in the Stanford orientation.

Saliency Mapping

Deep learning models are difficult to interpret due to their high dimensionality and non-linear operations. To better understand DROID-RV predictions, saliency maps were used to visualize the relative contributions of different regions of input video clips to final prediction of RVEDD and RV systolic dysfunction for randomly selected sample videos. Saliency maps were generated using the SmoothGrad method, which involves taking the gradient of an output prediction with respect to its given input video after the addition of random Gaussian noise, and converting the resulting gradients to overlays that signify the magnitude of influence of each pixel on the final prediction. For instance, since the resulting tensor of gradients has the same shape as the input video, it can be overlayed on the original input video for visualization.

The saliency maps were generated for selected random echocardiogram clips with normal RV systolic function, normal RV size (i.e., RVEDD<=41 mm), RV dysfunction, and RV dilation. The clip for RV dilated was randomly sampled twice due to incomplete deidentification of the initial randomly selected clip. Each input clip was normalized to a floating point tensor of shape (16, 224, 224, 3) with pixel values in the range of 0 to 1. Gradients were taken after addition of Gaussian noise with a standard deviation of 0.1 and were averaged over 25 repetitions.

To convert to a color overlay, the absolute value of each gradient value was taken and kept the maximum value across the red/green/blue channels, with resulting shape (16, 224, 224). To limit the range of values and allow for better visualization after conversion to a color heatmap, the gradients were then winsorized using the 0.0001 and 0.9999 percentile values. Single floating point values per pixel were then converted to red/green/blue values using the matplotlib 'magma' color map and averaged with the input image pixel values. The resulting tensors were converted to GIF images for visualization, and the frame with the highest summed saliency value was selected for visualization as a still image.

Qualitatively, the regions with the highest saliency appeared to include the RV free wall, tricuspid annulus, and interventricular septum, though high saliency can be seen throughout the heart, including the LV and atria.

Statistical Analysis

Model performance for RVEDD and RVEF estimation is reported using mean absolute error (MAE), $R^2$, Bland-Altman plots, and paired sample T tests. Performance for RV systolic dysfunction prediction is reported as area under the receiver operating characteristic curve (AUROC) and average precision.

The association between DROID-RV predictions and incident AF, HF, and all-cause mortality was tested using stratified cumulative incidence curves and Cox proportional hazards regression. Patients were censored on either the date of death (for AF and HF only), date of last follow up, or an administrative censoring date of Aug. 31, 2019. For cumulative incidence analyses, predicted RV dilation (i.e., predicted RVEDD>41 mm) and predicted RV systolic dysfunction were used to stratify patients using a probability threshold that maximized prediction accuracy in the model development sample, which was 0.302. Comparisons between strata were made using the log-rank test. For Cox models, associations of predicted RVEDD and probability of RV systolic dysfunction were tested with each outcome, with and without adjustment for age, sex, height, weight, and left ventricular ejection fraction (LVEF).

Statistical analyses were performed using R (version 4.2.1) with packages survival, survminer, cmprsk, yardstick, and pROC.

Results

Model Derivation and Validation Populations

The model derivation cohort, EWOC, is a longitudinal cohort of 97,251 ambulatory cardiology patients in which 17,141 patients (62.0% male, mean age 61.2±15.9 years) with 51,188 TTE studies for which video clips and RV size or function labels were available were identified (e.g., see the summary 2700 of FIG. 27). In total, the model derivation sample included 383,981 A4C or RV-focused video clips. The model derivation sample included 1,985 (11.0%) patients with RV dilation and 1,046 (6.1%) with RV systolic dysfunction (Table 9). Among patients in the derivation sample with available quantitative RVEDD measurements (n=3,774 [22.0%]), mean RVEDD was 41±7 mm. The derivation sample was split by patient into training (n=12,317), development (n=3,103), and internal validation (n=1,721) samples.

TABLE 9

| | Model Derivation & Internal Validation | External Validation & Outcomes |
|---|---|---|
| Study name | EWOC | C3PO |
| Patient population | Ambulatory Cardiology Patients | Ambulatory Primary Care Patients |
| N | 17,141 | 9,112 |
| Age (Y) | 61.2 ± 15.9 | 57.6 ± 17.5 |
| Sex | | |
| Female | 6,513 (38.0) | 4,527 (49.7) |
| Male | 10,628 (62.0) | 4,585 (50.3) |
| Race | | |
| Asian or Pacific Islander | 479 (2.8) | 456 (5.0) |
| Black | 417 (2.4) | 598 (6.6) |
| Hispanic or Latino | 281 (1.6) | 249 (2.7) |
| Other | 290 (1.7) | 376 (4.1) |
| Unknown | 375 (2.2) | 176 (1.9) |
| White | 15,299 (89.3) | 7,257 (79.6) |
| Atrial Fibrillation | 8,711 (50.8) | 2,813 (30.9) |
| Chronic Kidney Disease | 2,627 (15.3) | 1,854 (20.3) |
| Congenital Heart Disease | 3,639 (21.2) | 1,312 (14.4) |
| Coronary Artery Disease | 9,224 (53.8) | 3,541 (38.9) |
| Diabetes Mellitus | 3,043 (17.8) | 2,071 (22.7) |
| Heart Failure | 2,496 (14.6) | 1,065 (11.7) |
| Hypertension | 12,290 (71.7) | 6,260 (68.7) |
| Pulmonary Hypertension | 1,734 (10.1) | 844 (9.3) |
| Height (cm) | | |
| Mean ± SD | 170.4 ± 10.7 | 168.4 ± 10.7 |
| Missing | 300 (1.8) | 49 (0.5) |
| Weight (kg) | | |
| Mean ± SD | 82.7 ± 19.8 | 81.8 ± 21.5 |
| Missing | 503 (2.9) | 72 (0.8) |
| RV Cavity Size | | |
| Dilated | 1,885 (11.0) | 526 (5.8) |
| Not Dilated | 15,256 (89.0) | 8,532 (93.6) |
| Missing | 0 (0.0) | 54 (0.6) |

TABLE 9-continued

|  | Model Derivation & Internal Validation | External Validation & Outcomes |
|---|---|---|
| RVEDD (mm) | | |
| Mean ± SD | 40.9 ± 6.6 | 39.4 ± 6.9 |
| Missing | 13,367 (78.0) | 8,695 (95.4) |
| RV Systolic Function | | |
| Hypokinetic | 1,046 (6.1) | 267 (2.9) |
| Not Hypokinetic | 16,095 (93.9) | 8,786 (96.4) |
| Missing | 0 (0.0) | 59 (0.6) |

The first external validation sample was derived from C3PO, a cohort comprising 520,668 longitudinal primary care patients. Within C3PO, 9,112 patients (50.3% male, mean age 57.6±17.5 years) with at least 1 TTE and either RV size or function labels were identified. The C3PO external validation population had a lower prevalence of RV dilation (n=526 [5.8%]; n missing=54 [0.6%]) and dysfunction (n=267 [2.9%]; n missing=59 [0.6%]) compared to the model derivation population, with less frequent ascertainment of RVEDD (n=417 [4.6%] available) and mean RVEDD 39±7 mm.

The second external validation sample was RVENet, a dataset comprising 831 patients (61.5% male, mean age 45.2±22.8 years) with 944 TTE studies and paired RVEF measurements from 3-dimensional TTE. Median RVEF was 54.8% (interquartile range: 49.1-59.4%) and 135 (14.3%) had RVEF<45%.

RVEDD Estimation

DROID-RV was trained to first estimate RV size (i.e., dilated versus normal) in the training sample of 36,924 studies with qualitative RV size labels, and then fine-tuned it to estimate RVEDD in 4,025 studies with quantitative RVEDD measurements.

Figure 28:
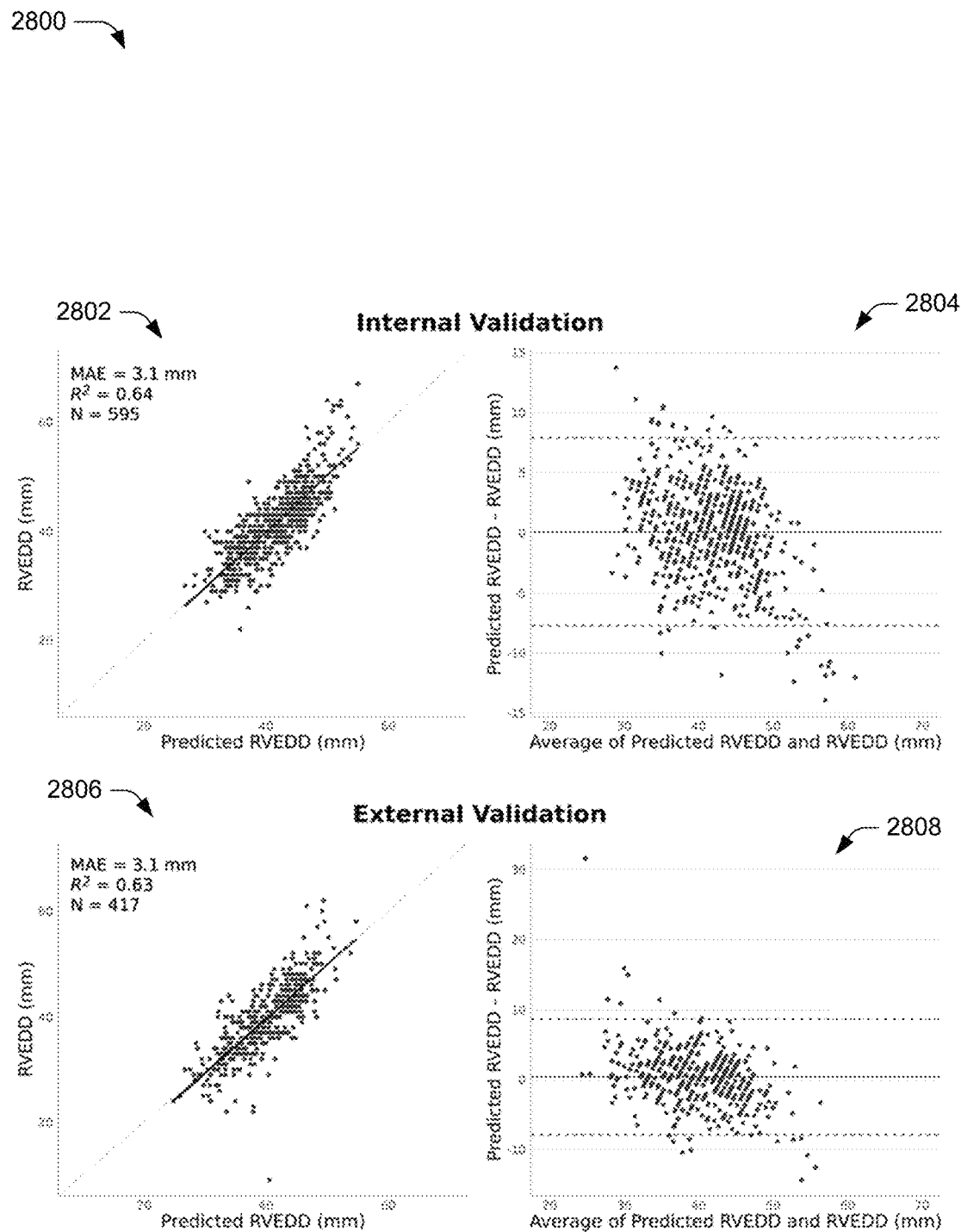
FIG. 28 shows show an example analysis of measurement prediction performance by an echocardiography deep learning model trained for right heart measurement predictions.

FIG. 28 shows show an example analysis 2800 of measurement prediction performance by an echocardiography deep learning model trained for right heart measurement predictions. The analysis 2800 includes a first correlation plot 2802 and a first Bland-Altman plot 2804 corresponding to the internal validation dataset (e.g., the internal validation sample 152). The analysis 2800 further includes a second correlation plot 2806 and a second Bland-Altman plot 2808 corresponding to the C3PO external validation dataset (e.g., part of the external validation subset 146). The first correlation plot 2802 and the second correlation plot 2806 show RVEDD estimated by DROID-RV (horizontal axis) versus measured RVEDD values (vertical axis), e.g., the associated ground truth label 206. The dashed lines in the first correlation plot 2802 and the second correlation plot 2806 represent perfect agreement, and the solid lines represent the best linear fit of the data. For the first Bland-Altman plot 2804 and the second Bland-Altman plot 2808, the horizontal (x-axis) depicts the average of the predicted RVEDD and the measured RVEDD for an individual, and the vertical (y-axis) plots the difference between the predicted RVEDD and the measured RVEDD. The solid horizontal line depicts the overall mean difference, and the dashed lines depict the estimated 95% limits of agreement.

As can be appreciated via the analysis 2800, DROID-RV accurately estimated RVEDD in the internal validation sample (n=595 studies with RVEDD measurements, MAE=3.1 mm, $R^2$=0.64; the first correlation plot 2802). Bland-Altman analysis demonstrated conservative estimates of RVEDD without statistically significant difference in the means (mean difference 0.1 [95% CI: −0.2-0.4] mm, p=0.583; and the first Bland-Altman plot 2804). Model performance was preserved in the C3PO external validation dataset (n=417 patients with RVEDD measurements, MAE=3.1 mm, $R^2$=0.63; the second correlation plot 2806). Bland-Altman plots again suggested conservative estimation errors with a modest overestimation bias (mean difference 0.4 [95% CI:0.0-0.8] mm, p=0.040; the second Bland-Altman plot 2808).

RV Systolic Dysfunction Prediction and RVEF Estimation

DROID-RV was then trained to classify RV systolic dysfunction (i.e., hypokinetic versus normal) along with RVEDD estimation.

Figure 29:
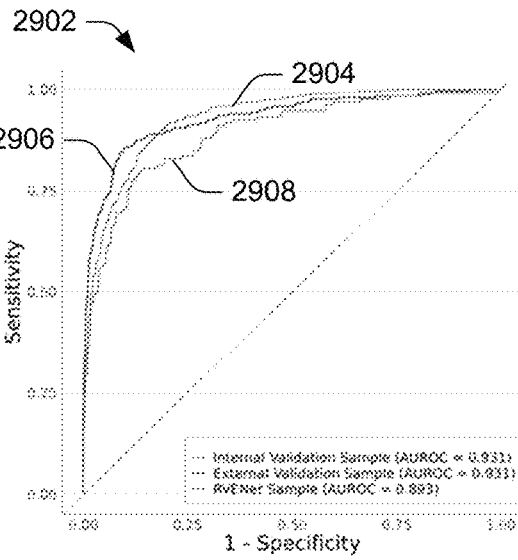
FIG. 29 shows an example analysis of deep learning model performance for predicting right ventricular systolic dysfunction and estimating right ventricular ejection fraction.

FIG. 29 shows an example analysis 2900 of deep learning model performance for predicting right ventricular systolic dysfunction and estimating right ventricular ejection fraction. The analysis 2900 includes receiver operating characteristic (ROC) curves 2902, including a first ROC curve 2904 corresponding to the internal validation sample, a second ROC curve 2906 corresponding to the C3PO external validation sample, and a third ROC curve 2908 corresponding to the RVENet external validation sample. The analysis 2900 further includes precision recall curves 2910, including a first precision recall curve 2912 corresponding to the internal validation sample, a second precision recall curve 2914 corresponding to the C3PO external validation sample, and a third precision recall curve 2916 corresponding to the RVENet external validation sample.

DROID-RV accurately predicted RV systolic function, achieving an internal validation AUROC of 0.931 (95% CI:0.921-0.941; the first ROC curve 2904) and an average precision of 0.701 (95% CI:0.662-0.736; prevalence 0.110; the first precision recall curve 2912) among 4,986 studies with RV function labels. The model generalized well to the C3PO external validation sample with AUROC of 0.931 (95% CI:0.913-0.949; the second ROC curve 2906) and an average precision of 0.580 (95% CI:0.521-0.637; prevalence 0.029; the second precision recall curve 2914) among 9,053 studies with RV function labels. DROID-RV prediction of RV systolic dysfunction also generalized well to the RVENet external validation sample, achieving an AUROC of 0.893 (95% CI:0.962-0.925; the third ROC curve 2908) and an average precision of 0.690 (95% CI:0.611-0.764, prevalence 0.142; the third precision recall curve 2916). DROID-RV performance on the RVENet sample was comparable to the internal validation performance of the RVENet model (AUROC 0.915 [95% CI:0.952-0.966]).

While DROID-RV was trained to estimate the probability of RV systolic dysfunction using qualitative RV systolic dysfunction labels, the training split of RVENet (n=764 studies) was used to fine-tune a second model, DROID-RVEF, that quantitatively estimates RVEF.

Accordingly, the analysis 2900 further includes a scatter plot 2918 and a Bland-Altman plot 2920 for RVEF estimation in the validation subset of the RVENet sample. In the scatter plot 2918, the dotted line represents the line of perfect agreement, and the solid line represent the best linear fit of the data. In the Bland-Altman plot 2920, the solid line represents the mean difference, and the dotted lines represent the 95% limits of agreement.

DROID-RVEF accurately predicted RVEF (MAE=3.9 percentage points, $R^2$=0.65; the scatter plot 2918) in the hold-out RVENet validation subset (n=180 studies), comparing favorably to the validation performance of the RVENet model on the same sample (MAE=4.57 percentage points, $R^2$=0.52). Bland-Altman analysis (the Bland-Altman plot 2920) demonstrated conservative estimates of RVEF without a significant difference in the means (mean difference 0.3 [95% CI: −0.4-1.0] percentage points, p=0.427).

Associations of Model Predictions with Cardiovascular Outcomes

After generating DROID-RV predictions of RVEDD and probability of RV systolic dysfunction, associations between the model predictions and incident mortality, AF, and HF were tested. Among 8,941 patients in the C3PO outcomes sample, there were 602 cases of incident AF, 362 cases of incident HF, and 931 deaths over median follow up of 3.4 (interquartile range: 1.4-6.3) years.

Figure 30A:
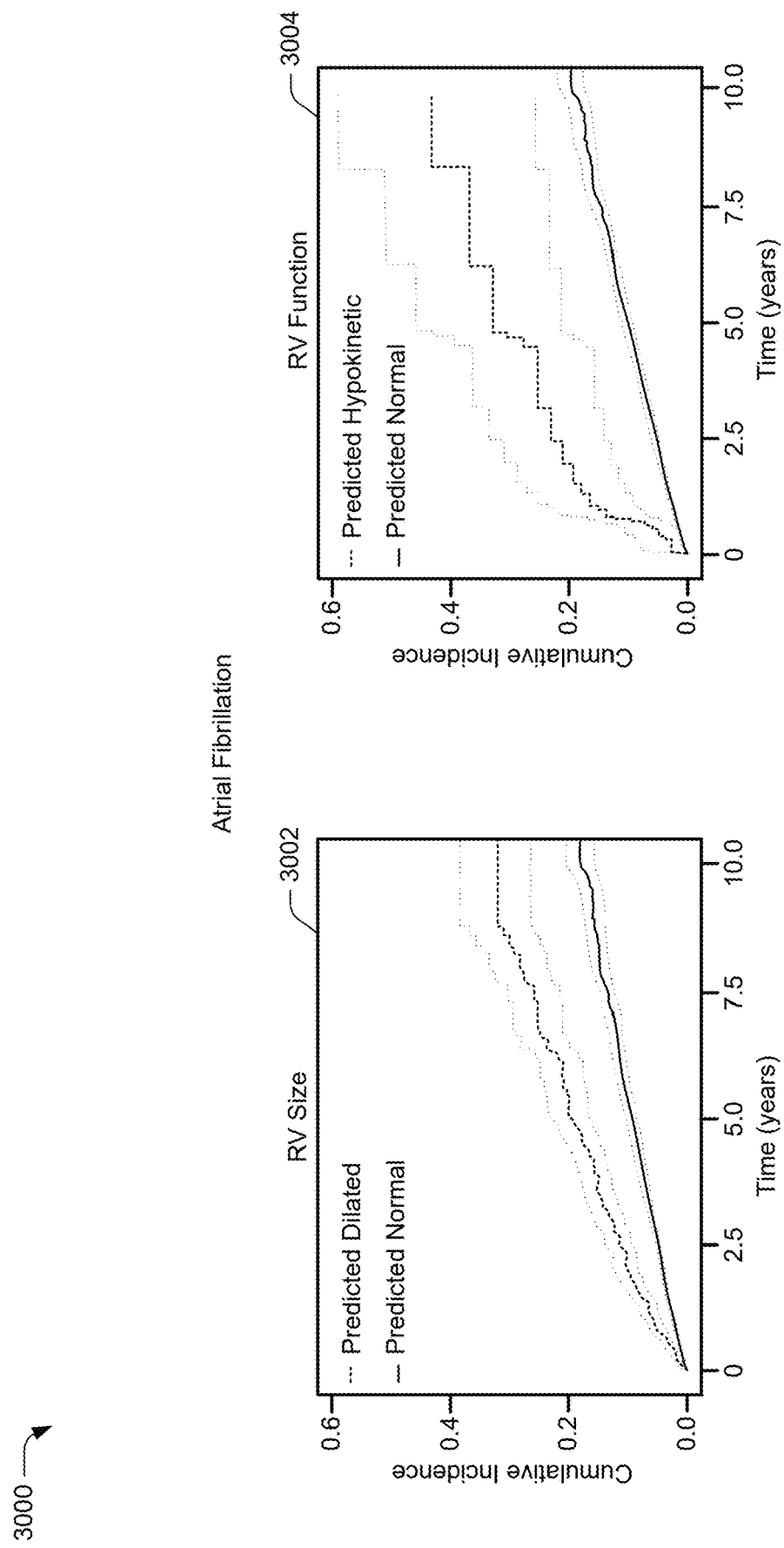
FIGS. 30A-30C show cause-specific cumulative incidence curves for atrial fibrillation, heart failure, and mortality.
Figure 30B:
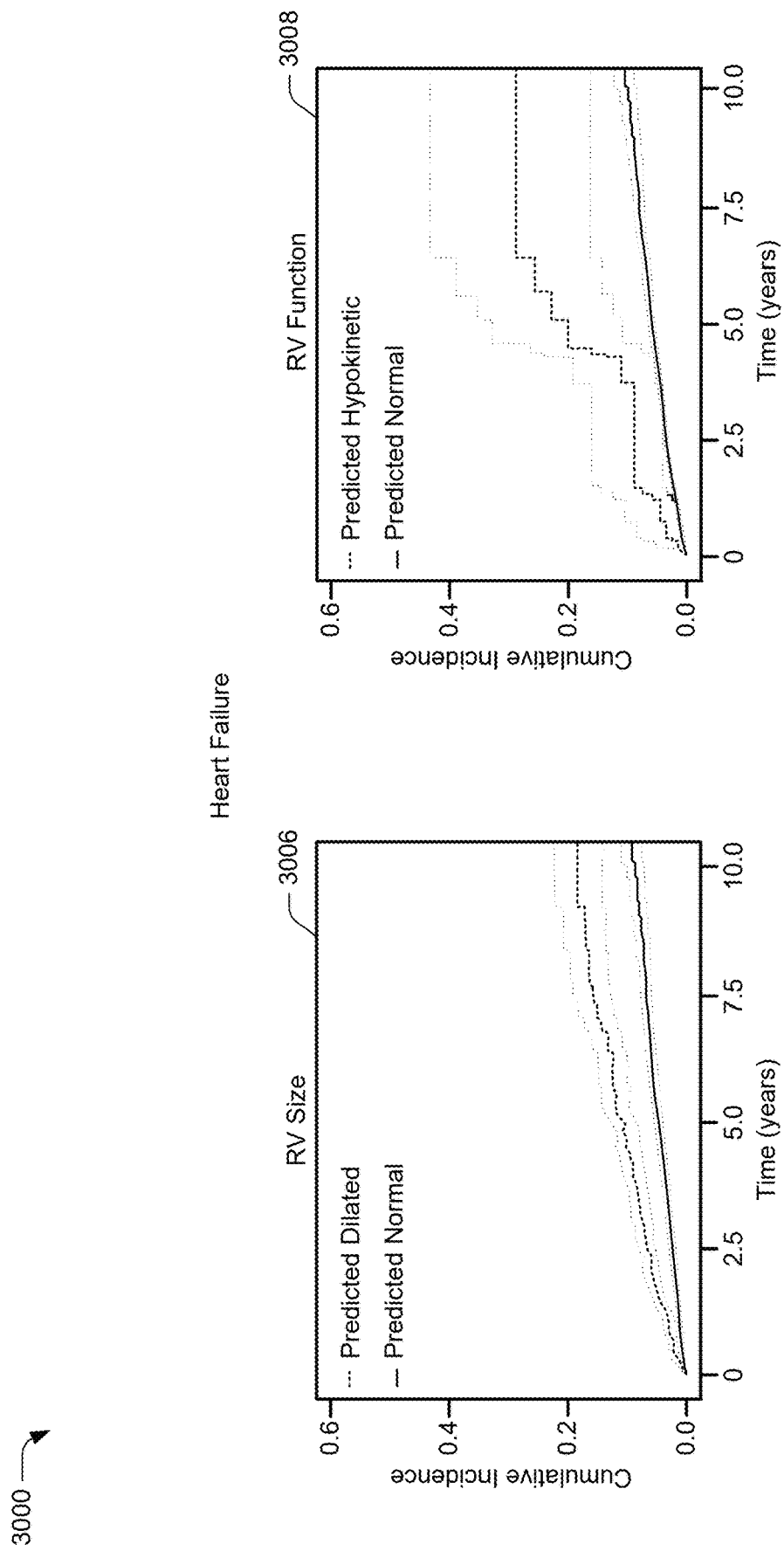
Figure 30C:
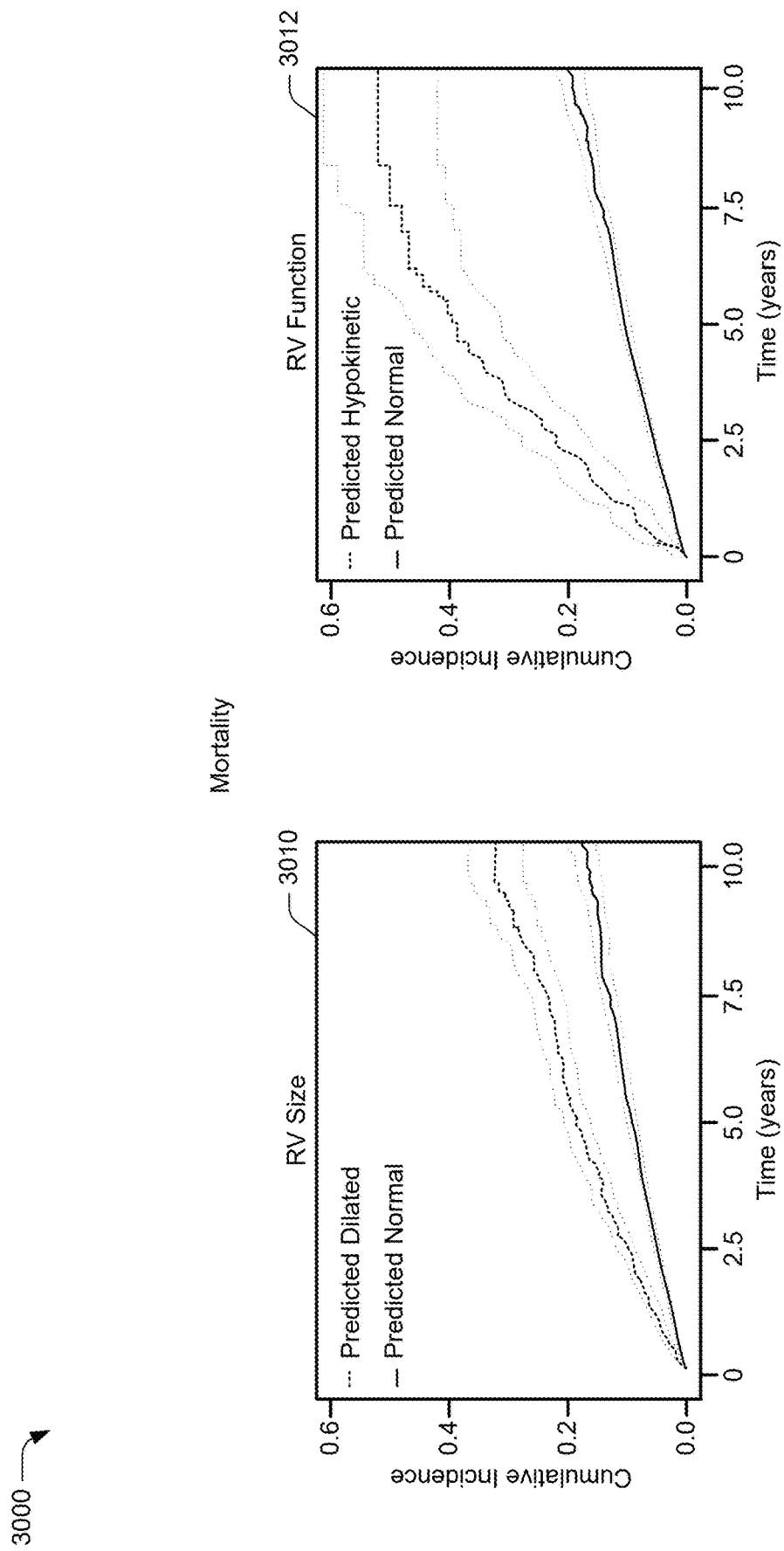

FIGS. 30A-30C show cause-specific cumulative incidence curves 3000 for atrial fibrillation (FIG. 30A), heart failure (FIG. 30B), and mortality (FIG. 30C). The cause-specific cumulative incidence curves 3000 include a first plot 3002 that stratifies the cumulative incidence of atrial fibrillation based on RV size (e.g., predicted dilated, indicated by a dashed line, versus predicted normal, indicated by a solid line), a second plot 3004 that stratifies the cumulative incidence of atrial fibrillation based on RV function (e.g., predicted hypokinetic, indicated by a dashed line, versus predicted normal, indicated by a solid line), a third plot 3006 that stratifies the cumulative incidence of heart failure based on RV size (e.g., predicted dilated, indicated by a dashed line, versus predicted normal, indicated by a solid line), a fourth plot 3008 that stratifies the cumulative incidence of heart failure based on RV function (e.g., predicted hypokinetic, indicated by a dashed line, versus predicted normal, indicated by a solid line), a fifth plot 3010 that stratifies the cumulative incidence of mortality based on RV size (e.g., predicted dilated, indicated by a dashed line, versus predicted normal, indicated by a solid line), and a sixth plot 3012 that stratifies the cumulative incidence of mortality based on RV function (e.g., predicted hypokinetic, indicated by a dashed line, versus predicted normal, indicated by a solid line).

The 5-year cumulative incidence of mortality was higher in patients with predicted RV dilation (18.4% [95% CI:16.2-20.7] versus 9.0% [95% CI:8.2-9.9] for normal predicted size) or abnormal predicted RV function (38.6% [95% CI:30.8-46.4] versus 10.2% [95% CI:9.4-11.0] for normal predicted function). Results were similar for incident HF and AF and are summarized in Table 10.

The association between the predicted RVEDD and RV systolic dysfunction probability and incident cardiovascular outcomes using Cox proportional hazards regression was assessed.

Figure 31:
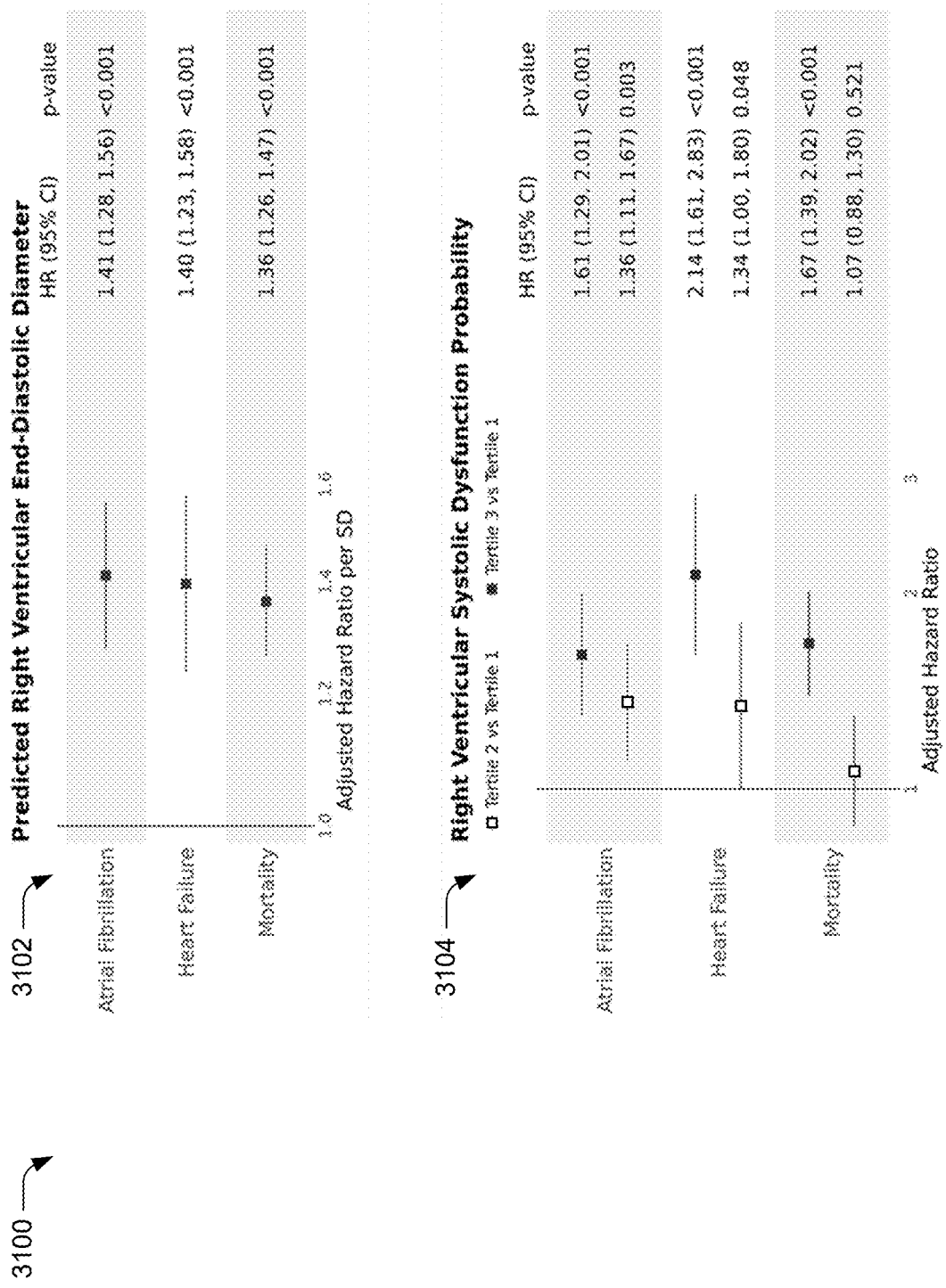
FIG. 31 shows an example analysis of the association of deep learning-derived measurements with incident outcomes using Cox proportional hazards models.

FIG. 31 shows an example analysis 3100 of the association of deep learning-derived measurements with incident outcomes using Cox proportional hazards models. A first forest plot 3102 demonstrates the association between RVEDD predictions with atrial fibrillation, heart failure, and mortality. A second forest plot 3104 shows tertiles of predicted RV dysfunction probability and incident AF, HF, and mortality after adjustment for age, sex, height, weight, and LVEF fraction. Tertile 2 versus tertile 1 is shown as open-filled (white) symbols, and tertile 3 versus tertile 1 is shown as black-filled symbols.

After adjustment for age, sex, height, weight, and LVEF, each standard deviation increase in predicted RVEDD was associated with a hazard ratio (HR) of 1.41 (95% CI:1.28-1.56) for incident AF, 1.40 (95% CI:1.23-1.58) for incident HF, and 1.36 (95% CI:1.26-1.47) for mortality (p<0.001 for all; the first forest plot 3102; Tables 11-13). Similarly, the highest tertile of predicted RV dysfunction risk was associated with a HR of 1.61 (95% CI:1.29-2.01) for incident AF, 2.14 (95% CI:1.61-2.83) for incident HF, and 1.67 (95% CI:1.39-2.02) for mortality, compared to the lowest tertile (p<0.001 for all; the second forest plot 3104; Tables 14-16).

TABLE 11

| Variable | N Observations | N Events | HR | 95% Lower CI | 95% Upper CI | p-value |
| --- | --- | --- | --- | --- | --- | --- |
| Mortality, adjusted | | | | | | |
| Predicted RVEDD (mm) | 8,941 | 831 | 1.36 | 1.26 | 1.47 | <0.001 |
| Age (Y) | 8,941 | 831 | 1.06 | 1.05 | 1.06 | <0.001 |
| Female | 4,449 | 336 | 1.00 | | | |
| Male | 4,492 | 495 | 1.14 | 0.94 | 1.39 | 0.192 |
| Height (cm) | 8,941 | 831 | 0.99 | 0.98 | 1.00 | 0.033 |

TABLE 10

| Characteristic | N | N Event | 5-Year Cumulative Incidence | 10-Year Cumulative Incidence | p-value[1] |
| --- | --- | --- | --- | --- | --- |
| Atrial Fibrillation | | | | | <0.001 |
| Predicted Dilated | 951 | 145 | 19.6% (16.4%, 23.1%) | 32.2% (26.2%, 38.2%) | |
| Predicted Normal | 5,862 | 457 | 9.1% (8.2%, 10.1%) | 17.5% (15.2%, 19.9%) | |
| Atrial Fibrillation | | | | | <0.001 |
| Predicted Hypokinetic | 93 | 23 | 33.0% (20.7%, 45.7%) | —% (—%, —%) | |
| Predicted Normal | 6,720 | 579 | 10.2% (9.3%, 11.2%) | 19.1% (17.0%, 21.3%) | |
| Heart Failure | | | | | <0.001 |
| Predicted Dilated | 1,432 | 121 | 10.7% (8.7%, 12.9%) | 17.9% (14.1%, 22.0%) | |
| Predicted Normal | 6,466 | 241 | 4.8% (4.1%, 5.5%) | 8.5% (7.0%, 10.1%) | |
| Heart Failure | | | | | <0.001 |
| Predicted Hypokinetic | 100 | 15 | 20.3% (10.5%, 32.2%) | 28.7% (16.1%, 42.6%) | |
| Predicted Normal | 7,798 | 347 | 5.6% (5.0%, 6.3%) | 9.9% (8.5%, 11.4%) | |
| Mortality | | | | | <0.001 |
| Predicted Dilated | 1,869 | 281 | 18.4% (16.2%, 20.7%) | 32.3% (27.6%, 37.1%) | |
| Predicted Normal | 7,072 | 550 | 9.0% (8.2%, 9.9%) | 16.2% (14.4%, 18.0%) | |
| Mortality | | | | | <0.001 |
| Predicted Hypokinetic | 238 | 75 | 38.6% (30.8%, 46.4%) | 52.1% (42.0%, 61.4%) | |
| Predicted Normal | 8,703 | 756 | 10.2% (9.4%, 11.0%) | 18.7% (16.9%, 20.5%) | |

[1]Logrank Test

TABLE 11-continued

| Variable | N Observations | N Events | HR | 95% Lower CI | 95% Upper CI | p-value |
|---|---|---|---|---|---|---|
| Weight (kg) | 8,941 | 831 | 0.99 | 0.99 | 1.00 | <0.001 |
| LV Ejection Fraction (%) | 8,941 | 831 | 0.98 | 0.97 | 0.98 | <0.001 |
| Mortality, unadjusted | | | | | | |
| Predicted RVEDD (mm) | 8,941 | 831 | 1.53 | 1.43 | 1.64 | <0.001 |

TABLE 12

| Variable | N Observations | N Events | HR | 95% Lower CI | 95% Upper CI | p-value |
|---|---|---|---|---|---|---|
| Heart Failure, adjusted | | | | | | |
| Predicted RVEDD (mm) | 7,898 | 362 | 1.40 | 1.23 | 1.58 | <0.001 |
| Age (Y) | 7,898 | 362 | 1.06 | 1.05 | 1.07 | <0.001 |
| Female | 4,066 | 164 | 1.00 | | | |
| Male | 3,832 | 198 | 0.80 | 0.59 | 1.08 | 0.146 |
| Height (cm) | 7,898 | 362 | 0.98 | 0.96 | 0.99 | <0.001 |
| Weight (kg) | 7,898 | 362 | 1.02 | 1.01 | 1.02 | <0.001 |
| LV Ejection Fraction (%) | 7,898 | 362 | 0.96 | 0.95 | 0.96 | <0.001 |
| Heart Failure, unadjusted | | | | | | |
| Predicted RVEDD (mm) | 7,898 | 362 | 1.54 | 1.39 | 1.72 | <0.001 |

TABLE 13

| Variable | N Observations | N Events | HR | 95% Lower CI | 95% Upper CI | p-value |
|---|---|---|---|---|---|---|
| Atrial Fibrillation, adjusted | | | | | | |
| Predicted RVEDD (mm) | 6,813 | 602 | 1.41 | 1.28 | 1.56 | <0.001 |
| Age (Y) | 6,813 | 602 | 1.06 | 1.05 | 1.06 | <0.001 |
| Female | 3,687 | 260 | 1.00 | | | |
| Male | 3,126 | 342 | 1.02 | 0.80 | 1.29 | 0.883 |
| Height (cm) | 6,813 | 602 | 0.99 | 0.98 | 1.00 | 0.120 |
| Weight (kg) | 6,813 | 602 | 1.01 | 1.00 | 1.01 | <0.001 |
| LV Ejection Fraction (%) | 6,813 | 602 | 0.98 | 0.97 | 0.98 | <0.001 |
| Atrial Fibrillation, unadjusted | | | | | | |
| Predicted RVEDD (mm) | 6,813 | 602 | 1.53 | 1.41 | 1.67 | <0.001 |

TABLE 14

| Variable | N Observations | N Events | HR | 95% Lower CI | 95% Upper CI | p-value |
|---|---|---|---|---|---|---|
| Mortality, adjusted | | | | | | |
| RV Systolic Dysfunction Probability | 8,941 | 831 | 1.18 | 1.13 | 1.24 | <0.001 |
| Age (Y) | 8,941 | 831 | 1.06 | 1.05 | 1.07 | <0.001 |
| Female | 4,449 | 336 | 1.00 | | | |
| Male | 4,492 | 495 | 1.40 | 1.16 | 1.69 | <0.001 |
| Height (cm) | 8,941 | 831 | 1.00 | 0.99 | 1.00 | 0.296 |
| Weight (kg) | 8,941 | 831 | 0.99 | 0.99 | 1.00 | 0.005 |
| LV Ejection Fraction (%) | 8,941 | 831 | 0.98 | 0.98 | 0.99 | <0.001 |
| Mortality, unadjusted | | | | | | |
| RV Systolic Dysfunction Probability | 8,941 | 831 | 1.29 | 1.24 | 1.33 | <0.001 |

TABLE 15

| Variable | N Observations | N Events | HR | 95% Lower CI | 95% Upper CI | p-value |
|---|---|---|---|---|---|---|
| Heart Failure, adjusted | | | | | | |
| RV Systolic Dysfunction Probability | 7,898 | 362 | 1.17 | 1.07 | 1.28 | <0.001 |
| Age (Y) | 7,898 | 362 | 1.06 | 1.05 | 1.07 | <0.001 |
| Female | 4,066 | 164 | 1.00 | | | |
| Male | 3,832 | 198 | 1.02 | 0.77 | 1.36 | 0.880 |
| Height (cm) | 7,898 | 362 | 0.98 | 0.97 | 0.99 | 0.007 |
| Weight (kg) | 7,898 | 362 | 1.02 | 1.01 | 1.02 | <0.001 |
| LV Ejection Fraction (%) | 7,898 | 362 | 0.96 | 0.95 | 0.97 | <0.001 |
| Heart Failure, unadjusted | | | | | | |
| RV Systolic Dysfunction Probability | 7,898 | 362 | 1.34 | 1.25 | 1.44 | <0.001 |

TABLE 16

| Variable | N Observations | N Events | HR | 95% Lower CI | 95% Upper CI | p-value |
|---|---|---|---|---|---|---|
| Atrial Fibrillation, adjusted | | | | | | |
| RV Systolic Dysfunction Probability | 6,813 | 602 | 1.15 | 1.07 | 1.23 | <0.001 |
| Age (Y) | 6,813 | 602 | 1.06 | 1.05 | 1.06 | <0.001 |
| Female | 3,687 | 260 | 1.00 | | | |
| Male | 3,126 | 342 | 1.31 | 1.05 | 1.63 | 0.018 |
| Height (cm) | 6,813 | 602 | 1.00 | 0.99 | 1.01 | 0.567 |
| Weight (kg) | 6,813 | 602 | 1.01 | 1.01 | 1.01 | <0.001 |
| LV Ejection Fraction (%) | 6,813 | 602 | 0.98 | 0.97 | 0.99 | <0.001 |
| Atrial Fibrillation, unadjusted | | | | | | |
| RV Systolic Dysfunction Probability | 6,813 | 602 | 1.25 | 1.17 | 1.33 | <0.001 |

Discussion

Disclosed herein is DROID-RV (e.g., the implementation 500 of FIG. 5), a deep learning model trained to predict RV size and function using the largest reported sample of paired TTE videos and RV labels to date, comprising over 380,000 echocardiogram videos and 50,000 studies from more than 17,000 cardiology patients. DROID-RV shows strong performance for estimating RVEDD and RV systolic dysfunction. DROID-RV was adapted to estimate RVEF using relatively few training examples with RVEF measurements. Using DROID-RV predictions, associations between RV size and function and incidence of AF, HF, and mortality were examined in over 55,000 primary care patients with long-term follow up.

The described techniques have several potential implications for RV assessment in clinical practice. First, the geometry of the RV makes RV assessment by TTE time consuming, relying on integration of information from multiple video clips. DROID-RV may streamline echocardiogram interpretation workflows by identifying studies or clips with RV abnormalities and providing preliminary measurements. Second, DROID-RV can be used to triage utilization of limited resources, such as 3-dimensional echocardiography or cardiac magnetic resonance imaging, which can better assess RV structure and function. Third, DROID-RV could augment echocardiogram interpretation at the point-of-care when rapid RV assessment is needed. The results described with respect to Example 2 demonstrate good performance across both primary care and cardiology cohorts, suggesting that DROID-RV is suitable to both screen a general population for RV abnormalities and to estimate RV size and function in patients with known cardiovascular disease.

Example 2 also demonstrates how deep learning-derived RV features can stratify cardiovascular risk at scale. One advantage of this technique is the use of large, high-quality EHR-derived cohorts with long-term follow up, which allows associations between model-predicted RV size and function and individual cardiovascular outcomes to be tested. When applied to the longitudinal primary care sample, DROID-RV enables the prognostic value of RV size and function to be assessed in a relatively unselected population with indications for TTE but not necessarily for detailed RV assessment. Despite the size of the C3PO primary care cohort, such an analysis is not feasible using clinically-derived RVEDD measurements due to their low availability. However, using DROID-RV, strong associations between predicted RVEDD and the probability of RV systolic dysfunction and the incidence of AF, HF, and mortality are indicated.

DROID-RV leverages the largest training sample of paired TTE videos and RV measurements to date, with 50% more patients and 5 times as many echocardiograms as the next largest training sample, and two orders of magnitude more training data than the next largest sample that reports clinical covariates. The large sample improves the performance of DROID-RV for prediction of RV systolic dysfunction compared to prior studies, which is sustained across two external validation samples. Moreover, DROID-RV provides quantitative estimates of RVEDD rather than predicting qualitative RV dilation. The results described with respect to Example 2 also highlight the effectiveness of a multi-step training approach that takes advantage of labels of varying granularity and frequency, a strategy which has not been applied to echocardiogram deep learning models. TTE interpretations may contain varying levels of detail depending on the patient, pathology, and indication for the study, which is challenging because the ultimate label of interest (e.g., RVEDD or RVEF) may be available in a small number of studies. DROID-RV addresses this problem via a multistep training process that first learns from qualitative labels (e.g., presence of RV dilation or systolic dysfunction), which are available for almost all studies, followed by fine-tuning using quantitative labels (e.g., RVEDD or RVEF), which are present for a smaller subset. This approach of combining qualitative and quantitative labels allows DROID-RV to accurately estimate RVEDD and improve estimation of RVEF.

Conclusions

A deep learning model was developed that predicts RVEDD and the probability of RV systolic dysfunction from echocardiogram videos in a sample of over 380,000 echocardiogram videos and 50,000 studies from over 17,000 longitudinal cardiology patients. This deep learning model generalizes well to two external validation samples, and model predictions of RV size and function are strongly associated with incidence of AF, HF, and mortality. Example 2 demonstrates the potential of deep learning to improve clinical workflows by enabling rapid and accurate assessment of RV structure and function from two-dimensional echocardiography.

Example 3: A Deep Learning Model to Identify Mitral Valve Prolapse from Echocardiogram Videos Mitral valve prolapse (MVP) affects an estimated 2-3% of the population and has been associated with heart failure, atrial and ventricular arrhythmias, and sudden cardiac death. MVP most often occurs due to myxomatous degeneration of the mitral valve (MV), and is characterized not only by prolapse of the MV into the left atrium (LA), but also by fibromyxomatous changes that can cause the valve to appear thickened. MVP is typically diagnosed by 2-dimensional transthoracic echocardiography (TTE) when the MV is displaced at least 2 mm into the LA during systole on a parasternal long axis (PLAX) view, and assessment of MVP is part of a standard comprehensive TTE exam. However, due to the complex 3-dimensional saddle shape of the MV, MVP has historically been over-diagnosed when assessed by 2-dimensional TTE. Achieving the correct diagnosis of MVP by TTE therefore relies on significant clinical expertise and knowledge of the geometry of the MV.

As demonstrated herein, deep learning techniques can be applied to digital TTE video clips to automatically and accurately estimate features such as left ventricular size and function (Example 1) and right ventricular function (Example 2). In Example 3, a deep learning model (Dimensional Reconstruction of Imaging Data—Mitral Valve Prolapse [DROID-MVP]) is trained to classify MVP using over 1,000,000 TTE video clips from over 50,000 studies performed on over 17,000 longitudinal cardiology patients, with additional validation in an independent sample of over 8,900 longitudinal primary care patients. DROID-MVP may correspond to the implementation 600 described with respect to FIG. 6, for example. As such, Example 3 applies deep learning to identify MVP in a general population. The echocardiographic features that influence DROID-MVP predictions are also investigated through detailed examination of incorrect predictions, multiple subgroup analyses, and visualization of model gradients. Furthermore, in Example 3, the capabilities of DROID-MVP are explored beyond MVP classification, including the ability of DROID-MVP to stratify MR severity without Doppler imaging and determine risk of future MV repair or replacement (MVR).

Methods
Study Populations

Figure 32:
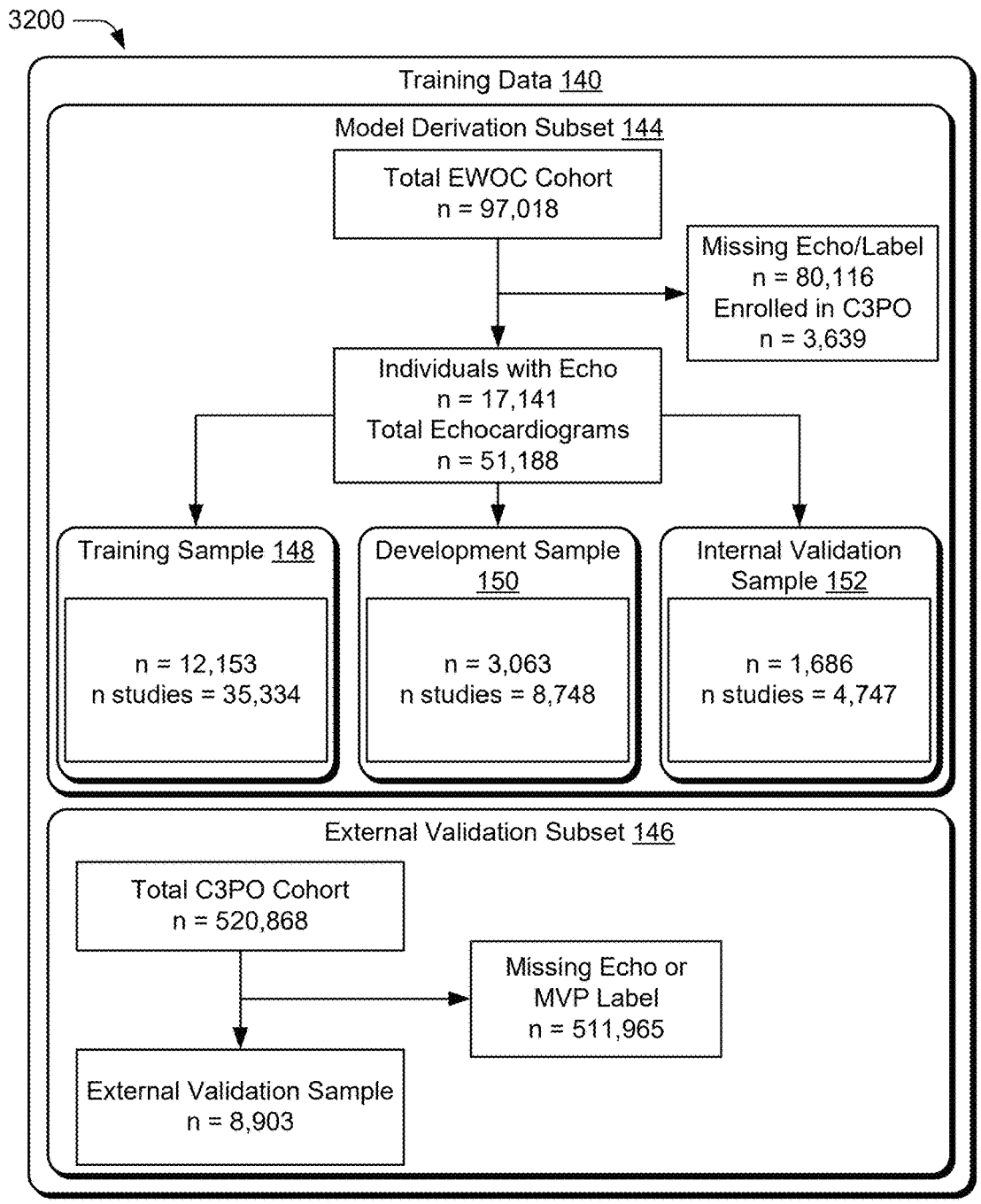
FIG. 32 illustrates a summary of the training data used for developing deep learning models for the assessment of mitral valve prolapse (MVP).

FIG. 32 illustrates a summary 3200 of the training data 140 used for developing deep learning models for the assessment of mitral valve prolapse. In Example 3, the study population for the training data 140 was derived from two electronic health record (EHR)-based cohorts of longitudinal cardiology and primary care patients within the Mass General Brigham (MGB) healthcare system. The DROID-MVP model was derived and internally validated (e.g., the model derivation subset 144) using echocardiograms from patients belonging to the Enterprise Warehouse of Cardiology (EWOC), a cohort of adults age 18 to 89 years receiving longitudinal cardiology care at MGB clinics between 2000 and 2019. Patients in this cohort were included during study training if they had at least one echocardiogram performed at Massachusetts General Hospital (MGH) with available PLAX, apical 4 chamber (A4C), apical 3 chamber (A3C), or apical 2 chamber (A2C) video clips and echocardiographer-adjudicated MVP labels.

External validation was performed using data from the Community Care Cohort Project (C3PO), a distinct cohort of patients aged 18 to 89 years receiving longitudinal primary care in the MGB system between 2001 and 2018. Patients in C3PO were included in the external validation sample (e.g., the external validation subset 146) if they had at least one echocardiogram performed at MGH within the 3 years prior to the start of follow up with available video clips for the appropriate views and MVP labels. Patients who were included in both the EWOC and C3PO cohorts (n=3, 639) were excluded from model training and included in the external validation sample.

As shown in the summary 3200, the training sample 148 included 35,334 echocardiogram videos obtained for 12,153 individuals, the development sample 150 included 8,748 echocardiogram videos obtained for 3,063 individuals, and the internal validation sample 152 included 4,747 echocardiogram videos obtained for 1,686 individuals. The external validation subset 146 included 8,903 individuals.

Echocardiogram and Training Label Acquisition and Pre-processing

Echocardiogram digital video clips and echocardiographer labels were derived from the MGH Echocardiography Laboratory Database, which contains data for all clinically indicated echocardiography studies performed at MGH since 1980. Studies performed on patients belonging to either the derivation (e.g., the model derivation subset 144) or validation (e.g., the external validation subset 146) cohorts were identified and cross-referenced with EHR-derived clinical data using medical record numbers.

Echocardiogram video clips were pre-processed as described with respect to Example 1 and Example 2. Each video clip was processed to remove patient identifying information and superimposed labels added by scanning equipment, sonographers or echocardiographers, such as by using the data preprocessor 132 introduced with respect to FIG. 1. A custom pipeline was developed to remove protected health information and data overlaid by scanning equipment including electrocardiogram and respirometer tracings.

TTE clips were processed (e.g., by the data preprocessor 132) to standardize resolution to 224 by 224 pixels, and 16 frames were chosen from each clip by selecting a starting frame and every 4th subsequent frame. During model training, if the total video length was greater than 64 (4×16) frames, the starting frame was randomly selected from the initial n frames where n=total # of frames−64. If the video length was shorter than 64 frames, the first frame was used as the starting frame and the clip was padded using frames from the beginning of the clip. During model evaluation, the first frame of each clip was always used as the starting frame to ensure reproducible results. The final input tensor to the model has the shape (16, 224, 224, 3).

Separate deep learning models were trained to 1) classify which of the standard echocardiographic views a clip represents, 2) whether the clip is on-axis or off-axis, 3) whether the clip represents a standard 2-dimensional B-mode clip, Doppler clip, or 3-dimensional clip, and 4) whether the clip is of interpretable quality (e.g., good versus poor). These labels were used to select clips for inclusion during model training of DROID-MVP. In Example 3, on-axis, interpretable, 2-dimensional B-mode (non-Doppler) video clips representing PLAX, A4C, A3C, and A2C views were included for DROID-MVP training.

Each study was classified by an interpreting echocardiographer into one of the following categories: 1) unspecified MVP, 2) anterior leaflet prolapse, 3) posterior leaflet prolapse, 4) bileaflet prolapse, 5) superior displacement of the MV not meeting criteria for MVP, and 6) normal. For model training and evaluation, patients with prolapse of any leaflet were classified as "MVP," and patients labeled as superior displacement of the MV or normal were classified as "normal." These echocardiographer-based classifications were used as the ground truth label 206 for the associated echocardiogram video 204 for a given training instance 202.

LV and LA measurements were filtered to remove non-physiologic values. For instance, left heart measurements, including left atrial anterior-posterior dimension (LAAPD), left ventricular (LV) ejection fraction (LVEF), LV end-systolic diameter (LVESD), and LV end-diastolic diameter (LVEDD), were obtained from the Massachusetts General Hospital EchoLab Database. LAAPD, LVESD, and LVEDD values were converted to millimeters, and values <0 or >150 mm were excluded.

Mitral valve regurgitation (MR) severity was reported on a seven-point scale, ranging from "none" to "severe," including intermediate steps (i.e., "moderate-severe"). Values indicating unknown severity or prosthetic valve regurgitation were removed, and MR severity was converted to a four-point scale (none/trace, mild, moderate, severe), with intermediate values classified as the higher severity level (i.e., moderate-severe MR was classified as severe).

Patient Characteristics and Outcomes

Patient demographics, measurements, comorbidities, and outcomes were derived from EHR and tabular echocardiogram data. Demographic data included age, race, ethnicity, and sex. Race and ethnicity were extracted from a combined field from the EHR database. Missing height and weight was obtained using the values from the most proximal echocardiogram study, when available. Presence of baseline comorbidities was determined by presence of a single International Classification of Diseases-9 or -10 code corresponding to the comorbidity on or prior to the start of cohort follow up, with the exception of heart failure, which was defined using codes corresponding to a primary diagnosis of HF for an inpatient encounter. MVR was determined using Current Procedural Terminology codes 33418, 33419, 33425, 33426, 33427, 33430, 0343T, and 0345T.

Height and weight were obtained from tabular data from the MGH EchoLab dataset. When reported at the patient level, the earliest available echocardiogram height or weight measurement was used. Height and weight values were processed to reconcile units, remove non-physiologic values, and limit missingness. Height and weight values were converted to kilograms and centimeters, respectively, and filtered to exclude likely non-physiologic values (i.e., height <121.92 cm [4 ft] or height >304.8 cm [10 ft]; weight <13.6 kg [30 lbs] or weight >454.5 kg [1000 lbs]).

Model Development

Patients in the model derivation sample (e.g., the model derivation subset 144) were divided into training (e.g., the training sample 148), development (e.g., the development sample 150), and internal validation (e.g., the internal validation sample 152) cohorts using an approximate 70%/20%/10% split. During model training, multiple TTE studies were used per patient when available. During internal validation, only the first study was used for each patient. One study per patient was available in the external validation sample. Since each echocardiogram study contains multiple video clips, and DROID-MVP generates a separate prediction for each input video clip, video-level predictions were aggregated into study-level predictions by taking the median of all predictions for each study. Model performance was evaluated at the study-level, except when reporting performance by view which was done at the video-level.

DROID-MVP is a convolutional neural network with two spatial dimension and one temporal dimension based on the MoViNet A2 architecture. An iterative approach to model development was used to develop a model trained to predict both binary MVP status and a six category prediction corresponding to the detailed MVP labels (e.g., unspecified MVP, anterior leaflet prolapse, posterior leaflet prolapse, bileaflet prolapse, superior displacement of the MV not meeting criteria for MVP, and normal); only binary MVP labels (e.g., "MVP" or "normal") were used for downstream analyses. Model training was performed using the ml4 h library (version 0.0.7 with modifications), 18 Python (version 3.8), and TensorFlow (version 2.5.0).

In the Example 3, DROID-MVP includes removal of the final convolutional layer and replacement with one or more classification and regression heads, each with a 256-node hidden dense layer followed by an output layer with a number of nodes equal to the number of classes or regression variables. Each model that was evaluated contained a classification head for binary classification of MVP, with the possible addition of other heads depending on the co-training tasks being evaluated. Each classification head has a number of nodes equal to the number of categories for that task, and a softmax activation function is applied. The pre-trained MoViNet weights were used for layers derived from MoViNet-A2, and other layer weights were initialized randomly.

An initial model was trained with a single mitral valve prolapse binary classification head, using only PLAX views, and taking every 4th frame to a total of 16 frames per view as input. An iterative search was performed to identify the set of hyperparameters (e.g., the hyperparameters 228), views, and co-training tasks that maximized performance of the model with respect to MVP classification. Hyperparameters to be optimized included the number of frames (16 versus 32) per video clip during model input and the number of frames to skip between selected frames (0, 1, 2, or 3). The set of views that were explored included the PLAX view plus 1) apical 4 chamber (A4C) view, 2) A4C, apical 3 chamber, and apical 2 chamber views, or 3) parasternal short axis views at the mitral valve level. The sets of co-training tasks that were explored, in addition to binary classification of MVP, included 1) multiclass MVP classification according to the detailed labels available in the MGH Echocardiography Laboratory database, 2) patient metrics including age, sex, height, weight, and body surface area, 3) mitral valve regurgitation severity, and 4) left heart measurements, including left ventricular (LV) ejection fraction, LV end-systolic diameter, LV end-diastolic diameter, and left atrial anterior-posterior dimension. The best set of hyperparameters was carried forward during view selection, and the best set of views was carried forward when selecting co-training tasks. The best performing model utilized the following parameters: 16 frames taking every 4th frame; inclusion of all apical views in addition to the PLAX view; and use of a second classification head for detailed MVP labels in addition to the binary MVP label during training. This is the model used with respect to the results described herein for Example 3.

The categorical cross-entropy loss function was minimized for classification tasks, and for regression tasks the mean square error loss function was minimized. Loss across all heads was summed and jointly minimized using the Adam optimizer with an initial learning rate of 1 e–4. A batch size of 16 was used. Early stopping was employed if the validation set loss failed to improve for 15 epochs, and the checkpoint with the lowest validation loss was used. For computational efficiency, each epoch was limited to 3000 training steps and 1000 validation steps.

Saliency Mapping

Saliency maps were generated by taking the gradient of the mitral valve prolapse output prediction with respect to its given input video and converting the resulting gradients to an overlay. Since the resulting tensor of gradients has the same shape as the input video, it can be overlayed on the original input video for visualization. Saliency maps were generated for randomly selected example videos in the internal test sample (e.g., the internal validation sample 152) for visualization. The process for converting gradients to the color overlay is as follows: for each pixel, the absolute value of each gradient was determined in the red/green/blue color channels, and the maximum value was selected. The values at the 0.0001 and 0.9999 thresholds were winsorized to better visualize a color heatmap. Floating point values between 0 and 1 were then converted to red/green/blue values using the matplotlib "magma" color map and averaged with the input image pixel values. The resulting arrays were converted to GIF images for visualization, and the GIF images depict the frame with the highest summed saliency value across all pictures for 2D visualization.

Statistical Analyses

Normally distributed data are reported as means+/−standard deviation (SD). Non-normally distributed data are reported as median (interquartile range [IQR]), and categorical data are reported as counts (%). Performance characteristics of the model with respect to binary classification of MVP are reported using area under the receiver-operator curve and area under the precision-recall curve, and using overall classification accuracy, sensitivity, specificity, precision, recall, and F1 score. To obtain a predicted MVP class, the continuous DROID-MVP prediction was dichotomized at a threshold that maximized classification accuracy in the model development sample (e.g., the development sample 150), which was 0.470. Fisher's exact test was used to compare the number of expected and observed cases when analyzing false positive and false negative predictions.

The test-retest variability of DROID-MVP and echocardiographer MVP classifications was examined on serial TTE studies using Cohen's kappa statistic. The p-values reported for the comparison between kappa statistics calculated for DROID-MVP and echocardiographer MVP classifications on serial studies was calculated as follows. First, the variances of the individual kappa statistics were averaged, and the square root was taken to obtain a pooled standard deviation. The probability of observing the difference between the kappa statistics under the null hypothesis of a mean difference of 0 with the pooled standard deviation was then calculated.

Associations with MR severity and left heart measurements were tested using multivariable logistic and linear regression performed on cases with complete covariate data. Associations between model-predicted MVP and incident MVR was tested using the Kaplan-Meier estimator and log-rank test and with multivariable Cox proportional hazards regression. Patients were censored at the date of last encounter available in the EHR, on the administrative censoring date of Aug. 31, 2019, or on the date of death. Statistical analyses were done using R (version 4.3.2) with packages pROC (version 1.18.5), survival (version 3.5-7), survminer (version 0.4.9), and yardstick (version 1.3.0).

White) with at least 1 TTE and echocardiographer-adjudicated MVP label were identified. The C3PO external validation population had a lower prevalence of MVP (n=197 [2.2%]) and moderate or greater MR (n=506 [5.7%]) compared to the model derivation population, and cardiovascular comorbidities and risk factors were generally less common (Table 17).

TABLE 17

| Characteristic | Model Derivation | Model Validation |
| --- | --- | --- |
| N | 17,454 | 8,903 |
| Age (y) | 61.4 ± 17.4 | 55.7 ± 17.6 |
| Sex | | |
| Female | 6,680 (38.3) | 4,436 (49.8) |
| Male | 10,774 (61.7) | 4,467 (50.2) |
| Race or Ethnicity | | |
| Asian or Pacific Islander | 481 (2.8) | 450 (5.1) |
| Black | 426 (2.4) | 593 (6.7) |
| Hispanic or Latino | 292 (1.7) | 251 (2.8) |
| Other/Unknown | 942 (5.4) | 550 (6.2) |
| White | 15,313 (87.7) | 7,059 (79.3) |
| Mitral Valve Prolapse | 813 (4.7) | 197 (2.2) |
| Moderate or Severe Mitral Regurgitation | 3,056 (17.5) | 506 (5.7) |
| Chronic Kidney Disease | 3,328 (19.1) | 2,053 (23.1) |
| Coronary Artery Disease | 9,905 (56.9) | 3,519 (39.5) |
| Diabetes Mellitus | 3,504 (20.1) | 1,943 (21.8) |
| Heart Failure | 2,468 (14.2) | 1,018 (11.4) |
| Hyperlipidemia | 10,887 (62.6) | 5,315 (59.7) |
| Hypertension | 12,318 (70.8) | 6,094 (68.4) |
| Left Ventricular Ejection Fraction (%) | 64.0 (56.0, 70.0) | 66.0 (61.0, 71.0) |
| Left Ventricular End Systolic Dimension (mm) | 32.5 ± 8.7 | 30.3 ± 6.5 |
| Left Ventricular End Diastolic Dimension (mm) | 47.1 ± 7.6 | 45.8 ± 6.3 |
| Left Atrial A-P Dimension (mm) | | |
| Mean ± SD | 40.7 ± 7.0 | 38.4 ± 6.7 |
| Missing | 6,501 (37.2) | 4,201 (47.2) |
| Height (cm) | | |
| Mean ± SD | 170.9 ± 10.7 | 169.3 ± 10.6 |
| Missing | 1,009 (5.8) | 1,001 (11.2) |
| Weight (kg) | | |
| Mean ± SD | 82.3 ± 21.0 | 81.4 ± 22.2 |
| Missing | 978 (5.6) | 976 (11.0) |

Results

Model Derivation and Validation Populations

DROID-MVP was trained and internally validated in longitudinal cohort of 97,018 ambulatory cardiology patients (Enterprise Warehouse of Cardiology, EWOC). Within the EWOC cohort, 51,188 TTE studies belonging to 17,141 patients (mean age at first echocardiogram 61.4±17.4 years; 6,680 [38.3%] women; 15,313 (87.7%) White) were identified for whom TTE video clips and echocardiographer-adjudicated MVP labels were available, which was used as the model derivation subset 144 (see the summary 3200 of FIG. 32). In total, the model derivation sample included 1,077,968 PLAX, A4C, A3C, and A2C video clips. A total of 913 (4.7%) patients had at least one TTE study demonstrating MVP, and 3,056 (17.5%) had at least one TTE study demonstrating moderate or greater MR.

For Example 3, the external validation subset 146 was derived from a cohort of 520,868 longitudinal primary care patients (Community Care Cohort Project, C3PO). Within C3PO, 8,903 patients (mean age at echocardiogram 55.7±17.6 years; 4,436 [49.8%] women; 7,059 (79.3%)

Model Performance for Mitral Valve Prolapse Classification

Figure 33:
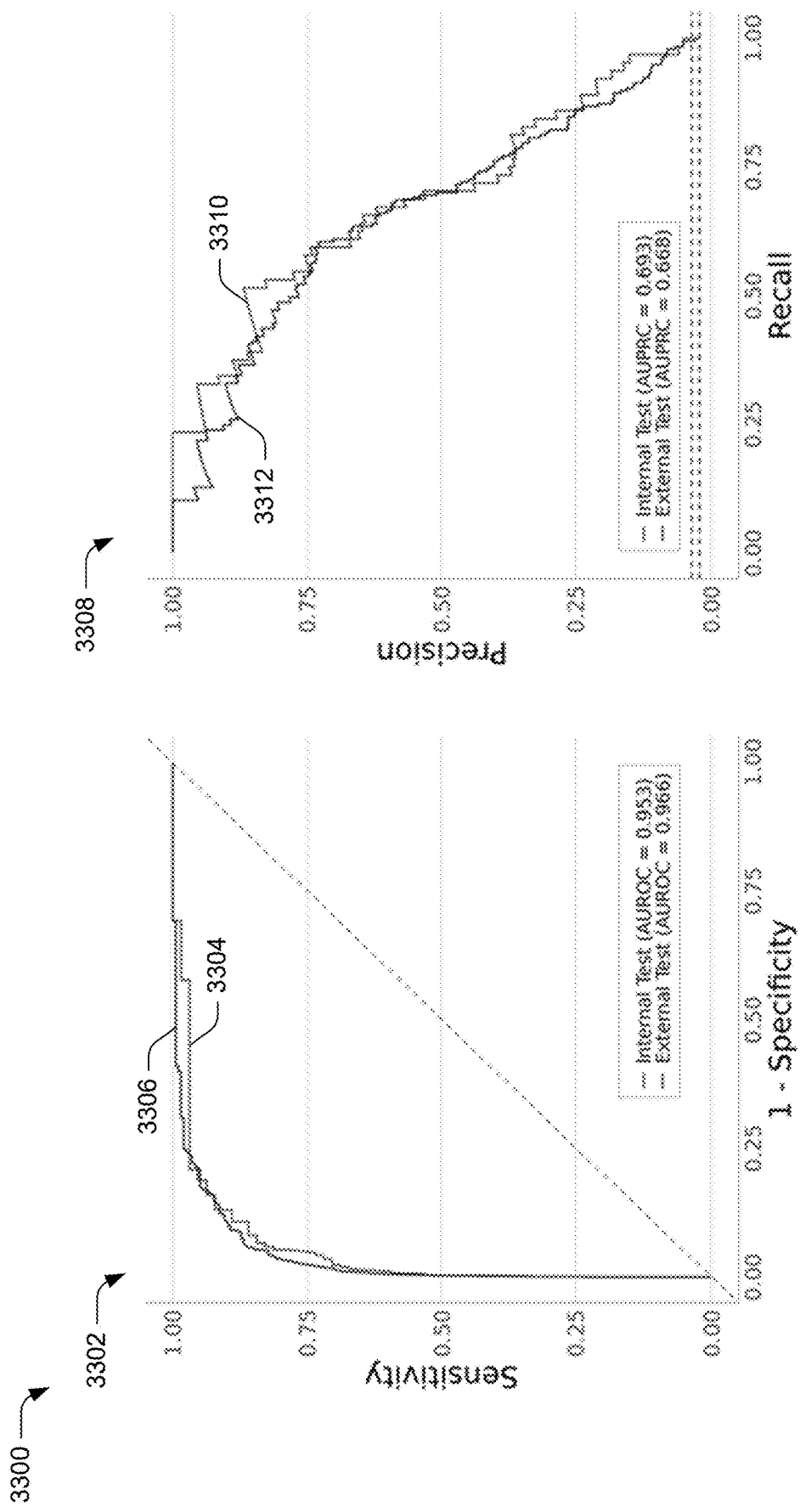
FIG. 33 shows an example analysis of deep learning model performance for predicting MVP classification.

FIG. 33 shows an example analysis 3300 of deep learning model performance for predicting MVP classification. The analysis 3300 includes receiver operating characteristic (ROC) curves 3302, including a first ROC curve 3304 corresponding to the internal validation sample (e.g., the internal validation sample 152) and a second ROC curve 3306 corresponding to the C3PO external validation sample (e.g., the external validation subset 146). The analysis 3300 further includes precision recall curves 3308, including a first precision recall curve 3310 corresponding to the internal validation sample and a second precision recall curve 3312 corresponding to the C3PO external validation sample.

DROID-MVP achieved excellent study-level discrimination of MVP in the internal test (area under the receiver-operator curve [AUROC] 0.953 [95% CI:0.924-0.978]; the first ROC curve 3304) and external test samples (AUROC 0.966 [0.955-0.978]; the second ROC curve 3306). Average precision was 0.693 (0.579-0.791; prevalence 0.037; the first precision recall curve 3310) in the internal test sample and 0.668 (0.601-0.730; prevalence 0.022; the second precision recall curve 3312) in the external test sample. Using the probability cutoff which maximized overall accuracy in the model development sample, the DROID-MVP achieved an overall study-level classification accuracy of 97.8% in the internal test sample and 98.6% in the external test sample. Confusion matrices and other model performance characteristics are provided in Tables 18-20.

TABLE 18

Internal Validation Sample Confusion Matrix

| Prediction | Reference Normal Mitral Valve | Mitral Valve Prolapse |
|---|---|---|
| Normal Mitral Valve | 1655 | 31 |
| Mitral Valve Prolapse | 7 | 33 |

TABLE 19

External Validation Sample Confusion Matrix

| Prediction | Reference Normal Mitral Valve | Mitral Valve Prolapse |
|---|---|---|
| Normal Mitral Valve | 8680 | 101 |
| Mitral Valve Prolapse | 26 | 96 |

TABLE 20

Additional Model Performance Characteristics

| Sample | Accuracy | Sensitivity | Specificity | PPV | NPV | F1 |
|---|---|---|---|---|---|---|
| Internal Test | 0.978 | 0.516 | 0.996 | 0.825 | 0.982 | 0.635 |
| External Test | 0.986 | 0.487 | 0.997 | 0.787 | 0.988 | 0.602 |

Given the inclusion of A4C, A3C, and A2C views during model training and evaluation, despite MVP typically being diagnosed from the PLAX view, model performance stratified by view was examined.

Figure 34:
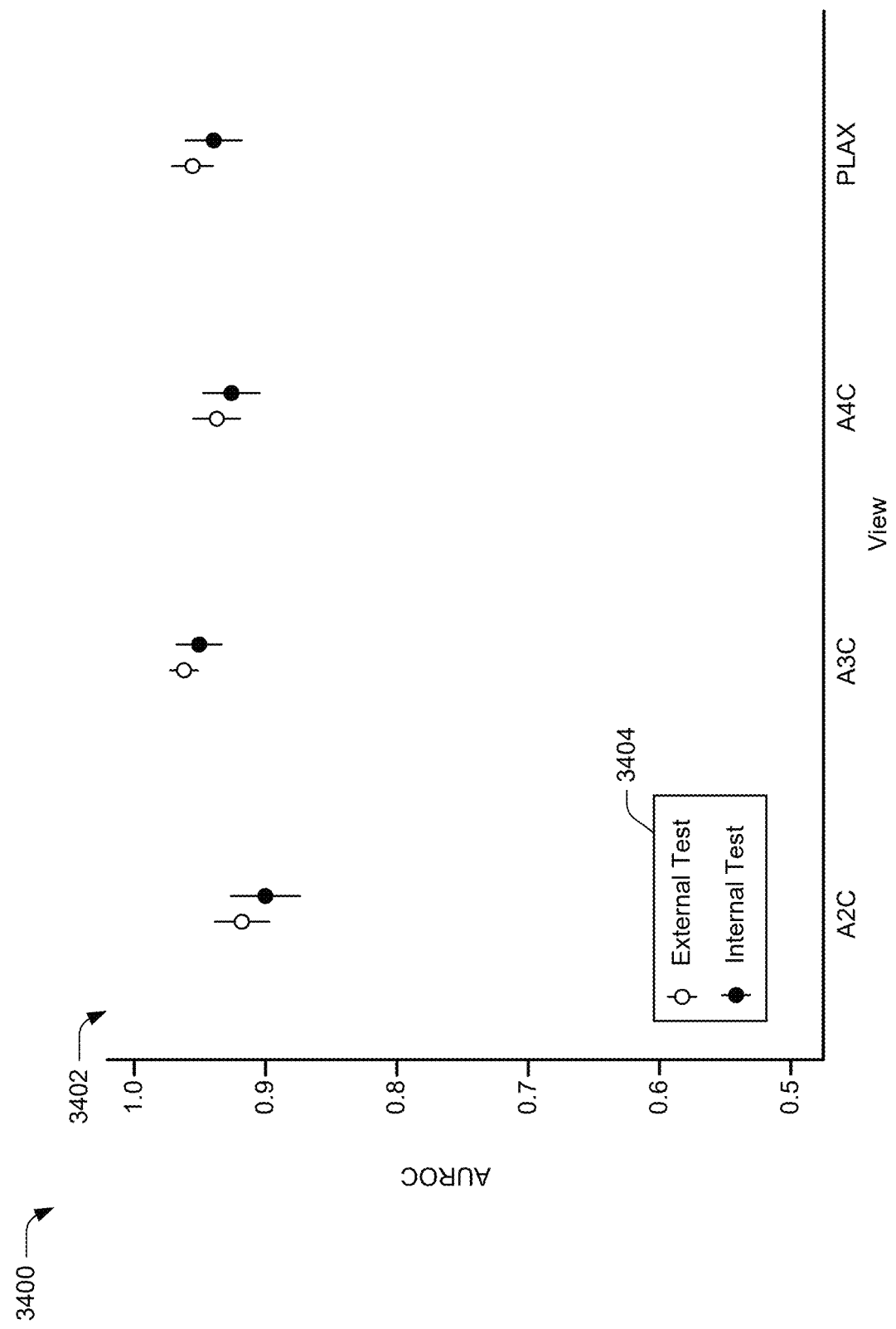
FIG. 34 shows an example analysis comparing view-level MVP classification in the internal and external test sets, as stratified by echocardiographic view.

FIG. 34 shows an example analysis 3400 comparing view-level MVP classification in the internal and external test sets, as stratified by echocardiographic view. The analysis 3400 includes a plot 3402 of the AUROC (vertical axis) for a given view (horizontal axis), as labeled, for the external validation subset 146 ("external test") and the internal validation sample 152 ("internal test"). A legend 3404 denotes that the external test data points are indicated by open or white-filled circles, whereas the internal test data points are indicated by black-filled circles.

As can be appreciated via the analysis 3400, model performance differed but remained strong across all views, with the lowest AUROC seen for the A2C view and the highest for the A3C view (internal test AUROC range: 0.900-0.951; external test AUROC range 0.919-0.963). Model performance was also assessed across subgroups of age, sex, and race, which were largely consistent and are shown in Table 21.

TABLE 21

| Sample | Subgroup | n | n MVP Cases | AUROC | Lower 95% CI | Upper 95% CI |
|---|---|---|---|---|---|---|
| Internal Validation | Female | 651 | 26 | 0.973 | 0.951 | 0.994 |
| Internal Validation | Male | 1,075 | 38 | 0.941 | 0.896 | 0.985 |
| External Validation | Female | 4,436 | 96 | 0.962 | 0.942 | 0.981 |
| External Validation | Male | 4,467 | 101 | 0.970 | 0.957 | 0.983 |
| Internal Validation | Age <65 | 871 | 26 | 0.938 | 0.889 | 0.987 |
| Internal Validation | Age >=65 | 855 | 38 | 0.965 | 0.931 | 0.999 |
| External Validation | Age <65 | 5,760 | 106 | 0.976 | 0.966 | 0.986 |
| External Validation | Age >=65 | 3,143 | 91 | 0.949 | 0.923 | 0.974 |
| Internal Validation | Non-White | 202 | 6 | 0.883 | 0.704 | 1.000 |
| Internal Validation | White | 1,524 | 58 | 0.961 | 0.938 | 0.985 |
| External Validation | Non-White | 1,844 | 24 | 0.976 | 0.958 | 0.994 |
| External Validation | White | 7,059 | 173 | 0.964 | 0.950 | 0.977 |

Analysis of Discordant Predictions

TTE studies where DROID-MVP predictions were discordant with echocardiographer-adjudicated MVP status were investigated. Thirty-three "false positive" studies were identified across the combined internal and external validation sets. In these thirty-three studies, the model classified as MVP but echocardiographers classified as normal (e.g., the model output 208 did not match the ground truth label 206). Of these thirty-three studies, 17 (51.5%) corresponded to studies adjudicated as superior displacement of the MV not meeting criteria for MVP. In comparison, only 259 (2.5%) of 10,335 true negative cases were labeled as superior displacement of the MV (p<0.001).

It was also assessed whether patients misclassified by DROID-MVP represent borderline cases that may have discordant echocardiographer adjudications on serial TTE studies. For this assessment, 999 patients in the internal validation set with multiple studies, excluding studies performed after MVR, were identified. The relationship between DROID-MVP predictions on the index study and changes in echocardiographer-adjudicated MVP status on future studies was studied. Among the thirty-three total patients with echocardiographer-adjudicated MVP on the index study, 8/13 (61.5%) with predicted normal MV (i.e., "false negatives") on the index study had a future study reporting a normal MV, as compared to 3/20 (15.0%) of patients with predicted MVP (p=0.009). Similarly, among 966 total patients with echocardiographer-adjudicated normal MV on the first study, 3/3 (100%) with predicted MVP on the index study (i.e., "false positives") had a future study with echocardiographer-adjudicated MVP, as compared to 17/963 (1.8%) with predicted normal MV (p<0.001).

The test-retest variability of both DROID-MVP and echocardiographer MVP classifications was assessed across repeated studies on the same patient using Cohen's kappa statistic. First, 10,594 unique pairs of studies performed on the same patient in the internal validation set were identified, excluding studies performed after MVR. Within this sample, the kappa statistic for test-retest agreement of serial echocardiographer assessments of MVP was 0.75 (95% CI:0.71-0.79), indicating substantial agreement. In comparison, the kappa statistic for serial DROID-MVP predictions was 0.80 (95% CI:0.75-0.85), indicating superior test-retest agreement (p=0.019).

severity (internal test AUROC range 0.941-0.988; external test AUROC range 0.921-0.987), indicating that DROID-MVP predictions are influenced by but not dependent on detection of MR. Note that there were only six cases of MVP with trace or no MR in the internal test set, resulting in wide confidence intervals.

Multivariable-adjusted associations between the MVP score and LV ejection fraction, end-systolic diameter, end-diastolic diameter, and LA anterior-posterior dimension were also examined among patients with echocardiographer-adjudicated MVP, which were not significantly different between MVP score groups among patients with MVP (Table 22).

TABLE 22

Associations between MVP Score and Left Heart Measurements

| Outcome | Comparison | Beta | Lower 95% CI | Upper 95% CI | P-value |
|---|---|---|---|---|---|
| LVEDD | Intermediate vs Low MVP Score | −0.915 | −2.849 | 1.020 | 0.352 |
| LVEDD | High vs Low MVP Score | 0.588 | −1.121 | 2.297 | 0.499 |
| LVESD | Intermediate vs Low MVP Score | −0.857 | −2.728 | 1.013 | 0.367 |
| LVESD | High vs Low MVP Score | −0.464 | −2.117 | 1.189 | 0.581 |
| LAAP | Intermediate vs Low MVP Score | −0.493 | −3.123 | 2.137 | 0.712 |
| LAAP | High vs Low MVP Score | 1.543 | −0.851 | 3.938 | 0.205 |
| LVEF | Intermediate vs Low MVP Score | 0.813 | −2.168 | 3.793 | 0.592 |
| LVEF | High vs Low MVP Score | 2.263 | −0.372 | 4.897 | 0.092 |

Association of Model Predictions with Mitral Valve Regurgitation

Due to the close relationship between MVP and MR, associations between DROID-MVP predictions and MR severity were examined.

Figure 35:
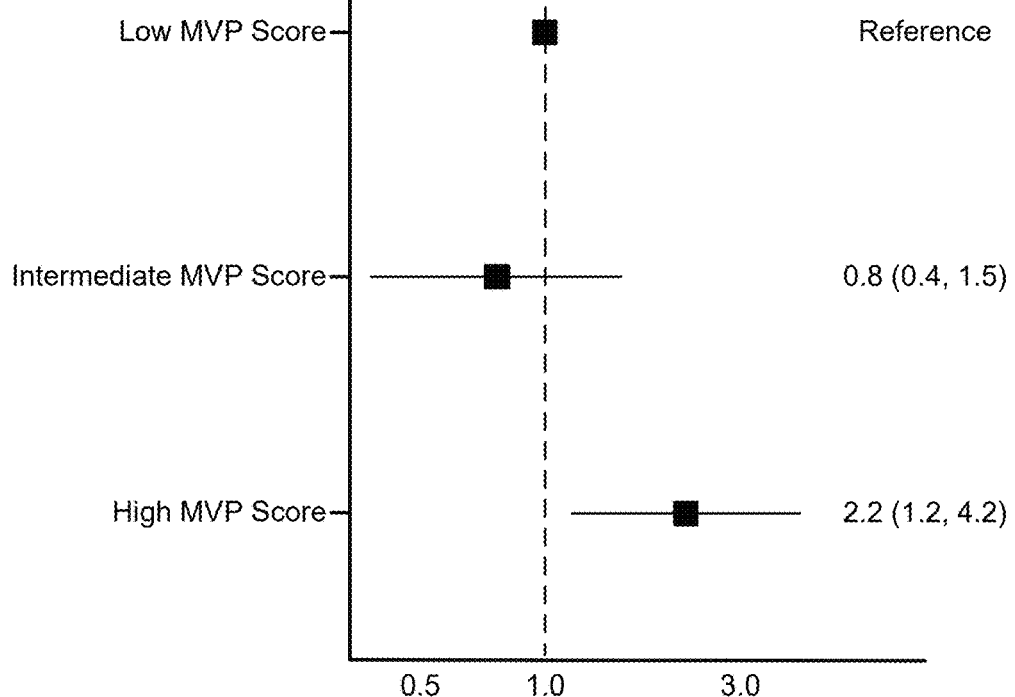
FIG. 35 shows an example analysis of the association between a deep learning model-predicted probability of MVP and a presence of moderate or severe mitral valve regurgitation, after adjustment for age, sex, height, and weight.

FIG. 35 shows an example analysis 3500 of the association between a DROID-MVP predicted probability of MVP (e.g., an MVP score) and a presence of moderate or severe mitral valve regurgitation, after adjustment for age, sex, height, and weight. The analysis 3500 includes a plot 3502 of the MVP score classified as low, intermediate, or high (vertical axis) versus an adjusted odds ratio for moderate or severe MR (horizontal axis). For the analysis 3500, the internal and external validation sets were combined. Patients were classified as having low (<0.33), intermediate (0.34-0.66), or high (>0.67) model-predicted probability of MVP ("MVP score"). Among patients with echocardiographer-adjudicated MVP and available covariates (n=236), a high versus low MVP score was associated with greater odds of moderate or severe MR (odds ratio 2.2 [1.2-4.2]; p=0.02), after adjustment for age, sex, height, and weight.

Although DROID-MVP was trained and evaluated exclusively on standard echocardiogram videos that do not include color Doppler imaging, given the strong associations between DROID-MVP predictions and MR severity, classification performance of DROID-MVP across strata of MR severity was also evaluated.

Figure 36:
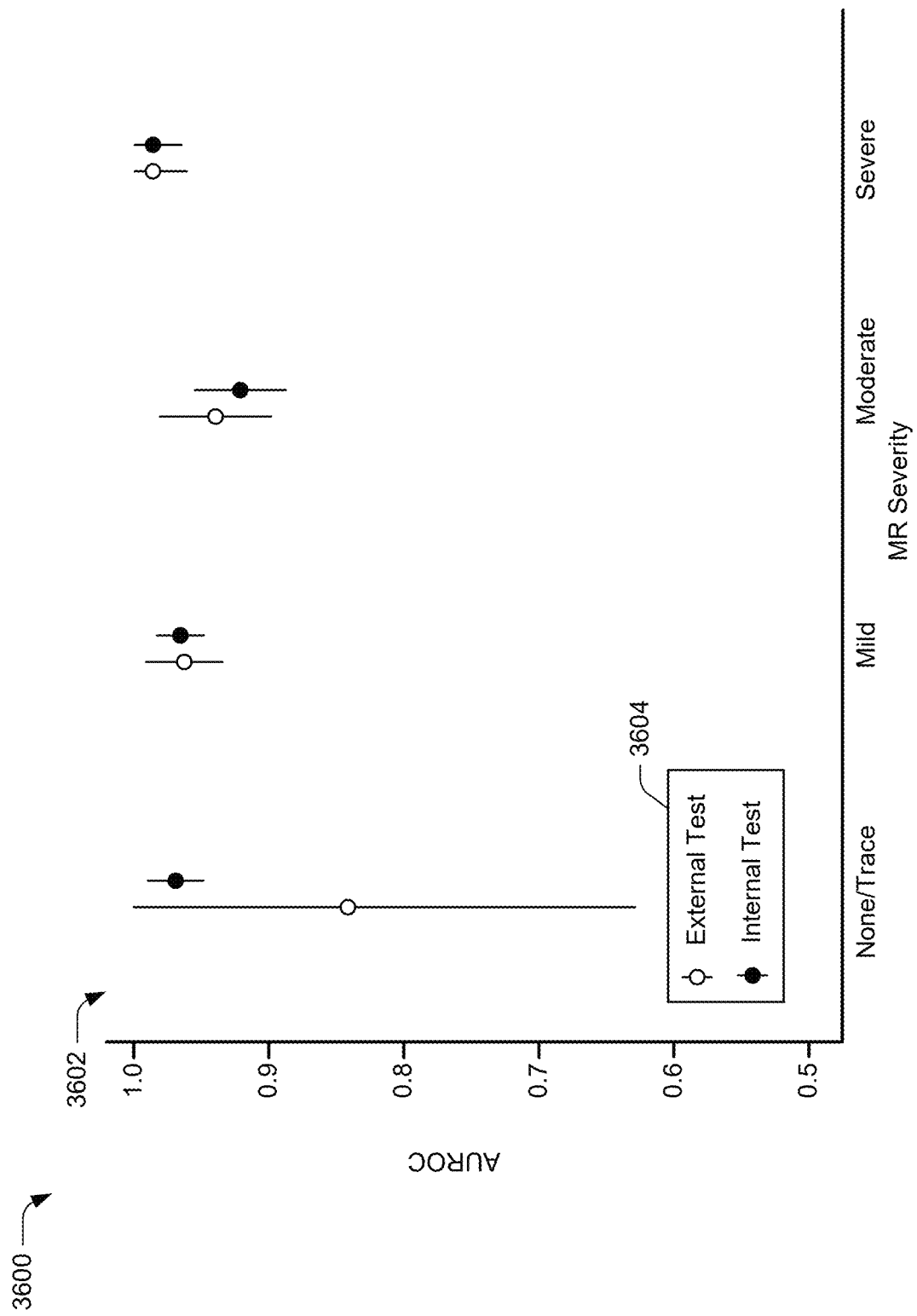
FIG. 36 shows an example analysis of deep learning model performance in internal and external test sets stratified by the presence of mitral valve regurgitation.

FIG. 36 shows an example analysis 3600 of deep learning model performance in internal and external test sets stratified by the presence of mitral valve regurgitation. The analysis 3600 includes a plot 3602 of the AUROC (vertical axis) for a given MR severity (horizontal axis), as labeled, for the external validation subset 146 ("external test") and the internal validation sample 152 ("internal test"). A legend 3604 denotes that the external test data points are indicated by open or white-filled circles, whereas the internal test data points are indicated by black-filled circles.

As can be appreciated via the analysis 3600, classification performance varied but remained strong across strata of MR Association of Model Predictions with Mitral Valve Repair or Replacement The association between MVP score and incidence of mitral valve repair or replacement (MVR) was assessed to explore whether the MVP score can identify patients with disease that will ultimately result in intervention.

Figure 37:
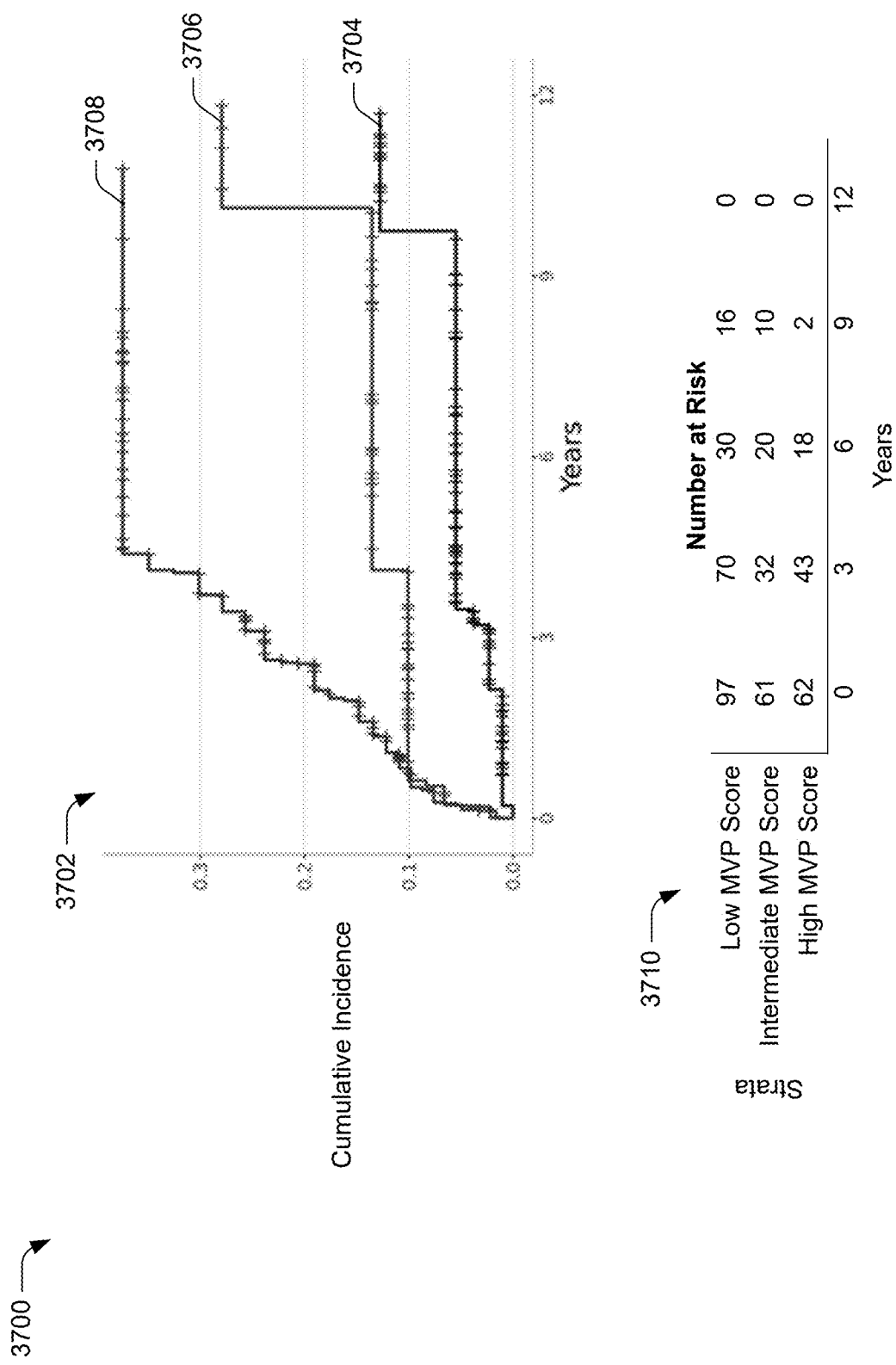
FIG. 37 shows an example analysis of the cumulative incidence of mitral valve repair or replacement, as stratified by a deep learning model-predicted probability of MVP.

FIG. 37 shows an example analysis 3700 of the cumulative incidence of mitral valve repair or replacement, as stratified by a DROID-MVP predicted probability of MVP (e.g., MVP score). The analysis 3700 includes a graph 3702 of cumulative incidence (vertical axis) relative to years (horizontal axis). The graph 3702 includes a first plot 3704 corresponding to patients having a low MVP score (e.g., as predicted by DROID-MVP), a second plot 3706 corresponding to patients having an intermediate MVP score, and a third plot 3708 corresponding to patients having a high MVP score. The analysis 3700 further includes a summary table 3710 indicating the number of individuals at risk per each year examined for the MVP score strata.

Among 250 patients in the combined internal and external validation sets with echocardiographer-adjudicated MVP, 38 (15.2%) underwent subsequent MVR over a median follow up time of 3.3 years from the index echocardiogram. When stratified by MVP score as shown in the analysis 3700, 25/92 (27.2%) patients with high MVP score underwent MVR (estimated 5-year cumulative incidence 37.5% [95% CI:23.4-48.9%]) as compared to 4/99 (4.1%) patients with low MVP score (estimated 5-year cumulative incidence 5.5% [95% CI: 0-10.7%]; p<0.001).

Figure 38:
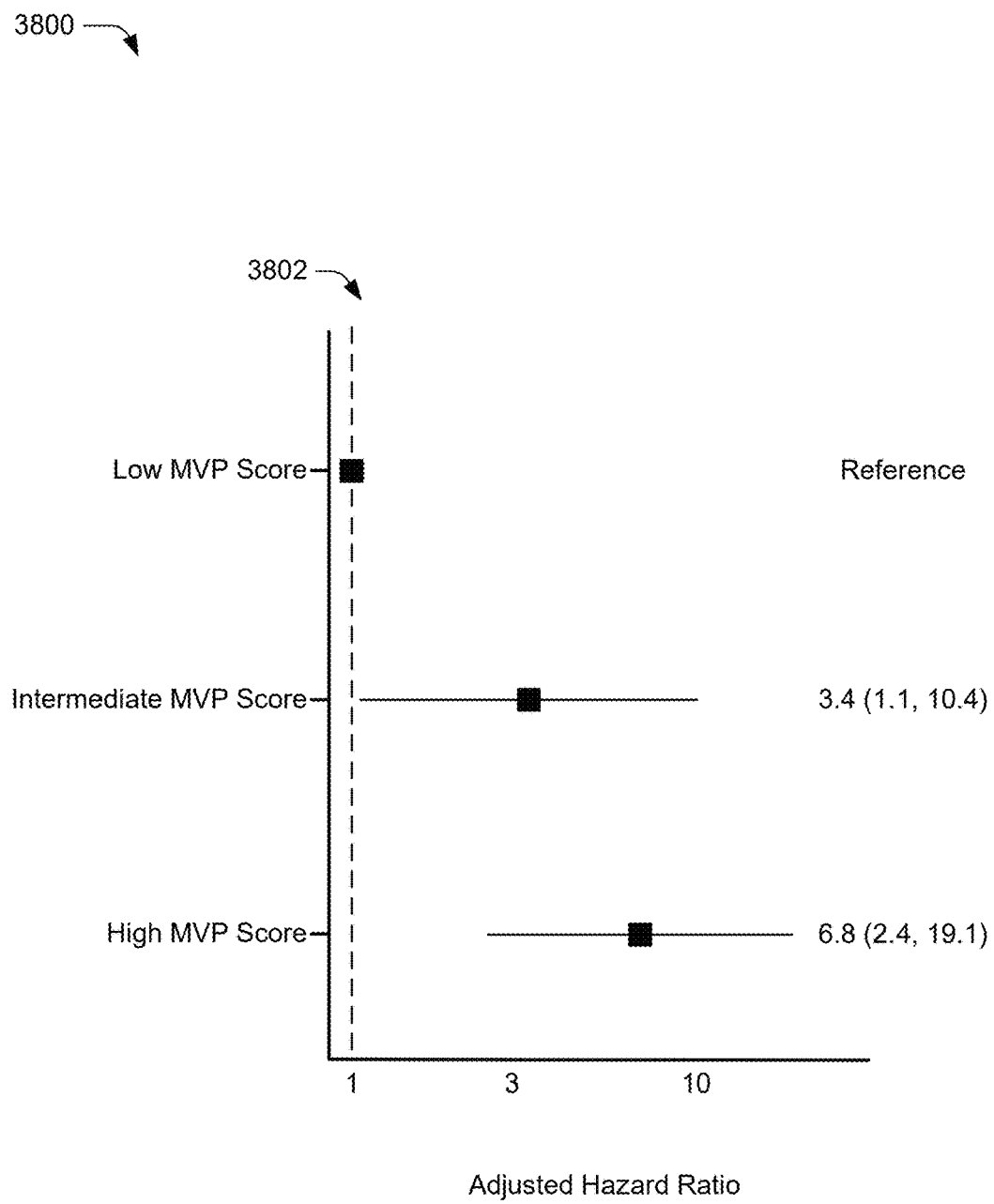
FIG. 38 depicts an example analysis of the association between MVP score and an incidence of mitral valve repair or replacement.

FIG. 38 depicts an example analysis 3800 of the association between MVP score and an incidence of mitral valve repair or replacement. The analysis 3800 includes a plot 3802 of the MVP score classified as low, intermediate, or high (vertical axis) versus an adjusted hazard ratio (horizontal axis). For the analysis 3800, the internal and external validation sets were combined. Patients were classified as having low (<0.33), intermediate (0.34-0.66), or high (>0.67) model-predicted probability of MVP ("MVP score"). Among patients with echocardiographer-adjudicated MVP and available covariates (n=236), a high versus low MVP score was associated with greater odds of moderate or severe MR (odds ratio 2.2 [1.2-4.2]; p=0.02), age, sex, LVESD, LVEF, and presence of moderate or severe MR, the latter of which reflect measurements influencing guideline indications for MVR.

The analysis 3800 includes a Cox proportional hazards regression model adjusted for age, sex, LVEF, LVESD, and presence of moderate or severe MR, the latter of which are elements of guideline indications for MVR in MVP. High MVP score was associated with a hazard ratio of 6.8 (95% CI:2.4-19.1) for MVR as compared to low MVP score (p<0.001), which was used as the reference. Intermediate MVP score was associated with a hazard ratio of 3.4 (95% CI:1.1-10.4) as compared to low MVP score.

To further explore the extent to which DROID-MVP predictions are specific to features of the MV, as opposed to being influenced by other cardiac structures present in the input video clips, changes in the MVP score after MVR were examined.

Figure 39:
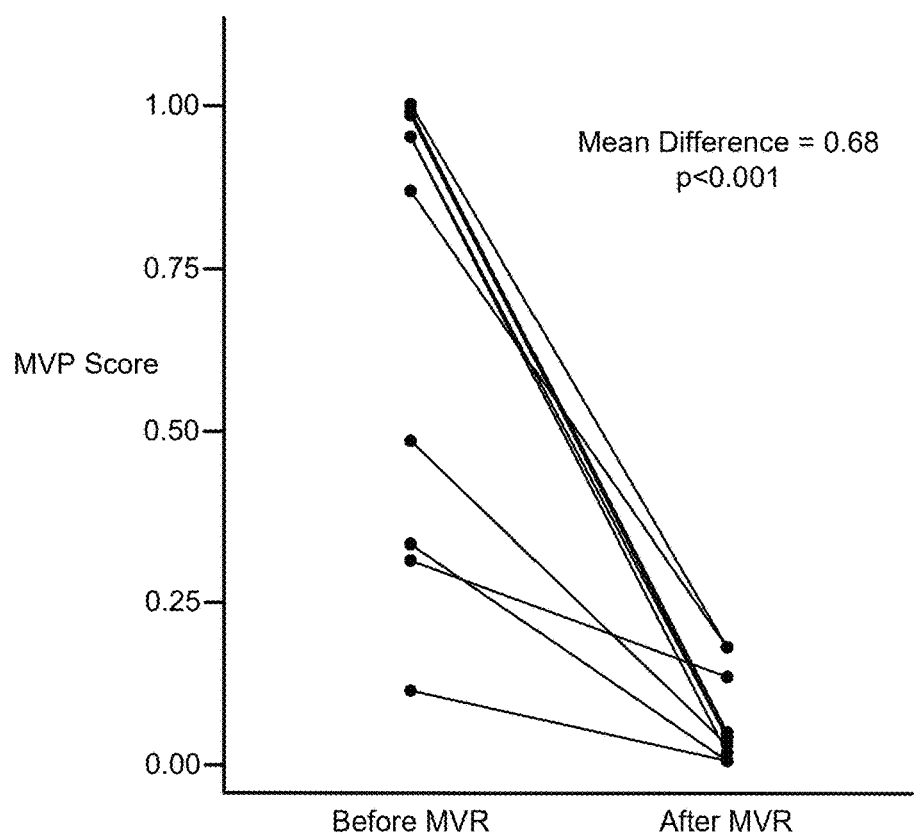
FIG. 39 depicts an example analysis of the change in MVP score following mitral valve repair or replacement.

FIG. 39 depicts an example analysis 3900 of the change in MVP score following mitral valve repair or replacement. For example, the analysis 3900 was performed using the subset of patients with pre- and post-MVR studies. The analysis 3900 includes a plurality of plots 3902, each of the plurality of plots 3902 corresponding to a different patient in the internal validation set with echocardiographer-adjudicated MVP and at least one available TTE performed before and after MVR. The DROID-MVP predicted MVP score (vertical axis) is plotted before MVR and after MVR, as indicated on the horizontal axis.

Among the eleven patients in the internal validation set with echocardiographer-adjudicated MVP and at least one available TTE performed before and after MVR, MVP score decreased by a mean of 0.68 (95% CI:0.44-0.91) following MVR (p<0.001).

Model Explainability

To understand which regions of the input video clip contribute to DROID-MVP predictions, saliency maps were generated which reflect the relative influence of different regions of the video clip on the final MVP prediction using an overlay. Qualitatively, the highest saliency was seen in the region of the MV, which was consistently identified regardless of the view or level of zoom of the clip.

Discussion

Example 3 describes DROID-MVP, a deep learning model for diagnosis of MVP that is trained and validated using over 1,000,000 TTE video clips from over 50,000 echocardiograms performed in over 17,000 longitudinal cardiology patients. It was found that in both cardiology and primary care patients, DROID-MVP exhibits excellent classification performance and has a higher agreement for MVP classification than echocardiographer adjudications.

DROID-MVP is a deep learning model that accurately identifies MVP from echocardiogram video clips. DROID-MVP predictions are associated with MR severity and incident MVR, and multiple approaches suggest that the model focuses on information from the MV to generate predictions. The results described in Example 3 suggest that deep learning methods can not only aid in automating identification of MVP from echocardiogram videos, but also potentially extend the abilities of clinicians by generating digital markers of MVP severity.

The use of deep learning in echocardiogram interpretation is interesting not only because it can automate tasks routinely done by highly trained clinicians, but also because it can improve upon human performance and enable use cases that are impractical and/or otherwise impossible. For example, diagnostic criteria for MVP focus on the degree of systolic displacement of the MV into the LA on the PLAX or A3C view because of the MV's saddle-shaped geometry and the need to standardize MVP diagnosis across echocardiographers and institutions. However, DROID-MVP can identify MVP with similar discriminative power even from A2C and A4C views. While the development of distinct diagnostic criteria for MVP in other views may be possible, they would be impractical to implement and standardize across echocardiography laboratories. Further, this would complicate already burdensome echocardiogram interpretation workflows to improve diagnostic yield of a relatively uncommon feature. An advantage of the deep learning approach to MVP identification described herein is that it incorporates information from the echocardiogram beyond a single measurement in the long-axis view, including data from other apical views and potentially other information on the appearance of the MV such as thickness. Moreover, DROID-MVP can incorporate this information without adding time or effort to the echocardiographer's workflow. In a hybrid workflow in which the model pre-reads studies prior to echocardiographer review, predictions can be easily revised based on clinical judgement as needed to minimize misclassification, which could include delayed diagnosis of MVP. The benefits of the techniques described herein are also apparent in the finding that the test-retest reliability of DROID-MVP is superior to the already highly reliable serial echocardiographer adjudications, suggesting that model predictions may help provide more reliable diagnoses of MVP in cases that are borderline by conventional diagnostic criteria.

The results described with respect to Example 3 also demonstrate the ways in which DROID-MVP can extend the capabilities of clinicians beyond streamlining MVP identification. Example 3 demonstrates that the MVP score is an independent predictor of moderate or severe MR among patients with MVP, a finding that is notable when considering that no Doppler imaging was used during training or inference. DROID-MVP also stratifies incidence of future MVR independently of demographics and other echocardiographic features that are included in the guideline recommendations for surgery. Taken together, these features of DROID-MVP suggest that it may be useful as a marker to stratify severity of MVP. Though MVP is often considered a clinically binary entity, it is increasingly recognized that there is a spectrum of degeneration of the MV with variable clinical prognosis. However, there are no standardized diagnostic criteria for these intermediate MVP phenotypes. The results described with respect to Example 3 indicate that higher DROID-MVP predictions correlate with more severe disease, suggesting that deep learning methods may be capable of generating a digital biomarker of MVP severity.

While model explainability is a challenge when using deep learning approaches, several approaches have been used to understand which components of the echocardiogram influence DROID-MVP predictions. First, DROID-MVP predictions are associated with MR severity despite the absence of Doppler color imaging, suggesting that the model identifies features of the MV (e.g., shape or coaptation) that are associated with MR. Moreover, the model performance remains good within strata of MR severity, suggesting that MR alone does not account for the high discriminative power of the model. Second, no association between model predictions and other structural left heart changes were observed among patients with MVP, suggesting that the model does not use changes in LA or LV size to assign higher scores independently of MVP status. Third, good model performance was also observed across subgroups based on race, age and sex, suggesting that these are not major contributors to model performance. Fourth, a large decrease in the predicted probability of MVP was observed in patients following MVR, suggesting that the predictions of the model are focused on the MV and respond appropriately to the change in appearance of the MV following surgery. Finally, saliency mapping techniques were employed to visualize the regions of the echocardiogram that most greatly influence the output of the model. While these techniques are limited in that they are linear visualizations of a highly non-linear model, they indicate that the area around the MV has the greatest influence on model predictions, with relatively little contribution from other regions. Also notable is the fact that DROID-MVP saliency maps consistently highlight the MV across different views and zoom levels, suggesting that the model localizes the MV regardless of where it appears in the video clip.

Conclusion

DROID-MVP is a deep learning model that accurately identifies MVP from echocardiogram video clips. DROID-MVP predictions are associated with MR severity and incident MVR, and multiple approaches suggest that the model focuses on information from the MV to generate predictions. The results described with respect to Example 3 suggest that deep learning methods can not only automate classification of MVP from echocardiogram videos, but also potentially extend the abilities of clinicians by generating digital markers of MVP severity.

Conclusion

Although the invention has been described in language specific to structural features and/or methodological acts, it is to be understood that the invention defined in the appended claims is not necessarily limited to the specific features or acts described. Rather, the specific features and acts are disclosed as example forms of implementing the claimed invention.

Features described above as well as those claimed below may be combined in various ways without departing from the scope hereof. The following examples illustrate some possible, non-limiting combinations:

(A1) A system comprising: an echocardiogram analysis module implemented in a non-transitory computer-readable storage medium, the echocardiogram analysis module comprising: a deep learning model to generate a video output for an input echocardiogram video, the deep learning model comprising a convolutional neural network and at least one dense layer; and a cardiac prediction generator to generate a cardiac prediction based on video outputs generated for a plurality of input echocardiogram videos of an echocardiogram study, the cardiac prediction comprising a measurement prediction or a classification prediction.

For example, as described herein, the deep learning model may be configured and/or trained to generate the single-video output. Similarly, the cardiac prediction generator may be configured and/or trained to generate a cardiac prediction.

The system may comprise one or more processors configured to perform operations, the operations comprising using a deep learning model to generate a single-video output for an input echocardiogram video, the deep learning model comprising a convolutional neural network and at least one dense layer; and using a cardiac prediction generator to generate a cardiac prediction based on single-video outputs generated for a plurality of input echocardiogram videos of a single echocardiogram study.

The cardiac prediction generator may be configured to generate the cardiac prediction based on single-video outputs generated by the deep learning model. Optionally, as described herein, the plurality of echocardiogram videos may comprise a plurality of different views. Further optionally, each input echocardiogram video may comprise a sequence of echocardiogram image frames obtained for a single view during a single acquisition process, and the input echocardiogram videos may comprise different view angles with respect to each other, such that the deep learning generates a plurality of single-video outputs each based on different view angles. In this way, information is extracted from a plurality of echocardiogram videos of a single study, including, optionally, from views that have previously been considered suboptimal or non-diagnostic for human analysis or which are not typically used during a manual clinical analysis workflow. As an illustrative example, information extracted from apical two chamber and/or apical four chamber views may be used in generating the cardiac prediction for mitral valve prolapse classification, even though apical two chamber and/or apical four chamber views are generally not used during a manual clinical analysis workflow for mitral valve prolapse. By leveraging this information, as described in greater detail herein, the cardiac predictions generated by the cardiac prediction generator are made more accurate.

(A2) For the system denoted as (A1), the video output comprises a video embedding, and wherein the deep learning model further comprises at least one multi-instance attention head to aggregate video embeddings generated for the plurality of echocardiogram videos of the echocardiogram study.

Optionally, the at least one multi-instance attention head may form part of the cardiac prediction generator.

(A3) For the system denoted as (A1) or (A2), the video output comprises a video cardiac prediction, and the cardiac prediction generator comprises an aggregation function to aggregate the video cardiac predictions generated for the plurality of echocardiogram videos of the echocardiogram study.

(A4) For the system denoted as any of (A1) through (A3), the cardiac prediction comprises the measurement prediction, and the measurement prediction comprises at least one of a left ventricular ejection fraction, a left ventricular dimension, or a left ventricular wall thickness.

(A5) For the system denoted as any of (A1) through (A4), the measurement prediction comprises the left ventricular dimension, and the left ventricular dimension comprises at least one of a left ventricular end-diastolic dimension or a left ventricular end-systolic dimension.

(A6) For the system denoted as any of (A1) through (A5), the measurement prediction comprises the left ventricular wall thickness, and the left ventricular wall thickness comprises at least one of an interventricular septal wall thickness or a posterior wall thickness.

(A7) For the system denoted as any of (A1) through (A6), the cardiac prediction comprises the measurement prediction, and the measurement prediction comprises a left atrial anteroposterior dimension.

(A8) For the system denoted as any of (A1) through (A7), the cardiac prediction comprises the measurement prediction, and the measurement prediction comprises at least one of a right ventricular end-diastolic diameter or a right ventricular ejection fraction.

(A9) For the system denoted as any of (A1) through (A8), the cardiac prediction comprises the classification prediction, and the classification prediction indicates unspecified mitral valve prolapse, anterior leaflet prolapse, posterior leaflet prolapse, bileaflet prolapse, or no mitral valve prolapse.

(A10) For the system denoted as any of (A1) through (A9), the cardiac prediction comprises the classification prediction, and the classification prediction comprises a probability score that a mitral valve prolapse is present.

(A11) For the system denoted as any of (A1) through (A10), the echocardiogram analysis module further comprises a data preprocessor to generate a standardized input video from the input echocardiogram video, and wherein the convolutional neural network extracts features of the standardized input video and outputs a video embedding summarizing the features.

(A12) For the system denoted as any of (A1) through (A11), further comprising a training module configured to: train the deep learning model using a training sample comprising a first portion of a first subset of echocardiogram training data; and refine the trained deep learning model using a development sample comprising a second portion of the first subset of the echocardiogram training data.

(A13) For the system denoted as (A12), to train the deep learning model using the training sample, the training module is further configured to: pre-train the deep learning model to output a qualitative classification as the cardiac prediction using an entirety of the training sample; and retrain the pre-trained deep learning model to output a quantitative value as the cardiac prediction using a subset of the training sample.

(A14) For the system denoted as any of (A12) through (A13), the training module is further configured to internally validate the trained and refined deep learning model using an internal validation sample comprising a third, remaining portion of the first subset of the echocardiogram training data.

(A15) For the system denoted as any of (A12) through (A14), the training module is further configured to externally validate the deep learning model using an external validation sample comprising a second subset of the echocardiogram training data, wherein the first subset of the echocardiogram training data and the second subset of the echocardiogram training data comprise echocardiogram videos from different data sources.

(A16) For the system denoted as any of (A1) through (A15), the cardiac prediction indicates a presence or absence of a cardiovascular condition.

(A17) For the system denoted as any of (A1) through (A16), the cardiac prediction comprises the classification prediction; the classification prediction comprises a mitral valve prolapse classification; and the plurality of input echocardiogram videos include at least one of an apical two chamber view or an apical four chamber view.

(B1) A method comprising: generating a standardized input video for an echocardiogram video to be processed by a deep learning model trained to output a cardiac prediction; extracting, via a convolutional neural network of the deep learning model, features of the standardized input video; outputting, by the convolutional neural network, a video embedding summarizing the features of the standardized input video; and generating the cardiac prediction based at least in part on video embeddings generated for a plurality of echocardiogram videos of an echocardiogram study, optionally wherein the plurality of echocardiogram videos comprises a plurality of different views, wherein the cardiac prediction comprises a measurement prediction or a classification prediction.

(B2) For the method denoted as (B1), wherein generating the cardiac prediction based at least in part on video embeddings generated for the plurality of echocardiogram videos of the echocardiogram study comprises: aggregating the video embeddings generated for the plurality of echocardiogram videos of the echocardiogram study via at least one trained multi-instance attention head; and generating the cardiac prediction based on an output of the at least one trained multi-instance attention head.

(B3) For the method denoted as (B1) or (B2), generating the cardiac prediction based at least in part on video embeddings generated for the plurality of echocardiogram videos of the echocardiogram study comprises: generating, via at least one dense layer, a video cardiac prediction based on the video embedding; and aggregating video cardiac predictions generated for the plurality of echocardiogram videos of the echocardiogram study using an aggregation function.

(B4) For the method denoted as any of (B1) through (B3), the aggregation function takes a median of the video cardiac predictions generated for the plurality of echocardiogram videos of the echocardiogram study.

(B5) For the method denoted as any of (B1) through (B4), the cardiac prediction comprises the measurement prediction, and the measurement prediction comprises a chamber dimension.

(B6) For the method denoted as any of (B1) through (B5), the cardiac prediction comprises the measurement prediction, and the measurement prediction comprises a wall thickness.

(B7) For the method denoted as any of (B1) through (B6), the cardiac prediction comprises the measurement prediction, and the measurement prediction comprises an ejection fraction.

(B8) For the method denoted as any of (B1) through (B7), wherein the cardiac prediction comprises the classification prediction, and the classification prediction comprises a mitral valve prolapse classification.

(C1) A method comprising: training a deep learning model to output a cardiac prediction, the training comprising: initially training the deep learning model using a training sample subset of a first portion of echocardiogram training data, the initially training including adjusting weights and bias of the deep learning model based on a loss calculated between a video output of the deep learning model for the cardiac prediction and a ground truth label; and refining the initially trained deep learning model using a development sample subset of the first portion of the echocardiogram training data, the refining including adjusting hyperparameters of the deep learning model; and generating the cardiac prediction for an echocardiogram video using the trained deep learning model, the generating comprising: preprocessing an echocardiogram video to be input to the deep learning model to generate a standardized input video; extracting, via a convolutional neural network of the deep learning model, features of the standardized input video; outputting, by the convolutional neural network, a video embedding summarizing the features of the standardized input video; and generating the cardiac prediction based on the video embedding.

(C2) For the method denoted as (C1), the training further comprises: internally validating the refined deep learning model using an internal validation sample subset of the first portion of the echocardiogram training data; and externally validating the internally validated deep learning model using an external validation sample comprising a second portion of the echocardiogram training data.

(C3) For the method denoted as (C1) or (C2), further comprising: selecting videos of a plurality of echocardiogram videos of an echocardiogram study based on a video classification output by the deep learning model for a given video of the plurality of echocardiogram videos; and generating a study-level cardiac prediction for the echocardiogram study by aggregating, via at least one multi-instance attention head, the video embedding output by the convolutional neural network for the selected videos.

(C4) For the method denoted as any of (C1) through (C3), further comprising: selecting videos of a plurality of echocardiogram videos of an echocardiogram study based on a video classification output by the deep learning model for a given video of the plurality of echocardiogram videos; and generating a study-level cardiac prediction for the echocardiogram study by aggregating, via an aggregation function, the cardiac prediction output by the convolutional neural network for the selected videos.

(C5) For the method denoted as any of (C1) through (C4), the cardiac prediction comprises a measurement prediction or a classification prediction.

What is claimed is:

1. A cardiac prediction system comprising:
   an echocardiogram analysis module implemented in a non-transitory computer-readable storage medium, the echocardiogram analysis module comprising:
      a data preprocessor that generates an input video for an echocardiogram video of a heart of a patient;
      a deep learning model comprising a convolutional neural network trained with a training dataset including echocardiogram videos of a plurality of echocardiogram studies to learn features of the echocardiogram videos, the convolutional neural network generating a video embedding summarizing features of the input video of the heart of the patient based on the learned features of the training dataset, the deep learning model further comprising at least one multi-instance attention head to aggregate video embeddings generated for a plurality of echocardiogram videos of an echocardiogram study of the heart of the patient; and
      a cardiac prediction generator that generates a cardiac prediction based upon the aggregated video embeddings, the cardiac prediction comprising a measurement prediction or a classification prediction for the heart of the patient, the measurement prediction, when generated, being selected from at least one of a left ventricular ejection fraction, a left ventricular dimension, a left ventricular wall thickness, a left atrial anteroposterior dimension, a right ventricular end-diastolic diameter, or a right ventricular ejection fraction, and the classification prediction, when generated, being selected from at least one of unspecified mitral valve prolapse, anterior leaflet prolapse, posterior leaflet prolapse, bileaflet prolapse, no mitral valve prolapse, or a probability score that a mitral valve prolapse is present.

2. The system of claim 1, wherein the cardiac prediction comprises the classification prediction.

3. The system of claim 1, wherein the cardiac prediction comprises the measurement prediction.

4. The system of claim 3, wherein the measurement prediction comprises the left ventricular dimension, and the left ventricular dimension comprises at least one of a left ventricular end-diastolic dimension or a left ventricular end-systolic dimension.

5. The system of claim 3, wherein the measurement prediction comprises the left ventricular wall thickness, and the left ventricular wall thickness comprises at least one of an interventricular septal wall thickness or a posterior wall thickness.

6. The system of claim 1, wherein the cardiac prediction comprises the measurement prediction, and the measurement prediction comprises the left atrial anteroposterior dimension.

7. The system of claim 1, wherein the cardiac prediction comprises the measurement prediction, and the measurement prediction comprises at least one of the right ventricular end-diastolic diameter or the right ventricular ejection fraction.

8. The system of claim 1, wherein the cardiac prediction comprises the classification prediction, and the classification prediction indicates the unspecified mitral valve prolapse, the anterior leaflet prolapse, the posterior leaflet prolapse, the bileaflet prolapse, or the no mitral valve prolapse.

9. The system of claim 1, wherein the cardiac prediction comprises the classification prediction, and the classification prediction comprises the probability score that a mitral valve prolapse is present.

10. The system of claim 1, further comprising a training module configured to:
    train the deep learning model using a training sample comprising a first portion of a first subset of the training data; and
    refine the trained deep learning model using a development sample comprising a second portion of the first subset of the training data.

11. The system of claim 10, wherein to train the deep learning model using the training sample, the training module is further configured to:
    pre-train the deep learning model to output a qualitative classification as the cardiac prediction using an entirety of the training sample; and
    retrain the pre-trained deep learning model to output a quantitative value as the cardiac prediction using a subset of the training sample.

12. The system of claim 10, wherein the training module is further configured to internally validate the trained and refined deep learning model using an internal validation sample comprising a third portion of the first subset of the training data.

13. The system of claim 10, wherein the training module is further configured to externally validate the deep learning model using an external validation sample comprising a second subset of the training data, wherein the first subset of the training data and the second subset of the training data comprise echocardiogram videos from different data sources.

14. The system of claim 1, wherein the cardiac prediction indicates a presence or absence of a cardiovascular condition.

15. The system of claim 1, wherein:
    the cardiac prediction comprises the classification prediction;
    the classification prediction comprises a mitral valve prolapse classification; and
    the plurality of input echocardiogram videos includes at least one of an apical two chamber view or an apical four chamber view.

16. A method for generating a cardiac prediction, said method comprising:
generating a standardized input video for an echocardiogram video of a heart of a patient to be processed by a deep learning model trained to output a cardiac prediction, the deep learning model having been trained on standardized input videos generated for echocardiogram videos of a plurality of echocardiogram studies;
using the deep learning model to analyze the standardized input video by:
extracting, via a convolutional neural network of the deep learning model, features of the standardized input video, the features learned from the plurality of echocardiogram studies during training; and
outputting, by the convolutional neural network, a video embedding summarizing the features of the standardized input video; and
generating the cardiac prediction based at least in part on video embeddings generated for a plurality of echocardiogram videos of an echocardiogram study, the plurality of echocardiogram videos comprising a plurality of different views, the video embeddings being aggregated using at least one multi-instance attention head of the deep learning model,
wherein the cardiac prediction comprises a measurement prediction or a classification prediction for the heart of the patient, the measurement prediction, when generated, being selected from at least one of a left ventricular ejection fraction, a left ventricular dimension, a left ventricular wall thickness, a left atrial anteroposterior dimension, a right ventricular end-diastolic diameter, or a right ventricular ejection fraction, and the classification prediction, when generated, being selected from at least one of unspecified mitral valve prolapse, anterior leaflet prolapse, posterior leaflet prolapse, bileaflet prolapse, no mitral valve prolapse, or a probability score that a mitral valve prolapse is present.

17. The method of claim 16, wherein the aggregating takes a median of the video embeddings generated for the plurality of echocardiogram videos of the echocardiogram study.

18. The method of claim 16, wherein the cardiac prediction comprises the measurement prediction, and the measurement prediction comprises the left ventricular dimension, and the left ventricular dimension comprises at least one of a left ventricular end-diastolic dimension or a left ventricular end-systolic dimension.

19. The method of claim 16, wherein the cardiac prediction comprises the measurement prediction, and the measurement prediction comprises the left ventricular wall thickness, and the left ventricular wall thickness comprises at least one of an interventricular septal wall thickness or a posterior wall thickness.

20. The method of claim 16, wherein the cardiac prediction comprises the measurement prediction, and the measurement prediction comprises at least one of a left ventricular ejection fraction, a left ventricular dimension, or a left ventricular wall thickness.

21. The method of claim 16, wherein the cardiac prediction comprises the classification prediction, and the classification prediction comprises the mitral valve prolapse classification.

22. A cardiac prediction method comprising:
training a deep learning model to output a cardiac prediction based on learned features of echocardiogram training data, the echocardiogram training data including a plurality of input echocardiogram videos of a plurality of echocardiogram studies, the training comprising:
initially training the deep learning model using a training sample subset of a first portion of the echocardiogram training data, the initially training including adjusting weights and biases of the deep learning model based on a loss calculated between an output of the deep learning model for the cardiac prediction and a ground truth label; and
refining the initially trained deep learning model using a development sample subset of the first portion of the echocardiogram training data, the refining including adjusting hyperparameters of the deep learning model; and
generating the cardiac prediction for an echocardiogram study of a heart of a patient using the trained deep learning model, the generating comprising:
preprocessing an echocardiogram video of the echocardiogram study to be input to the deep learning model to generate a standardized input video;
extracting, via a convolutional neural network of the deep learning model, features of the standardized input video based on the learned features;
outputting, by the convolutional neural network, a video embedding summarizing the features of the standardized input video;
aggregating video embeddings generated for a plurality of echocardiogram videos of the echocardiogram study using at least one multi-instance attention head of the deep learning model; and
generating the cardiac prediction based on the aggregated video embeddings, the cardiac prediction comprising a measurement prediction or a classification prediction for the heart of the patient, the measurement prediction, when generated, being selected from at least one of a left ventricular ejection fraction, a left ventricular dimension, a left ventricular wall thickness, a left atrial anteroposterior dimension, a right ventricular end-diastolic diameter, or a right ventricular ejection fraction, and the classification prediction, when generated, being selected from at least one of unspecified mitral valve prolapse, anterior leaflet prolapse, posterior leaflet prolapse, bileaflet prolapse, no mitral valve prolapse, or a probability score that a mitral valve prolapse is present.

23. The method of claim 22, wherein the training further comprises:
internally validating the refined deep learning model using an internal validation sample subset of the first portion of the echocardiogram training data; and
externally validating the internally validated deep learning model using an external validation sample comprising a second portion of the echocardiogram training data.

24. The method of claim 22, further comprising:
selecting videos of the plurality of echocardiogram videos of the echocardiogram study based on a video classification output by the deep learning model for a given video of the plurality of echocardiogram videos; and
generating a study-level cardiac prediction for the echocardiogram study by aggregating, via the at least one multi-instance attention head, the video embedding output by the convolutional neural network for the selected videos.

25. The method of claim 22, further comprising:
selecting videos of the plurality of echocardiogram videos of the echocardiogram study based on a video classification output by the deep learning model for a given video of the plurality of echocardiogram videos; and
generating a study-level cardiac prediction for the echocardiogram study by aggregating, via an aggregation function, the cardiac prediction output by the convolutional neural network for the selected videos.

26. The method of claim 22, wherein the cardiac prediction comprises the probability score that the mitral valve prolapse is present.

* * * * *